US011180741B2

(12) United States Patent
Heron et al.

(10) Patent No.: US 11,180,741 B2
(45) Date of Patent: Nov. 23, 2021

(54) MODIFIED ENZYMES

(71) Applicant: Oxford Nanopore Technologies Ltd., Oxford (GB)

(72) Inventors: Andrew John Heron, Oxford (GB); Rebecca Victoria Bowen, Oxford (GB); Mark Bruce, Oxford (GB); Lakmal Jayasinghe, Oxford (GB); Joseph Hargreaves Lloyd, Oxford (GB); Szabolcs Soeroes, Oxford (GB); Elizabeth Jayne Wallace, Oxford (GB); Christopher Peter Youd, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 15/517,592

(22) PCT Filed: Oct. 6, 2015

(86) PCT No.: PCT/GB2015/052916
§ 371 (c)(1),
(2) Date: Apr. 7, 2017

(87) PCT Pub. No.: WO2016/055777
PCT Pub. Date: Apr. 14, 2016

(65) Prior Publication Data
US 2018/0179500 A1    Jun. 28, 2018

(30) Foreign Application Priority Data
Oct. 7, 2014    (GB) ...................................... 1417712

(51) Int. Cl.
*C12N 9/14* (2006.01)
*C12Q 1/6869* (2018.01)
*C12Q 1/68* (2018.01)

(52) U.S. Cl.
CPC ................. *C12N 9/14* (2013.01); *C12Q 1/68* (2013.01); *C12Q 1/6869* (2013.01); *C12Y 306/04012* (2013.01)

(58) Field of Classification Search
None
See application file for complete search history.

(56) References Cited

U.S. PATENT DOCUMENTS

| | | |
|---|---|---|
| 7,338,807 B2 | 3/2008 | Harris et al. |
| 7,625,706 B2 | 12/2009 | Akeson et al. |
| 7,745,116 B2 | 6/2010 | Williams |
| 7,851,203 B2 | 12/2010 | Letant et al. |
| 7,947,454 B2 | 5/2011 | Akeson et al. |
| 8,105,846 B2 | 1/2012 | Bayley et al. |
| 8,785,211 B2 | 7/2014 | Bayley et al. |
| 8,828,208 B2 | 9/2014 | Canas et al. |
| 9,617,591 B2 | 4/2017 | Moysey et al. |
| 9,758,823 B2 | 9/2017 | Moysey et al. |
| 9,797,009 B2 | 10/2017 | Heron et al. |
| 10,221,450 B2 | 3/2019 | Heron et al. |
| 10,322,150 B2 | 6/2019 | Honda et al. |
| 10,385,382 B2 | 8/2019 | Heron et al. |
| 10,392,658 B2 | 8/2019 | Heron et al. |
| 10,443,097 B2 | 10/2019 | Jayasinghe et al. |
| 10,724,018 B2 | 7/2020 | Bruce et al. |
| 10,724,087 B2 | 7/2020 | Moysey et al. |
| 10,808,231 B2 | 10/2020 | Heron et al. |
| 10,844,432 B2 | 11/2020 | Jayasinghe et al. |
| 2003/0010638 A1 | 1/2003 | Hansford et al. |
| 2004/0058378 A1 | 3/2004 | Kong et al. |
| 2004/0248114 A1 | 12/2004 | Taira et al. |
| 2006/0063171 A1 | 3/2006 | Akeson et al. |
| 2008/0293045 A1 | 11/2008 | Piepenburg et al. |
| 2009/0256116 A1 | 10/2009 | Shumaker-Parry et al. |
| 2010/0035260 A1 | 2/2010 | Olasagasti et al. |
| 2010/0092960 A1 | 4/2010 | Fehr |
| 2010/0120098 A1 | 5/2010 | Grunenwald et al. |
| 2010/0221212 A1 | 9/2010 | Stagliano et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0107802 A1 | 5/2012 | Stoddart et al. |
| 2013/0048499 A1 | 2/2013 | Mayer et al. |
| 2013/0149769 A1 | 6/2013 | Kizaki et al. |
| 2013/0225421 A1 | 8/2013 | Li et al. |
| 2014/0051069 A1 | 2/2014 | Jayasinghe et al. |
| 2014/0186823 A1 | 7/2014 | Clarke et al. |

(Continued)

FOREIGN PATENT DOCUMENTS

| | | |
|---|---|---|
| CA | 2927728 | 4/2015 |
| CA | 2937411 | 7/2015 |

(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
(H. Guo et al., "Protein Tolerance to Random Amino Acid Change", PNAS 101(25): 9205-9210, Jun. 2004.*
Sequence ID No. 2 Search Results. US-14-351-038-2. Sep. 16, 2015. 69 pages.
Blast® NCBI. Sequence ID No. 10; ZSYBNHWV114. Sep. 18, 2015.
Blast® NCBI. Sequence ID No. 52; ZT1133A811N. Sep. 18, 2015.
Genbank Submission. NCBI; Accession No. AM778123. Richards et al.; Sep. 18, 2008.
Genbank accession No. AEA72977 sequence. Apr. 6, 2011. Gregoracci et al.
GenPept Accession No. XP 003728286. Jun. 7, 2012.

(Continued)

*Primary Examiner* — Richard G Hutson
(74) *Attorney, Agent, or Firm* — Wolf, Greenfield & Sacks, P.C.

(57) ABSTRACT

The invention relates to modified Dda helicases which can be used to control the movement of polynucleotides and are particularly useful for sequencing polynucleotides.

30 Claims, 15 Drawing Sheets

Specification includes a Sequence Listing.

(56) References Cited

U.S. PATENT DOCUMENTS

| | | |
|---|---|---|
| 2014/0255921 A1 | 9/2014 | Moysey et al. |
| 2014/0262784 A1 | 9/2014 | Clarke et al. |
| 2014/0335512 A1 | 11/2014 | Moysey et al. |
| 2015/0008126 A1 | 1/2015 | Maglia et al. |
| 2015/0031020 A1 | 1/2015 | Jayasinghe et al. |
| 2015/0065354 A1 | 3/2015 | Moysey et al. |
| 2015/0152492 A1 | 6/2015 | Brown et al. |
| 2015/0191709 A1 | 7/2015 | Heron et al. |
| 2015/0197796 A1 | 7/2015 | White et al. |
| 2015/0218629 A1 | 8/2015 | Heron et al. |
| 2016/0257942 A1 | 9/2016 | Bruce et al. |
| 2017/0002406 A1 | 1/2017 | Bowen et al. |
| 2018/0030530 A1 | 2/2018 | Moysey et al. |
| 2018/0037874 A9 | 2/2018 | Bruce et al. |
| 2018/0230526 A1 | 8/2018 | Heron et al. |
| 2019/0203288 A1 | 7/2019 | Gutierrez et al. |
| 2019/0345550 A1 | 11/2019 | Bowen et al. |
| 2021/0009971 A1 | 1/2021 | Bruce et al. |

FOREIGN PATENT DOCUMENTS

| | | |
|---|---|---|
| CN | 104039979 A | 9/2014 |
| JP | 2006-500028 A | 1/2006 |
| WO | 2000/028312 | 5/2000 |
| WO | 2002/092821 | 11/2002 |
| WO | 2004/027025 A2 | 4/2004 |
| WO | 2005/124888 | 12/2005 |
| WO | 2006/028508 | 3/2006 |
| WO | 2006/100484 | 9/2006 |
| WO | 2007/057668 | 5/2007 |
| WO | 2008/102120 | 8/2008 |
| WO | 2008/102121 | 8/2008 |
| WO | 2008/124107 A1 | 10/2008 |
| WO | 2009/035647 | 3/2009 |
| WO | 2009/044170 A1 | 4/2009 |
| WO | 2009/077734 A2 | 6/2009 |
| WO | 2010/004265 | 1/2010 |
| WO | 2010/004273 | 1/2010 |
| WO | 2010/034018 | 3/2010 |
| WO | 2010/086602 A1 | 8/2010 |
| WO | 2010/086603 | 8/2010 |
| WO | 2010/086622 | 8/2010 |
| WO | 2010/109197 | 9/2010 |
| WO | 2010/117470 A2 | 10/2010 |
| WO | 2010/122293 | 10/2010 |
| WO | 2011/067559 | 6/2011 |
| WO | 2012/033524 A2 | 3/2012 |
| WO | 2012/164270 A1 | 12/2012 |
| WO | 2013/014451 A1 | 1/2013 |
| WO | 2013/041878 | 3/2013 |
| WO | 2013/057495 A2 | 4/2013 |
| WO | 2013/098561 A1 | 7/2013 |
| WO | 2013/098562 A2 | 7/2013 |
| WO | 2013/153359 | 10/2013 |
| WO | 2013/185137 A1 | 12/2013 |
| WO | 2014/013259 A1 | 1/2014 |
| WO | 2014/013260 A1 | 1/2014 |
| WO | 2014/013262 A1 | 1/2014 |
| WO | 2014/064443 A2 | 5/2014 |
| WO | 2014/064444 A1 | 5/2014 |
| WO | 2014/135838 A1 | 9/2014 |
| WO | WO 2014/135838 * | 9/2014 |
| WO | 2014/158665 A1 | 10/2014 |
| WO | 2015/022544 A1 | 2/2015 |
| WO | 2015/055981 A2 | 4/2015 |
| WO | 2015/110777 A1 | 7/2015 |
| WO | 2015/110813 A1 | 7/2015 |
| WO | 2015/124935 A1 | 8/2015 |
| WO | 2015/150786 A1 | 10/2015 |
| WO | 2016/034591 A2 | 3/2016 |
| WO | 2016/055777 A2 | 4/2016 |
| WO | 2016/059363 A1 | 4/2016 |
| WO | 2018/060740 A1 | 4/2018 |
| WO | 2018/100370 A1 | 6/2018 |

OTHER PUBLICATIONS

Press release: Oxford Nanopore introduces DNA 'strand sequencing' on the high-throughput GridlON platform and presents MinlON, a sequencer the size of a USB; memory stick, Feb. 2012.

[No. Author Listed] Antibodies bind specific molecules through their hypervariable loops. 33.3 Antibody Binding. 6th edition. 2007;953-954.

Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Arslan et al., Protein structure. Engineering of a superhelicase through conformational control. Science. Apr. 17, 2015;348(6232):344-7. doi: 10.1126/science.aaa0445.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Braha et al., Designed protein pores as components for biosensors. Chem Biol. Jul. 1997;4(7):497-505.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Buttner et al., Structural basis for DNA duplex separation by a superfamily-2 helicase. Nat Struct Mol Biol. Jul. 2007;14(7):647-52.

Byrd et al., A parallel quadruplex DNA is bound tightly but unfolded slowly by pif1 helicase. J Biol Chem. Mar. 6, 2015;290(10):6482-94. doi: 10.1074/jbc.M114.630749. Epub Jan. 14, 2015.

Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.

Colas et al., Microscopical investigations of nisin-loaded nanoliposomes prepared by Mozafari method and their bacterial targeting. Micron. 2007;38(8):841-7.

Comer et al., Microscopic mechanics of hairpin DNA translocation through synthetic nanopores. Biophys J. Jan. 2009;96(2):593-608. doi: 10.1016/j.bpj.2008.09.023.

Deamer, Nanopore analysis of nucleic acids bound to exonucleases and polymerases. Annu Rev Biophys. 2010;39:79-90. doi:10.1146/annurev.biophys.093008.131250.

Derrington et al., Nanopore DNA sequencing with MspA. Proc Natl Acad Sci U S A. Sep. 14, 2010; 107(37):16060-5. doi: 10.1073/pnas.1001831107. Epub Aug. 26, 2010.

Devereux et al., A comprehensive set of sequence analysis programs for the VAX. Nucleic Acids Res. Jan. 11, 1984;12(1 Pt 1):387-95.

Dostal et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.

Dou et al., The DNA binding properties of the *Escherichia coli* RecQ helicase. J Biol Chem. Feb. 20, 2004;279(8):6354-63. Epub Dec. 9, 2003.

Durrieu et al., Interactions between neuronal fusion proteins explored by molecular dynamics. Biophys J. May 1, 2008;94(9):3436-46. doi:10.1529/biophysj.107.123117. Epub Jan. 22, 2008.

(56) References Cited

OTHER PUBLICATIONS

Eliseev et al., Molecular Recognition of Nucleotides, Nucleosides, and Sugars by Aminocyclodextrins. J. Am. Chem. Soc., vol. 116:6081-6088 (1994).
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Garalde et al., Highly parallel direct RNA sequencing on an array of nanopores. bioRxiv. 2016. doi: http://dx.doi.org/10.1101/068809.
Garcillan-Barcia et al., The diversity of conjugative relaxases and its application in plasmid classification. FEMS Microbiol Rev. May 2009;33(3):657-87.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.
Grant et al., A facile method for attaching nitroxide spin labels at the 5' terminus of nucleic acids. Nucleic Acids Res. 2007;35(10):e77. Epub May 21, 2007.
Green et al., Quantitative evaluation of the lengths of homobifunctional protein cross-linking reagents used as molecular rulers. Protein Sci. Jul. 2001;10(7):1293-304.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al., The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Hornblower et al., Single-molecule analysis of DNA-protein complexes using nanopores. Nat Methods. Apr. 2007;4(4):315-7. Epub Mar. 4, 2007.
Howorka et al., Nanopore analytics: sensing of single molecules. Chem Soc Rev. Aug. 2009;38(8):2360-84. doi: 10.1039/b813796j. Epub Jun. 15, 2009.
Ivanov et al., DNA tunneling detector embedded in a nanopore. Nano Lett. Jan. 12, 2011;11(1):279-85. doi: 10.1021/nl103873a. Epub Dec. 6, 2010.
James, Aptamers. Encyclopedia of Analytical Chemistry. R.A. Meyers (Ed.). 4848-4871. John Wiley & Sons Ltd, Chichester, 2000.
Jezewska et al., Interactions of Escherichia coli replicative helicase PriA protein with single-stranded DNA. Biochemistry. Aug. 29, 2000;39(34):10454-67.
Kafri et al., Dynamics of molecular motors and polymer translocation with sequence heterogeneity. Biophys J. Jun. 2004;86(6):3373-91.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316. Epub Oct. 31, 2013.
Kar et al., Defining the structure-function relationships of bluetongue virus helicase protein VP6. J Virol. Nov. 2003;77(21):11347-56.
Keyser, Controlling molecular transport through nanopores. J R Soc Interface. Oct. 7, 2011;8(63):1369-78. doi: 10.1098/rsif.2011.0222. Epub Jun. 29, 2011.
Khafizov, Single Molecule Force Spectroscopy Of Single Stranded Dna Binding Protein And Rep Helicase. University of Illinois at Urbana-Champaign Dissertation. 2012.
Korolev et al., Major domain swiveling revealed by the crystal structures of complexes of E. coli Rep helicase bound to single-stranded DNA and ADP. Cell. Aug. 22, 1997;90(4):635-47.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.
Langecker et al., Synthetic lipid membrane channels formed by designed DNA nanostructures. Science. Nov. 16, 2012;338(6109):932-6. doi: 10.1126/science.1225624.
Lee et al., Direct imaging of single UvrD helicase dynamics on long single-stranded DNA. Nat Commun. 2013;4:1878. doi:10.1038/ncomms2882.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008; 133(5):801-12. doi: 10.1016/j.cell.2008.04.029.
Lohman et al., Mechanisms of helicase-catalyzed DNA unwinding. Annu Rev Biochem. 1996;65:169-214.
Lohman et al., Non-hexameric DNA helicases and translocases:mechanisms and regulation. Nat Rev Mol Cell Biol. May 2008;9(5):391-401. doi:10.1038/nrm2394.
Ma et al., Bright functional rotaxanes. Chem Soc Rev. Jan. 2010;39(1):70-80. doi: 10.1039/b901710k. Epub Jul. 21, 2009.
Maddox et al., Elevated serum levels in human pregnancy of a molecule immunochemically similar to eosinophil granule major basic protein. J Exp Med. Oct. 1, 1983;158(4):1211-26.
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Marini et al., A human DNA helicase homologous to the DNA cross-link sensitivity protein Mus308. J Biol Chem. Mar. 8, 2002;277(10):8716-23. Epub Dec. 18, 2001.
Miles et al., Properties of Bacillus cereus hemolysin II: a heptameric transmembrane pore. Protein Sci. Jul. 2002;11(7):1813-24.
Montal et al., Formation of bimolecular membranes from lipid monolayers and a study of their electrical properties. Proc Natl Acad Sci U S A. Dec. 1972;69(12):3561-6.
Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.
Nikolov et al., Behavior of giant vesicles with anchored DNA molecules. Biophys J. Jun. 15, 2007;92(12):4356-68. Epub Mar. 23, 2007.
O'Shea et al., X-ray structure of the GCN4 leucine zipper, a two-stranded, parallel coiled coil. Science. Oct. 25, 1991;254(5031):539-44.
Pfeiffer et al., Bivalent cholesterol-based coupling of oligonucletides to lipid membrane assemblies. J Am Chem Soc. Aug. 25, 2004;126(33):10224-5.
Pinero-Fernandez et al., Indole transport across Escherichia coli membranes. J Bacteriol. Apr. 2011;193(8):1793-8. doi:10.1128/JB.01477-10. Epub Feb. 4, 2011.
Portakal et al., Construction of recB-recD genetic fusion and functional analysis of RecBDC fusion enzyme in Escherichia coli. BMC Biochem. Oct. 10, 2008;9:27. doi: 10.1186/1471-2091-9-27.
Raney et al., Structure and Mechanisms of SF1 DNA Helicases. Adv Exp Med Biol. 2013;767:17-46. doi: 10.1007/978-1-4614-5037-5_2.
Remaut et al., Protein-protein interaction through beta-strand addition. Trends Biochem Sci. Aug. 2006;31(8):436-44. Epub Jul. 7, 2006.

(56) References Cited

OTHER PUBLICATIONS

Richards et al., Structure of the DNA repair helicase hel308 reveals DNA binding and autoinhibitory domains. J Biol Chem. Feb. 22, 2008;283(8):5118-26. Epub Dec. 4, 2007.

Rudolf et al., The DNA repair helicases XPD and FancJ have essential iron-sulfur domains. Mol Cell. Sep. 15, 2006;23(6):801-8.

Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.

Saariaho et al., Characteristics of MuA transposase-catalyzed processing of model transposon end DNA hairpin substrates. Nucleic Acids Res. Jun. 6, 2006;34(10):3139-49. Print 2006.

Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.

Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.

Schneider et al., DNA sequencing with nanopores. Nat Biotechnol. Apr. 10, 2012;30(4):326-8. doi: 10.1038/nbt.2181.

Singleton et al., Structure and mechanism of helicases and nucleic acid translocases. Annu Rev Biochem. 2007;76:23-50.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.

Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.

UniProt Database accession No. a4s1e1 sequence. May 15, 2007.
UniProt Database accession No. b4kac8 sequence. Sep. 23, 2008.
UniProt Database accession No. D0KN27. Dec. 15, 2009.
UniProt Database accession No. D7RM26 sequence. Aug. 10, 2010.
UniProt Database accession No. e1qus6 sequence. Nov. 30, 2010.
UniProt Database accession No. i3d0e7 sequence. Jul. 11, 2012.
UniProt Database accession No. I6ZR75 sequence. Oct. 3, 2012.
UniProt Database accession No. I7J3V8 sequence. Oct. 3, 2012.
UniProt Database accession No. k0im99 sequence. Nov. 28, 2012.
UniProt Database accession No. k7nri8 sequence. Feb. 6, 2013.
UniProt Database accession No. Q12WZ6 sequence. Apr. 12, 2017.
UniProt Database accession No. Q7Y5C3 sequence. Oct. 1, 2003.

Van Heel et al., Single-particle electron cryo-microscopy:towards atomic resolution. Q Rev Biophys. Nov. 2000;33(4):307-69.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Venkatesan et al., Nanopore sensors for nucleic acid analysis. Nat Nanotechnol. Sep. 18, 2011;6(10):615-24. doi: 10.1038/nnano.2011.129.

Vinson, Proteins in motion. Introduction. Science. Apr. 10, 2009;324(5924):197. doi: 10.1126/science.324.5924.197.

Wang et al., DNA helicase activity of the RecD protein from Deinococcus radiodurans. J Biol Chem. Dec. 10, 2004;279(50):52024-32.

White, Structure, function and evolution of the XPD family of iron-sulfur-containing 5'→3' DNA helicases. Biochem Soc Trans. 2009;37:547-551.

Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.

Woodman et al., Molecular biology of Hel308 helicase in archaea. Biochem Soc Trans. Feb. 2009;37(Pt 1):74-8. doi: 10.1042/BST0370074.

Woodman et al., Winged helix domains with unknown function in Hel308 and related helicases. Biochem Soc Trans. Jan. 2011;39(1):140-4. doi:10.1042/BST0390140.

Yoshina-Ishii et al., Arrays of mobile tethered vesicles on supported lipid bilayers. J Am Chem Soc. Apr. 2, 2003;125(13):3696-7.

Zhang et al., Structural evidence for consecutive Hel308-like modules in the spliceosomal ATPase Brr2. Nat Struct Mol Biol. Jul. 2009;16(7):731-9. doi: 10.1038/nsmb.1625.

U.S. Appl. No. 15/441,695, filed Feb. 24, 2017, Moysey et al.
U.S. Appl. No. 15/704,395, filed Sep. 14, 2017, Heron et al.
PCT/GB2015/052916, May 6, 2016, International Search Report and Written Opinion.
PCT/GB2015/052916, Apr. 20, 2017, International Preliminary Report on Patentability.

[No. Author Listed] Data sheet SEQ ID No. 10 search results from STIC, printed on Oct. 29, 2018, pp. 1-38 (Year: 2018).

[No. Author Listed] Data sheet SEQ ID No. 2 search results from STIC, printed on Oct. 29, 2018, pp. 1-24 (Year: 2018).

Balakrishnan et al., Dna2 exhibits a unique strand end-dependent helicase function. J Biol Chem Dec. 10, 2010;285(50):38861-8. doi: 10.1074/jbc.M110.165191. Epub Oct. 6, 2010.

Bennett et al., Association of yeast DNA topoisomerase III and Sgs1 DNA helicase: studies of fusion proteins. Proc Natl Acad Sci U S A. Sep. 25, 2001;98(20):11108-13. Epub Sep. 11, 2001.

Bessler et al., The amino terminus of the *Saccharomyces cerevisiae* DNA helicase Rrm3p modulates protein function ltering replication and checkpoint activity. Genetics. Nov. 2004;168(3):1205-18.

Byrd et al., Superfamily 2 helicases. Front Biosci (Landmark Ed). Jun. 1, 2012;17:2070-88.

Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.

Eoff et al., The Kinetic Mechanism for DNA Unwinding by Multiple Molecules of Dda Helicase Aligned on DNA. Biochemistry. Jun. 1, 2010; 49(21): 4543-4553. doi: 10.1021/bi100061v. Author Manuscript.

Farah et al., The RecBCD enzyme initiation complex for DNA unwinding:enzyme positioning and DNA opening. J Mol Biol. Oct. 10, 1997;272(5):699-715.

Guo et al., The linker region between the helicase and primase domains of the bacteriophage T7 gene 4 protein is critical for hexamer formation. J Biol Chem. Oct. 15, 1999;274(42):30303-9.

Heron et al., Simultaneous measurement of ionic current and fluorescence from single protein pores. J Am Chem Soc. Feb. 11, 2009;131(5):1652-3. doi: 10.1021/ja808128s.

Jankowsky, RNA helicases at work: binding and rearranging. Trends Biochem Sci. Jan. 2011;36(1):19-29. doi: 10.1016/j.tibs.2010.07.008.

Japrung et al., Urea facilitates the translocation of single-stranded DNA and RNA through the alpha-hemolysin nanopore. Biophys J. May 19, 2010;98(9):1856-63. doi: 10.1016/j.bpj.2009.12.4333.

Kankia et al., Folding of the thrombin aptamer into a G-quadruplex with Sr(2+): stability, heat, and hydration. J Am Chem Soc. Nov. 7, 2001; 123(44):10799-804.

Kutyavin et al., Oligonucleotides containing 2-aminoadenine and 2-thiothymine act as selectively binding complementary agents. Biochemistry. Aug. 27, 1996;35(34):11170-6.

Lee et al., Cooperative translocation enhances the unwinding of duplex DNA by SARS coronavirus helicase nsP13. Nucleic Acids Res. Nov. 2010;38(21):7626-36. doi: 10.1093/nar/gkq647. Epub Jul. 29, 2010.

LEVIN et al., Helicase from hepatitis C virus, energetics of DNA binding. J Biol Chem. Aug. 16, 2002;277(33):29377-85. Epub May 28, 2002.

(56) References Cited

OTHER PUBLICATIONS

Marathias et al., Structures of the potassium-saturated, 2:1, and intermediate, 1:1, forms of a quadruplex DNA. Nucleic Acids Res. May 1, 2000;28(9):1969-77.

Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.

Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.

Mechanic et al., *Escherichia coli* DNA helicase II is active as a monomer. J Biol Chem. Apr. 30, 1999;274(18):12488-98.

Ngo et al., Computational complexity, protein structure prediction, and the levinthal paradox. 14. The protein folding problem teritary structure prediction. Ed(s):Merz et al. Birkhauser, Boston, Ma. 1994. 433, 492-5.

Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.

Berger, Snapshot: nucleic acid helicases and translocases. Cell. Sep. 5, 2008;134(5):888-888.e1. doi: 10.1016/j.cell.2008.08.027.

Jia et al., Rotations of the 2B Sub-domain of *E. coli* UvrD Helicase/Translocase Coupled to Nucleotide and DNA Binding. J Mol Biol. Aug. 19, 2011; 411(3): 633-648. EPub Jun. 17, 2011. doi: 10.1016/j.jmb.2011.06.019.

Nishikiori et al., Crystal structure of the superfamily 1 helicase from Tomato mosaic virus. J Virol. Jul. 2012;86(14):7565-76. doi: 10.1128/JVI.00118-12. Epub May 9, 2012.

Stelter et al., Structural and mechanistic insight into DNA unwinding by Deinococcus radiodurans UvrD. PLoS One. Oct. 15, 2013;8(10):e77364. doi: 10.1371/journal.pone.0077364.

Zhang et al., DNA Binding and Unwinding Functional Analyses of Recombinant *E. coli* Helicase II (UvrD). Chinese J. of Biochem. Mol. Biol. 2007;23(9):764-9.

Ali et al., Kinetic measurement of the step size of DNA unwinding by *Escherichia coli* UvrD helicase. Science. Jan. 17, 1997;275(5298):377-80. doi: 10.1126/science.275.5298.377. Erratum in: Science Apr. 4, 1997;276(5309):21.

Dong et al., Wza the translocon for *E. coli* capsular polysaccharides defines a new class of membrane protein. Nature. Nov. 9, 2006;444(7116):226-9. doi: 10.1038/nature05267. Epub Nov. 1, 2006.

Jones et al., Protein secondary structure prediction based on position-specific scoring matrices. J Mol Biol. Sep. 17, 1999;292(2):195-202. doi: 10.1006/jmbi.1999.3091.

Kabsch et al., Dictionary of protein secondary structure: pattern recognition of hydrogen-bonded and geometrical features. Biopolymers. Dec. 1983;22(12):2577-637. doi: 10.1002/bip.360221211.

Theissen et al., Cooperative binding of ATP and RNA induces a closed conformation in a DEAD box RNA helicase. Proc Natl Acad Sci U S A. Jan. 15, 2008;105(2):548-53. doi: 10.1073/pnas.0705488105. Epub Jan. 9, 2008.

U.S. Appl. No. 16/902,301, filed Jun. 16, 2020, Moysey et al.
U.S. Appl. No. 17/064,329, filed Oct. 6, 2020, Heron et al.
U.S. Appl. No. 17/075,017, filed Oct. 20, 2020, Jayasinghe et al.
U.S. Appl. No. 16/893,332, filed Jun. 4, 2020, Bruce et al.

\* cited by examiner

MODIFIED ENZYMES

RELATED APPLICATIONS

This Application is a national stage filing under 35 U.S.C. § 371 of PCT International Application No. PCT/GB2015/052916, which has an international filing date of Oct. 6, 2015; is a continuation-in-part of PCT International Application No. PCT/GB2015/051291, which has an international filing date of May 1, 2015; and claims foreign priority benefits under 35 U.S.C. § 119(a)-(d) or 35 U.S.C. § 365(b) of British application number 1417712.5, filed Oct. 7, 2014, the contents of each of which are herein incorporated by reference in their entireties.

FIELD OF THE INVENTION

The invention relates to modified Dda helicases which can be used to control the movement of polynucleotides and are particularly useful for sequencing polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "strand sequencing" method, a single polynucleotide strand is passed through the pore and the identities of the nucleotides are derived. Strand sequencing can involve the use of a nucleotide handling protein, such as a helicase, to control the movement of the polynucleotide through the pore.

SUMMARY OF THE INVENTION

The inventors have surprisingly identified specific Dda mutants which have an improved ability to control the movement of a polynucleotide through a pore. The mutants of the invention display reduced forward slipping. This is a phenomenon where the DNA moves forwards relative to the pore by at least 4 consecutive nucleotides and typically by more than 10 consecutive nucleotides. Slipping forward may involve movement forward of 100 consecutive nucleotides or more and this may happen more than once for each polynucleotide. Slipping forward can be problematic for polynucleotide sequencing. The mutants identified by the inventors typically comprise a combination of mutations, namely (1) one or more substitutions of the amino acids which interact with nucleotides in single stranded DNA (ssDNA) and (2) one or more modifications in the part of the mutant which interacts with a transmembrane pore.

Accordingly, the invention provides a DNA-dependent ATPase (Dda) helicase in which (a) at least one amino acid which interacts with one or more nucleotides in single stranded DNA (ssDNA) is substituted and (b) the part of the helicase which interacts with a transmembrane pore comprises one or more modifications, wherein the helicase has the ability to control the movement of a polynucleotide.

The invention also provides:

a construct comprising a helicase of the invention and an additional polynucleotide binding moiety, wherein the helicase is attached to the polynucleotide binding moiety and the construct has the ability to control the movement of a polynucleotide;

a polynucleotide comprising a sequence which encodes a helicase of the invention or a construct of the invention;

a vector which comprises a polynucleotide of the invention operably linked to a promoter;

a host cell comprising a vector of the invention;

a method of making a helicase of the invention or a construct of the invention, which comprises expressing a polynucleotide of the invention, transfecting a cell with a vector of the invention or culturing a host cell of the invention;

a method of controlling the movement of a polynucleotide, comprising contacting the polynucleotide with a helicase of the invention or a construct of the invention and thereby controlling the movement of the polynucleotide;

a method of characterising a target polynucleotide, comprising (a) contacting the target polynucleotide with a transmembrane pore and a helicase of the invention or a construct of the invention such that the helicase controls the movement of the target polynucleotide through the pore and (b) taking one or more measurements as the polynucleotide moves with respect to the pore wherein the measurements are indicative of one or more characteristics of the target polynucleotide and thereby characterising the target polynucleotide;

a method of forming a sensor for characterising a target polynucleotide, comprising forming a complex between (a) a pore and (b) a helicase of the invention or a construct of the invention and thereby forming a sensor for characterising the target polynucleotide;

sensor for characterising a target polynucleotide, comprising a complex between (a) a pore and (b) a helicase of the invention or a construct of the invention;

use of a helicase of the invention or a construct of the invention to control the movement of a target polynucleotide through a pore;

a kit for characterising a target polynucleotide comprising (a) a pore and (b) a helicase of the invention or a construct of the invention;

an apparatus for characterising target polynucleotides in a sample, comprising (a) a plurality of pores and (b) a plurality of helicases of the invention or a plurality of constructs of the invention; and a series of two or more helicases attached to a polynucleotide, wherein at least one of the two or more helicases is a helicase of the invention.

DESCRIPTION OF THE FIGURES

FIG. 6 (B) shows a region of a plot (y-axis label (a1)=pore amino acid residue number, y-axis label (a2)=number of pore/enzyme contacts, x-axis label=enzyme amino acid residue number) which shows which amino acids in the pore (MspA mutant 2) interact with particular amino acids in the enzyme (enzyme mutant 1) from run 3. The grey bands in the plots indicate an interaction between amino acids. The darkness of the grey band corresponds to the number of interactions between enzyme/pore, with dark grey=many interactions and light grey=fewer interactions. The first amino acid in each box corresponds to the interacting amino acid in the MspA mutant 2 and the second amino acid corresponds to the interacting amino acids in enzyme mutant 1.

DESCRIPTION OF THE SEQUENCE LISTING

Figure 1:
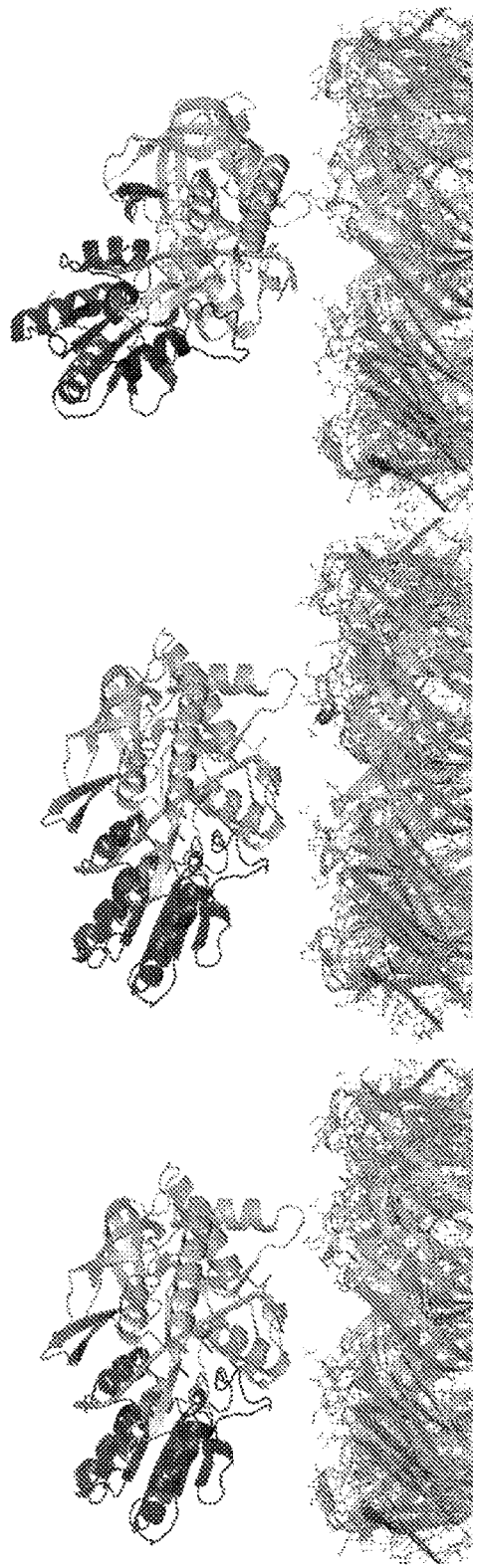
FIG. 1 shows the three different initial simulation orientations of T4 Dda-E94C/A360C/C109A/C136A (SEQ ID NO: 8 with mutations E94C/A360C/C109A/C136A) with respect to either MspA-(G75S/G77S/L88N/D90N/D91N/D118R/Q126R/D134R/E139K)8 (SEQ ID NO: 2 with mutations G75S/G77S/L88N/D90N/D91N/D118R/Q126R/D134R/E139K=MspA mutant 1) or MspA-((Del-L74/G75/D118/L119)D56N/E59R/L88N/D90N/D91N/Q126R/D134R/E139K)8 (SEQ ID NO: 2 with mutations D56N/E59R/L88N/D90N/D91N/Q126R/D134R/E139K and deletion of the amino acids L74/G75/D118/L119=MspA mutant 2). The difference between run 1 and run 2 was that both the enzyme and pore had different side chain conformations despite the pore and enzyme being in the same position. In run three the enzyme has been tilted slightly with respect to the nanopore.
Figure 2:
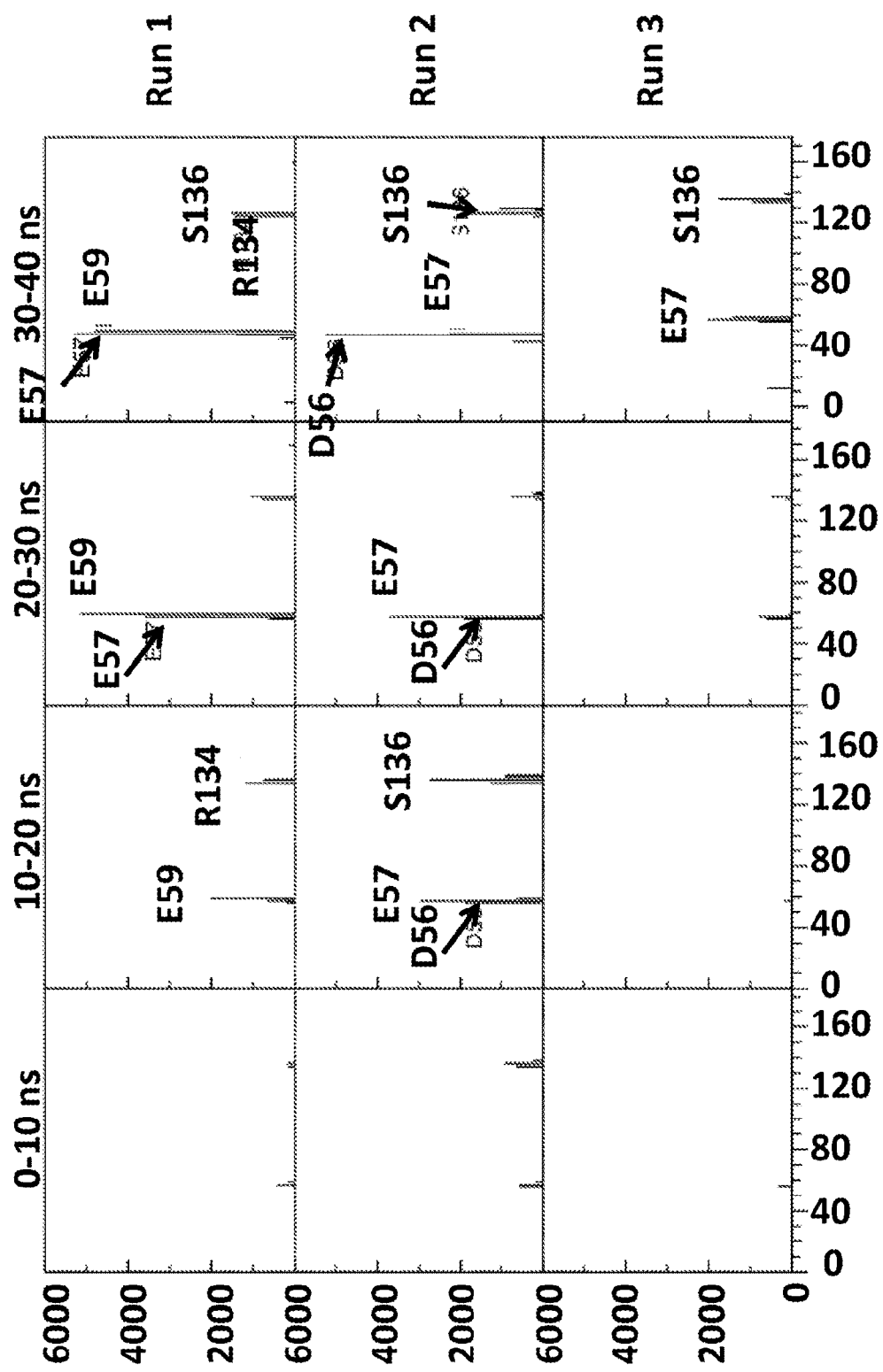
FIG. 2 shows a plot (y-axis label=number of pore/enzyme contacts, x-axis label=pore amino acid residue number) of the interaction points of the nanopore MspA mutant 1 with enzyme mutant 1. Each row of the plot shows the interaction points for the different enzyme/nanopore orientations e.g. runs 1-3.
Figure 3:
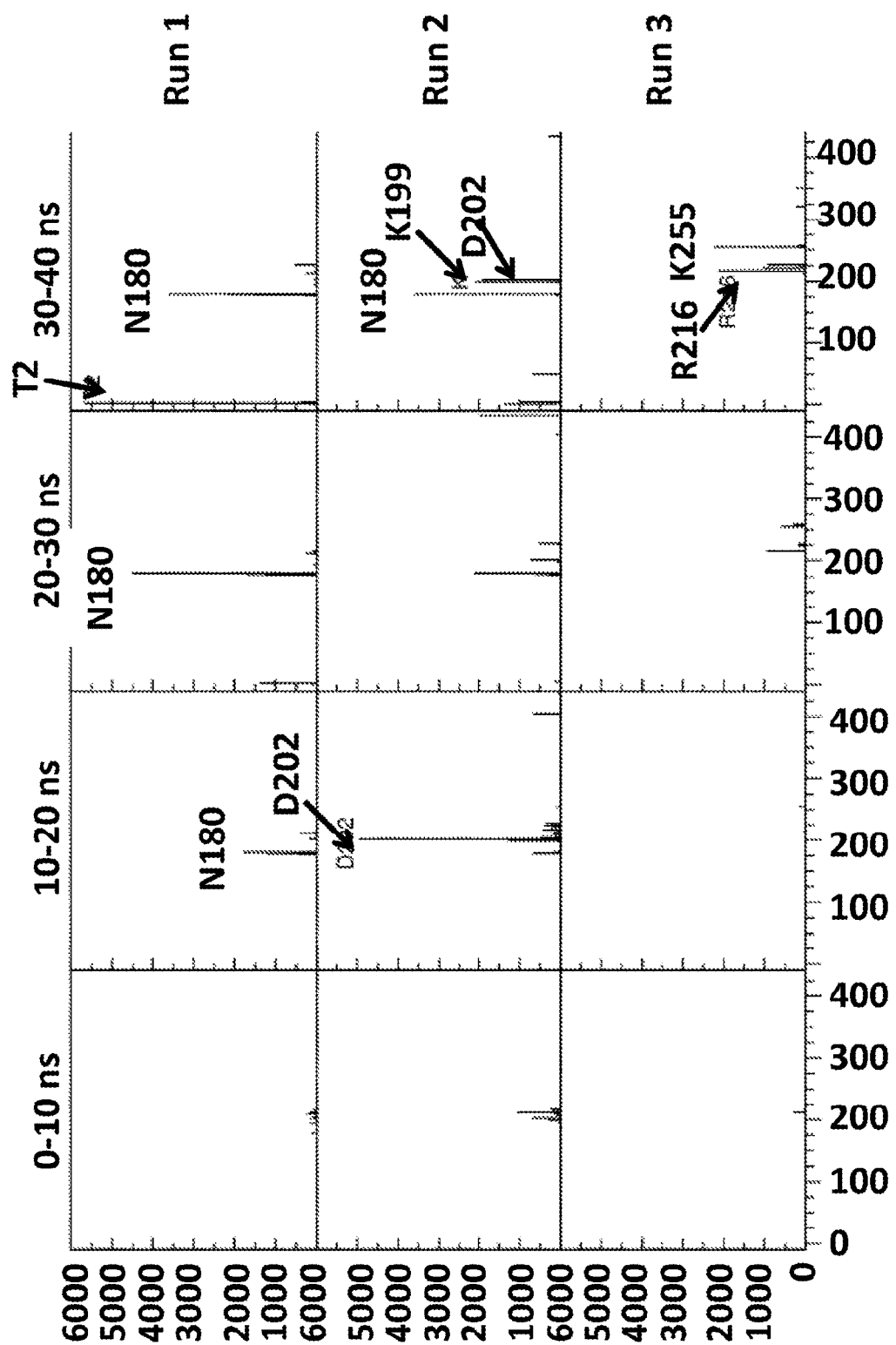
FIG. 3 shows a plot (y-axis label=number of pore/enzyme contacts, x-axis label=enzyme amino acid residue number) of the interaction points of the enzyme mutant 1 with MspA mutant 1. Each row of the plot shows the interaction points for the different enzyme/nanopore orientations e.g. runs 1-3.
Figure 4:
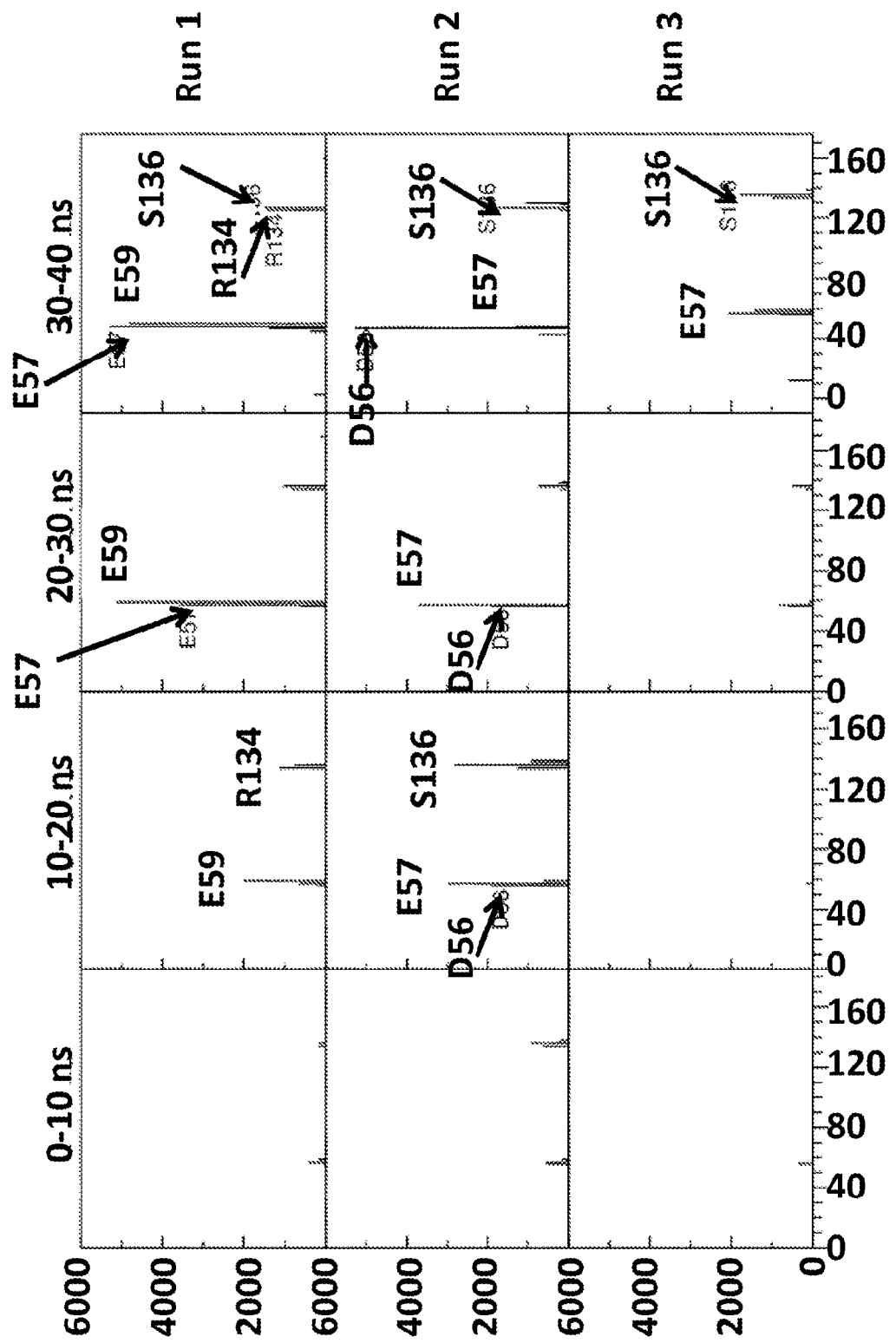
FIG. 4 shows a plot (y-axis label=number of pore/enzyme contacts, x-axis label=pore amino acid residue number) of the interaction points of the nanopore MspA mutant 2 with enzyme mutant 1. Each row of the plots shows the interaction points for the different enzyme/nanopore orientations e.g. runs 1-3.
Figure 5:
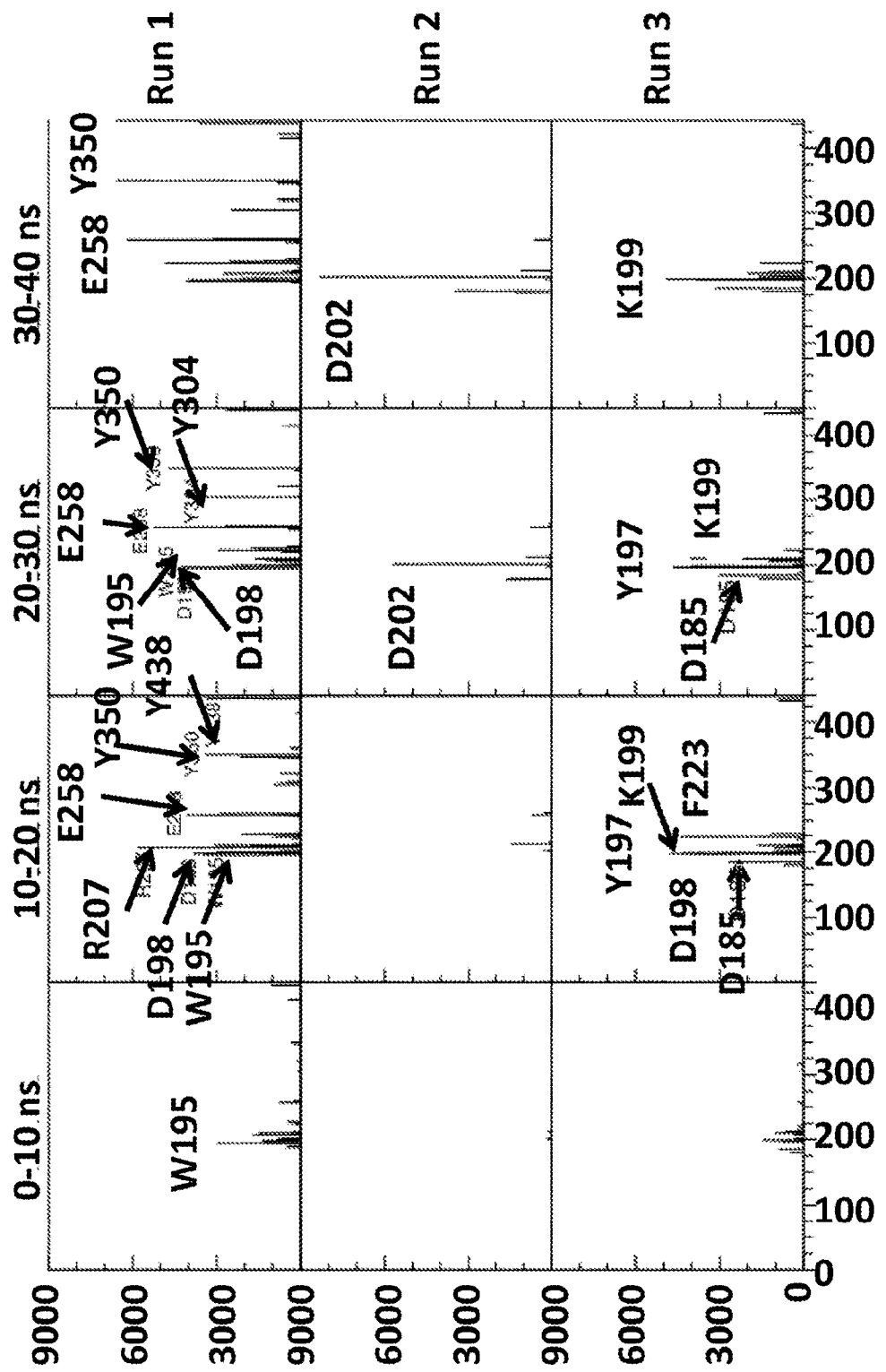
FIG. 5 shows a plot (y-axis label=number of pore/enzyme contacts, x-axis label=enzyme amino acid residue number) of the interaction points of the enzyme mutant 1 with MspA mutant 2. Each row of the plot shows the interaction points for the different enzyme/nanopore orientations e.g. runs 1-3.

SEQ ID NO: 1 shows the codon optimised polynucleotide sequence encoding the wild-type MspA monomer. This mutant lacks the signal sequence.

SEQ ID NO: 2 shows the amino acid sequence of the mature form of the wild-type MspA monomer. This mutant lacks the signal sequence.

SEQ ID NO: 3 shows the polynucleotide sequence encoding one monomer of α-hemolysin-E111N/K147N ((α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NOs: 8 to 23 show the amino acid sequences of the Dda helicases shown in Tables 1 and 2.

SEQ ID NO: 24 shows the amino acid sequence of a preferred HhH domain.

SEQ ID NO: 25 shows the amino acid sequence of the ssb from the bacteriophage RB69, which is encoded by the gp32 gene.

SEQ ID NO: 26 shows the amino acid sequence of the ssb from the bacteriophage T7, which is encoded by the gp2.5 gene.

SEQ ID NO: 27 shows the amino acid sequence of the UL42 processivity factor from Herpes virus 1.

SEQ ID NO: 28 shows the amino acid sequence of subunit 1 of PCNA.

SEQ ID NO: 29 shows the amino acid sequence of subunit 2 of PCNA.

SEQ ID NO: 30 shows the amino acid sequence of subunit 3 of PCNA.

SEQ ID NO: 31 shows the amino acid sequence of Phi29 DNA polymerase.

SEQ ID NO: 32 shows the amino acid sequence (from 1 to 319) of the UL42 processivity factor from the Herpes virus 1.

SEQ ID NO: 33 shows the amino acid sequence of the ssb from the bacteriophage RB69, i.e. SEQ ID NO: 25, with its C terminus deleted (gp32RB69CD).

SEQ ID NO: 34 shows the amino acid sequence (from 1 to 210) of the ssb from the bacteriophage T7 (gp2.5T7-R211Del). The full length protein is shown in SEQ ID NO: 96.

SEQ ID NO: 35 shows the amino acid sequence of the 5$^{th}$ domain of Hel308 Hla.

SEQ ID NO: 36 shows the amino acid sequence of the 5$^{th}$ domain of Hel308 Hvo.

SEQ ID NO: 37 shows the amino acid sequence of the (HhH)2 domain.

SEQ ID NO: 38 shows the amino acid sequence of the (HhH)2-(HhH)2 domain.

SEQ ID NO: 39 shows the amino acid sequence of the human mitochondrial SSB (HsmtSSB).

SEQ ID NO: 40 shows the amino acid sequence of the p5 protein from Phi29 DNA polymerase.

SEQ ID NO: 41 shows the amino acid sequence of the wild-type SSB from *E. coli*.

SEQ ID NO: 42 shows the amino acid sequence of the ssb from the bacteriophage T4, which is encoded by the gp32 gene.

SEQ ID NO: 43 shows the amino acid sequence of EcoSSB-CterAla.

SEQ ID NO: 44 shows the amino acid sequence of EcoSSB-CterNGGN.

SEQ ID NO: 45 shows the amino acid sequence of EcoSSB-Q152del.

SEQ ID NO: 46 shows the amino acid sequence of EcoSSB-G117del.

SEQ ID NO: 47 shows the amino acid sequence of Topoisomerase V Mka (*Methanopyrus Kandleri*).

SEQ ID NO: 48 shows the amino acid sequence of domains H-L of Topoisomerase V Mka (*Methanopyrus Kandleri*).

SEQ ID NO: 49 shows the amino acid sequence of Mutant S (*Escherichia coli*).

SEQ ID NO: 50 shows the amino acid sequence of Sso7d (*Sufolobus solfataricus*).

SEQ ID NO: 51 shows the amino acid sequence of Sso10b1 (*Sulfolobus solfataricus* P2).

SEQ ID NO: 52 shows the amino acid sequence of Sso10b2 (*Sulfolobus solfataricus* P2).

SEQ ID NO: 53 shows the amino acid sequence of Tryptophan repressor (*Escherichia coli*).

SEQ ID NO: 54 shows the amino acid sequence of Lambda repressor (*Enterobacteria phage* lambda).

SEQ ID NO: 55 shows the amino acid sequence of Cren7 (*Histone crenarchaea* Cren7 Sso).

SEQ ID NO: 56 shows the amino acid sequence of human histone (*Homo sapiens*).

SEQ ID NO: 57 shows the amino acid sequence of dsbA (*Enterobacteria phage* T4).

SEQ ID NO: 58 shows the amino acid sequence of Rad51 (*Homo sapiens*).

SEQ ID NO: 59 shows the amino acid sequence of PCNA sliding clamp (*Citromicrobium bathyomarinum* JL354).

SEQ ID NOs: 60 to 64 show a polynucleotide sequences used in Example 3.

SEQ ID NO: 65 shows the codon optimised polynucleotide sequence encoding the wild-type CsgG monomer from *Escherichia coli* Str. K-12 substr. MC4100. This monomer lacks the signal sequence.

SEQ ID NO: 66 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NO: 67 shows the amino acid sequence of StepII(C).

SEQ ID NOs: 68 to 73 shows the polynucleotide sequences used in Example 5.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a helicase" includes "helicases", reference to "a modification" includes two or more such modifications, reference to "a transmembrane protein pore" includes two or more such pores, and the like.

All publications, patents and patent applications cited herein, whether supra or infra, are hereby incorporated by reference in their entirety.

Modified Dda Helicases

The present invention provides a modified Dda helicase. The one or more specific modifications are discussed in more detail below. Modifications according to the invention include one or more substitutions as discussed below.

Characterisation, such as sequencing, of a polynucleotide using a transmembrane pore and helicase typically involves analysing polymer units made up of k nucleotides where k is a positive integer (i.e. 'k-mers'). This is discussed in International Application No. PCT/GB2012/052343 (published as WO 2013/041878). As the target polynucleotide moves with respect to, or through the pore, different k-mers within the polynucleotide are analysed, typically by measuring the current flowing through the pore. The movement of the polynucleotide with respect to, such as through, the pore can be viewed as movement from one k-mer to another or from k-mer to k-mer.

The modified helicases of the invention provide more consistent movement of the target polynucleotide with respect to, such as through, the transmembrane pore. The helicases preferably provide more consistent movement from one k-mer to another or from k-mer to k-mer as the target polynucleotide moves with respect to, such as through, the pore. The helicases allow the target polynucleotide to move with respect to, such as through, the transmembrane pore more smoothly. The helicases preferably provide more regular or less irregular movement of the target polynucleotide with respect to, such as through, the transmembrane pore.

The modification(s), particularly the substitution of one or more amino acids which interact with one or more nucleotides in ssDNA), allow the modified helicase to display reduced forward slipping. This is a phenomenon where the DNA moves forwards relative to the pore by at least 4 consecutive nucleotides and typically by more than 10 consecutive nucleotides. Slipping forward may involve movement forward of 100 consecutive nucleotides or more and this may happen more than once for each polynucleotide. Slipping forward can be problematic for polynucleotide sequencing.

The modification(s) typically reduces the frequency of forward slipping displayed by the helicase by at least 10%, at least 20%, at least 30%, at least 40%, at least 50%, at least 60%, at least 70%, at least 80% or at least 90%. The modification(s) typically abolishes forward slipping, i.e. reduces the frequency of forward slipping displayed by the helicase by 100%. The modification(s) typically reduces the length of forward slipping displayed by the helicase to 10 nucleotides or fewer, such as 9 nucleotides or fewer, 8 nucleotides or fewer, 7 nucleotides or fewer, 6 nucleotides or fewer, 5 nucleotides or fewer, 4 nucleotides or fewer, 3 nucleotides or fewer, 2 nucleotides or fewer or 1 nucleotide.

The modification(s) preferably reduce the frequency and length of forward slipping displayed by the helicase.

Forward slipping can be measured using any method known in the art. The ability of a helicase to control the movement of a polynucleotide and the incidence of forward slipping is typically assayed in a nanopore system, such as the ones described below. The ability of a helicase to control the movement of a polynucleotide and the incidence of forward slipping can be determined as described in the Examples.

The modifications (s), particularly the modification(s) in the the the part of the helicase which interacts with a transmembrane pore, typically reduce the noise associated with the movement of the target polynucleotide with respect to, such as through, the transmembrane pore. Unwanted movement of the target polynucleotide in any dimension as a k-mer is being analysed typically results in noise in the current signature or level for the k-mer. The helicases of the invention may reduce this noise by reducing unwanted movement associated with one or more k-mers, such as each k-mer, in the target polynucleotide. The helicases may reduce the noise associated with the current level or signature for one or more k-mers, such as each k-mer, in the target polynucleotide.

In a preferred embodiment, the target polynucleotide is double stranded and the helicase reduces the noise associated with the movement of the complement strand to a greater degree than it reduces the noise associated with the movement of the template strand and/or increases the consistency of the movement of the complement strand to a greater degree than it increases the consistency of the movement of the template strand. This is advantageous for strand sequencing of double stranded target polynucleotides. The two stands of the double stranded polynucleotide are preferably linked by a bridging moiety, such as a hairpin loop or hairpin loop adaptor. This is discussed in more detail below. In other words, the modified helicases of the invention are better at controlling the movement of a polynucleotide. The extent to which the helicases can control the movement of a polynucleotide is typically altered by the modifications as discussed in more detail below.

The helicase of the invention is modified. The modified helicase is typically modified compared with the corresponding wild-type helicase or natural helicase. The helicase of the invention is artificial or non-natural.

A modified helicase of the invention is a useful tool for controlling the movement of a polynucleotide during Strand Sequencing. The helicase can control the movement of DNA in at least two active modes of operation (when the helicase is provided with all the necessary components to facilitate movement e.g. ATP and $Mg^{2+}$) and one inactive mode of operation (when the helicase is not provided with the necessary components to facilitate movement).

When provided with all the necessary components to facilitate movement the helicase moves along the DNA in the 5'-3' direction, but the orientation of the DNA in the nanopore (dependent on which end of the DNA is captured) means that the enzyme can be used to either move the DNA out of the nanopore against the applied field, or move the DNA into the nanopore with the applied field. When the 3' end of the DNA is captured the helicase works against the direction of the field applied by the voltage, pulling the threaded DNA out of the nanopore and into the cis chamber. However, when the DNA is captured 5'-down in the nanopore, the helicase works with the direction of the field applied by the voltage, pushing the threaded DNA into the nanopore and into the trans chamber. When the helicase is not provided with the necessary components to facilitate movement it can bind to the DNA and act as a brake slowing the movement of the DNA when it is pulled into the pore by the applied field. In the inactive mode it does not matter whether the DNA is captured either 3' or 5' down, it is the applied field which pulls the DNA into the nanopore towards the trans side with the enzyme acting as a brake. When in the inactive mode the movement control of the DNA by the helicase can be described in a number of ways including ratcheting, sliding and braking.

A problem which occurs in sequencing polynucleotides, particularly those of 500 nucleotides or more, is that the molecular motor which is controlling the movement of the polynucleotide may disengage from the polynucleotide. This allows the polynucleotide to be pulled through the pore rapidly and in an uncontrolled manner in the direction of the applied field. A modified helicase of the invention is less likely to unbind or disengage from the polynucleotide being sequenced. The modified helicase can provide increased read lengths of the polynucleotide as they control the movement of the polynucleotide through a nanopore. The ability to move an entire polynucleotide through a nanopore under the control of a modified helicase of the invention allows characteristics of the polynucleotide, such as its sequence, to be estimated with improved accuracy and speed over known methods. This becomes more important as strand lengths increase and molecular motors are required with improved processivity. A modified helicase of the invention is particularly effective in controlling the movement of target polynucleotides of 500 nucleotides or more, for example 1000 nucleotides, 5000, 10000, 20000, 50000, 100000 or more.

A modified helicase of the invention is also a useful tool for isothermal polymerase chain reaction (PCR). In such methods, the strands of double stranded DNA are typically first separated by a helicase of the invention and coated by single stranded DNA (ssDNA)-binding proteins. In the second step, two sequence specific primers typically hybridise to each border of the DNA template. DNA polymerases may then be used to extend the primers annealed to the templates to produce a double stranded DNA and the two newly synthesized DNA products may then be used as substrates by the helicases of the invention, entering the next round of the reaction. Thus, a simultaneous chain reaction develops, resulting in exponential amplification of the selected target sequence.

The modified helicase has the ability to control the movement of a polynucleotide. The ability of a helicase to control the movement of a polynucleotide can be assayed using any method known in the art. For instance, the helicase may be contacted with a polynucleotide and the position of the polynucleotide may be determined using standard methods. The ability of a modified helicase to control the movement of a polynucleotide is typically assayed in a nanopore system, such as the ones described below and, in particular, as described in the Examples.

A modified helicase of the invention may be isolated, substantially isolated, purified or substantially purified. A helicase is isolated or purified if it is completely free of any other components, such as lipids, polynucleotides, pore monomers or other proteins. A helicase is substantially isolated if it is mixed with carriers or diluents which will not interfere with its intended use. For instance, a helicase is substantially isolated or substantially purified if it is present in a form that comprises less than 10%, less than 5%, less than 2% or less than 1% of other components, such as lipids, polynucleotides, pore monomers or other proteins.

Any Dda helicase may be modified in accordance with the invention. Preferred Dda helicases are discussed below.

Dda helicases typically comprises the following five domains: 1A (RecA-like motor) domain, 2A (RecA-like motor) domain, tower domain, pin domain and hook domain (Xiaoping He et al., 2012, Structure; 20: 1189-1200). The domains may be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, NNicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307-69). Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

Simulations can be performed to assess which amino acids make contact with the nucleotides in ssDNA within the enzyme binding site. The simulations may be performed using the GROMACS package version 4.0.5, with the AMBER-99SB force field and the TIP3P water model. A preferred method is disclosed in the Examples.

Modifications of the Invention

The helicase of the invention is one in which at least one amino acid which interacts with one or more nucleotides in single stranded DNA (ssDNA) is substituted. Any number of amino acids may substituted, such as 1 or more, 2 or more, 3 or more, 4 or more, 5 or more or 6 or more amino acids. As the helicase moves along ssDNA or as the ssDNA moves through the helicase, amino acids may sequentially interact with different nucleotides. Each amino which is substituted may interact with any number of nucleotides at a time, such as one, two, three or more nucleotides at a time. The amino acids which interact with one or more nucleotides in single stranded DNA can be identified using protein modelling as discussed above.

Base and/or Sugar Interactions

The helicase of the invention is preferably one in which at least one amino acid which interacts with the sugar and/or base of one or more nucleotides in single stranded DNA (ssDNA) is substituted with an amino acid which comprises a larger side chain (R group). Any number of amino acids may substituted, such as 1 or more, 2 or more, 3 or more, 4 or more, 5 or more or 6 or more amino acids. Each amino acid may interact with the base, the sugar or the base and the sugar. The amino acids which interact with the sugar and/or base of one or more nucleotides in single stranded DNA can be identified using protein modelling as discussed above.

Table 1 below summarises the preferred Dda helicases which may be modified in accordance with the invention.

TABLE 1

| Dda Homologue (SEQ ID NO:) | | Habitat | Uniprot | Length | Sequence Identity to 1993/% | Number of D/E vs. K/R amino acids | # C |
|---|---|---|---|---|---|---|---|
| Rma-DSM (SEQ ID NO: 9) | *Rhodothermus marinus* | Mild halophile, moderate thermophile > 65° C. | D0MKQ2 | 678 | 21 | −84/+85 | 2 |
| Csp (SEQ ID NO: 10) | *Cyanothece* sp. (strain ATCC 51142) | Marine bacterium | B1X365 | 496 | 24 | −76/+76 | 5 |
| Sru (SEQ ID NO: 11) | *Salinibacter ruber* | Extremely halophilic, 35-45° C. | Q2S429 | 421 | 26 | −78/+54 | 3 |
| Sgo (SEQ ID NO: 12) | *Sulfurimonas gotlandica* GD1 | Habitat: hydrothermal vents, coastal sediments | B6BJ43 | 500 | 27 | −72/+64 | 2 |
| Vph12B8 (SEQ ID NO: 13) | *Vibrio* phage henriette 12B8 | Host found in saltwater, stomach bug | M4MBC3 | 450 | 27 | −62/+47 | 6 |
| Vph (SEQ ID NO: 14) | *Vibrio* phage phi-pp2 | Host found in saltwater, stomach bug | I6XGX8 | 421 | 39 | −55/+45 | 5 |
| Aph65 (SEQ ID NO: 15) | *Aeromonas* phage 65 | Host found in fresh/brackish water, stomach bug | E5DRP6 | 434 | 40 | −57/+48 | 4 |

TABLE 1-continued

| Dda Homologue (SEQ ID NO:) | Habitat | Uniprot | Length | Sequence Identity to 1993/% | Number of D/E vs. K/R amino acids | # C |
|---|---|---|---|---|---|---|
| AphCC2 (SEQ ID NO: 16) | *Aeromonas* phage CC2 | Host found in fresh/brackish water, stomach bug | I6XH64 | 420 | 41 | −53/+44 | 4 |
| Cph (SEQ ID NO: 17) | *Cronobacter* phage vB CsaM GAP161 | Host member of enterobacteriaceae | K4FBD0 | 443 | 42 | −59/+57 | 4 |
| Kph (SEQ ID NO: 18) | *Klebsiella* phage KP15 | Host member of enterobacteriaceae | D5JF67 | 442 | 44 | −59/+58 | 5 |
| SphIME13 (SEQ ID NO: 19) | *Stenotrophomonas* phage IME13 | Host found in soil | J7HXT5 | 438 | 51 | −58/+59 | 7 |
| AphAc42 (SEQ ID NO: 20) | *Acinetobacter* phage Ac42 | Host found in soil | E5EYE6 | 442 | 59 | −53/+49 | 9 |
| SphSP18 (SEQ ID NO: 21) | *Shigella* phage SP18 | Host member of enterobacteriaceae | E3SFA5 | 442 | 59 | −55/+55 | 9 |
| Yph (SEQ ID NO: 22) | *Yersinia* phage phiR1-RT | Host member of enterobacteriaceae | I7J3V8 | 439 | 64 | −52/+52 | 7 |
| SphS16 (SEQ ID NO: 23) | *Salmonella* phage S16 | Host member of enterobacteriaceae | M1EA88 | 441 | 72 | −56/+55 | 5 |
| 1993 (SEQ ID NO: 8) | Enterobateria phage T4 | Host member of enterobacteriaceae | P32270 | 439 | 100 | −57/+58 | 5 |

The helicase of the invention preferably comprises a variant of SEQ ID NO: 8 wherein the at least one amino acid which interacts with the sugar and/or base of one or more nucleotides in ssDNA is at least one of H82, N88, P89, F98, D121, V150, P152, F240, F276, S287, H396 and Y415. These numbers correspond to the relevant positions in SEQ ID NO: 8 and may need to be altered in the case of variants where one or more amino acids have been inserted or deleted compared with SEQ ID NO: 8. A skilled person can determine the corresponding positions in a variant as discussed above. The helicase of the invention preferably comprises a variant of SEQ ID NO: 8 wherein the at least one amino acid which interacts with the sugar and/or base of one or more nucleotides in ssDNA is F98 and one or more H82, N88, P89, D121, V150, P152, F240, F276, S287, H396 and Y415, such as F98/H82, F98/N88, F98/P89, F98/D121, F98/V150, F98/P152, F98/F240, F98/F276, F98/S287 or F98/H396.

The helicase of the invention is preferably a variant of SEQ ID NO: 9, 10, 11, 12, 13, 14, 15, 16, 17, 18, 19, 20, 21, 22 or 23 wherein the at least one amino acid which interacts with the sugar and/or base of one or more nucleotides in ssDNA is at least one of the amino acids which correspond to H82, N88, P89, F98, D121, V150, P152, F240, F276, S287, H396 and Y415 in SEQ ID NO: 8. The helicase of the invention preferably comprises a variant of SEQ ID NO: 9, 10, 11, 12, 13, 14, 15, 16, 17, 18, 19, 20, 21, 22 or 23 wherein the at least one amino acid which interacts with the sugar and/or base of one or more nucleotides in ssDNA is the amino acid which corresponds to F98 in SEQ ID NO: 8 and one or more of the amino acids which correspond to H82, N88, P89, D121, V150, P152, F240, F276, S287, H396 and Y415 in SEQ ID NO: 8, such as the amino acids which correspond to F98/H82, F98/N88, F98/P89, F98/D121, F98/V150, F98/P152, F98/F240, F98/F276, F98/S287 or F98/H396.

Table 2 shows the amino acids in SEQ ID NOs: 9 to 23 which correspond to H82, N88, P89, F98, D121, V150, P152, F240, F276, S287, H396 and Y415 in SEQ ID NO: 8.

TABLE 2

| SEQ ID NO: | | | | | | | | | | | | |
|---|---|---|---|---|---|---|---|---|---|---|---|---|
| 8 | H82 | N88 | P89 | F98 | D121 | V150 | P152 | F240 | F276 | S287 | H396 | Y415 |
| 9 | H81 | F87 | D88 | S105 | S131 | V181 | Q183 | R274 | H313 | G314 | H428 | H447 |
| 10 | A144 | Q150 | P151 | G158 | N187 | V217 | K218 | W307 | F344 | K355 | H455 | H473 |
| 11 | H87 | R93 | L94 | G100 | G126 | V154 | N155 | Y240 | Y277 | G280 | H377 | R395 |
| 12 | H112 | K118 | P119 | E128 | G154 | I185 | N187 | Y273 | F309 | K310 | H414 | H433 |
| 13 | H93 | V99 | M100 | D106 | N132 | I159 | Q160 | Y267 | M302 | G303 | H400 | K419 |
| 14 | H74 | N80 | P81 | F90 | D114 | V143 | H145 | Y230 | M266 | P273 | H378 | Y397 |
| 15 | H78 | H84 | P85 | F94 | S117 | E147 | A149 | Y235 | M271 | I279 | H387 | Y406 |
| 16 | H65 | H71 | P72 | F81 | S104 | V133 | H135 | F222 | M258 | I266 | H373 | Y392 |
| 17 | H84 | S90 | P91 | F100 | D126 | V155 | A157 | Y243 | V279 | T290 | H399 | A418 |
| 18 | H84 | S90 | P91 | F100 | D126 | V155 | T157 | Y243 | V279 | V290 | H398 | A417 |
| 19 | Q82 | N88 | P89 | F98 | T121 | V150 | E152 | Y237 | M274 | K285 | H393 | Q412 |
| 20 | H88 | N94 | P95 | F104 | D127 | V156 | P158 | F246 | I282 | S293 | H399 | K418 |
| 21 | H84 | N90 | P91 | F100 | D123 | V152 | P154 | Y242 | M278 | S289 | H399 | M418 |

TABLE 2-continued

| SEQ ID NO: | | | | | | | | | | | |
|---|---|---|---|---|---|---|---|---|---|---|---|
| 22 | H83 | N89 | P90 | F99 | D122 | V151 | P153 | Y241 | M277 | H288 | H396 | M415 |
| 23 | H83 | N89 | P90 | F99 | D122 | V151 | P153 | F241 | M277 | H288 | H397 | M416 |

The at least one amino acid which interacts with the sugar and/or base of one or more nucleotides in ssDNA is preferably at least one amino acid which intercalates between the nucleotides in ssDNA. Amino acids which intercalate between nucleotides in ssDNA can be modeled as discussed above. The at least one amino acid which intercalates between the nucleotides in ssDNA is preferably at least one of P89, F98 and V150 in SEQ ID NO: 8, such as P89, F98, V150, P89/F98, P89/V150, F98/V150 or P89/F98/V150.

The at least one amino acid which intercalates between the nucleotides in ssDNA in SEQ ID NO: 9, 10, 11, 12, 13, 14, 15, 16, 17, 18, 19, 20, 21, 22 or 23 is preferably at least one of the amino acids which correspond to P89, F98 and V150 in SEQ ID NO: 8, such as P89, F98, V150, P89/F98, P89/V150, F98/V150 or P89/F98/V150. Corresponding amino acids are shown in Table 2 above.

Larger R Groups

The larger side chain (R group) preferably (a) contains an increased number of carbon atoms, (b) has an increased length, (c) has an increased molecular volume and/or (d) has an increased van der Waals volume. The larger side chain (R group) preferably (a); (b); (c); (d); (a) and (b); (a) and (c); (a) and (d); (b) and (c); (b) and (d); (c) and (d); (a), (b) and (c); (a), (b) and (d); (a), (c) and (d); (b), (c) and (d); or (a), (b), (c) and (d). Each of (a) to (d) may be measured using standard methods in the art.

The larger side chain (R group) preferably increases the (i) electrostatic interactions (ii) hydrogen bonding and/or (iii) cation-pi (cation-π) interactions between the at least one amino acid and the one or more nucleotides in ssDNA, such as increases (i); (ii); (iii); (i) and (ii); (i) and (iii); (ii) and (iii); and (i), (ii) and (iii). A skilled person can determine if the R group increases any of these interactions. For instance in (i), positively charged amino acids, such as arginine (R), histidine (H) and lysine (K), have R groups which increase electrostatic interactions. For instance in (ii), amino acids such as asparagine (N), serine (S), glutamine (Q), threonine (T) and histidine (H) have R groups which increase hydrogen bonding. For instance in (iii), aromatic amino acids, such as phenylalanine (F), tryptophan (W), tyrosine (Y) or histidine (H), have R groups which increase cation-pi (cation-π) interactions. Specific substitutions below are labelled (i) to (iii) to reflect these changes. Other possible substitutions are labelled (iv). These (iv) substitutions typically increase the length of the side chain (R group).

The amino acid which comprises a larger side chain (R) may be a non-natural amino acid. The non-natural amino acid may be any of those discussed below.

The amino acid which comprises a larger side chain (R group) is preferably not alanine (A), cysteine (C), glycine (G), selenocysteine (U), methionine (M), aspartic acid (D) or glutamic acid (E).

Histidine (H) is preferably substituted with (i) arginine (R) or lysine (K), (ii) glutamine (Q) or asparagine (N) or (iii) phenylalanine (F), tyrosine (Y) or tryptophan (W). Histidine (H) is more preferably substituted with (a) N, Q or W or (b) Y, F, Q or K.

Asparagine (N) is preferably substituted with (i) arginine (R) or lysine (K), (ii) glutamine (Q) or histidine (H) or (iii) phenylalanine (F), tyrosine (Y) or tryptophan (W). Asparagine (N) is more preferably substituted with R, H, W or Y.

Proline (P) is preferably substituted with (i) arginine (R) or lysine (K), (ii) glutamine (Q), asparagine (N), threonine (T) or histidine (H), (iii) tyrosine (Y), phenylalanine (F) or tryptophan (W) or (iv) leucine (L), valine (V) or isoleucine (I). Proline (P) is more preferably substituted with (i) arginine (R) or lysine (K), (ii) glutamine (Q), asparagine (N), threonine (T) or histidine (H), (iii) phenylalanine (F) or tryptophan (W) or (iv) leucine (L), valine (V) or isoleucine (I). Proline (P) is more preferably substituted with (a) F, (b) L, V, I, T or F or (c) W, F, Y, H, I, L or V.

Valine (V) is preferably substituted with (i) arginine (R) or lysine (K), (ii) glutamine (Q), asparagine (N) or histidine (H), (iii) phenylalanine (F), tyrosine (Y) or tryptophan (W) or (iv) isoleucine (I) or leucine (L). Valine (V) is more preferably substituted with (i) arginine (R) or lysine (K), (ii) glutamine (Q), asparagine (N) or histidine (H), (iii) tyrosine (Y) or tryptophan (W) or (iv) isoleucine (I) or leucine (L). Valine (V) is more preferably substituted with I or H or I, L, N, W or H.

Phenylalanine (F) is preferably substituted with (i) arginine (R) or lysine (K), (ii) histidine (H) or (iii) tyrosine (Y) or tryptophan (W). Phenylalanine (F) is more preferably substituted with (a) W, (b) W, Y or H, (c) W, R or K or (d) K, H, W or R.

Glutamine (Q) is preferably substituted with (i) arginine (R) or lysine (K) or (iii) phenylalanine (F), tyrosine (Y) or tryptophan (W).

Alanine (A) is preferably substituted with (i) arginine (R) or lysine (K), (ii) glutamine (Q), asparagine (N) or histidine (H), (iii) phenylalanine (F), tyrosine (Y) or tryptophan (W) or (iv) isoleucine (I) or leucine (L).

Serine (S) is preferably substituted with (i) arginine (R) or lysine (K), (ii) glutamine (Q), asparagine (N) or histidine (H), (iii) phenylalanine (F), tyrosine (Y) or tryptophan (W) or (iv) isoleucine (I) or leucine (L). Serine (S) is preferably substituted with K, R, W or F Lysine (K) is preferably substituted with (i) arginine (R) or (iii) tyrosine (Y) or tryptophan (W).

Arginine (R) is preferably substituted with (iii) tyrosine (Y) or tryptophan (W).

Methionine (M) is preferably substituted with (i) arginine (R) or lysine (K), (ii) glutamine (Q), asparagine (N) or histidine (H) or (iii) phenylalanine (F), tyrosine (Y) or tryptophan (W).

Leucine (L) is preferably substituted with (i) arginine (R) or lysine (K), (ii) glutamine (Q) or asparagine (N) or (iii) phenylalanine (F), tyrosine (Y) or tryptophan (W).

Aspartic acid (D) is preferably substituted with (i) arginine (R) or lysine (K), (ii) glutamine (Q), asparagine (N) or histidine (H) or (iii) phenylalanine (F), tyrosine (Y) or tryptophan (W). Aspartic acid (D) is more preferably substituted with H, Y or K.

Glutamic acid (E) is preferably substituted with (i) arginine (R) or lysine (K), (ii) glutamine (Q), asparagine (N) or histidine (H) or (iii) phenylalanine (F), tyrosine (Y) or tryptophan (W).

Isoleucine (I) is preferably substituted with (i) arginine (R) or lysine (K), (ii) glutamine (Q), asparagine (N) or histidine (H), (iii) phenylalanine (F), tyrosine (Y) or tryptophan (W) or (iv) leucine (L).

Tyrosine (Y) is preferably substituted with (i) arginine (R) or lysine (K) or (iii) tryptophan (W). Tyrosine (Y) is more preferably substituted with W or R.

The helicase more preferably comprises a variant of SEQ ID NO: 8 and comprises (a) P89F, (b) F98W, (c) V150I, (d) V150H, (e) P89F and F98W, (f) P89F and V150I, (g) P89F and V150H, (h) F98W and V150I, (i) F98W and V150H (j) P89F, F98W and V150I or (k) P89F, F98W and V150H.

The helicase more preferably comprises a variant of SEQ ID NO: 8 which comprises:

H82N;
H82Q;
H82W;
N88R;
N88H;
N88W;
N88Y;
P89L;
P89V;
P89I;
P89E;
P89T;
P89F;
D121H;
D121Y;
D121K;
V150I;
V150L;
V150N;
V150W;
V150H;
P152W;
P152F;
P152Y;
P152H;
P152I;
P152L;
P152V;
F240W;
F240Y;
F240H;
F276W;
F276R;
F276K;
F276H;
S287K;
S287R;
S287W;
S287F;
H396Y;
H396F;
H396Q;
H396K;
Y415W;
Y415R;
F98W/H82N;
F98W/H82Q;
F98W/H82W;
F98W/N88R;
F98W/N88H;
F98W/N88W;
F98W/N88Y;
F98W/P89L;
F98W/P89V;
F98W/P89I;
F98W/P89T;
F98W/P89F;
F98W/D121H;
F98W/D121Y;
F98W/D121K;
F98W/V150I;
F98W/V150L;

-continued

F98W/V150N;
F98W/V150W;
F98W/V150H;
F98W/P152W;
F98W/P152F;
F98W/P152Y;
F98W/P152H;
F98W/P152I;
F98W/P152L;
F98W/P152V;
F98W/F240W;
F98W/F240Y;
F98W/F240H;
F98W/F276W;
F98W/F276R;
F98W/F276K;
F98W/F276H;
F98W/S287K;
F98W/S287R;
F98W/S287W;
F98W/S287F;
F98W/H396Y;
F98W/H396F;
F98W/H396Q;
F98W/Y415W; or
F98W/Y415R.

Phosphate Interactions

The helicase of the invention is preferably one in which at least one amino acid which interacts with one or more phosphate groups in one or more nucleotides in ssDNA is substituted. Any number of amino acids may substituted, such as 1 or more, 2 or more, 3 or more, 4 or more, 5 or more or 6 or more amino acids. Nucleotides in ssDNA each comprise three phosphate groups. Each amino which is substituted may interact with any number of the phosphate groups at a time, such as one, two or three phosphate groups at a time. The amino acids which interact with one or more phosphate groups can be identified using protein modelling as discussed above.

The substitution preferably increases the (i) electrostatic interactions, (ii) hydrogen bonding and/or (iii) cation-pi (cation-π) interactions between the at least one amino acid and the one or more phosphate groups in ssDNA. Preferred substitutions which increase (i), (ii) and (iii) are discussed below using the labelling (i), (ii) and (iii).

The substitution preferably increases the net positive charge of the position. The net charge at any position can be measured using methods known in the art. For instance, the isolectric point may be used to define the net charge of an amino acid. The net charge is typically measured at about 7.5. The substitution is preferably the substitution of a negatively charged amino acid with a positively charged, uncharged, non-polar or aromatic amino acid. A negatively charged amino acid is an amino acid with a net negative charge. Negatively charged amino acids include, but are not limited to, aspartic acid (D) and glutamic acid (E). A positively charged amino acid is an amino acid with a net positive charge. The positively charged amino acid can be naturally-occurring or non-naturally-occurring. The positively charged amino acid may be synthetic or modified. For instance, modified amino acids with a net positive charge may be specifically designed for use in the invention. A number of different types of modification to amino acids are well known in the art. Preferred naturally-occurring positively charged amino acids include, but are not limited to, histidine (H), lysine (K) and arginine (R).

The uncharged amino acid, non-polar amino acid or aromatic amino acid can be naturally occurring or nonnaturally-occurring. It may be synthetic or modified. Uncharged amino acids have no net charge. Suitable uncharged amino acids include, but are not limited to, cysteine (C), serine (S), threonine (T), methionine (M), asparagines (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y).

The helicase preferably comprises a variant of SEQ ID NO: 8 wherein the at least one amino acid which interacts with one or more phosphates in one or more nucleotides in ssDNA is at least one of H64, T80, S83, N242, K243, N293, T394 and K397. These numbers correspond to the relevant positions in SEQ ID NO: 8 and may need to be altered in the case of variants where one or more amino acids have been inserted or deleted compared with SEQ ID NO: 8. A skilled person can determine the corresponding positions in a variant as discussed above.

The helicase preferably comprises a variant of SEQ ID NO: 9, 10, 11, 12, 13, 14, 15, 16, 17, 18, 19, 20, 21, 22 or 23 and wherein the at least one amino acid which interacts with one or more phosphates in one or more nucleotides in ssDNA is at least one of the amino acids which correspond to H64, T80, S83, N242, K243, N293, T394 and K397 in SEQ ID NO: 8.

Table 3 shows the amino acids in SEQ ID NOs: 9 to 23 which correspond to H64, T80, S83, N242, K243, N293, T 394 and K397 in SEQ ID NO: 8.

TABLE 3

| SEQ ID NO: | | | | | | | | |
|---|---|---|---|---|---|---|---|---|
| 8 | H64 | T80 | S83 | N242 | K243 | N293 | T394 | K397 |
| 9 | G63 | T79 | S82 | N276 | A277 | N317 | T426 | K429 |
| 10 | N121 | T142 | K145 | N309 | K310 | N361 | T453 | K456 |
| 11 | H66 | T85 | S88 | N242 | K243 | N286 | T375 | R378 |
| 12 | H89 | T110 | S113 | N275 | K276 | V315 | T412 | K415 |
| 13 | H68 | T91 | S94 | N269 | A270 | N308 | T398 | K401 |
| 14 | H56 | T72 | S75 | N232 | D233 | N279 | T376 | K379 |
| 15 | H60 | T76 | S79 | N237 | K238 | N285 | T385 | K388 |
| 16 | H47 | T63 | S66 | N224 | K225 | N272 | T371 | K374 |
| 17 | H66 | T82 | S85 | N245 | D246 | N296 | T397 | K400 |
| 18 | H66 | T82 | S85 | N245 | A246 | N296 | T396 | K399 |
| 19 | H64 | T80 | S83 | N239 | N240 | N291 | T391 | K394 |
| 20 | H70 | T86 | S89 | N248 | K249 | N299 | T397 | K400 |
| 21 | H66 | T82 | S85 | N244 | K245 | N295 | T397 | K400 |
| 22 | H65 | T81 | S84 | N243 | K244 | N294 | T394 | K397 |
| 23 | H65 | T81 | K84 | N243 | K244 | N294 | T395 | K398 |

Histidine (H) is preferably substituted with (i) arginine (R) or lysine (K), (ii) asparagine (N), serine (S), glutamine (Q) or threonine (T), (iii) phenylalanine (F), tryptophan (W) or tyrosine (Y). Histidine (H) is preferably substituted with (a) N, Q, K or F or (b) N, Q or W.

Threonine (T) is preferably substituted with (i) arginine (R), histidine (H) or lysine (K), (ii) asparagine (N), serine (S), glutamine (Q) or histidine (H) or (iii) phenylalanine (F), tryptophan (W), tyrosine (Y) or histidine (H). Threonine (T) is more preferably substituted with (a) K, Q or N or (b) K, H or N.

Serine (s) is preferably substituted with (i) arginine (R), histidine (H) or lysine (K), (ii) asparagine (N), glutamine (Q), threonine (T) or histidine (H) or (iii) phenylalanine (F), tryptophan (W), tyrosine (Y) or histidine (H). Serine (S) is more preferably substituted with H, N, K, T, R or Q.

Asparagine (N) is preferably substituted with (i) arginine (R), histidine (H) or lysine (K), (ii) serine (S), glutamine (Q), threonine (T) or histidine (H) or (iii) phenylalanine (F), tryptophan (W), tyrosine (Y) or histidine (H). Asparagine (N) is more preferably substituted with (a) H or Q or (b) Q, K or H.

Lysine (K) is preferably substituted with (i) arginine (R) or histidine (H), (ii) asparagine (N), serine (S), glutamine (Q), threonine (T) or histidine (H) or (iii) phenylalanine (F), tryptophan (W), tyrosine (Y) or histidine (H). Lysine (K) is more preferably substituted with (a) Q or H or (b)R, H or Y.

The helicase more preferably comprises a variant of SEQ ID NO: 8 and comprises one or more of, such as all of, (a) H64N, H64Q, H64K or H64F, (b) T80K, T80Q or T80N, (c) S83H, S83N, S83K, S83T, S83R, or S83Q (d) N242H or N242Q, (e) K243Q or K243H, (f) N293Q, N293K or N293H, (g) T394K, T394H or T394N or (h) K397R, K397H or K397Y.

Combinations

The helicase may be one in which (a) at least one amino acid which interacts with the sugar and/or base of one or more nucleotides in ssDNA is substituted with an amino acid which comprises a larger side chain (R group) and (b) at least one amino acid which interacts with one or more phosphate groups in one or more nucleotides in ssDNA is substituted. The helicase preferably comprises:

(a) a variant of SEQ ID NO: 8 comprising a substitution at F98 as defined above and a substitution at one or more of H64, T80, S83, N242, K243, N293, T394 and K397; or (b) a variant of SEQ ID NO: 9, 10, 11, 12, 13, 14, 15, 16, 17, 18, 19, 20, 21, 22 or 23 comprising a substitution at the amino acid which corresponds to F98 and a substitution at one of more of the amino acids which correspond to H64, T80, S83, N242, K243, N293, T394 and K397 in SEQ ID NO: 8.

The helicase is preferably a variant of SEQ ID NO: 8 which comprises substitutions at:

F98/H64, such as F98W/H64N, F98W/H64Q, F98W/H64K or F98W/H64F;

F98/T80, such as F98W/T80K, F98W/T80Q, F98W/T80N;

F98/1H82, such as F98W/H82N, F98W/H82Q or F98W/H82W;

F98/S83, such as F98W/S83H, F98W/S83N, F98W/S83K, F98W/S83T, F98W/S83R or F98W/S83Q;

F981N242, such as F98W/N242H, F98W/N242Q, F98W/K243Q or F98W/K243H;

F98/N293, such as F98W/N293Q, F98W/N293K, F98W/N293H, F98W/T394K, F98W/T394H, F98W/T394N, F98W/H396Y, F98W/H396F, F98W/H396Q or F98W/H396K; or F98/K397, such as F98W/K397R, F98W/K397H or F98W/K397Y.

Preferred combinations in SEQ ID NO: 9, 10, 11, 12, 13, 14, 15, 16, 17, 18, 19, 20, 21, 22 or 23 include the combinations of amino acids which correspond to the combinations in SEQ ID NO: 8 listed above.

Pore Interaction

The helicase of the invention is further one in which the part of the helicase which interacts with a transmembrane pore comprises one or more modifications, preferably one or more substitutions. The part of the helicase which interacts with a transmembrane pore is typically the part of the helicase which interacts with a transmembrane pore when the helicase is used to control the movement of a polynucleotide through the pore, for instance as discussed in more detail below. The part typically comprises the amino acids that interact with or contact the pore when the helicase is used to control the movement of a polynucleotide through the pore, for instance as discussed in more detail below. The part typically comprises the amino acids that interact with or contact the pore when the helicase is bound to or attached to a polynucleotide which is moving through the pore under an applied potential.

In SEQ ID NO: 8, the part which interacts with the transmembrane pore typically comprises the amino acids at positions 1, 2, 3, 4, 5, 6, 51, 176, 177, 178, 179, 180, 181, 185, 189, 191, 193, 194, 195, 197, 198, 199, 200, 201, 202, 203, 204, 207, 208, 209, 210, 211, 212, 213, 216, 219, 220, 221, 223, 224, 226, 227, 228, 229, 247, 254, 255, 256, 257, 258, 259, 260, 261, 298, 300, 304, 308, 318, 319, 321, 337, 347, 350, 351, 405, 415, 422, 434, 437, 438. These numbers correspond to the relevant positions in SEQ ID NO: 8 and may need to be altered in the case of variants where one or more amino acids have been inserted or deleted compared with SEQ ID NO: 8. A skilled person can determine the corresponding positions in a variant as discussed above. The part which interacts with the transmembrane pore preferably comprises the amino acids at (a) positions 1, 2, 4, 51, 177, 178, 179, 180, 185, 193, 195, 197, 198, 199, 200, 202, 203, 204, 207, 208, 209, 210, 211, 212, 216, 221, 223, 224, 226, 227, 228, 229, 254, 255, 256, 257, 258, 260, 304, 318, 321, 347, 350, 351, 405, 415, 422, 434, 437 and 438 in SEQ ID NO: 8; or (b) positions 1, 2, 178, 179, 180, 185, 195, 197, 198, 199, 200, 202, 203, 207, 209, 210, 212, 216, 221, 223, 226, 227, 255, 258, 260, 304, 350 and 438 in SEQ ID NO: 8.

The part which interacts with the transmembrane pore preferably comprises one or more of, such as 2, 3, 4 or 5 of, the amino acids at positions K194, W195, K198, K199 and E258 in SEQ ID NO: 8. The variant of SEQ ID NO: 8 preferably comprises a modification at one or more of (a), K194, (b) W195, (c) D198, (d) K199 and (d) E258. The variant of SEQ ID NO: 8 preferably comprises a substitution at one or more of (a) K194, such as K194L, (b) W195, such as W195A, (c) D198, such as D198V, (d) K199, such as K199L and (d) E258, such as E258L. The variant may comprise {a}; {b}; {c}; {d}; {e}; {a,b}; {a,c}; {a,d}; {a,e}; {b,c}; {b,d}; {b,e}; {c,d}; {c,e}; {d,e}; {a,b,c}; {a,b,d}; {a,b,e}; {a,c,d}; {a,c,e}; {a,d,e}; {b,c,d}; {b,c,e}; {b,d,e}; {c,d,e}; {a,b,c,d}; {a,b,c,e}; {a,b,d,e}; {a,c,d,e}; {b,c,d,e}; or {a,b,c,d,e}. The modifications or substitutions set out in this paragraph are preferred when the modified polynucleotide binding protein interacts with a pore derived from MspA, particularly any of the modified pores discussed below.

The part of the polynucleotide binding protein which interacts with the transmembrane pore preferably comprises the amino acid at position 194 or 199 of SEQ ID NO: 8. The variant preferably comprises K194A, K194V, K194F, K194D, K194S, K194W or K194L and/or K199A, K199V, K199F, K199D, K199S, K199W or K199L. In SEQ ID NO: 9, 10, 11, 12, 13, 14, 15, 16, 17, 18, 19, 20, 21, 22 or 23, the part which interacts with the transmembrane pore typically comprises the amino acids at positions which correspond to those in SEQ ID NO: 8 listed above. Amino acids in SEQ ID NOs: 9, 10, 11, 12, 13, 14, 15, 16, 17, 18, 19, 20, 21, 22 and 23 which correspond to these positions in SEQ ID NO: 9 can be identified using the alignment shown below.

| | | | | | |
|---|---|---|---|---|---|
| SEQ ID NO: 8 | K194 | W195 | D198 | K199 | E258 |
| SEQ ID NO: 9 | L230 | E231 | H234 | Y235 | R293 |
| SEQ ID NO: 10 | W259 | N260 | T263 | Y264 | E326 |
| SEQ ID NO: 11 | A192 | D193 | F196 | G197 | A259 |
| SEQ ID NO: 12 | I224 | K225 | D228 | F229 | Q292 |
| SEQ ID NO: 13 | Q213 | D214 | Y217 | A218 | A286 |
| SEQ ID NO: 14 | Q185 | W186 | T189 | N190 | N248 |
| SEQ ID NO: 15 | G190 | W191 | P194 | N195 | K253 |
| SEQ ID NO: 16 | G177 | W178 | Q181 | N182 | K240 |
| SEQ ID NO: 17 | K200 | M201 | P204 | M205 | K261 |
| SEQ ID NO: 18 | K200 | P201 | P204 | L205 | K261 |
| SEQ ID NO: 19 | K193 | W194 | E197 | K198 | A256 |
| SEQ ID NO: 20 | N200 | W201 | E204 | N205 | N264 |
| SEQ ID NO: 21 | G196 | W197 | D200 | C201 | E260 |
| SEQ ID NO: 22 | G195 | W196 | E199 | N200 | E259 |
| SEQ ID NO: 23 | S195 | W196 | E199 | K200 | Q259 |

Preferred Combinations

The helicase of the invention preferably comprises a variant of SEQ ID NO: 8 which comprises a substitution at F98, such as F98R, F98K, F98Q, F98N, F98H, F98Y, F98F or F98W, and a substitution at K194, such as K194A, K194V, K194F, K194D, K194S, K194W or K194L, and/or K199, such as K199A, K199V, K199F, K199D, K199S, K199W or K199L. The helicase of the invention preferably comprises a variant of SEQ ID NO: 9, 10, 11, 12, 13, 14, 15, 16, 17, 18, 19, 20, 21, 22 or 23 which comprises a substitution at the position which corresponds to F98 in SEQ ID NO: 8 and a substitution at the position(s) which correspond to K194 and/or K199 in SEQ ID NO: 8. These corresponding positions may be replaced with any of the amino acids listed above for F98, K194 and K119 in SEQ ID NO: 8.

The helicase is preferably a variant of SEQ ID NO: 8 which comprises substitutions at:

F98/K194/H64, such as F98W/K194L/H64N, F98W/K194L/H64Q, F98W/K194L/H64K or F98W/K194L/H64F;

F98/K194/T80, such as F98W/K194L/T80K, F98W/K194L/T80Q or F98W/K194L/T80N;

F98/K194/H82, such as F98W/K194L/H82N, F98W/K194L/H82Q or F98W/K194L/H82W

F98/S83/K194, such as F98W/S83H/K194L, F98W/S83T/K194L, F98W/S83R/K194L, F98W/S83Q/K194L, F98W/S83N/K194L, F98W/S83K/K194L, F98W/N88R/K194L, F98W/N88H/K194L, F98W/N88W/K194L or F98W/N88Y/K194L;

F98/S83/K194/F276, such as F98W/S83H/K194L/F276K;

F98/P89/K194, such as F98W/P89L/K194L, F98W/P89V/K194L, F98W/P89I/K194L or F98W/P89T/K194L;

F98/D121/K194, such as F98W/D121H/K194L, F98W/D121Y/K194L or F98W/D121K/K194L;

F98/V150/K194, such as F98W/V150I/K194L, F98W/V150L/K194L, F98W/V150N/K194L, F98W/V150W/K194L or F98W/V150H/K194L;

F98/P152/K194, such as F98W/P152W/K194L, F98W/P152F/K194L, F98W/P152Y/K194L, F98W/P152H/K194L, F98W/P152I/K194L, F98W/P152L/K194L or F98W/P152V/K194L;

F98/F240/K194, such as F98W/F240W/K194L, F98W/F240Y/K194L or F98W/F240H/K194L;

F98/N242/K194, such as F98W/N242H/K194L or F98W/N242Q/K194L;

F98/K194/F276, such as F98W/K194L/F276K, F98W/K194L/F276H, F98W/K194L/F276W or F98W/K194L/F276R;

F98/K194/S287, such as F98W/K194L/S287K, F98W/ K194L/S287R, F98W/K194L/S287W or F98W/ K194L/S287F;

F98/N293/K194, such as F98W/N293Q/K194L, F98W/ N293K/K194L or F98W/N293H/K194L;

F98/T394/K194, such as F98W/T394K/K194L, F98W/ T394H/K194L or F98W/T394N/K194L;

F98/H396/K194, such as F98W/H396Y/K194L, F98W/ H396F/K194L, F98W/H396Q/K194L or F98W/ H396K/K194L;

F98/K397/K194, such as F98W/K397R/K194L, F98W/ K397H/K194L or F98W/K397Y/K194L; or F98/Y415/K194, such as F98W/Y415W/K194L or F98W/Y415R/K194L.

In any of the above combinations, K194 may be replaced with any of W195, D198, K199 and E258.

The helicase is preferably a variant of SEQ ID NO: 9, 10, 11, 12, 13, 14, 15, 16, 17, 18, 19, 20, 21, 22 or 23 which comprises substitutions at amino acids which correspond to the combinations in SEQ ID NO: 8 listed above.

Modifications in the Tower Domain and/or Pin Domain and/or 1A Domain

The helicase of the invention is preferably one in which at least one cysteine residue (i.e. one or more cysteine residues) and/or at least one non-natural amino acid (i.e. one or more non-natural amino acids) have been introduced into (i) the tower domain and/or (ii) the pin domain and/or the (iii) 1A (RecA-like motor) domain, wherein the helicase has the ability to control the movement of a polynucleotide. These types of modification are disclosed in PCT/GB2014/ 052736 (WO 2015/055981). At least one cysteine residue and/or at least one non-natural amino acid may be introduced into the tower domain, the pin domain, the 1A domain, the tower domain and the pin domain, the tower domain and the 1A domain or the tower domain, the pin domain and the 1A domain.

The helicase of the invention is preferably one in which at least one cysteine residue and/or at least one non-natural amino acid have been introduced into each of (i) the tower domain and (ii) the pin domain and/or the 1A (RecA-like motor) domain, i.e. into the tower domain and the pin domain, the tower domain and the 1A domain or the tower domain, the pin domain and the 1A domain.

Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced. Only one or more cysteine residues may be introduced. Only one or more non-natural amino acids may be introduced. A combination of one or more cysteine residues and one or more non-natural amino acids may be introduced.

The at least one cysteine residue and/or at least one non-natural amino acid are/is preferably introduced by substitution. Methods for doing this are known in the art.

These modifications do not prevent the helicase from binding to a polynucleotide. These modifications decrease the ability of the polynucleotide to unbind or disengage from the helicase. In other words, the one or more modifications increase the processivity of the helicase by preventing dissociation from the polynucleotide strand. The thermal stability of the enzyme is typically also increased by the one or more modifications giving it an improved structural stability that is beneficial in Strand Sequencing.

A non-natural amino acid is an amino acid that is not naturally found in a helicase. The non-natural amino acid is preferably not histidine, alanine, isoleucine, arginine, leucine, aspara-gine, lysine, aspartic acid, methionine, cysteine, phenylalanine, glutamic acid, threonine, glutamine, tryptophan, glycine, valine, proline, serine or tyrosine. The non-natural amino acid is more preferably not any of the twenty amino acids in the previous sentence or selenocysteine.

Preferred non-natural amino acids for use in the invention include, but are not limited, to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl) carbonyl]-L-phenylalanine, (2S)-2-amino-3-4-[(propan-2-ylsulfanyl)carbonyl]phenyl;propanoic acid, (2S)-2-amino-3-4-[(2-amino-3-sulfanylpropanoyl)amino]phenyl;
propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl) norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, 0-(4,5-Dimethoxy-2-nitrobenzyl)-L-serine, (2S)-2-amino-6-([(2-nitrobenzyl)oxy]carbonyl;amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-[(2R,3R)-3-Methyl-3,4-dihydro-2H-pyrrol-2-yl]carbonyl;-L-lysine, $N^6$-[(Benzyloxy)carbonyl]lysine, (2S)-2-amino-6-[(cyclopentylcarbonyl)amino] hexanoic acid, $N^6$-[(Cyclopentyloxy)carbonyl]-L-lysine, (2S)-2-amino-6-[(2R)-tetrahydrofuran-2-ylcarbonyl]amino; hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-([(2-methyl-2-propanyl) oxy]carbonyl;amino)hexanoic acid, $N^6$-[(Allyloxy) carbonyl]lysine, (2S)-2-amino-6-([(2-azidobenzyl)oxy] carbonyl;amino)hexanoic acid, $N^6$-L-Prolyl-L-lysine, (2S)-2-amino-6-[(prop-2-yn-1-yloxy)carbonyl]amino;hexanoic acid and $N^6$-[(2-Azidoethoxy)carbonyl]-L-lysine. The most preferred non-natural amino acid is 4-azido-L-phenylalanine (Faz).

Table 4 below (which is separated in two parts) identifies the residues making up each domain in each Dda homologue (SEQ ID NOs: 8 to 23).

TABLE 4

| Homologue | SEQ ID NO | 1A | 2A |
|---|---|---|---|
| Dda-Rma-DSM | 9 | M1-I84 + R113-Y211 | R212-E294 + G422-S678 |
| Dda-Csp | 10 | M1-L147 + S166-V240 | R241-N327 + A449-G496 |
| Dda-Sru | 11 | M1-L90 + E108-H173 | R174-D260 + A371-V421 |
| Dda-S go | 12 | M1-L115 + N136-V205 | R206-K293 + I408-L500 |
| Dda-Vph12B8 | 13 | M1-L96 + F114-V194 | R195-D287 + V394-Q450 |
| Dda-Vph | 14 | M1-L77 + V96-V166 | R167-T249 + L372-N421 |
| Dda-Aph65 | 15 | M1-M81 + L99-M171 | R172-T254 + L381-K434 |
| Dda-AphCC2 | 16 | M1-M68 + M86-M158 | R159-T241 + L367-K420 |
| Dda-Cph | 17 | M1-L87 + A108-M181 | R182-T262 + L393-V443 |
| Dda-Kph | 18 | M1-L87 + A108-M181 | R182-T262 + L392-V442 |
| Dda-SphIME13 | 19 | M1-L85 + T103-K176 | R177-N257 + L387-V438 |
| Dda-AphAc42 | 20 | M1-L91 + V109-M183 | R184-T265 + L393-I442 |
| Dda-SphSP18 | 21 | M1-L87 + M105-M179 | R180-T261 + L393-V442 |
| Dda-Yph | 22 | M1-L86 + V104-K178 | R179-T260 + L390-I439 |
| Dda-SphS16 | 23 | M1-L86 + V104-M178 | R179-T260 + L391-V441 |
| Dda-1993 | 8 | M1-L85 + V103-K177 | R178-T259 + L390-V439 |

| Homologue | SEQ ID | tower | pin | hook |
|---|---|---|---|---|
| Dda-Rma-DSM | 9 | G295-N309 + F316-Y421 | Y85-L112 | A310-L315 |
| Dda-Csp | 10 | V328-P342 + N360-Y448 | K148-N165 | V343-L359 |
| Dda-Sru | 11 | A261-T275 + T285-Y370 | G91-E107 | W276-L284 |
| Dda-Sgo | 12 | G294-I307 + T314-Y407 | G116-T135 | R308-Y313 |
| Dda-Vph12B8 | 13 | V288-E301 + N307-N393 | G97-P113 | M302-W306 |
| Dda-Vph | 14 | S250-P264 + E278-S371 | K78-E95 | V265-I277 |
| Dda-Aph65 | 15 | K255-P269 + T284-S380 | K82-K98 | V270-F283 |
| Dda-AphCC2 | 16 | D242-P256 + T271-S366 | K69-K85 | V257-F270 |
| Dda-Cph | 17 | T263-P277 + N295-P392 | K88-K107 | L278-Y294 |
| Dda-Kph | 18 | D263-P277 + N295-A391 | K88-K107 | L278-Y294 |
| Dda-SphIME13 | 19 | A258-P272 + N290-P386 | K86-G102 | L273-F289 |
| Dda-AphAc42 | 20 | L266-P280 + N298-A392 | K92-D108 | L281-F297 |
| Dda-SphSP18 | 21 | D262-P276 + N294-A392 | K88-E104 | H277-F293 |
| Dda-Yph | 22 | D261-P275 + N293-A389 | K87-E103 | L276-F292 |
| Dda-SphS16 | 23 | E261-P275 + T293-A390 | K87-E103 | L276-F292 |
| Dda-1993 | 8 | D260-P274 + N292-A389 | K86-E102 | L275-F291 |

The helicase of the invention preferably comprises a variant of SEQ ID NO: 8 in which at least one cysteine residue and/or at least one non-natural amino acid have been introduced into (i) the tower domain (residues D260-P274 and N292-A389) and/or (ii) the pin domain (residues K86-E102) and/or the (iii) 1A domain (residues M1-L85 and V103-K177). The at least one cysteine residue and/or at least one non-natural amino acid are preferably introduced into residues N292-A389 of the tower domain.

The helicase of the invention preferably comprises a variant of SEQ ID NO: 9 in which at least one cysteine residue and/or at least one non-natural amino acid have been introduced into (i) the tower domain (residues G295-N309 and F316-Y421) and/or (ii) the pin domain (residues Y85-L112) and/or the (iii) 1A domain (residues M1-I84 and R113-Y211). The at least one cysteine residue and/or at least one non-natural amino acid are preferably introduced into residues F316-Y421 of the tower domain.

The helicase of the invention preferably comprises a variant of SEQ ID NO: 10 in which at least one cysteine residue and/or at least one non-natural amino acid have been introduced into (i) the tower domain (residues V328-P342 and N360-Y448) and/or (ii) the pin domain (residues K148-N165) and/or the (iii) 1A domain (residues M1-L147 and S166-V240). The at least one cysteine residue and/or at least one non-natural amino acid are preferably introduced into residues N360-Y448 of the tower domain.

The helicase of the invention preferably comprises a variant of SEQ ID NO: 11 in which at least one cysteine residue and/or at least one non-natural amino acid have been introduced into (i) the tower domain (residues A261-T275 and T285-Y370) and/or (ii) the pin domain (residues G91-E107) and/or the (iii) 1A domain (residues M1-L90 and E108-H173). The at least one cysteine residue and/or at least one non-natural amino acid are preferably introduced into residues T285-Y370 of the tower domain.

The helicase of the invention preferably comprises a variant of SEQ ID NO: 12 in which at least one cysteine residue and/or at least one non-natural amino acid have been introduced into (i) the tower domain (residues G294-I307 and T314-Y407) and/or (ii) the pin domain (residues G116-T135) and/or the (iii) 1A domain (residues M1-L115 and N136-V205). The at least one cysteine residue and/or at least one non-natural amino acid are preferably introduced into residues T314-Y407 of the tower domain.

The helicase of the invention preferably comprises a variant of SEQ ID NO: 13 in which at least one cysteine residue and/or at least one non-natural amino acid have been introduced into (i) the tower domain (residues V288-E301 and N307-N393) and/or (ii) the pin domain (residues G97-P113) and/or the (iii) 1A domain (residues M1-L96 and F114-V194). The at least one cysteine residue and/or at least one non-natural amino acid are preferably introduced into residues N307-N393 of the tower domain.

The helicase of the invention preferably comprises a variant of SEQ ID NO: 14 in which at least one cysteine residue and/or at least one non-natural amino acid have been introduced into (i) the tower domain (residues 5250-P264 and E278-S371) and/or (ii) the pin domain (residues K78-E95) and/or the (iii) 1A domain (residues M1-L77 and V96-V166). The at least one cysteine residue and/or at least one non-natural amino acid are preferably introduced into residues E278-S371 of the tower domain.

The helicase of the invention preferably comprises a variant of SEQ ID NO: 15 in which at least one cysteine residue and/or at least one non-natural amino acid have been introduced into (i) the tower domain (residues K255-P269 and T284-S380) and/or (ii) the pin domain (residues K82-K98) and/or the (iii) 1A domain (residues M1-M81 and L99-M171). The at least one cysteine residue and/or at least one non-natural amino acid are preferably introduced into residues T284-S380 of the tower domain.

The helicase of the invention preferably comprises a variant of SEQ ID NO: 16 in which at least one cysteine residue and/or at least one non-natural amino acid have been introduced into (i) the tower domain (residues D242-P256 and T271-S366) and/or (ii) the pin domain (residues K69-K85) and/or the (iii) 1A domain (residues M1-M68 and M86-M158). The at least one cysteine residue and/or at least one non-natural amino acid are preferably introduced into residues T271-S366 of the tower domain.

The helicase of the invention preferably comprises a variant of SEQ ID NO: 17 in which at least one cysteine residue and/or at least one non-natural amino acid have been introduced into (i) the tower domain (residues T263-P277 and N295-P392) and/or (ii) the pin domain (residues K88-K107) and/or the (iii) 1A domain (residues M1-L87 and A108-M181). The at least one cysteine residue and/or at least one non-natural amino acid are preferably introduced into residues N295-P392 of the tower domain.

The helicase of the invention preferably comprises a variant of SEQ ID NO: 18 in which at least one cysteine residue and/or at least one non-natural amino acid have been introduced into (i) the tower domain (residues D263-P277 and N295-A391) and/or (ii) the pin domain (residues K88-K107) and/or the (iii) 1A domain (residues M1-L87 and A108-M181). The at least one cysteine residue and/or at least one non-natural amino acid are preferably introduced into residues N295-A391 of the tower domain.

The helicase of the invention preferably comprises a variant of SEQ ID NO: 19 in which at least one cysteine residue and/or at least one non-natural amino acid have been introduced into (i) the tower domain (residues A258-P272 and N290-P386) and/or (ii) the pin domain (residues K86-G102) and/or the (iii) 1A domain (residues M1-L85 and T103-K176). The at least one cysteine residue and/or at least one non-natural amino acid are preferably introduced into residues N290-P386 of the tower domain.

The helicase of the invention preferably comprises a variant of SEQ ID NO: 20 in which at least one cysteine residue and/or at least one non-natural amino acid have been introduced into (i) the tower domain (residues L266-P280 and N298-A392) and/or (ii) the pin domain (residues K92-D108) and/or the (iii) 1A domain (residues M1-L91 and V109-M183). The at least one cysteine residue and/or at least one non-natural amino acid are preferably introduced into residues N298-A392 of the tower domain.

The helicase of the invention preferably comprises a variant of SEQ ID NO: 21 in which at least one cysteine residue and/or at least one non-natural amino acid have been introduced into (i) the tower domain (residues D262-P276 and N294-A392) and/or (ii) the pin domain (residues K88-E104) and/or the (iii) 1A domain (residues M1-L87 and M105-M179). The at least one cysteine residue and/or at least one non-natural amino acid are preferably introduced into residues N294-A392 of the tower domain.

The helicase of the invention preferably comprises a variant of SEQ ID NO: 22 in which at least one cysteine residue and/or at least one non-natural amino acid have been introduced into (i) the tower domain (residues D261-P275 and N293-A389) and/or (ii) the pin domain (residues K87-E103) and/or the (iii) 1A domain (residues M1-L86 and V104-K178). The at least one cysteine residue and/or at least one non-natural amino acid are preferably introduced into residues N293-A389 of the tower domain.

The helicase of the invention preferably comprises a variant of SEQ ID NO: 23 in which at least one cysteine residue and/or at least one non-natural amino acid have been introduced into (i) the tower domain (residues E261-P275 and T293-A390) and/or (ii) the pin domain (residues K87-E103) and/or the (iii) 1A domain (residues M1-L86 and V104-M178). The at least one cysteine residue and/or at least one non-natural amino acid are preferably introduced into residues T293-A390 of the tower domain.

The helicase of the invention preferably comprises a variant of any one of SEQ ID NOs: 8 to 23 in which at least one cysteine residue and/or at least one non-natural amino acid have been introduced into each of (i) the tower domain and (ii) the pin domain and/or the 1A domain. The helicase of the invention more preferably comprises a variant of any one of SEQ ID NOs: 8 to 23 in which at least one cysteine residue and/or at least one non-natural amino acid have been introduced into each of (i) the tower domain, (ii) the pin domain and (iii) the 1A domain. Any number and combination of cysteine residues and non-natural amino acids may be introduced as discussed above.

The helicase of the invention preferably comprises a variant of SEQ ID NO: 8 which comprises (i) E94C and/or A360C; (ii) E93C and/or K358C; (iii) E93C and/or A360C; (iv) E93C and/or E361C; (v) E93C and/or K364C; (vi) E94C and/or L354C; (vii) E94C and/or K358C; (viii) E93C and/or L354C; (ix) E94C and/or E361C; (x) E94C and/or K364C; (xi) L97C and/or L354C; (xii) L97C and/or K358C; (xiii) L97C and/or A360C; (xiv) L97C and/or E361C; (xv) L97C and/or K364C; (xvi) K123C and/or L354C; (xvii) K123C and/or K358C; (xviii) K123C and/or A360C; (xix) K123C and/or E361C; (xx) K123C and/or K364C; (xxi) N155C and/or L354C; (xxii) N155C and/or K358C; (xxiii) N155C and/or A360C; (xxiv) N155C and/or E361C; (xxv) N155C and/or K364C; (xxvi) any of (i) to (xxv) and G357C; (xxvii) any of (i) to (xxv) and Q100C; (xxviii) any of (i) to (xxv) and I127C; (xxix) any of (i) to (xxv) and Q100C and I127C; (xxx) E94C and/or F377C; (xxxi) N95C; (xxxii) T91C; (xxxiii) Y92L, E94Y, Y350N, A360C and Y363N; (xxxiv) E94Y and A360C; (xxxv) A360C; (xxxvi) Y92L, E94C, Y350N, A360Y and Y363N; (xxxvii) Y92L, E94C and A360Y; (xxxviii) E94C and/or A360C and F276A; (xxxix) E94C and/or L356C; (xl) E93C and/or E356C; (xli) E93C and/or G357C; (xlii) E93C and/or A360C; (xliii) N95C and/or W378C; (xliv) T91C and/or S382C; (xlv) T91C and/or W378C; (xlvi) E93C and/or N353C; (xlvii) E93C and/or S382C; (xlviii) E93C and/or K381C; (xlix) E93C and/or D379C; (l) E93C and/or S375C; (li) E93C and/or W378C; (lii) E93C and/or W374C; (liii) E94C and/or N353C; (liv) E94C and/or S382C; (lv) E94C and/or K381C; (lvi) E94C and/or D379C; (lvii) E94C and/or S375C; (lviii) E94C and/or W378C; (lix) E94C and/or W374C; (lx) E94C and A360Y; (lxi) E94C, G357C and A360C or (lxii) T2C, E94C and A360C. In any one of (i) to (lxii), and/or is preferably and.

The helicase of the invention preferably comprises a variant of any one of SEQ ID NOs: 9 to 23 which comprises a cysteine residue at the positions which correspond to those in SEQ ID NO: 8 as defined in any of (i) to (lxii). Positions in any one of SEQ ID NOs: 9 to 23 which correspond to those in SEQ ID NO: 8 can be identified using the alignment of SEQ ID NOs: 8 to 23 below. The helicase of the invention preferably comprises a variant of SEQ ID NO: 11 which comprises (a) D99C and/or L341C, (b) Q98C and/or L341C or (d) Q98C and/or A340C. The helicase of the invention preferably comprises a variant of SEQ ID NO: 15 which comprises D90C and/or A349C. The helicase of the invention preferably comprises a variant of SEQ ID NO: 21 which comprises D96C and/or A362C.

The helicase of the invention preferably comprises a variant of any one of SEQ ID NOs: 8 to 23 as defined in any one of (i) to (lxii) in which Faz is introduced at one or more of the specific positions instead of cysteine. Faz may be introduced at each specific position instead of cysteine. The helicase of the invention preferably comprises a variant of SEQ ID NO: 8 which comprises (i) E94Faz and/or A360C; (ii) E94C and/or A360Faz; (iii) E94Faz and/or A360Faz; (iv) Y92L, E94Y, Y350N, A360Faz and Y363N; (v) A360Faz; (vi) E94Y and A360Faz; (vii) Y92L, E94Faz, Y350N, A360Y and Y363N; (viii) Y92L, E94Faz and A360Y; (ix) E94Faz and A360Y; and (x) E94C, G357Faz and A360C.

The helicase of the invention preferably further comprises one or more single amino acid deletions from the pin domain. Any number of single amino acid deletions may be made, such as 1, 2, 3, 4, 5, 6, 7, 8, 9, 10 or more. The helicase more preferably comprises a variant of SEQ ID NO: 8 which comprises deletion of E93, deletion of E95 or deletion of E93 and E95. The helicase more preferably comprises a variant of SEQ ID NO: 8 which comprises (a) E94C, deletion of N95 and A360C; (b) deletion of E93, deletion of E94, deletion of N95 and A360C; (c) deletion of E93, E94C, deletion of N95 and A360C or (d) E93C, deletion of N95 and A360C. The helicase of the invention preferably comprises a variant of any one of SEQ ID NOs: 9 to 23 which comprises deletion of the position corresponding to E93 in SEQ ID NO: 8, deletion of the position corresponding to E95 in SEQ ID NO: 8 or deletion of the positions corresponding to E93 and E95 in SEQ ID NO: 8.

The helicase of the invention preferably further comprises one or more single amino acid deletions from the hook domain. Any number of single amino acid deletions may be made, such as 1, 2, 3, 4, 5, 6, 7, 8, 9, 10 or more. The helicase more preferably comprises a variant of SEQ ID NO: 8 which comprises deletion of any number of positions T278 to S287. The helicase more preferably comprises a variant of SEQ ID NO: 8 which comprises (a) E94C, deletion of Y279 to K284 and A360C, (b) E94C, deletion of T278, Y279, V286 and S287 and A360C, (c) E94C, deletion of I281 and K284 and replacement with a single G and A360C, (d) E94C, deletion of K280 and P2845 and replacement with a single G and A360C, or (e) deletion of Y279 to K284, E94C, F276A and A230C. The helicase of the invention preferably comprises a variant of any one of SEQ ID NOs: 9 to 23 which comprises deletion of any number of the positions corresponding to 278 to 287 in SEQ ID NO: 8.

The helicase of the invention preferably further comprises one or more single amino acid deletions from the pin domain and one or more single amino acid deletions from the hook domain.

The helicase of the invention is preferably one in which at least one cysteine residue and/or at least one non-natural amino acid have been further introduced into the hook domain and/or the 2A (RecA-like) domain. Any number and combination of cysteine residues and non-natural amino acids may be introduced as discussed above for the tower, pin and 1A domains.

The helicase of the invention preferably comprises a variant of SEQ ID NO: 8 in which at least one cysteine residue and/or at least one non-natural amino acid have further been introduced into the hook domain (residues L275-F291) and/or the 2A (RecA-like) domain (residues R178-T259 and L390-V439).

The helicase of the invention preferably comprises a variant of SEQ ID NO: 9 in which at least one cysteine residue and/or at least one non-natural amino acid have further been introduced into the hook domain (residues A310-L315) and/or the 2A (RecA-like) domain (residues R212-E294 and G422-S678).

The helicase of the invention preferably comprises a variant of SEQ ID NO: 10 in which at least one cysteine residue and/or at least one non-natural amino acid have further been introduced into the hook domain (residues V343-L359) and/or the 2A (RecA-like) domain (residues R241-N327 and A449-G496).

The helicase of the invention preferably comprises a variant of SEQ ID NO: 11 in which at least one cysteine residue and/or at least one non-natural amino acid have further been introduced into the hook domain (residues W276-L284) and/or the 2A (RecA-like) domain (residues R174-D260 and A371-V421).

The helicase of the invention preferably comprises a variant of SEQ ID NO: 12 in which at least one cysteine residue and/or at least one non-natural amino acid have further been introduced into the hook domain (residues R308-Y313) and/or the 2A (RecA-like) domain (residues R206-K293 and I408-L500).

The helicase of the invention preferably comprises a variant of SEQ ID NO: 13 in which at least one cysteine residue and/or at least one non-natural amino acid have further been introduced into the hook domain (residues M302-W306) and/or the 2A (RecA-like) domain (residues R195-D287 and V394-Q450).

The helicase of the invention preferably comprises a variant of SEQ ID NO: 14 in which at least one cysteine residue and/or at least one non-natural amino acid have further been introduced into the hook domain (residues V265-I277) and/or the 2A (RecA-like) domain (residues R167-T249 and L372-N421).

The helicase of the invention preferably comprises a variant of SEQ ID NO: 15 in which at least one cysteine residue and/or at least one non-natural amino acid have further been introduced into the hook domain (residues V270-F283) and/or the 2A (RecA-like) domain (residues R172-T254 and L381-K434).

The helicase of the invention preferably comprises a variant of SEQ ID NO: 16 in which at least one cysteine residue and/or at least one non-natural amino acid have further been introduced into the hook domain (residues V257-F270) and/or the 2A (RecA-like) domain (residues R159-T241 and L367-K420).

The helicase of the invention preferably comprises a variant of SEQ ID NO: 17 in which at least one cysteine residue and/or at least one non-natural amino acid have further been introduced into the hook domain (residues L278-Y294) and/or the 2A (RecA-like) domain (residues R182-T262 and L393-V443).

The helicase of the invention preferably comprises a variant of SEQ ID NO: 18 in which at least one cysteine residue and/or at least one non-natural amino acid have further been introduced into the hook domain (residues L278-Y294) and/or the 2A (RecA-like) domain (residues R182-T262 and L392-V442).

The helicase of the invention preferably comprises a variant of SEQ ID NO: 19 in which at least one cysteine residue and/or at least one non-natural amino acid have further been introduced into the hook domain (residues L273-F289) and/or the 2A (RecA-like) domain (residues R177-N257 and L387-V438).

The helicase of the invention preferably comprises a variant of SEQ ID NO: 20 in which at least one cysteine residue and/or at least one non-natural amino acid have further been introduced into the hook domain (residues L281-F297) and/or the 2A (RecA-like) domain (residues R184-T265 and L393-I442).

The helicase of the invention preferably comprises a variant of SEQ ID NO: 21 in which at least one cysteine residue and/or at least one non-natural amino acid have further been introduced into the hook domain (residues H277-F293) and/or the 2A (RecA-like) domain (residues R180-T261 and L393-V442).

The helicase of the invention preferably comprises a variant of SEQ ID NO: 22 in which at least one cysteine residue and/or at least one non-natural amino acid have further been introduced into the hook domain (residues L276-F292) and/or the 2A (RecA-like) domain (residues R179-T260 and L390-I439).

The helicase of the invention preferably comprises a variant of SEQ ID NO: 23 in which at least one cysteine residue and/or at least one non-natural amino acid have further been introduced into the hook domain (residues L276-F292) and/or the 2A (RecA-like) domain (residues R179-T260 and L391-V441).

The helicase of the invention preferably comprises a variant of SEQ ID NO: 8 which comprises one or more of (i) I181C; (ii) Y279C; (iii) I281C; and (iv) E288C. The helicase may comprise any combination of (i) to (iv), such as (i); (ii); (iii); (iv); (i) and (ii); (i) and (iii); (i) and (iv); (ii) and (iii); (ii) and (iv); (iii) and (iv); or (i), (ii), (iii) and (iv). The helicase more preferably comprises a variant of SEQ ID NO: 8 which comprises (a) E94C, I281C and A360C or (b) E94C, I281C, G357C and A360C. The helicase of the invention preferably comprises a variant of any one of SEQ ID NOs: 9 to 23 which comprises a cysteine residue at one or more of the position(s) which correspond to those in SEQ ID NO: 8 as defined in (i) to (iv), (a) and (b). The helicase may comprise any of these variants in which Faz is introduced at one or more of the specific positions (or each specific position) instead of cysteine.

The helicase of the invention is further modified to reduce its surface negative charge. Surface residues can be identified in the same way as the Dda domains disclosed above. Surface negative charges are typically surface negatively-charged amino acids, such as aspartic acid (D) and glutamic acid (E).

The helicase is preferably modified to neutralise one or more surface negative charges by substituting one or more negatively charged amino acids with one or more positively charged amino acids, uncharged amino acids, non-polar amino acids and/or aromatic amino acids or by introducing one or more positively charged amino acids, preferably adjacent to one or more negatively charged amino acids. Suitable positively charged amino acids include, but are not limited to, histidine (H), lysine (K) and arginine (R). Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y).

Preferred substitutions include, but are not limited to, substitution of E with R, substitution of E with K, substitution of E with N, substitution of D with K and substitution of D with R.

The helicase of the invention preferably comprises a variant of SEQ ID NO: 8 and the one or more negatively charged amino acids are one or more of D5, E8, E23, E47, D167, E172, D202, D212 and E273. Any number of these amino acids may be neutralised, such as 1, 2, 3, 4, 5, 6, 7 or 8 of them. Any combination may be neutralised. The helicase of the invention preferably comprises a variant of any one of SEQ ID NOs: 9 to 23 and the one or more negatively charged amino acids correspond to one or more of D5, E8, E23, E47, D167, E172, D202, D212 and E273 in SEQ ID NO: 8. Amino acids in SEQ ID NOs: 9 to 23 which correspond to D5, E8, E23, E47, D167, E172, D202, D212 and E273 in SEQ ID NO: 8 can be determined using the alignment below. The helicase of the invention preferably comprises a variant of SEQ ID NO: 8 which comprises (a) E94C, E273G and A360C or (b) E94C, E273G, N292G and A360C.

The helicase of the invention is preferably further modified by the removal of one or more native cysteine residues. Any number of native cysteine residues may be removed. The number of cysteine residues in each of SEQ ID NOs: 9 to 23 is shown in Table 1 (as #C). The one or more cysteine residues are preferably removed by substitution. The one or more cysteine residues are preferably substituted with alanine (A), serine (S) or valine (V). The helicase of the invention preferably comprises a variant of SEQ ID NO: 8 and the one or more native cysteine residues are one or more of C109, C114, C136, C171 and C412. Any number and combination of these cysteine residues may be removed. For instance, the variant of SEQ ID NO: 8 may comprise C109; C114; C136; C171; C412; C109 and C114; C109 and C136; C109 and C171; C109 and C412; C114 and C136; C114 and C171; C114 and C412; C136 and C171; C136 and C412; C171 and C412; C109, C114 and C136; C109, C114 and C171; C109, C114 and C412; C109, C136 and C171; C109, C136 and C412; C109, C171 and C412; C114, C136 and C171; C114, C136 and C412; C114, C171 and C412; C136, C171 and C412; C109, C114, C136 and C171; C109, C114, C136 and C412; C109, C114, C171 and C412; C109, C136, C171 and C412; C114, C136, C171 and C412; or C109, C114, C136, C171 and C412.

The helicase of the invention is preferably one in which at least one cysteine residue (i.e. one or more cysteine residues) and/or at least one non-natural amino acid (i.e. one or more non-natural amino acids) have been introduced into the tower domain only. Suitable modifications are discussed above.

The helicase of the invention preferably comprises a variant of SEQ ID NO: 8 comprising the following mutations:

E93C and K364C;
E94C and K364C;
E94C and A360C;
L97C and E361C;
L97C and E361C and C412A;
K123C and E361C;
K123C, E361C and C412A;
N155C and K358C;
N155C, K358C and C412A;
N155C and L354C;
N155C, L354C and C412A;
deltaE93, E94C, deltaN95 and A360C;
E94C, deltaN95 and A360C;

E94C, Q100C, I127C and A360C;
L354C;
G357C;
E94C, G357C and A360C;
E94C, Y279C and A360C;
E94C, I281C and A360C;
E94C, Y279Faz and A360C;
Y279C and G357C;
I281C and G357C;
E94C, Y279C, G357C and A360C;
E94C, I281C, G357C and A360C;
E8R, E47K, E94C, D202K and A360C;
D5K, E23N, E94C, D167K, E172R, D212R and A360C;
D5K, E8R, E23N, E47K, E94C, D167K, E172R, D202K, D212R and A360C;
E94C, C114A, C171A, A360C and C412D;
E94C, C114A, C171A, A360C and C412S;
E94C, C109A, C136A and A360C;
E94C, C109A, Cl 14A, C136A, C171A, A360C and C412S;
E94C, C109V, C114V, C171A, A360C and C412S;
C109A, C114A, C136A, G153C, C171A, E361C and C412A;
C109A, C114A, C136A, G153C, C171A, E361C and C412D;
C109A, C114A, C136A, G153C, C171A, E361C and C412S;
C109A, C114A, C136A, G153C, C171A, K358C and C412A;
C109A, C114A, C136A, G153C, C171A, K358C and C412D
C109A, C114A, C136A, G153C, C171A, K358C and C412S;
C109A, C114A, C136A, N155C, C171A, K358C and C412A;
C109A, C114A, C136A, N155C, C171A, K358C and C412D;
C109A, C114A, C136A, N155C, C171A, K358C and C412S;
C109A, C114A, C136A, N155C, C171A, L354C and C412A;
C109A, C114A, C136A, N155C, C171A, L354C and C412D;
C109A, C114A, C136A, N155C, C171A, L354C and C412S;
C109A, C114A, K123C, C136A, C171A, E361C and C412A;
C109A, C114A, K123C, C136A, C171A, E361C and C412D;
C109A, C114A, K123C, C136A, C171A, E361C and C412S;
C109A, C114A, K123C, C136A, C171A, K358C and C412A;
C109A, C114A, K123C, C136A, C171A, K358C and C412D;
C109A, C114A, K123C, C136A, C171A, K358C and C412S;
C109A, C114A, C136A, G153C, C171A, E361C and C412A;
E94C, C109A, C114A, C136A, C171A, A360C and C412D;
E94C, C109A, C114V, C136A, C171A, A360C and C412D;
E94C, C109V, C114A, C136A, C171A, A360C and C412D;
L97C, C109A, C114A, C136A, C171A, E361C and C412A;
L97C, C109A, C114A, C136A, C171A, E361C and C412D; or
L97C, C109A, C114A, C136A, C171A, E361C and C412S.

Modifications in the Hook Domain and/or 2A Domain

In one embodiment, the helicase of the invention is one in which at least one cysteine residue and/or at least one non-natural amino acid have been introduced into the hook domain and/or the 2A (RecA-like motor) domain, wherein the helicase has the ability to control the movement of a polynucleotide. At least one cysteine residue and/or at least one non-natural amino acid is preferably introduced into the hook domain and the 2A (RecA-like motor) domain.

Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced.

Only one or more cysteine residues may be introduced. Only one or more non-natural amino acids may be introduced. A combination of one or more cysteine residues and one or more non-natural amino acids may be introduced.

The at least one cysteine residue and/or at least one non-natural amino acid are preferably introduced by substitution. Methods for doing this are known in the art. Suitable modifications of the hook domain and/or the 2A (RecA-like motor) domain are discussed above.

The helicase of the invention is preferably a variant of SEQ ID NO: 8 comprising (a) Y279C, I181C, E288C, Y279C and I181C, (b) Y279C and E288C, (c) I181C and E288C or (d) Y279C, I181C and E288C. The helicase of the invention preferably comprises a variant of any one of SEQ ID NOs: 9 to 23 which comprises a mutation at one or more of the position(s) which correspond to those in SEQ ID NO: 8 as defined in (a) to (d).

Surface Modification

In one embodiment, the helicase is modified to reduce its surface negative charge, wherein the helicase has the ability to control the movement of a polynucleotide. Suitable modifications are discussed above. Any number of surface negative charges may be neutralised.

The helicase of the invention preferably comprises a variant of SEQ ID NO: 8 comprising the following mutations:
E273G;
E8R, E47K and D202K;
D5K, E23N, D167K, E172R and D212R; or
D5K, E8R, E23N, E47K, D167K, E172R, D202K and D212R.

Other Modified Helicases

In one embodiment, the helicase of the invention comprises a variant of SEQ ID NO: 8 comprising:
A360K;
Y92L and/or A360Y;
Y92L, Y350N and Y363N;
Y92L and/or Y363N; or
Y92L.

Other Modifications

In addition to the specific mutations disclosed above, a variant of SEQ ID NO: 8 may comprise one or more of the following mutations:
K38A;
T91F;
T91N;
T91Q;
T91W;
V96E;

V96F;
V96L
V96Q;
V96R;
V96W;
V96Y;
P274G;
V286F;
V286W;
V286Y;
F291G;
N292F;
N292G;
N292P;
N292Y;
G294Y;
G294F;
K364A; and
W378A.

In addition to the specific mutations disclosed above, a variant of SEQ ID NO: 8 may comprise:

K38A, E94C and A360C;
H64K; E94C and A360C;
H64N; E94C and A360C;
H64Q; E94C and A360C;
H64S; E94C and A360C;
H64W, E94C and A360C;
T80K, E94C and A360C;
T80K, S83K, E94C, N242K, N293K and A360C;
T80K, S83K, E94C, N242K, N293K, A360C and T394K;
T80K, S83K, E94C, N293K and A360C;
T80K, S83K, E94C, A360C and T394K;
T80K, S83K, E94C, A360C and T394N;
T80K, E94C, N242K and A360C;
T80K, E94C, N242K, N293K and A360C;
T80K, E94C, N293K and A360C;
T80N, E94C and A360C;
H82A, E94C and A360C;
H82A, P89A, E94C, F98A and A360C;
H82F, E94C and A360C;
H82Q, E94C, A360C;
H82R, E94C and A360C;
H82W, E94C and A360C;
H82W, P89W, E94C, F98W and A360C;
H82Y, E94C and A360C;
S83K, E94C and A360C;
S83K, T80K, E94C, A360C and T394K;
S83N, E94C and A360C;
S83T, E94C and A360C;
N88H, E94C and A360C;
N88Q, E94C and A360C;
P89A, E94C and A360C;
P89A, F98W, E94C and A360C;
P89A, E94C, F98Y and A360C;
P89A, E94C, F98A and A360C;
P89F, E94C and A360C;
P89S, E94C and A360C;
P89T, E94C and A360C;
P89W, E94C, F98W and A360C;
P89Y, E94C and A360C;
T91F, E94C and A360C;
T91N, E94C and A360C;
T91Q, E94C and A360C;
T91W, E94C and A360C;
E94C, V96E and A360C;
E94C, V96F and A360C;
E94C, V96L and A360C;
E94C, V96Q and A360C;
E94C, V96R and A360C;
E94C, V96W and A360C;
E94C, V96Y and A360C;
E94C, F98A and A360C;
E94C, F98L and A360C;
E94C, F98V and A360C;
E94C, F98Y and A360C;
E94C; F98W and A360C;
E94C, V150A and A360C;
E94C, V150F and A360C;
E94C, V150I and A360C;
E94C, V150K and A360C;
E94C, V150L and A360C;
E94C, V150S and A360C;
E94C, V150T and A360C;
E94C, V150W and A360C;
E94C, V150Y and A360C;
E94C, F240Y and A360C;
E94C, F240W and A360C;
E94C, N242K and A360C;
E94C, N242K, N293K and A360C;
E94C, P274G and A360C;
E94C, L275G and A360C
E94C, F276A and A360C;
E94C, F276I and A360C;
E94C, F276M and A360C;
E94C, F276V and A360C;
E94C, F276W and A360C;
E94C, F276Y and A360C;
E94C, V286F and A360C;
E94C, V286W and A360C;
E94C, V286Y and A360C;
E94C, S287F and A360C;
E94C, S287W and A360C;
E94C, S287Y and A360C;
E94C, F291G and A360C;
E94C, N292F and A360C;
E94C, N292G and A360C;
E94C, N292P and A360C;
E94C, N292Y and A360C;
E94C, N293F and A360C;
E94C, N293K and A360C;
E94C, N293Q and A360C;
E94C, N293Y and A360C;
E94C, G294F and A360C;
E94C, G294Y and A360C;
E94C, A36C and K364A;
E94C, A360C, W378A;
E94C, A360C and T394K;
E94C, A360C and H396Q;
E94C, A360C and H396S;
E94C, A360C and H396W;
E94C, A360C and Y415F;
E94C, A360C and Y415K;
E94C, A360C and Y415M; or
E94C, A360C and Y415W.

The helicase of the invention preferably comprises a variant of SEQ ID NO: 8 which comprises (a) E94C/A360C/W378A or (b) E94C/A360C/C109A/C136A/W378A or (d) E94C/A360C/C109A/C136A/W378A and then (ΔM1) G1G2 (i.e. deletion of M1 and then addition G1 and G2).

Preferred variants of any one of SEQ ID NOs: 8 to 23 have (in addition to the modifications of the invention) the N-terminal methionine (M) replaced with one glycine residue (G). In the examples this is shown as (ΔM1)G1. It may also be termed M1G. Any of the variants discussed above may further comprise M1G.

The most preferred helicases of the invention comprise a variant of SEQ ID NO: 8 which comprises (a) E94C/F98W/A360C/C109A/C136A/K194L; (b) M1G/E94C/F98W/A360C/C109A/C136A/K194L; (c) E94C/F98W/A360C/C109A/C136A/K199L; or (d) M1G/E94C/F98W/A360C/C109A/C136A/K199L.

Variants

A variant of a helicase is an enzyme that has an amino acid sequence which varies from that of the wild-type helicase and which has polynucleotide binding activity. In particular, a variant of any one of SEQ ID NOs: 8 to 23 is an enzyme that has an amino acid sequence which varies from that of any one of SEQ ID NOs: 8 to 23 and which has polynucleotide binding activity. Polynucleotide binding activity can be determined using methods known in the art.

Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant has helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature.

Over the entire length of the amino acid sequence of any one of SEQ ID NOs: 8 to 23, a variant will preferably be at least 20% homologous to that sequence based on amino acid similarity or identity. More preferably, the variant polypeptide may be at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 8 to 23 over the entire sequence. There may be at least 70%, for example at least 80%, at least 85%, at least 90% or at least 95%, amino acid identity over a stretch of 100 or more, for example 150, 200, 300, 400 or 500 or more, contiguous amino acids ("hard homology"). Homology is determined as described below. The variant may differ from the wild-type sequence in any of the ways discussed below with reference to SEQ ID NOs: 2 and 4. In particular, in addition to the specific modifications discussed above, the variant of any one of SEQ ID NOs: 8 to 23 may comprise one or more substitutions, one or more deletions and/or one or more additions as discussed below.

Preferred variants of any one of SEQ ID NOs: 8 to 23 have a non-natural amino acid, such as Faz, at the amino- (N-) terminus and/or carboxy (C-) terminus. Preferred variants of any one of SEQ ID NOs: 8 to 23 have a cysteine residue at the amino- (N-) terminus and/or carboxy (C-) terminus. Preferred variants of any one of SEQ ID NOs: 8 to 23 have a cysteine residue at the amino- (N-) terminus and a non-natural amino acid, such as Faz, at the carboxy (C-) terminus or vice versa.

Preferred variants of SEQ ID NO: 8 contain one or more of, such as all of, the following modifications E54G, D151E, I196N and G357A.

No Connection

In one preferred embodiment, none of the introduced cysteines and/or non-natural amino acids in a modified helicase of the invention are connected to one another.

Connecting Two More of the Introduced Cysteines and/or Non-Natural Amino Acids

In another preferred embodiment, two more of the introduced cysteines and/or non-natural amino acids in a modified helicase of the invention are connected to one another. This typically reduces the ability of the helicase of the invention to unbind from a polynucleotide.

Any number and combination of two more of the introduced cysteines and/or non-natural amino acids may be connected to one another. For instance, 3, 4, 5, 6, 7, 8 or more cysteines and/or non-natural amino acids may be connected to one another. One or more cysteines may be connected to one or more cysteines. One or more cysteines may be connected to one or more non-natural amino acids, such as Faz. One or more non-natural amino acids, such as Faz, may be connected to one or more non-natural amino acids, such as Faz.

The two or more cysteines and/or non-natural amino acids may be connected in any way. The connection can be transient, for example non-covalent. Even transient connection will reduce unbinding of the polynucleotide from the helicase.

The two or more cysteines and/or non-natural amino acids are preferably connected by affinity molecules. Suitable affinity molecules are known in the art. The affinity molecules are preferably (a) complementary polynucleotides (International Application No. PCT/GB10/000132 (published as WO 2010/086602), (b) an antibody or a fragment thereof and the complementary epitope (Biochemistry 6th Ed, W.H. Freeman and co (2007) pp 953-954), (c) peptide zippers (O'Shea et al., Science 254 (5031): 539-544), (d) capable of interacting by β-sheet augmentation (Remaut and Waksman Trends Biochem. Sci. (2006) 31 436-444), (e) capable of hydrogen bonding, pi-stacking or forming a salt bridge, (f) rotaxanes (Xiang Ma and He Tian Chem. Soc. Rev., 2010, 39, 70-80), (g) an aptamer and the complementary protein (James, W. in Encyclopedia of Analytical Chemistry, R. A. Meyers (Ed.) pp. 4848-4871 John Wiley & Sons Ltd, Chichester, 2000) or (h) half-chelators (Hammerstein et al. J Biol Chem. 2011 April 22; 286(16): 14324-14334). For (e), hydrogen bonding occurs between a proton bound to an electronegative atom and another electronegative atom. Pi-stacking requires two aromatic rings that can stack together where the planes of the rings are parallel. Salt bridges are between groups that can delocalize their electrons over several atoms, e.g. between aspartate and arginine.

The two or more parts may be transiently connected by a hexa-his tag or Ni-NTA.

The two or more cysteines and/or non-natural amino acids are preferably permanently connected. In the context of the invention, a connection is permanent if is not broken while the helicase is used or cannot be broken without intervention on the part of the user, such as using reduction to open —S—S— bonds.

The two or more cysteines and/or non-natural amino acids are preferably covalently-attached. The two or more cysteines and/or non-natural amino acids may be covalently attached using any method known in the art.

The two or more cysteines and/or non-natural amino acids may be covalently attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two or more cysteines and/or non-natural amino acids may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), any one of the amino acids numbered 1-71 included in FIG. 1 of Liu C. C. and Schultz P. G., Annu. Rev. Biochem., 2010, 79, 413-444 or any one of the amino acids listed below. The introduced amino acids may be modified as discussed above.

In a preferred embodiment, the two or more cysteines and/or non-natural amino acids are connected using linkers. Linker molecules are discussed in more detail below. One suitable method of connection is cysteine linkage. This is discussed in more detail below. The two or more cysteines and/or non-natural amino acids are preferably connected using one or more, such as two or three, linkers. The one or more linkers may be designed to reduce the size of, or close, the opening as discussed above. If one or more linkers are being used to close the opening as discussed above, at least a part of the one or more linkers is preferably oriented such that it is not parallel to the polynucleotide when it is bound by the helicase. More preferably, all of the linkers are oriented in this manner. If one or more linkers are being used to close the opening as discussed above, at least a part of the one or more linkers preferably crosses the opening in an orientation that is not parallel to the polynucleotide when it bound by the helicase. More preferably, all of the linkers cross the opening in this manner. In these embodiments, at least a part of the one or more linkers may be perpendicular to the polynucleotide. Such orientations effectively close the opening such that the polynucleotide cannot unbind from the helicase through the opening.

Each linker may have two or more functional ends, such as two, three or four functional ends. Suitable configurations of ends in linkers are well known in the art.

One or more ends of the one or more linkers are preferably covalently attached to the helicase. If one end is covalently attached, the one or more linkers may transiently connect the two or more cysteines and/or non-natural amino acids as discussed above. If both or all ends are covalently attached, the one or more linkers permanently connect the two or more cysteines and/or non-natural amino acids.

The one or more linkers are preferably amino acid sequences and/or chemical crosslinkers.

Suitable amino acid linkers, such as peptide linkers, are known in the art. The length, flexibility and hydrophilicity of the amino acid or peptide linker are typically designed such that it reduces the size of the opening, but does not to disturb the functions of the helicase. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline. The amino acid sequence of a linker preferably comprises a polynucleotide binding moiety. Such moieties and the advantages associated with their use are discussed below.

Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG 11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S-S-PEG3-biotin, DBCO-S-S-PEG3-biotin, DBCO-S-S-PEG11-biotin, (succinimidyl 3-(2-pyridyldithio)propionate (SPDP) and maleimide-PEG(2 kDa)-maleimide (ALPHA,OMEGA-BIS-MALEIMIDO POLY(ETHYLENE GLYCOL)). The most preferred crosslinker is maleimide-propyl-SRDFWRS-(1,2-diaminoethane)-propyl-maleimide.

The one or more linkers may be cleavable. This is discussed in more detail below.

The two or more cysteines and/or non-natural amino acids may be connected using two different linkers that are specific for each other. One of the linkers is attached to one part and the other is attached to another part. The linkers should react to form a modified helicase of the invention. The two or more cysteines and/or non-natural amino acids may be connected using the hybridization linkers described in International Application No. PCT/GB10/000132 (published as WO 2010/086602). In particular, the two or more cysteines and/or non-natural amino acids may be connected using two or more linkers each comprising a hybridizable region and a group capable of forming a covalent bond. The hybridizable regions in the linkers hybridize and link the two or more cysteines and/or non-natural amino acids. The linked cysteines and/or non-natural amino acids are then coupled via the formation of covalent bonds between the groups. Any of the specific linkers disclosed in International Application No. PCT/GB10/000132 (published as WO 2010/086602) may be used in accordance with the invention.

The two or more cysteines and/or non-natural amino acids may be modified and then attached using a chemical cross-linker that is specific for the two modifications. Any of the crosslinkers discussed above may be used.

The linkers may be labeled. Suitable labels include, but are not limited to, fluorescent molecules (such as Cy3 or AlexaFluor®555), radioisotopes, e.g. $^{125}$I, $^{35}$S, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of connecting two or more cysteines is via cysteine linkage. This can be mediated by a bi-functional chemical crosslinker or by an amino acid linker with a terminal presented cysteine residue.

The length, reactivity, specificity, rigidity and solubility of any bi-functional linker may be designed to ensure that the size of the opening is reduced sufficiently and the function of the helicase is retained. Suitable linkers include bisma-leimide crosslinkers, such as 1,4-bis(maleimido)butane (BMB) or bis(maleimido)hexane. One drawback of bi-functional linkers is the requirement of the helicase to contain no further surface accessible cysteine residues if attachment at specific sites is preferred, as binding of the bi-functional linker to surface accessible cysteine residues may be difficult to control and may affect substrate binding or activity. If the helicase does contain several accessible cysteine residues, modification of the helicase may be required to remove them while ensuring the modifications do not affect the folding or activity of the helicase. This is discussed in International Application No. PCT/GB10/000133 (published as WO 2010/086603). The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S$^-$ group. The reactivity of cysteine residues may be protected by thiol protective groups such as 5,5'-dithiobis-(2-nitrobenzoic acid) (dTNB). These may be reacted with one or more cysteine residues of the helicase before a linker is attached. Selective deprotection of surface accessible cysteines may be possible using reducing reagents immobilized on beads (for example immobilized tris(2-carboxyethyl) phosphine, TCEP). Cysteine linkage is discussed in more detail below.

Another preferred method of attachment via Faz linkage. This can be mediated by a bi-functional chemical linker or by a polypeptide linker with a terminal presented Faz residue.

Other Modifications

The helicase of the invention may also be modified to increase the attraction between (i) the tower domain and (ii) the pin domain and/or the LA domain. Any known chemical modifications can be made in accordance with the invention. These types of modification are disclosed in PCT/GB2014/052736 (WO 2015/055981).

In particular, the invention provides a helicase of the invention in which at least one charged amino acid has been introduced into (i) the tower domain and/or (ii) the pin domain and/or (iii) the 1A (RecA-like motor) domain, wherein the helicase has the ability to control the movement of a polynucleotide. The ability of the helicase to control the movement of a polynucleotide may be measured as discussed above. The invention preferably provides a helicase of the invention in which at least one charged amino acid has been introduced into (i) the tower domain and (ii) the pin domain and/or the 1A domain.

The at least one charged amino acid may be negatively charged or positively charged. The at least one charged amino acid is preferably oppositely charged to any amino acid(s) with which it interacts in the helicase. For instance, at least one positively charged amino acid may be introduced into the tower domain at a position which interacts with a negatively charged amino acid in the pin domain. The at least one charged amino acid is typically introduced at a position which is not charged in the wild-type (i.e. unmodified) helicase. The at least one charged amino acid may be used to replace at least one oppositely charged amino acid in the helicase. For instance, a positively charged amino acid may be used to replace a negatively charged amino acid.

Suitable charged amino acids are discussed above. The at least one charged amino acid may be natural, such as arginine (R), histidine (H), lysine (K), aspartic acid (D) or glutamic acid (D). Alternatively, the at least one charged amino acid may be artificial or non-natural. Any number of charged amino acids may be introduced into each domain. For instance, 1, 2, 3, 4, 5, 6, 7, 8, 9, 10 or more charged amino acids may be introduced into each domain.

The helicase preferably comprises a variant of SEQ ID NO: 8 which comprises a positively charged amino acid at one or more of the following positions: (i) 93; (ii) 354; (iii) 360; (iv) 361; (v) 94; (vi) 97; (vii) 155; (viii) 357; (ix) 100; and (x) 127. The helicase preferably comprises a variant of SEQ ID NO: 8 which comprises a negatively charged amino acid at one or more of the following positions: (i) 354; (ii) 358; (iii) 360; (iv) 364; (v) 97; (vi) 123; (vii) 155; (viii); 357; (ix) 100; and (x) 127. The helicase preferably comprises a variant of any one of SEQ ID NOs: 9 to 23 which comprises a positively charged amino acid or negatively charged amino acid at the positions which correspond to those in SEQ ID NO: 8 as defined in any of (i) to (x). Positions in any one of SEQ ID NOs: 9 to 23 which correspond to those in SEQ ID NO: 8 can be identified using the alignment of SEQ ID NOs: 8 to 23 below.

The helicase preferably comprises a variant of SEQ ID NO: 8 which is modified by the introduction of at least one charged amino acid such that it comprises oppositely charged amino acid at the following positions: (i) 93 and 354; (ii) 93 and 358; (iii) 93 and 360; (iv) 93 and 361; (v) 93 and 364; (vi) 94 and 354; (vii) 94 and 358; (viii) 94 and 360; (ix) 94 and 361; (x) 94 and 364; (xi) 97 and 354; (xii) 97 and 358; (xiii) 97 and 360; (xiv) 97 and 361; (xv) 97 and 364; (xvi) 123 and 354; (xvii) 123 and 358; (xviii) 123 and 360; (xix) 123 and 361; (xx) 123 and 364; (xxi) 155 and 354; (xxii) 155 and 358; (xxiii) 155 and 360; (xxiv) 155 and 361; (xxv) 155 and 364. The helicase of the invention preferably comprises a variant of any one of SEQ ID NOs: 9 to 23 which comprises oppositely charged amino acids at the positions which correspond to those in SEQ ID NO: 8 as defined in any of (i) to (xxv).

The invention also provides a helicase in which (i) at least one charged amino acid has been introduced into the tower domain and (ii) at least one oppositely charged amino acid has been introduced into the pin domain and/or the 1A (RecA-like motor) domain, wherein the helicase has the ability to control the movement of a polynucleotide. The at least one charged amino acid may be negatively charged and the at least one oppositely charged amino acid may be positively charged or vice versa. Suitable charged amino acids are discussed above. Any number of charged amino acids and any number of oppositely charged amino acids may be introduced. For instance, 1, 2, 3, 4, 5, 6, 7, 8, 9, 10 or more charged amino acids may be introduced and/or 1, 2, 3, 4, 5, 6, 7, 8, 9, 10 or more oppositely charged amino acids may be introduced.

The charged amino acids are typically introduced at positions which are not charged in the wild-type helicase. One or both of the charged amino acids may be used to replace charged amino acids in the helicase. For instance, a positively charged amino acid may be used to replace a negatively charged amino acid. The charged amino acids may be introduced at any of the positions in the (i) tower domain and (ii) pin domain and/or 1A domain discussed above. The oppositely charged amino acids are typically introduced such that they will interact in the resulting helicase. The helicase preferably comprises a variant of SEQ ID NO: 8 in which oppositely charged amino acids have been introduced at the following positions: (i) 97 and 354; (ii) 97 and 360; (iii) 155 and 354; or (iv) 155 and 360. The helicase of the invention preferably comprises a variant of any one of SEQ ID NOs: 9 to 23 which comprises oppositely charged amino acids at the positions which correspond to those in SEQ ID NO: 8 as defined in any of (i) to (iv).

Construct

The invention also provides a construct comprising a modified helicase of the invention and an additional polynucleotide binding moiety, wherein the helicase is attached to the polynucleotide binding moiety and the construct has the ability to control the movement of a polynucleotide. The construct is artificial or non-natural.

A construct of the invention is a useful tool for controlling the movement of a polynucleotide during Strand Sequencing. A construct of the invention is even less likely than a modified helicase of the invention to disengage from the polynucleotide being sequenced. The construct can provide even greater read lengths of the polynucleotide as it controls the translocation of the polynucleotide through a nanopore.

A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

The construct has the ability to control the movement of a polynucleotide. This can be determined as discussed above.

A construct of the invention may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

The helicase may be any of the helicases of the invention discussed above.

The helicase is preferably covalently attached to the additional polynucleotide binding moiety. The helicase may be attached to the moiety at more than one, such as two or three, points.

The helicase can be covalently attached to the moiety using any method known in the art. Suitable methods are discussed above with reference to connecting the two or more parts.

The helicase and moiety may be produced separately and then attached together. The two components may be attached in any configuration. For instance, they may be attached via their terminal (i.e. amino or carboxy terminal) amino acids. Suitable configurations include, but are not limited to, the amino terminus of the moiety being attached to the carboxy terminus of the helicase and vice versa. Alternatively, the two components may be attached via amino acids within their sequences. For instance, the moiety may be attached to one or more amino acids in a loop region of the helicase. In a preferred embodiment, terminal amino acids of the moiety are attached to one or more amino acids in the loop region of a helicase.

In a preferred embodiment, the helicase is chemically attached to the moiety, for instance via one or more linker molecules as discussed above. In another preferred embodiment, the helicase is genetically fused to the moiety. A helicase is genetically fused to a moiety if the whole construct is expressed from a single polynucleotide sequence. The coding sequences of the helicase and moiety may be combined in any way to form a single polynucleotide sequence encoding the construct. Genetic fusion of a pore to a nucleic acid binding protein is discussed in International Application No. PCT/GB09/001679 (published as WO 2010/004265).

The helicase and moiety may be genetically fused in any configuration. The helicase and moiety may be fused via their terminal amino acids. For instance, the amino terminus of the moiety may be fused to the carboxy terminus of the helicase and vice versa. The amino acid sequence of the moiety is preferably added in frame into the amino acid sequence of the helicase. In other words, the moiety is preferably inserted within the sequence of the helicase. In such embodiments, the helicase and moiety are typically attached at two points, i.e. via the amino and carboxy terminal amino acids of the moiety. If the moiety is inserted within the sequence of the helicase, it is preferred that the amino and carboxy terminal amino acids of the moiety are in close proximity and are each attached to adjacent amino acids in the sequence of the helicase or variant thereof. In a preferred embodiment, the moiety is inserted into a loop region of the helicase.

The helicase may be attached directly to the moiety. The helicase is preferably attached to the moiety using one or more, such as two or three, linkers as discussed above. The one or more linkers may be designed to constrain the mobility of the moiety. The helicase and/or the moiety may be modified to facilitate attachment of the one or more linker as discussed above.

Cleavable linkers can be used as an aid to separation of constructs from non-attached components and can be used to further control the synthesis reaction. For example, a heterobifunctional linker may react with the helicase, but not the moiety. If the free end of the linker can be used to bind the helicase protein to a surface, the unreacted helicases from the first reaction can be removed from the mixture. Subsequently, the linker can be cleaved to expose a group that reacts with the moiety. In addition, by following this sequence of linkage reactions, conditions may be optimised first for the reaction to the helicase, then for the reaction to the moiety after cleavage of the linker. The second reaction would also be much more directed towards the correct site of reaction with the moiety because the linker would be confined to the region to which it is already attached.

The helicase may be covalently attached to the bifunctional crosslinker before the helicase/crosslinker complex is covalently attached to the moiety. Alternatively, the moiety may be covalently attached to the bifunctional crosslinker before the bifunctional crosslinker/moiety complex is attached to the helicase. The helicase and moiety may be covalently attached to the chemical crosslinker at the same time.

Preferred methods of attaching the helicase to the moiety are cysteine linkage and Faz linkage as described above. In a preferred embodiment, a reactive cysteine is presented on a peptide linker that is genetically attached to the moiety. This means that additional modifications will not necessarily be needed to remove other accessible cysteine residues from the moiety.

Cross-linkage of helicases or moieties to themselves may be prevented by keeping the concentration of linker in a vast excess of the helicase and/or moiety. Alternatively, a "lock and key" arrangement may be used in which two linkers are used. Only one end of each linker may react together to form a longer linker and the other ends of the linker each react with a different part of the construct (i.e. helicase or moiety). This is discussed in more detail below.

The site of attachment is selected such that, when the construct is contacted with a polynucleotide, both the helicase and the moiety can bind to the polynucleotide and control its movement.

Figure 10A:
FIG. 10A shows an example of complementary polynucleotides that may be used to bind helicase.
Figure 10B:
FIG. 10B shows an example of DNA that could be used for helicase-Phi29 constructs.

Attachment can be facilitated using the polynucleotide binding activities of the helicase and the moiety. For instance, complementary polynucleotides can be used to bring the helicase and moiety together as they hybridize. The helicase can be bound to one polynucleotide and the moiety can be bound to the complementary polynucleotide. The two polynucleotides can then be allowed to hybridise to each other. This will bring the helicase into close contact with the moiety, making the linking reaction more efficient. This is especially helpful for attaching two or more helicases in the correct orientation for controlling movement of a target polynucleotide. An example of complementary polynucleotides that may be used is shown in FIG. 10A. For helicase-Phi29 constructs the DNA in FIG. 10B could be used.

Tags can be added to the construct to make purification of the construct easier. These tags can then be chemically or enzymatically cleaved off, if their removal is necessary. Fluorophores or chromophores can also be included, and these could also be cleavable.

A simple way to purify the construct is to include a different purification tag on each protein (i.e. the helicase and the moiety), such as a hexa-His-tag and a Strep-Tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs of the invention can also be purified from unreacted proteins on the basis of a different DNA processivity property. In particular, a construct of the invention can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

Polynucleotide Binding Moiety

The constructs of the invention comprise a polynucleotide binding moiety. A polynucleotide binding moiety is a polypeptide that is capable of binding to a polynucleotide. The moiety is preferably capable of specific binding to a defined polynucleotide sequence. In other words, the moiety preferably binds to a specific polynucleotide sequence, but displays at least 10 fold less binding to different sequences or more preferably at least 100 fold less binding to different sequences or most preferably at least 1000 fold less binding to different sequences. The different sequence may be a random sequence. In some embodiments, the moiety binds to a specific polynucleotide sequence, but binding to different sequences cannot be measured. Moieties that bind to specific sequences can be used to design constructs that are targeted to such sequences.

The moiety typically interacts with and modifies at least one property of a polynucleotide. The moiety may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

It is preferred that the tertiary structure of the moiety is known. Knowledge of the three dimensional structure of the moiety allows modifications to be made to the moiety to facilitate its function in the construct of the invention.

The moiety may be any size and have any structure. For instance, the moiety may be an oligomer, such as a dimer or trimer. The moiety is preferably a small, globular polypeptide formed from one monomer. Such moieties are easy to handle and are less likely to interfere with the ability of the helicase to control the movement of the polynucleotide, particularly if fused to or inserted into the sequence of the helicase.

The amino and carboxy terminii of the moiety are preferably in close proximity. The amino and carboxy terminii of the moiety are more preferably presented on same face of the moiety. Such embodiments facilitate insertion of the moiety into the sequence of the helicase. For instance, if the amino and carboxy terminii of the moiety are in close proximity, each can be attached by genetic fusion to adjacent amino acids in the sequence of the helicase.

It is also preferred that the location and function of the active site of the moiety is known. This prevents modifications being made to the active site that abolish the activity of the moiety. It also allows the moiety to be attached to the helicase so that the moiety binds to the polynucleotide and controls its movement. Knowledge of the way in which a moiety may bind to and orient polynucleotides also allows an effective construct to be designed.

The constructs of the invention are useful in Strand Sequencing. The moiety preferably binds the polynucleotide in a buffer background which is compatible with Strand Sequencing and the discrimination of the nucleotides. The moiety preferably has at least residual activity in a salt concentration well above the normal physiological level, such as from 100 mM to 2M. The moiety is more preferably modified to increase its activity at high salt concentrations. The moiety may also be modified to improve its processivity, stability and shelf life.

Suitable modifications can be determined from the characterisation of polynucleotide binding moieties from extremophiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The polynucleotide binding moiety preferably comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers and proliferating cell nuclear antigens (PCNAs).

The helix-hairpin-helix (HhH) domains are polypeptide motifs that bind DNA in a sequence non-specific manner. They have been shown to confer salt stability and processivity when fused to polymerases, as well as increasing their thermal stability. Suitable domains include domain H (residues 696-751) and domain HI (residues 696-802) from Topoisomerase V from *Methanopyrus kandleri* (SEQ ID NO: 47). As discussed below, the polynucleotide binding moiety may be domains H-L of SEQ ID NO: 47 as shown in SEQ ID NO: 48. Topoisomerase V from *Methanopyrus kandleri* is an example of a double-stranded binding protein as discussed below.

The HhH domain preferably comprises the sequence shown in SEQ ID NO: 24 or 37 or 38 or a variant thereof. This domain increases the processivity and the salt tolerance of a helicase when used in a construct of the invention. A variant of SEQ ID NO: 24 or 37 or 38 is a protein that has an amino acid sequence which varies from that of SEQ ID NO: 24 or 37 or 38 and which has polynucleotide binding activity. This can be measured as described above. A variant typically has at least 50% homology to SEQ ID NO: 24 or 37 or 38 based on amino acid identity over its entire sequence (or any of the % homologies discussed above in relation to helicases) and has polynucleotide binding activity. A variant may differ from SEQ ID NO: 24 or 37 or 38 in any of the ways discussed above in relation to helicases or below in relation to pores. A variant preferably comprises one or more substituted cysteine residues and/or one or more substituted Faz residues to facilitate attachment to the helicase as discussed above. SSBs bind single stranded DNA with high affinity in a sequence non-specific manner.

They exist in all domains of life in a variety of forms and bind DNA either as monomers or multimers. Using amino acid sequence alignment and logorithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class; All beta proteins, Fold; OB-fold, Superfamily: Nucleic acid-binding proteins, Family; Single strand DNA-binding domain, SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukariotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Thermotoga maritima*). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs. In some of these species they have been shown to be monomeric (*Methanococcus jannaschii* and *Methanothermobacter thermoautotrophicum*). Still, other species of Archaea, including

*Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e.g. cysteines, unnatural amino-acids). This is discussed in more detail below.

The SSB is preferably either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 39, the human replication protein A 70 kDa subunit, the human replication protein A 14 kDa subunit, the telomere end binding protein alpha subunit from *Oxytricha nova*, the core domain of telomere end binding protein beta subunit from *Oxytricha nova*, the protection of telomeres protein 1 (Pot1) from *Schizosaccharomyces pombe*, the human Pot1, the OB-fold domains of BRCA2 from mouse or rat, the p5 protein from phi29 (SEQ ID NO: 40) or a variant of any of those proteins. A variant is a protein that has an amino acid sequence which varies from that of the wild-type protein and which has single stranded polynucleotide binding activity. Polynucleotide binding activity can be determined using methods known in the art (and as described above). For instance, the ability of a variant to bind a single stranded polynucleotide can be determined as described in the Examples.

A variant of SEQ ID NO: 39 or 40 typically has at least 50% homology to SEQ ID NO: 39 or 40 based on amino acid identity over its entire sequence (or any of the % homologies discussed above in relation to helicases) and has single stranded polynucleotide binding activity. A variant may differ from SEQ ID NO: 39 or 40 in any of the ways discussed above in relation to helicases. In particular, a variant may have one or more conservative substitutions as shown in Tables 7 and 8.

Examples of SSBs which require one or more modifications in their C-terminal region to decrease the net negative charge include, but are not limited to, the SSB of *E. coli* (EcoSSB; SEQ ID NO: 41, the SSB of *Mycobacterium tuberculosis*, the SSB of *Deinococcus radiodurans*, the SSB of *Thermus thermophiles*, the SSB from *Sulfolobus solfataricus*, the human replication protein A 32 kDa subunit (RPA32) fragment, the CDC13 SSB from *Saccharomyces cerevisiae*, the Primosomal replication protein N (PriB) from *E. coli*, the PriB from *Arabidopsis thaliana*, the hypothetical protein At4g28440, the SSB from T4 (gp32; SEQ ID NO: 42), the SSB from RB69 (gp32; SEQ ID NO: 25), the SSB from T7 (gp2.5; SEQ ID NO: 26) or a variant of any of these proteins. Hence, the SSB used in the method of the invention may be derived from any of these proteins.

In addition to the one or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which has single stranded polynucleotide binding activity. Polynucleotide binding activity can be determined as discussed above.

The SSB used in the invention may be derived from a variant of SEQ ID NO: 25, 26, 41 or 42. In other words, a variant of SEQ ID NO: 25, 26, 41 or 42 may be used as the starting point for the SSB used in the invention, but the SSB actually used further includes one or more modifications in its C-terminal region which decreases the net negative charge of the C-terminal region. A variant of SEQ ID NO: 25, 26, 41 or 42 typically has at least 50% homology to SEQ ID NO: 25, 26, 41 or 42 based on amino acid identity over its entire sequence (or any of the % homologies discussed above in relation to helicases) and has single stranded polynucleotide binding activity. A variant may differ from SEQ ID NO: 25, 26, 41 or 42 in any of the ways discussed above in relation to helicases. In particular, a variant may have one or more conservative substitutions as shown in Tables 7 and 8.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

Related to DNA sliding clamps, processivity factors are viral proteins that anchor their cognate polymerases to DNA, leading to a dramatic increase in the length of the fragments generated. They can be monomeric (as is the case for UL42 from Herpes simplex virus 1) or multimeric (UL44 from Cytomegalovirus is a dimer), they do not form closed rings around the DNA strand and they contact DNA directly. UL42 has been shown to increase processivity without reducing the rate of its corresponding polymerase, suggesting that it interacts with DNA in a different mode to SSBs. The UL42 preferably comprises the sequence shown in SEQ ID NO: 27 or SEQ ID NO: 32 or a variant thereof. A variant of SEQ ID NO: 27 or 32 is a protein that has an amino acid sequence which varies from that of SEQ ID NO: 27 or 32 and which has polynucleotide binding activity. This can be measured as described above. A variant typically has at least 50% homology to SEQ ID NO: 27 or 32 based on amino acid identity over its entire sequence (or any of the % homologies discussed above in relation to helicases) and has polynucleotide binding activity. A variant may differ from SEQ ID NO: 27 or SEQ ID NO: 32 in any of the ways discussed above in relation to helicases or below in relation to pores. A variant preferably comprises one or more substituted cysteine residues and/or one or more substituted Faz residues to facilitate attachment to the helicase as discussed above.

Attaching UL42 to a helicase could be done via genetic fusion or chemical attachment (cysteines, unnatural amino-acids). As the polymerase polypeptide that binds UL42 is visible in the crystal structure, these 35 amino acids (residues 1200-1235) could be fused onto the C-terminus of the helicase and the natural affinity between this polypeptide and the processivity factor used to form a complex. The interaction could be stabilized by introducing a covalent interaction (cysteines or unnatural amino-acids). One option is to utilize a natural UL42 cysteine (C300) that is located close to the polypeptide interaction site and introduce a point mutation into the polymerase polypeptide (e.g. L1234C).

A reported method of increasing polymerase processivity is by exploiting the interaction between *E. coli* thioredoxin (Trx) and the thioredoxin binding domain (TBD) of bacteriophage T7 DNA polymerase (residues 258-333). The binding of Trx to TBD causes the polypeptide to change conformation to one that binds DNA. TBD is believed to clamp down onto a DNA strand and limit the polymerase off-rate, thus increasing processivity. Chimeric polymerases have been made by transferring TBD onto a non-processive polymerase, resulting in 1000 fold increase in polymerised fragment length. There were no attempts to attach TBD to any other class of proteins, but a covalent link between TBD and Trx was engineered and can be used to stabilise the interaction.

Some helicases use accessory proteins in-vivo to achieve processivity (e.g. cisA from phage Φx174 and geneII protein from phage M13 for *E. coli* Rep helicase). Some of these proteins have been shown to interact with more than one helicase (e.g. MutL acts on both UvrD and Rep, though not to the same extent). These proteins have intrinsic DNA binding capabilities, some of them recognizing a specific DNA sequence. The ability of some of these accessory proteins to covalently attach themselves to a specific DNA sequence could also be used to create a set starting point for the helicase activity.

The proteins that protect the ends of chromosomes bind to telomeric ssDNA sequences in a highly specific manner. This ability could either be exploited as is or by using point mutations to abolish the sequence specificity.

Small DNA binding motifs (such as helix-turn-helix) recognize specific DNA sequences. In the case of the bacteriophage 434 repressor, a 62 residue fragment was engineered and shown to retain DNA binding abilities and specificity.

An abundant motif in eukaryotic proteins, zinc fingers consist of around 30 amino-acids that bind DNA in a specific manner. Typically each zinc finger recognizes only three DNA bases, but multiple fingers can be linked to obtain recognition of a longer sequence.

Proliferating cell nuclear antigens (PCNAs) form a very tight clamp (doughnut) which slides up and down the dsDNA or ssDNA. The PCNA from crenarchaeota is unique in being a hetero-trimer so it is possible to functionalise one subunit and retain activity. Its subunits are shown in SEQ ID NOs: 28, 29 and 30. The PCNA is preferably a trimer comprising the sequences shown in SEQ ID NOs: 28, 29 and 30 or variants thereof. PCNA sliding clamp (NCBI Reference Sequence: ZP_06863050.1; SEQ ID NO: 59) forms a dimer. The PCNA is preferably a dimer comprising SEQ ID NO: 59 or a variant thereof. A variant is a protein that has an amino acid sequence which varies from that of SEQ ID NO: 28, 29, 30 or 59 and which has polynucleotide binding activity. This can be measured as described above. A variant is typically a trimer comprising sequences that have at least 50% homology to SEQ ID NOs: 28, 29 and 30 or a dimer comprising sequences that have at least 50% homology to SEQ ID NO: 59 based on amino acid identity over each entire sequence (or any of the % homologies discussed above in relation to helicases) and which has polynucleotide binding activity. A variant may comprise sequences which differ from SEQ ID NO: 28, 29, 30 or 59 in any of the ways discussed above in relation to helicases or below in relation to pores. A variant preferably comprises one or more substituted cysteine residues and/or one or more substituted Faz residues to facilitate attachment to the helicase as discussed above. In a preferred embodiment, subunits 1 and 2 of the PCNA from crenarchaeota (i.e. SEQ ID NOs: 28 and 29 or variants thereof) are attached, such as genetically fused, and the resulting protein is attached to a helicase to form a construct of the invention. During use of the construct, subunit 3 (i.e. SEQ ID NO: 30 or a variant thereof) may be added to complete the PCNA clamp (or doughnut) once the construct has bound the polynucleotide. In a preferred embodiment, one monomer of the PCNA sliding clamp (i.e. SEQ ID NO: 59 or a variant thereof) is attached, such as genetically fused, to a helicase to form a construct of the invention. During use of the construct, the second monomer (i.e. SEQ ID NO: 59 or a variant thereof) may be added to complete the PCNA clamp (or doughnut) once the construct has bound the polynucleotide.

The polynucleotide binding motif may be selected from any of those shown in Table 5 below.

TABLE 5

Suitable polynucleotide binding motifs

| No. | Name | Class | Organism | Structure | Sequence | Functional form | MW (Da) | Notes |
|---|---|---|---|---|---|---|---|---|
| 1 | SSBEco | ssb | *Escherichia coli* | 1QVC, 1EYG | P0AGE0 | homo-tetramer | 18975 | |
| 2 | SSBBhe | ssb | *Bartonella henselae* | 3LGJ, 3PGZ | Q6G302 | homo-tetramer | 16737 | structure only |
| 3 | SSBCbu | ssb | *Coxiella burnetii* | 3TQY | Q83EP4 | homo-tetramer | 17437 | structure only |
| 4 | SSBTma | ssb | *Thermathoga maritima* | 1Z9F | Q9WZ73 | homo-dimer | 16298 | small, thermostable, salt independent DNA binding |

TABLE 5-continued

Suitable polynucleotide binding motifs

| No. | Name | Class | Organism | Structure | Sequence | Functional form | MW (Da) | Notes |
|---|---|---|---|---|---|---|---|---|
| 5 | SSBHpy | ssb | *Helicobacter pylori* | 2VW9 | O25841 | homo-tetramer | 20143 | |
| 6 | SSBDra | ssb | *Deinococcus radiodurans* | 1SE8 | Q9RY51 | homo-dimer | 32722 | |
| 7 | SSBTaq | ssb | *Thermus aquaticus* | 2FXQ | Q9KH06 | homo-dimer | 30026 | |
| 8 | SSBMsm | ssb | *Mycobacterium smegmatis* | 3A5U, 1X3E | Q9AFI5 | homo-tetramer | 17401 | tetramer more stable than *E. coli*, binding less salt dependent |
| 9 | SSBSso | ssb/RPA | *Sulfolobus solfataricus* | 1O7I | Q97W73 | homo-tetramer | 16138 | similarities with RPA |
| 10 | SSBMHsmt | ssb | *Homo sapiens* | 3ULL | Q04837 | homo-tetramer | 17260 | |
| 11 | SSBMle | ssb | *Mycobacterium leprae* | 3AFP | P46390 | homo-tetramer | 17701 | |
| 12 | gp32T4 | ssb | Bacteriophage T4 | 1GPC | P03695 | monomer | 33506 | Homo-dimer in the absence of DNA, monomer when binding DNA. |
| 13 | gp32RB69 | ssb | Bacteriophage RB69 | 2A1K | Q7Y265 | monomer | 33118 | |
| 14 | gp2.5T7 | ssb | Bacteriophage T7 | 1JE5 | P03696 | monomer | 25694 | |
| 15 | UL42 | processivity factor | Herpes virus 1 | 1DML | P10226 | monomer | 51159 | binds ssDNA dsDNA, structure shows link with polymerase |
| 16 | UL44 | processivity factor | Herpes virus 5 (cytomegalovirus) | 1YYP | P16790 | homo-dimer | 46233 | forms C shaped clamp on DNA |
| 17 | pf8 | processivity factor | KSHV | 3I2M | Q77ZG5 | homo-dimer | 42378 | |
| 18 | RPAMja | RPA | *Methanococcus jannaschii* | 3DM3 | Q58559 | monomer | 73842 | contains 4 OB folds. Structure of fragment |
| 19 | RPAMma | RPA | *Methanococcus maripaludis* | 3E0E, 2K5V | Q6LYF9 | monomer | 71388 | Core domain structure |
| 20 | RPAMth | RPA | *Methanothermobacter thermoautotrophicus* | | | monomer | 120000 | Shown to interact directly with Hel308. Sequence from paper. |
| 21 | RPA70Sce | RPA | *Saccharomyces cerevisiae* | 1YNX | P22336 | hetero-trimer | 70348 | unit has two OB folds and binds DNA |
| 22 | RPAMbu1 | RPA | *Methanococcoides burtonii* | | Q12V72 | ? | 41227 | three OB folds identified |
| 23 | RPAMbu2 | RPA | *Methanococcoides burtonii* | | Q12W96 | ? | 47082 | two OB folds identified |
| 24 | RPA70Hsa | RPA | *Homo sapiens* | 1JMC | P27694 | hetero-trimer | 68138 | |
| 25 | RPA14Hsa | RPA | *Homo sapiens* | 3KDF | P35244 | hetero-trimer | 13569 | in complex with RPA32 |
| 26 | gp45T4 | sliding clamp | Bacteriophage T4 | 1CZD | P04525 | homo-trimer | 24858 | ring shape threads DNA |
| 27 | BetaEco | sliding clamp | *E. coli* | 3BEP | P0A988 | homo-dimer | 40587 | ring shape threads DNA, may bind ssDNA in pocket |
| 28 | PCNASce | sliding clamp | *Saccharomyces cerevisiae* | 1PLQ, 3K4X | P15873 | homo-dimer | 28916 | ring shape threads DNA |
| 29 | PCNATko | sliding clamp | *Thermococcus kodakaraensis* | 3LX1 | Q5JF32 | homo-dimer | 28239 | |
| 30 | PCNAHvo | sliding clamp | *Haloferax volcanii* | 3IFV | D0VWY8 | homo-dimer | 26672 | |
| 31 | PCNAPfu | sliding clamp | *Pyrococcus furiosus* | 1GE8 | O73947 | homo-dimer | 28005 | |
| 32 | PCNAMbu | sliding clamp | *Methanococcoides burtonii* | | Q12U18 | homo-dimer | 27121 | Inferred from homology |
| 33 | BetaMtu | sliding clamp | *Mycobacterium tuberculosis* | 3P16 | Q50790 | homo-dimer | 42113 | |
| 34 | BetaTma | sliding clamp | *Thermotoga maritima* | 1VPK | Q9WYA0 | homo-dimer | 40948 | |
| 35 | BetaSpy | sliding clamp | *Streptococcus pyrogenes* | 2AVT | Q9EVR1 | homo-dimer | 41867 | |

TABLE 5-continued

Suitable polynucleotide binding motifs

| No. | Name | Class | Organism | Structure | Sequence | Functional form | MW (Da) | Notes |
|---|---|---|---|---|---|---|---|---|
| 36 | gp45RB69 | sliding clamp | Bacteriophage RB69 | 1B77 | O80164 | homo-trimer | 25111 | Structure shows interaction with polypeptide from polymerase |
| 37 | p55Hsa | DNA binding protein | Homo sapiens (mitochondrial) | 2G4C, 3IKL, 3IKM | Q9UHN | monomer | 54911 | interacts with specific polymerase domain |
| 38 | p55Dme | DNA binding protein | Drosophylla melanogaster | | Q9VJV8 | monomer | 41027 | associates with polymerase Gamma conferring salt tolerance, processivity and increased activity |
| 39 | p55Xla | DNA binding protein | Xenopus laevis | | Q9W6G7 | monomer | 52283 | |
| 40 | RepDSau | replication initiation protein | Staphylococcus aureus | | P08115 | homo-dimer | 37874 | increases processivity of PcrA, covalently and specifically links DNA |
| 41 | G2P | replication initiation protein | Enterobacteria phage 1 | | P69546 | monomer | 46168 | increases processivity of Rep, covalently and specifically links DNA |
| 42 | MutLEco | mismatch repair protein | Escherichia coli | 1BKN, 1B62, 1B63 | P23367 | homo-dimer | 67924 | increases processivity of UvrD (and Rep) |
| 43 | KuMtu | DNA repair protein | Mycobacterium tuberculosis | | O05866 | homo-dimer | 30904 | increases processivity of UvrD1. Structure available for human Ku |
| 44 | OnTEBP | telomere binding protein | Oxytricha nova-Alpha | 1OTC | P29549 | hetero-dimer | 56082 | Specific biding to 3' end T4G4T4G4. Alpha subunit may be enough |
| | | | Oxytricha nova-Beta | | P16458 | | 41446 | |
| 45 | EcrTEBP | telomere binding protein | Euplotes crassus | | Q06183 | monomer | 53360 | Homolog to OnTEBP with no Beta subunit in genome |
| 46 | TteTEBP | telomere binding protein | Tetrachymena termophila Alpha | | Q23FB9 | hetero-dimer | 53073 | Homolog to OnTEBP-Alpha |
| | | | Tetrachymena termophila Beta | | Q23FH0 | | 54757 | May be homolog to OnTEBP Beta |
| 47 | pot1Spo | telomere binding proteins | Schizosaccharomyces pombe | | O13988 | monomer | 64111 | related to TEBP |
| 48 | Cdc13pSce | telomere binding proteins | Saccharomyces cerevisiae | | C7GSV7 | monomer | 104936 | specific binding to telomeric DNA |
| 49 | C1 | repressor | Bacteriophage 434 | | P16117 | homo-dimer | 10426 | binds DNA specifically as homo-dimer |
| 50 | LexA | repressor | Escherichia coli | 1LEB | P0A7C2 | homo-dimer | 22358 | binds DNA specifically as homo-dimer |

The polynucleotide binding moiety is preferably derived from a polynucleotide binding enzyme. A polynucleotide binding enzyme is a polypeptide that is capable of binding to a polynucleotide and interacting with and modifying at least one property of the polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding moiety does not need to display enzymatic activity as long as it is capable of binding the polynucleotide and controlling its movement. For instance, the moiety may be derived from an enzyme that has been modified to remove its enzymatic activity or may be used under conditions which prevent it from acting as an enzyme.

The polynucleotide binding moiety is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are exonucleases, polymerases, helicases and topoisomerases, such as gyrases. Suitable exonucleases include, but are not limited to, exonuclease I from *E. coli*, exonuclease III enzyme from *E. coli*, RecJ from *T. thermophilus* and bacteriophage lambda exonuclease, TatD exonuclease and variants thereof.

The polymerase is preferably a member of any of the Moiety Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The polymerase may be PyroPhage® 3173 DNA Polymerase (which is commercially available from Lucigen® Corporation), SD Polymerase (commercially available from Bioron®) or variants thereof. The polynucleotide binding moiety is preferably derived from Phi29 DNA polymerase (SEQ ID NO: 31). The moiety may comprise the sequence shown in SEQ ID NO: 101 or a variant thereof. A variant of SEQ ID NO: 31 is an enzyme that has an amino acid sequence which varies from that of SEQ ID NO: 31 and which has polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NO: 31, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 31 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

The helicase may be any of those discussed above, including any of SEQ ID NOs: 8 to 23. Helicase dimers and multimers are discussed in detail below. The polynucleotide binding moiety may be a polynucleotide binding domain derived from a helicase. For instance, the polynucleotide binding moiety preferably comprises the sequence shown in SEQ ID NOs: 35 or 36 or a variant thereof. A variant of SEQ ID NOs: 35 or 36 is a protein that has an amino acid sequence which varies from that of SEQ ID NOs: 35 or 36 and which has polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NOs: 35 or 36, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NOs: 35 or 36 over the entire sequence. There may be at least 80%, for example at least 85%, 90% or 95%, amino acid identity over a stretch of 40 or more, for example 50, 60, 70 or 80 or more, contiguous amino acids ("hard homology"). Homology is determined as described below. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The polynucleotide binding moiety may be any of the enzymes discussed above.

The moiety may be labelled with a revealing label. The label may be any of those described above.

The moiety may be isolated from any moiety-producing organism, such as *E. coli, T. thermophilus* or bacteriophage, or made synthetically or by recombinant means. For example, the moiety may be synthesized by in vitro translation and transcription as described below. The moiety may be produced in large scale following purification as described below.

Helicase Oligomers

As will be clear from the discussion above, the polynucleotide binding moiety is preferably derived from a helicase. For instance, it may be a polynucleotide domain from a helicase. The moiety more preferably comprises one or more helicases. The helicases may be any of those discussed above with reference to the constructs of the invention, including the helicases of the invention and helicases which are not modified in accordance with the invention. In such embodiments, the constructs of the invention of course comprise two or more helicases attached together. At least one of the helicases is modified in accordance with the invention. The constructs may comprise two, three, four, five or more helicases. In other words, the constructs of the invention may comprise a helicase dimer, a helicase trimer, a helicase tetramer, a helicase pentamer and the like.

The two or more helicases can be attached together in any orientation. Identical or similar helicases may be attached via the same amino acid position or spatially proximate amino acid positions in each helicase. This is termed the "head-to-head" formation. Alternatively, identical or similar helicases may be attached via positions on opposite or different sides of each helicase. This is termed the "head-to-tail" formation. Helicase trimers comprising three identical or similar helicases may comprise both the head-to-head and head-to-tail formations.

The two or more helicases may be different from one another (i.e. the construct is a hetero-dimer, -trimer, -tetramer or -pentamer etc.). For instance, the constructs of the invention may comprise (a) one or more helicases of the invention and one or more helicases which are not modified in accordance with the invention or (b) two or more different helicases of the invention. The construct may comprise two different variants of the same Dda helicase. For instance, the construct may comprise two variants of one of the helicases discussed above with one or more cysteine residues or Faz residues introduced at different positions in each variant. In this instance, the helicases can be in a head-to-tail formation.

Hetero-dimers can be formed in two possible ways. The first involves the use of a homo-bifunctional linker as discussed above. One of the helicase variants can be modified with a large excess of linker in such a way that one linker is attached to one molecule of the protein. This linker modified variant can then be purified away from unmodified proteins, possible homo-dimers and unreacted linkers to react with the other helicase variant. The resulting dimer can then be purified away from other species.

The second involves the use of hetero-bifunctional linkers. For example, one of the helicase variants can be modified with a first PEG linker containing maleimide or iodoacetamide functional group at one end and a cyclooctyne functional group (DIBO) at the other end. An example of this is shown below:

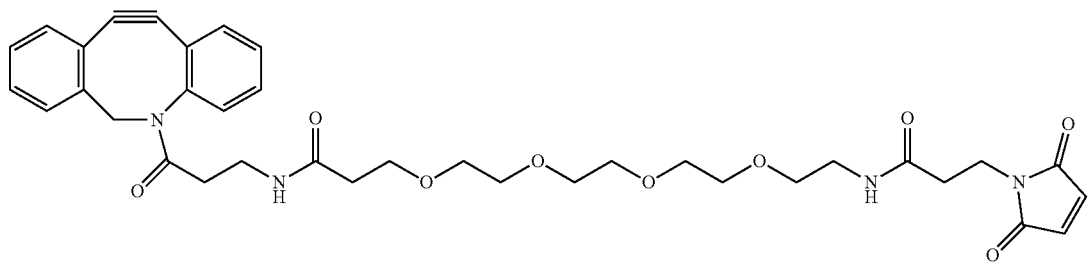

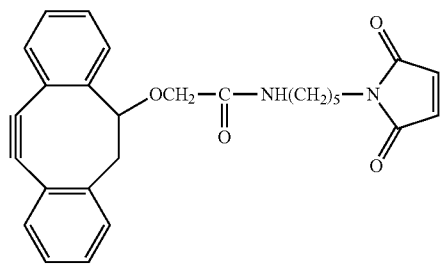

The second helicase variant can be modified with a second PEG linker containing maleimide or iodoacetamide functional group at one end and an azide functional group at the other end. An example is shown below:

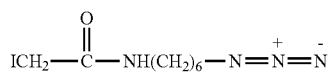

The two helicase variants with two different linkers can then be purified and clicked together (using copper free click chemistry) to make a dimer. Copper free click chemistry has been used in these applications because of its desirable properties. For example, it is fast, clean and not poisonous towards proteins. However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

These two ways of linking two different variants of the same helicase are also valid for any of the constructs discussed above in which the helicase and the moiety are different from one another, such as dimers of two different helicases and a helicase-polymerase dimer.

Similar methodology may also be used for linking different Faz variants. One Faz variant can be modified with a large excess of linker in such a way that one linker is attached to one molecule of the protein. This linker modified Faz variant can then be purified away from unmodified proteins, possible homo-dimers and unreacted linkers to react with the second Faz variant. The resulting dimer can then be purified away from other species.

Hetero-dimers can also be made by linking cysteine variants and Faz variants of the same helicase or different helicases. Hetero-bifunctional PEG linkers with maleimide or iodoacetamide functionalities at one end and DBCO functionality at the other end can be used in this combination of mutants. An example of such a linker is shown below (DBCO-PEG4-maleimide):

The length of the linker can be varied by changing the number of PEG units between the two functional groups.

Helicase hetero-trimers can comprise three different types of helicases. The same is true for oligomers comprising more than three helicases. The two or more helicases within a construct may be different variants of the same helicase, such as different variants of any one of SEQ ID NOs: 8 to 23. The different variants may be modified at different positions to facilitate attachment via the different positions. The hetero-trimers may therefore be in a head-to-tail and head-to-head formation.

The two or more helicases in the constructs of the invention may be the same as one another (i.e. the construct is a homo-dimer, -trimer, -tetramer or -pentamer etc.) In such embodiments, the helicases are preferably attached using the same position in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

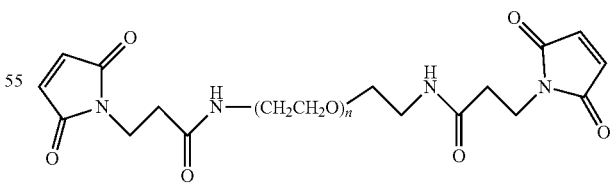

The length of the linker can be varied to suit the required applications. For example, n can be 2, 3, 4, 8, 11, 12, 16 or more. PEG linkers are suitable because they have favourable properties such as water solubility. Other non PEG linkers can also be used in cysteine linkage.

By using similar approaches, identical Faz variants can also be made into homo-dimers. Homo-bifunctional linkers with DIBO functional groups can be used to link two molecules of the same Faz variant to make homo-dimers using Cu²⁺ free click chemistry. An example of a linker is given below:

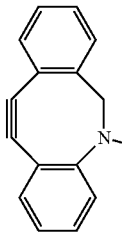 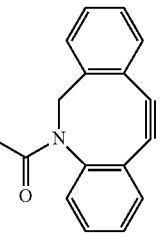

The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

Homo-dimers or longer homo-oligomers may also be prepared in the head-to-tail formation if two or more cysteine residues or non-natural amino acids are introduced in the helicase in accordance with the invention and different cysteines or non-natural amino acids in the different helicase monomers are attached together. For instance, homo-oligomers may be formed from variants of SEQ ID NO: 8 comprising Y279C and G357C and the C at 279 in one monomer may be attached to the C at 357 in another monomer. Similarly, homo-oligomers may be formed from variants of SEQ ID NO: 8 comprising I281C and G357C and the C at 281 in one monomer may be attached to the C at 357 in another monomer. The same is true when Faz is introduced at these positions instead of C. Such C and Faz mutants allow series or trains of helicases to be created.

Polynucleotide Sequences

The invention provides a polynucleotide comprising a sequence which encodes a helicase of the invention or a construct of the invention. The polynucleotide may consist of such a sequence. The polynucleotide may be any of those discussed above.

Any of the proteins described herein may be expressed using methods known in the art. Polynucleotide sequences may be isolated and replicated using standard methods in the art. Chromosomal DNA may be extracted from a helicase producing organism, such as *Methanococcoides burtonii*, and/or a SSB producing organism, such as *E. coli*. The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or λ promoter is typically used.

The host cell typically expresses the construct at a high level. Host cells transformed with a polynucleotide sequence will be chosen to be compatible with the expression vector used to transform the cell. The host cell is typically bacterial and preferably *E. coli*. Any cell with a λ DE3 lysogen, for example Rosetta2(DE3)pLys, C41 (DE3), BL21 (DE3), JM109 (DE3), B834 (DE3), TUNER, Origami and Origami B, can express a vector comprising the T7 promoter.

Series

The invention also provides a series of two or more helicases attached (or bound) to a polynucleotide, wherein at least one of the two or more helicases is a helicase of the invention. The series may comprise any number of helicases such as 2, 3, 4, 5, 6, 7, 8, 9, 10 or more helicases. Any number of the helicases may be helicases of the invention. All of the two or more helicases are preferably helicases of the invention. The one or more helicases of the invention may be any of those discussed above.

The two or more helicases may be the same helicase or may be different helicases. For instance, if the series comprises two or more helicases of the invention, they may be the same or may be different.

The series may comprise any number and any combination of helicases of the invention. The series of two or more helicases preferably comprises at least two helicases of the invention. The series may comprise two or more helicases each of which comprises a variant of SEQ ID NO: 8 comprising (or only comprising) (a) P89F, (b) V150I, (c) V150H, (d) P89F and F98W, (e) P89F and V150I, (f) P89F and V150H, (g) F98W and V150I, (h) F98W and V150H (i) P89F, F98W and V150I or (j) P89F, F98W and V150H.

The series may comprise two or more helicases each of which comprises a variant of SEQ ID NO: 8 comprising (i) E94C/A360C, (ii) E94C/A360C and then (ΔM1)G1G2 (i.e. deletion of M1 and then addition G1 and G2), (iii) E94C/A360C/C109A/C136A, (iv) E94C/A360C/C109A/C136A and then (ΔM1)G1G2 (i.e. deletion of M1 and then addition G1 and G2), (v) E94C/A360C/W378A, (vi) E94C/A360C/W378A and then (ΔM1)G1G2 (i.e. deletion of M1 and then addition G1 and G2), (vii) E94C/A360C/C109A/C136A/W378A or (viii) E94C/A360C/C109A/C136A/W378A and then (AMI)G1G2 (i.e. deletion of M1 and then addition G1 and G2). One helicase of the invention in the series preferably comprises a variant of SEQ ID NO: 8 comprising one of (i) to (iv) and another helicase of the invention in the series preferably comprises a variant of SEQ ID NO: 8 comprising one of (v) to (viii).

In addition to one or more helicases of the invention, the series may comprise one or more helicases which are not part of the invention. The one or more helicases may be or be derived from a Hel308 helicase, a RecD helicase, such as TraI helicase or a TrwC helicase, a XPD helicase or a Dda helicase (such as any one of SEQ ID NOs: 8 to 23). The one or more helicases may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013/098561); PCT/GB2013/051925 (published as WO 2014/013260); PCT/GB2013/051924 (published as WO 2014/013259) and PCT/GB2013/051928 (published as WO 2014/013262); and PCT/GB2014/052736 (WO 2015/055981). In particular, the one or more helicases are preferably modified to reduce the size of an opening in the polynucleotide binding domain through which in at least one conformational state the polynucleotide can unbind from the helicase. This is disclosed in WO 2014/013260.

The two or more helicases in the series may be separate from one another. The two or more helicases in the series may be brought together by a transmembrane pore as the polynucleotide moves through the pore. The two or more helicases in the series may contact one another.

The two or more helicases are preferably not attached to one another except via the polynucleotide. The two or more helicases are preferably not covalently attached to one another.

The two or more helicases may be attached or covalently attached to one another. The helicases may be attached in any order and using any method. A series of attached helicases may be called a train.

Polynucleotides to which the series of the invention may be attached/bound are discussed in more detail below.

Methods of the invention The invention provides a method of controlling the movement of a target polynucleotide.

The method comprises contacting the target polynucleotide with a modified helicase of the invention or a construct of the invention and thereby controlling the movement of the polynucleotide. The method is preferably carried out with a potential applied across the pore. As discussed in more detail below, the applied potential typically results in the formation of a complex between the pore and the helicase or construct. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The invention also provides a method of characterising a target polynucleotide. The method comprises (a) contacting the target polynucleotide with a transmembrane pore and a modified helicase of the invention or a construct of the invention such that the helicase or construct controls the movement of the target polynucleotide through the pore. The method also comprises (b) taking one or more measurements as the polynucleotide moves with respect to the pore wherein the measurements are indicative of one or more characteristics of the target polynucleotide and thereby characterising the target polynucleotide.

In all of the methods of the invention, the helicases or constructs may be any of those discussed above.

Any number of helicases of the invention may be used in these methods. For instance, 1, 2, 3, 4, 5, 6, 7, 8, 9, 10 or more helicases may be used. If two or more helicases of the invention are used, they may be the same or different. Suitable numbers and combinations are discussed above with reference to the series of the invention. These equally apply to the methods of the invention.

If two or more helicases are used, they may be attached to one another. The two or more helicases may be covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259) and PCT/GB2013/051928 (published as WO 2014/013262); and PCT/GB2014/052736 (WO 2015/055981).

If two or more helicases are used, they are preferably not attached to one another except via the polynucleotide. The two or more helicases are more preferably not covalently attached to one another.

Steps (a) and (b) are preferably carried out with a potential applied across the pore as discussed above. In some instances, the current passing through the pore as the polynucleotide moves with respect to the pore is used to determine the sequence of the target polynucleotide.

This is Strand Sequencing.

The method of the invention is for characterising a target polynucleotide. A polynucleotide is defined above.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The sample may be a non-biological sample. The non-biological sample is preferably a fluid sample. Examples of a non-biological sample include surgical fluids, water such as drinking water, sea water or river water, and reagents for laboratory tests.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane.

Each polynucleotide may be coupled to the membrane using any number of anchors, such as 2, 3, 4 or more anchors. For instance, one polynucleotide may be coupled to the membrane using two anchors each of which separately couples (or binds) to both the polynucleotide and membrane.

The one or more anchors may comprise the one or more helicases and/or the one or more molecular brakes.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the detector.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalized, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut to broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore, then some sequence data will be lost as the sequencing run cannot continue to the end of the polynucleotide due to the distance between the membrane and the detector. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

For certain applications, such as aptamer detection, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 6 below.

TABLE 6

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g.Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either Suitable modifications for decreasing the net negative charge are disclosed in International Application No. PCT/GB2013/051924 (published as WO 2014/013259). The SSB may be any of the SSBs disclosed in this International application.

The modified SSB most preferably comprises a sequence selected from those shown in SEQ ID NOs: 33, 34, 43 to 46.

Double-stranded binding proteins bind double stranded DNA with high affinity. Suitable double-stranded binding proteins include, but are not limited to Mutator S (MutS; NCBI Reference Sequence: NP_417213.1; SEQ ID NO: 49), Sso7d (*Sufolobus solfataricus* P2; NCBI Reference Sequence: NP_343889.1; SEQ ID NO: 50; Nucleic Acids Research, 2004, Vol 32, No. 3, 1197-1207), Sso10b1 (NCBI Reference Sequence: NP_342446.1; SEQ ID NO: 51), Sso10b2 (NCBI Reference Sequence: NP_342448.1; SEQ ID NO: 52), Tryptophan repressor (Trp repressor; NCBI Reference Sequence: NP_291006.1; SEQ ID NO: 53), Lambda repressor (NCBI Reference Sequence: NP_040628.1; SEQ ID NO: 54), Cren7 (NCBI Reference Sequence: NP_342459.1; SEQ ID NO: 55), major histone classes H1/H5, H2A, H2B, H3 and H4 (NCBI Reference Sequence: NP_066403.2, SEQ ID NO: 56), dsbA (NCBI Reference Sequence: NP_049858.1; SEQ ID NO: 57), Rad51 (NCBI Reference Sequence: NP_002866.2; SEQ ID NO: 58), sliding clamps and Topoisomerase V Mka (SEQ ID NO: 47) or a variant of any of these proteins. A variant of SEQ ID NO: 47, 49, 50, 51, 52, 53, 54, 55, 56, 57 or 58 typically has at least 50% homology to SEQ ID NO: 47, 49, 50, 51, 52, 53, 54, 55, 56, 57 or 58 based on amino acid identity over its entire sequence (or any of the % homologies discussed above in relation to helicases) and has single stranded polynucleotide binding activity. A variant may differ from SEQ ID NO: 47, 49, 50, 51, 52, 53, 54, 55, 56, 57 or 58 in any of the ways discussed above in relation to helicases. In particular, a variant may have one or more conservative substitutions as shown in Tables 7 and 8. Most polymerases achieve processivity by interacting with sliding clamps. In general, these are multimeric proteins (homodimers or homo-trimers) that encircle dsDNA. These sliding clamps require accessory proteins (clamp loaders) to assemble them around the DNA helix in an ATP-dependent process. They also do not contact DNA directly, acting as a topological tether. As sliding clamps interact with their cognate polymerases in a specific manner via a polymerase domain, this fragment could be fused to the helicase in order to incite recruitment of helicases onto the sliding clamp. This interaction could be further stabilized by the generation of a covalent bond (introduction of cysteines or unnatural amino-acids). end of a polynucleotide has been reported previously. A thiol group can be added to the 5' of ssDNA or dsDNA using T4 polynucleotide kinase and ATPyS (Grant, G. P. and P. Z. Qin (2007). "A facile method for attaching nitroxide spin labels at the 5' terminus of nucleic acids." Nucleic Acids Res 35(10): e77). An azide group can be added to the 5'-phosphate of ssDNA or dsDNA using T4 polynucleotide kinase and γ-[2-Azidoethyl]-ATP or γ-[6-Azidohexyl]-ATP.

Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the polynucleotide to the membrane via hybridisation. Hybridisation in the one or more anchors allows coupling in a transient manner as discussed above. The hybridisation may be present in any part of the one or more anchors, such as between the one or more anchors and the polynucleotide, within the one or more anchors or between the one or more anchors and the membrane. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide or directly to a Y adaptor and/or leader sequence attached to the polynucleotide or directly to a bridging moiety adaptor, such as a hairpin loop adaptor, attached to the polynucleotide (as discussed below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a bridging moiety adaptor attached to the polynucleotide (as discussed below).

The one or more anchors may comprise a single stranded or double stranded polynucleotide. One part of the anchor may be ligated to a single stranded or double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, E. coli single stranded binding protein, P5 single stranded binding protein, T4 gp32 single stranded binding protein, the TOPO V dsDNA binding region, human histone proteins, E. coli HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalized.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before contacting with the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8 or at least 9 subunits. The pore is preferably made up of 6, 7, 8 or 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from lysenin are disclosed in International Application No. PCT/GB2013/050667 (published as WO 2013/153359). Suitable pores derived from CsgG are disclosed in International Application No. PCT/EP2015/069965. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is wild-type MspA monomer. A variant of SEQ ID NO: 2 is a polypeptide that has an amino acid sequence which varies from that of SEQ ID NO: 2 and which has the ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP, BLAST and PSIBLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih-.gov/).

The variant may comprise the following mutations: D90N, D91N, D93N, D118R, D134R and E139K. The variant may be any of the variants disclosed in International Application No. PCT/GB2012/050301 (WO 2012/107778).

The variant preferably (a) does not comprise aspartic acid (D) at position 90; (b) does not comprise aspartic acid (D) at position 91; (c) comprises aspartic acid (D) or glutamic acid (E) at position 93; and (d) comprises one or more modifications which decrease the net negative charge of the inward facing amino acids in the cap forming region and/or the barrel forming region of the monomer. Preferred mutations in (d) include, but are not limited to, D118R, Q126R, D134R and E139K. The variant preferably comprises D90N, D91N, D or E at 93, D118R, D134R and E139K. The variant may be any of the variants disclosed in International Application No. PCT/GB2015/051290.

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 7 below. Where amino acids have similar polarity, this can also be determined by reference to the hydropathy scale for amino acid side chains in Table 8.

TABLE 7

Chemical properties of amino acids

| | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

TABLE 8

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which has its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant has the ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL).

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase or construct may be covalently attached to the pore. The helicase or construct is preferably not covalently attached to the pore. The application of a voltage to the pore and helicase or construct typically results in the formation of a sensor that is capable of sequencing target polynucleotides. This is discussed in more detail below.

Any of the proteins described herein, i.e. the helicases, the transmembrane protein pores or constructs, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase, pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The helicase, pore or construct may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

Proteins may be made synthetically or by recombinant means. For example, the helicase, pore or construct may be synthesized by in vitro translation and transcription (IVTT). The amino acid sequence of the helicase, pore or construct may be modified to include non-naturally occurring amino acids or to increase the stability of the protein. When a protein is produced by synthetic means, such amino acids may be introduced during production. The helicase, pore or construct may also be altered following either synthetic or recombinant production.

The helicase, pore or construct may also be produced using D-amino acids. For instance, the pore or construct may comprise a mixture of L-amino acids and D-amino acids. This is conventional in the art for producing such proteins or peptides.

The helicase, pore or construct may also contain other non-specific modifications as long as they do not interfere with pore formation or helicase or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

The helicase, pore and construct can be produced using standard methods known in the art. Polynucleotide sequences encoding a helicase, pore or construct may be derived and replicated using standard methods in the art. Polynucleotide sequences encoding a helicase, pore or construct may be expressed in a bacterial host cell using standard techniques in the art. The helicase, pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The helicase, pore and/or construct may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the target polynucleotide with a transmembrane pore and a helicase of the invention or a construct of the invention such that the target polynucleotide moves through the pore and the helicase or construct controls the movement of the target polynucleotide through the pore; and (b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffer include, but are not limited to, HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $CO^{2+}$. The enzyme cofactor is most preferably $Mg^{2+}$.

The target polynucleotide may be contacted with the helicase or construct and the pore in any order. In is preferred that, when the target polynucleotide is contacted with the helicase or construct and the pore, the target polynucleotide firstly forms a complex with the helicase or construct. When the voltage is applied across the pore, the target polynucleotide/helicase or construct complex then forms a complex with the pore and controls the movement of the polynucleotide through the pore.

Other Methods

The invention also provides a method of forming a sensor for characterising a target polynucleotide. The method comprises forming a complex between a pore and a helicase of the invention or a construct of the invention. The helicase may be any of those discussed above. Any number and combination of helicases of the invention discussed above with reference to the series and methods of the invention may be used.

The complex may be formed by contacting the pore and the helicase or construct in the presence of the target polynucleotide and then applying a potential across the pore. The applied potential may be a chemical potential or a voltage potential as described above. Alternatively, the complex may be formed by covalently attaching the pore to the helicase or construct. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a helicase of the invention or a construct of the invention. Any of the embodiments discussed above with reference to the methods of the invention equally apply to this method. The invention also provides a sensor produced using the method of the invention.

Kits

The present invention also provides kits for characterising a target polynucleotide.

In one embodiment, the kit comprises (a) a pore and (b) a helicase of the invention of the invention or a construct of the invention. The pore may be any of those discussed above.

In another embodiment, the kit comprises (a) a helicase of the invention or a construct of the invention and (b) one or more loading moieties. Each loading moiety may be any moiety that is capable of being attached to the target polynucleotide. Each loading moiety may be any length as long as the helicase or construct may bind and it can be attached to the target polynucleotide.

The one or more loading moieties are preferably synthetic or artificial. The one or more loading moieties are preferably non-natural.

Suitable loading moieties include, but are not limited to a polymeric linker, a chemical linker, a polynucleotide or a polypeptide. The one or more loading moieties preferably comprise a polynucleotide or a loading polynucleotide. In such embodiments, the helicase or construct are preferably bound to (or attached to) the polynucleotide. Any of the polynucleotides discussed above may be used. Preferably, the one or more loading moieties comprise DNA, RNA, modified DNA (such as abasic DNA), RNA, PNA, LNA, BNA or PEG. The one or more loading moieties more preferably comprise single stranded or double stranded DNA or RNA.

The one or more loading moieties preferably comprise a single stranded polynucleotide to which the one or more polynucleotide binding proteins are bound (or attached).

At least one of the one or more loading moieties is preferably a Y adaptor. The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor preferably comprises one or more anchors capable of coupling the Y adaptor to a membrane. Anchors are discussed in more detail above. A preferred anchor is cholesterol.

The Y adaptor preferably comprises a leader sequence which preferentially threads into the pore. The leader sequence facilitates the method of the invention. The leader sequence is designed to preferentially thread into the pore and thereby facilitate the movement of target polynucleotide with respect to the pore, such as through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, BNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises a spacer as discussed below.

The leader sequence can be any length, but is typically 10 to 150 nucleotides in length, such as from 20 to 150 nucleotides in length. The length of the leader typically depends on the transmembrane pore used in the method.

At least one of the one or more loading moieties is preferably a bridging moiety. The bridging moiety is most preferably a hairpin loop or a hairpin loop adaptor. Suitable hairpin loop adaptors can be designed using methods known in the art. The hairpin loop may be any length. If used as a loading moiety, the hairpin loop is typically 400 or fewer nucleotides, such as 350 or fewer nucleotides, 300 or fewer nucleotides, 250 or fewer nucleotides, 200 or fewer nucleotides, 150 or fewer nucleotides, 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 400, from 2 to 300, from 5 to 200, from 6 to 100 nucleotides in length. Hairpin loops are formed when two complementary parts of a polynucleotide hybridise to form a double stranded sequence (called a stem). If used as a loading moiety, the stem of the hairpin loop is preferably 200 or fewer nucleotide pairs, such as 150 or fewer nucleotide pairs, 100 or fewer nucleotide pairs, 90 or fewer nucleotide pairs, 80 or fewer nucleotide pairs, 70 or fewer nucleotide pairs, 60 or fewer nucleotide pairs, 50 or fewer nucleotide pairs, 40 or fewer nucleotide pairs, 30 or fewer nucleotide pairs, 20 or fewer nucleotide pairs or 10 or fewer nucleotide pairs, in length. The one or more polynucleotide binding proteins typically bind to the loop of the hairpin, i.e. not the stem.

If the target polynucleotide is double stranded, the one or more loading moieties preferably comprise a Y adaptor and optionally a bridging moiety, such as a hairpin loop adaptor. If at least one or more of the loading moieties is Y adaptor, it may be used in combination with a bridging adaptor that does not have any polynucleotide binding proteins bound or attached.

The helicase or construct may be stalled at one or more spacers on the one or more loading moieties. Spacers are defined in PCT/GB2014/050175 (WO 2014/135838). Preferred spacers include, but are not limited to, nitroindoles, 5-nitroindoles, inosines, acridines, 2-aminopurines, 2-6-di-aminopurines, 5-bromo-deoxyuridines, inverted thymidines (inverted dTs), inverted dideoxy-thymidines (ddTs), dideoxy-cytidines (ddCs), 5-methylcytidines, 5-hydroxymethyl-cytidines, 2'-O-Methyl RNA bases, Iso-deoxycytidines (Iso-dCs), Iso-deoxyguanosines (Iso-dGs), iSpC3 groups (i.e. nucleotides which lack sugar and a base), photo-cleavable (PC) groups, hexandiol groups, spacer 9 (iSp9) groups, spacer 18 (iSp18) groups, a polymer or thiol connections. The spacer may comprise any combination of these groups. Many of these groups are commercially available from IDT® (Integrated DNA Technologies®).

Any number of one or more loading moieties may be used. The method may comprise attaching two or more loading moieties each having a helicase or construct bound (attached) thereto. For instance, a loading moiety may be attached to each end of the target polynucleotide. In such embodiments, one loading moiety is preferably a Y adaptor and the other loading moiety may be a bridging moiety, such as a hairpin loop adaptor.

The one or more loading moieties may be attached to the target polynucleotide in any manner. The one or more loading moieties are preferably covalently attached to the target polynucleotide.

The one or more loading moieties are most preferably ligated to the target polynucleotide. The one or more loading moieties may be ligated to either end of the polynucleotide, i.e. the 5' or the 3' end. Loading moieties may be ligated to both ends of the target polynucleotide. The one or more loading moieties may be ligated to the polynucleotide using any method known in the art. The one or more loading moieties may be ligated to the polynucleotide in the absence of ATP or using gamma-S-ATP (ATPyS) instead of ATP.

The one or more loading moieties may be ligated using a ligase, such as T4 DNA ligase, E. coli DNA ligase, Taq DNA ligase, Tma DNA ligase and 9° N DNA ligase. The ligase is preferably used under the conditions set out in Example 3.

The helicase or construct preferably remains bound (attached) to the loading moiety once the loading moiety has been attached to the target polynucleotide. After it has been attached in accordance with the invention, the helicase or construct may unbind from the one or more loading moieties.

Any of the embodiments discussed above with reference to the method of the invention equally apply to the kits. The helicase may be any of those discussed. The kit may comprise any number and combination of helicases of the invention discussed above with reference to the series and methods of the invention.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of helicases of the invention or a plurality of constructs of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention. The helicase may be any of those discussed above with reference to the constructs of the invention, including the helicases of the invention and helicases which are not modified in accordance with the invention. The apparatus may comprise any number and combination of helicases of the invention.

The apparatus is preferably set up to carry out the method of the invention.

The apparatus preferably comprises:

a sensor device that is capable of supporting the plurality of pores and membranes and being operable to perform polynucleotide characterisation using the pores and membranes; and at least one port for delivery of the material for performing the characterisation.

Alternatively, the apparatus preferably comprises:

a sensor device that is capable of supporting the plurality of pores and membranes being operable to perform polynucleotide characterisation using the pores and membranes; and at least one reservoir for holding material for performing the characterisation.

The apparatus more preferably comprises:

a sensor device that is capable of supporting the membrane and plurality of pores and membranes and being operable to perform polynucleotide characterising using the pores and membranes;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

Methods of Producing Helicases of the Invention

The invention also provides methods of producing a modified helicase of the invention. The method comprises providing a Dda helicase and modifying the helicase to form a modified helicase of the invention.

The method preferably further comprises determining whether or not the helicase is capable of controlling the movement of a polynucleotide. Assays for doing this are described above. If the movement of a polynucleotide can be controlled, the helicase has been modified correctly and a helicase of the invention has been produced. If the movement of a polynucleotide cannot be controlled, a helicase of the invention has not been produced.

Methods of Producing Constructs of the Invention

The invention also provides a method of producing a construct of the invention. The method comprises attaching, preferably covalently attaching, a helicase of the invention to an additional polynucleotide binding moiety. Any of the helicases and moieties discussed above can be used in the methods. The site of and method of covalent attachment are selected as discussed above.

The method preferably further comprises determining whether or not the construct is capable of controlling the movement of a polynucleotide. Assays for doing this are described above. If the movement of a polynucleotide can be controlled, the helicase and moiety have been attached correctly and a construct of the invention has been produced. If the movement of a polynucleotide cannot be controlled, a construct of the invention has not been produced.

The following Examples illustrate the invention.

EXAMPLES

Example 1

This example describes the simulations which were run to investigate the interaction between MspA-(G75S/G77S/L88N/D90N/D91N/D118R/Q126R/D134R/E139K)8 (SEQ ID NO: 2 with mutations G75S/G77S/L88N/D90N/D91N/D118R/Q126R/D134R/E139K=MspA mutant 1) or MspA-((Del-L74/G75/D118/L119)D56N/E59R/L88N/D90N/D91N/Q126R/D134R/E139K)8 (SEQ ID NO: 2 with mutations D56N/E59R/L88N/D90N/D91N/Q126R/D134R/E139K and deletion of the amino acids L74/G75/D118/L119=MspA mutant 2) with T4 Dda-E94C/A360C/C109A/C136A (SEQ ID NO: 8 with mutations E94C/A360C/C114A/C171A/C421D)=enzyme mutant 1a).

Simulations were performed using the GROMACS package version 4.0.5, with the GROMOS 53a6 forcefield and the SPC water model.

The MspA mutant 1 and MspA mutant 2 models were based on the crystal structure of MspA found in the protein data bank, accession code 1UUN. The relevant mutations were made using PyMOL, and in the case of MspA mutant 2 the residues L74/G75/D118/L119 were deleted from the barrel. The resultant pore models were then energy minimised using the steepest descents algorithm. The enzyme mutant 1a model was based on the Dda1993 structure found in the protein data bank, accession code 3UPU. Again, relevant mutations were made using PyMOL, and the model was energy minimised using the steepest descents algorithm.

The enzyme mutant 1a model was then placed above MspA mutant 1 and MspA mutant 2. Three simulations were performed for the enzyme mutant 1a/MspA mutant 1 and enzyme mutant 1a/MspA mutant 2 systems, with the orientation of enzyme mutant 1a differing in each simulation (See FIG. 1 for cartoon representations of the three different simulation orientations). The pore was placed into a lipid membrane comprising DPPC molecules and the simulation box was solvated. Throughout the simulation, restraints were applied to the backbone of the pore. However, the enzyme was unrestrained. The system was simulated in the NPT ensemble for 40 ns, using the Berendsen thermostat and Berendsen barostat to 300 K.

Figure 6:
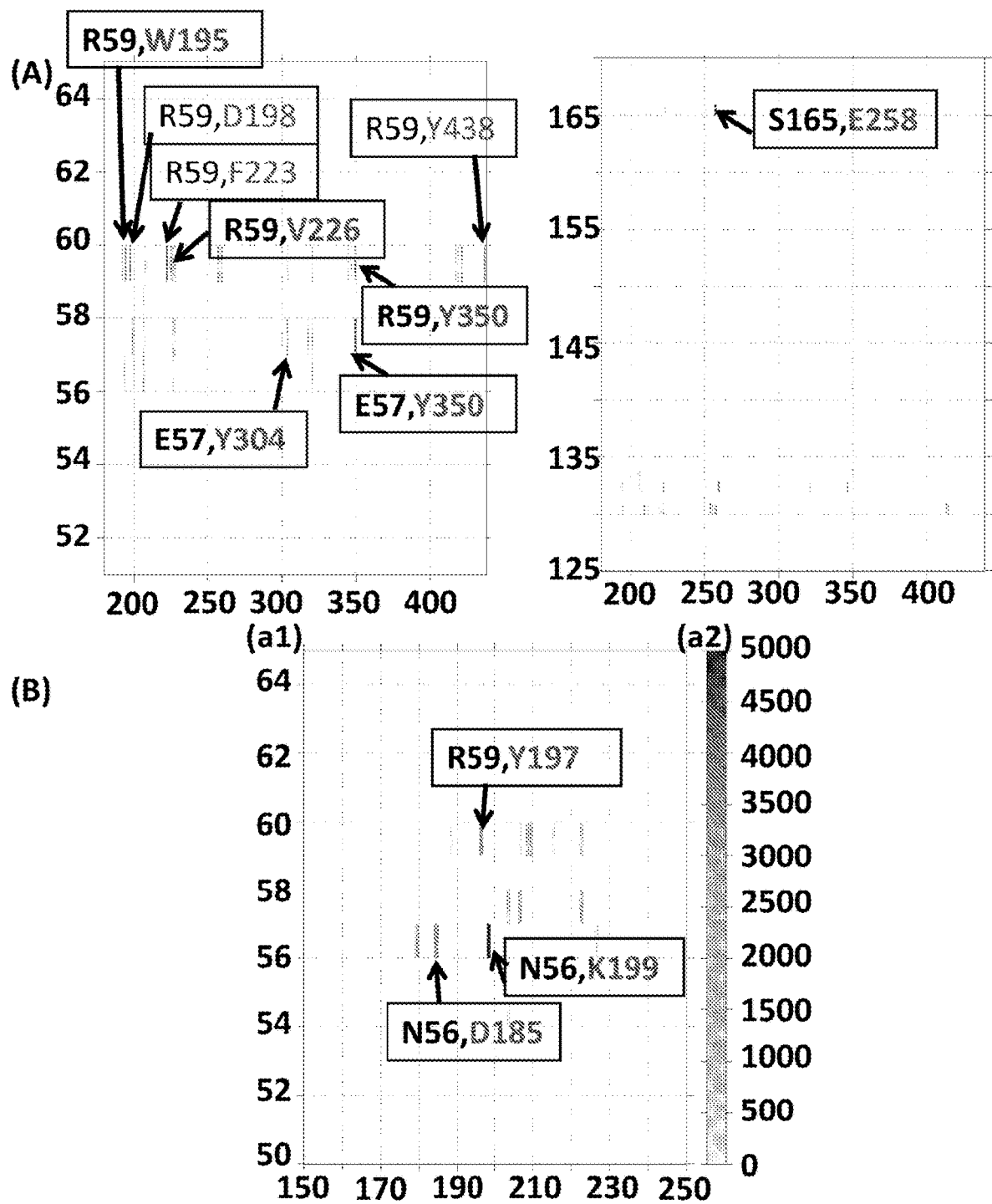
FIG. 6 (A) shows two regions of a plot (y-axis label=pore amino acid residue number, x-axis label=enzyme amino acid residue number) which shows which amino acids in the pore (MspA mutant 2) interact with particular amino acids in the enzyme (enzyme mutant 1) from run 1.

The contacts between the enzyme and pore were analysed using both GROMACS analysis software and also locally written code. FIGS. 2 to 5 showed the amino acid residues which interacted in MspA mutant 1 (FIGS. 2 and 3) and MspA mutant 2 (FIGS. 4 and 5) with the enzyme mutant 1a. The tables below show the amino acid positions in both the pore and the enzyme which were found to interact (Table 9 shows the MspA mutant 1 amino acid contact points observed when the interactions were measured between MspA mutant 1 and enzyme mutant 1a, Table 10 shows the enzyme mutant 1a amino acid contact points observed when the interactions were measured between MspA mutant 1 and enzyme mutant 1a, Table 11 shows the MspA mutant 2 amino acid contact points observed when the interactions were measured between MspA mutant 2 and enzyme mutant 1a, Table 12 shows the enzyme mutant La amino acid contact points observed when the interactions were measured between MspA mutant 2 and enzyme mutant 1a). FIG. 6 shows which amino acids in the pore (MspA mutant 2) interacted with particular amino acids in the enzyme (enzyme mutant 1a). The simulation data can be used to identify parts of enzyme mutant 1a which could be modified in order to improve the interaction between the enzyme and the nanopore in order to provide more consistent movement of the target polynucleotide with respect to, such as through, the transmembrane pore.

TABLE 9

| Run 1 Pore Amino Acid Residue | Run 2 Pore Amino Acid Residue | Run 3 Pore Amino Acid Residue |
|---|---|---|
| 57 | 56 | 57 |
| 59 | 57 | 136 |
| 136 | 136 | 59 |
| 134 | 139 | 134 |
| 56 | 52 | 56 |
| 54 | 134 | 12 |
| 12 | 138 | 139 |
| 169 | 55 | 58 |
| 14 | 59 | 137 |
| 58 | | 14 |
| 55 | | 48 |
| 52 | | 169 |
| 138 | | |
| 139 | | |
| 137 | | |

TABLE 10

| Run 1 Enzyme Amino Acid Residue | Run 2 Enzyme Amino Acid Residue | Run 3 Enzyme Amino Acid Residue |
|---|---|---|
| 2 | 180 | 255 |
| 180 | 199 | 216 |
| 179 | 202 | 221 |

TABLE 10-continued

| Run 1 Enzyme Amino Acid Residue | Run 2 Enzyme Amino Acid Residue | Run 3 Enzyme Amino Acid Residue |
|---|---|---|
| 178 | 1 | 227 |
| 227 | 4 | 351 |
| 4 | 51 | 321 |
| 177 | 434 | 254 |
| 212 | 179 | 258 |
| 1 | 178 | 224 |
| 194 | 177 | 257 |
| 204 | 197 | 256 |
| 176 | 5 | 223 |
| 213 | 201 | 212 |
| 3 | 181 | 308 |
| 216 | 200 | 207 |
| 211 | 6 | 350 |
| 202 | | 228 |
| 224 | | 210 |
| 223 | | 319 |
| 191 | | 304 |
| 199 | | 209 |
| 201 | | 347 |
| 434 | | 261 |
| 405 | | 260 |
| 255 | | 247 |

TABLE 11

| Run 1 Pore Amino Acid Residue | Run 2 Pore Amino Acid Residue | Run 3 Pore Amino Acid Residue |
|---|---|---|
| 59 | 59 | 56 |
| 57 | 57 | 59 |
| 134 | 169 | 57 |
| 136 | 134 | 136 |
| 169 | 136 | 12 |
| 56 | 56 | 14 |
| 137 | 54 | 134 |
| 58 | 14 | 54 |
| 14 | 12 | 169 |
| 135 | | 53 |
| 60 | | |
| 170 | | |

TABLE 12

| Run 1 Enzyme Amino Acid Residue | Run 2 Enzyme Amino Acid Residue | Run 3 Enzyme Amino Acid Residue |
|---|---|---|
| 350 | 202 | 199 |
| 258 | 180 | 197 |
| 223 | 179 | 185 |
| 195 | 212 | 198 |
| 198 | 258 | 207 |
| 438 | 211 | 202 |
| 260 | 198 | 223 |
| 207 | 265 | 180 |
| 226 | 260 | 209 |
| 304 | 259 | 210 |
| 200 | 255 | 203 |
| 227 | 1 | 204 |
| 347 | 200 | 437 |
| 321 | 300 | 200 |
| 422 | 203 | 211 |
| 318 | 261 | 405 |
| 415 | 216 | 227 |
| 210 | 177 | 258 |
| 229 | 213 | 212 |
| 255 | 207 | 256 |

TABLE 12-continued

| Run 1 Enzyme Amino Acid Residue | Run 2 Enzyme Amino Acid Residue | Run 3 Enzyme Amino Acid Residue |
|---|---|---|
| 224 | 337 | 216 |
| 228 | 204 | 189 |
| 208 | 434 | 228 |
| 193 | 298 | 220 |
| 256 |  | 219 |

Example 2

This example describes the simulations which were run to investigate the interaction between two different enzymes (wild-type Dda 1993 (SEQ ID NO: 8)) and T4 Dda-E94C/A360C (SEQ ID NO: 8 with mutations E94C/A360C) =enzyme mutant 18) and a polynucleotide.

Simulations were performed to assess which residues made contact with the DNA that was within the enzyme binding site. The simulations were performed using the GROMACS package version 4.0.5, with the AMBER-99SB force field and the TIP3P water model.

Two enzymes were simulated, wild-type Dda1993 and enzyme mutant 18. Enzyme mutant 18 was simulated in its closed-complex form, such that a disulphide bond was present between E94C and A360C. The initial structure of wild-type Dda1993 was based on the structure available in the protein data bank, with accession code 3UPU. The structure in this PDB file is Dda1993-K38A. Hence, in the wild-type Dda1993 simulations, residue 38 was mutated back to lysine using PyMOL. The enzyme mutant 18 model was also based on the structure in 3UPU, with the relevant mutations made in PyMOL. The DNA simulated in both enzyme simulations was the DNA present in the crystal structure of 3UPU (DNA sequence is poly(dT)). The resultant enzyme/DNA models were then energy minimised using the steepest descents algorithm. The simulation box was then solvated and another round of energy minimisation was performed. Throughout the simulation the enzyme and DNA were unrestrained. The system was simulated in the NPT ensemble for 20 ns, using the Berendsen thermostat and Berendsen barostat to 300 K.

The contacts between the enzyme and DNA were analysed using both GROMACS analysis software and also locally written code. The tables below show the amino acids in the two enzymes which interacted with the DNA present in the crystal structure 3UPU (Tables 13 and 14 show the wild-type Dda 1993 amino acid contact points observed when the interactions were measured between wild-type Dda1993 and the DNA and Tables 15 and 16 show enzyme mutant 18 amino acid contact points observed when the interactions were measured between enzyme mutant 18 and the DNA). The simulation data can be used to identify positions in the Dda1993 enzyme and enzyme mutant 18 which could be mutated in order to improve the interaction between the enzyme and the DNA in order to provide more consistent movement of the target polynucleotide with respect to, such as through, the transmembrane pore.

TABLE 13

| Amino Acid Residue WT Dda1993 |
|---|
| N242 |
| K397 |
| H396 |
| N293 |
| H82 |
| H64 |
| F98 |
| V150 |
| Y415 |
| T63 |
| F240 |
| T241 |
| T394 |
| T80 |
| F276 |
| P89 |
| N88 |
| S83 |
| I289 |
| P152 |
| P274 |

TABLE 14

| Amino Acid Residue WT Dda1993 |
|---|
| I87 |
| D417 |
| P62 |
| S287 |
| H414 |
| K243 |
| M119 |
| A416 |
| L420 |
| K86 |
| N292 |
| V96 |
| D151 |
| N155 |
| W378 |
| E288 |
| T278 |
| V286 |
| K123 |
| R148 |
| L97 |

TABLE 15

| Amino Acid Residue Enzyme Mutant 18 |
|---|
| H82 |
| K397 |
| N242 |
| H64 |
| V150 |
| H396 |
| T241 |
| N293 |
| T63 |
| N88 |
| F98 |
| F240 |
| T80 |
| S83 |

TABLE 15-continued

Amino Acid
Residue
Enzyme Mutant
18

P89
T394
S287
F276
Y415
I87
D417

TABLE 16

Amino Acid
Residue
Enzyme
Mutant 18

V286
I289
P62
N292
R148
K101
K243
A416
K86
L420
N155
E288
P274
D151
P152
P285
M119
T278
D121
K284
Q272

Example 3

Figure 7:
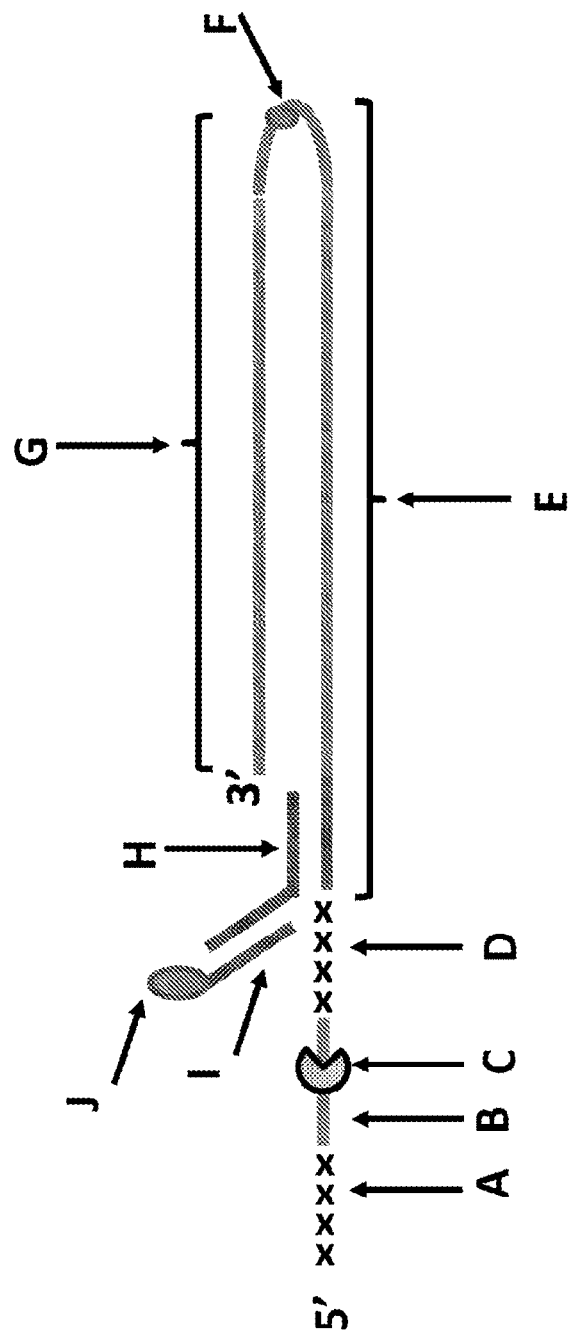
FIG. 7 shows DNA construct X used in Example 3. Section A corresponded to thirty iSpC3 spacers. Section B corresponded to SEQ ID NO: 60. Label C corresponded to the enzyme mutant used in the experiment. Section D corresponded to four iSp18 spacers. Section E corresponded to SEQ ID NO: 61. Section F corresponded to four iSpC3 spacers. Section G corresponded to SEQ ID NO: 62. Section H corresponded to SEQ ID NO: 63. Section I corresponded to SEQ ID NO: 64. Section J corresponded to a 3' cholesterol.

This example compares movement control of DNA construct X (see FIG. 7) through a nanopore using T4 Dda-E94C/C109A/C136A/A360C (SEQ ID NO: 8 with mutations E94C/C109A/C136A/A360C and then (ΔM1)G1)) (Enzyme mutant 1) with a number of different helicases. All of the helicases tested controlled the movement of the DNA through the nanopore and changes in current as the DNA translocated through the nanopore were observed. The helicases tested had either a) at least one amino acid substitution which interacted with one or more nucleotides in single stranded DNA (ssDNA) or b) one or more modifications in the part of the helicase which interacted with the transmembrane pore or both changes a) and b). This example investigates the number of complement slips forward per 3.6 kb, number of complement slips forward per kb, the % of bases missed in construct X due to slipping forward, total length of slips forward in the complement and average length of slip forward. The helicases investigated in the example moved along the polynucleotide in a 5' to 3' direction. When the 5'end of the polynucleotide (the end away from which the helicase moves) was captured by the pore, the helicase worked with the direction of the field resulting from the applied potential and moved the threaded polynucleotide into the pore and into the trans chamber. In this Example, slipping forward involved the DNA moving forwards relative to the pore (i.e. towards its 3' and away from it 5' end) at least 4 consecutive nucleotides.

Materials and Methods

Prior to setting up the experiment, DNA construct X (final concentration 0.1 nM) was pre-incubated at room temperature for five minutes with the appropriate enzyme (see list of enzymes provided below (final concentration added to the nanopore system 10 nM, which was provided in buffer (253 mM KCl, 50 mM potassium phosphate, pH 8.0, 2 mM EDTA)). After five minutes, TMAD (100 μM final concentration added to the nanopore system) was added to the pre-mix and the mixture incubated for a further 5 minutes. Finally, MgCl2 (2 mM final concentration added to the nanopore system), ATP (2 mM final concentration added to the nanopore system) and KCl (500 mM final concentration added to the nanopore system) were added to the pre-mix.

Electrical measurements were acquired from single MspA nanopores (MspA-((Del-L74/G75/D118/L119)D56F/E59R/L88N/D90N/D91N/Q126R/D134R/E139K)8 (SEQ ID NO: 2 with mutations D56F/E59R/L88N/D90N/D91N/Q126R/D134R/E139K and deletion of the amino acids L74/G75/D118/L119) (MspA mutant 3)) inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 150 uL of 500 mM KCl, 25 mM K Phosphate, pH8.0 was then flowed through the system. After 10 minutes a further 150 uL of 500 mM KCl, 25 mM K Phosphate, pH8.0 was flowed through the system and then the enzyme (see list below, 10 nM final concentration), DNA construct X (0.1 nM final concentration), fuel (MgCl2 2 mM final concentration, ATP 2 mM final concentration) pre-mix (150 μL total) was then flowed into the single nanopore experimental system. The experiment was run at −140 mV and helicase-controlled DNA movement monitored.

Results

A number of different helicases were investigated in order to determine the effect of at least one or more substitutions to regions of the helicase which were thought to interact with the DNA construct X or one or more modifications which were thought to interact with the nanopore. Five different parameters were investigated in order to identify helicases which exhibited improved helicase controlled DNA translocation 1) the number of complement slips forward per 3.6 kb, 2) number of complement slips forward per kb, 3) the % of bases missed in construct X due to slipping forward, 4) total length of slips forward in the complement and 5) average length of slip forward.

The measurement of slips forward per kilobase or per 3.6 kb were calculated using the following procedure 1) the helicase controlled DNA movements were mapped to a model using an HMM algorithm, 2) the helicase-controlled DNA movements were then subjected to filtering, 3) the mapped helicase controlled DNA movements were checked to ensure accurate mapping, 4) the transitions that were classified as a slipping forward movement of at least four consecutive nucleotides were determined per kilobase or per 3.6 kb. The % bases missed in construct X due to slipping forward is a measure of the number of bases in construct X which are missed as a result of slips forward along DNA construct X expressed as a percentage. The total length of complement slips is the sum of all slips in the complement section of the strand. Average slip length is the sum of all slips in the complement section of the strand divided by the total number of slips in the complement.

Table 17 below shows the different enzymes tested which were compared to enzyme mutant 1. Of the enzymes tested, mutants 2 to 13 and 15 to 17 exhibited an improvement in at least one of the parameters 1 to 5 when compared to enzyme mutant 1.

Mutants 5 to 13 have at least one amino acid, which interacted with the sugar and/or base of one or more nucleotides in single stranded DNA (ssDNA), substituted with an amino acid which comprised a larger side chain (R group) and had no one or more modifications in the part of the helicase which interacted with the transmembrane pore. All of mutants 5 to 13 exhibited an improvement in at least one of parameters 1 to 5 when compared with enzyme mutant 1 which was attributed to the amino acid substitution which comprised a larger side chain (R group) and which interacted with the sugar and/or base of one or more nucleotides in single stranded DNA (ssDNA). Clearly, making at least one substitution with a larger side chain group at positions which interacted with the sugar and or base of one or more nucleotides in the single stranded (ssDNA) resulted in improved movement control.

Mutant 14 has at least one amino acid, which interacted with the sugar and/or base of one or more nucleotides in single stranded DNA (ssDNA), substituted with an amino acid which comprised a smaller side chain (R group) and had no one or more modifications in the part of the helicase which interacted with the transmembrane pore. Mutant 14 exhibited no improvement in any of parameters 1 to 5 when compared with enzyme mutant 1 which was attributed to the amino acid substitution which comprised a smaller side chain (R group) and which interacted with the sugar and/or base of one or more nucleotides in single stranded (ssDNA). Clearly, making at least one substitution with a smaller side chain groups at positions which interacted with the sugar and or base of one or more nucleotides in single stranded DNA (ssDNA) resulted in poorer movement control.

Mutant 4 has at least one amino acid substitution which interacted with one or more phosphate groups in one or more nucleotides in single stranded DNA (ssDNA), at least one amino acid, which interacted with the sugar and/or base of one or more nucleotides in single stranded DNA (ssDNA), substituted with an amino acid which comprised a larger side chain (R group) and had no one or more modifications in the part of the helicase which interacted with the transmembrane pore. Mutant 4 exhibited an improvement in at least one of parameters 1 to 5 when compared with enzyme mutant 1 which was attributed to the combination of amino acid substitutions e.g. one which interacted with one or more phosphate groups in one or more nucleotides in single stranded DNA (ssDNA) and the second which interacted with the sugar and/or base of one or more nucleotides in single stranded DNA (ssDNA). Furthermore, Mutant 4 exhibited an improvement in at least one of parameters 1 to 5 when compared with enzyme mutant 9 which was attributed to the amino acid substitution which interacted with one or more phosphate groups in one or more nucleotides in single stranded DNA (ssDNA). Clearly, making substitutions with larger side chain groups at positions which interacted with the sugar and/or base of one or more nucleotides and making substitutions which interacted with one or more phosphate groups in one or more nucleotides in single stranded DNA (ssDNA) resulted in improved movement control.

Mutant 2 had at least one amino acid, which interacted with the sugar and/or base of one or more nucleotides in single stranded DNA (ssDNA), substituted with an amino acid which comprised a larger side chain (R group) and had one or more modifications in the part of the helicase which interacted with the transmembrane pore. Mutant 2 exhibited an improvement in at least one of parameters 1 to 5 when compared with enzyme mutant 1 which was attributed to the combination of changes e.g. the first at least one substitution which interacted with the sugar and/or base of one or more nucleotides in single stranded DNA (ssDNA) and the second one or more modifications in the part of the helicase which interacted with the transmembrane pore. Mutant 2 also exhibited an improvement in at least one of parameters 1 to 5 when compared with enzyme mutant 9 which was attributed to the second one or more modifications in the part of the helicase which interacted with the transmembrane pore. Furthermore, mutant 2 exhibited an improvement in at least one of parameters 1 to 5 when compared with enzyme mutant 16 which was attributed to the first at least one substitution which interacted with the sugar and/or base of one or more nucleotides in single stranded DNA (ssDNA). Clearly, making the combination of changes (the first at least one substitution which interacted with the sugar and/or base of one or more nucleotides in single stranded DNA (ssDNA) and the second one or more modifications in the part of the helicase which interacted with the transmembrane pore) resulted in an enzyme which exhibited improved movement control.

Mutant 3 had at least one amino acid, which interacted with the sugar and/or base of one or more nucleotides in single stranded DNA (ssDNA), substituted with an amino acid which comprised a larger side chain (R group) and had one or more modifications in the part of the helicase which interacted with the transmembrane pore. Mutant 3 exhibited an improvement in at least one of parameters 1 to 5 when compared with enzyme mutant 1 which was attributed to the combination of changes e.g. the first at least one substitution which interacted with the sugar and/or base of one or more nucleotides in single stranded DNA (ssDNA) and the second one or more modifications in the part of the helicase which interacted with the transmembrane pore. Mutant 3 also exhibited an improvement in at least one of parameters 1 to 5 when compared with enzyme mutant 9 which was attributed to the second one or more modifications in the part of the helicase which interacted with the transmembrane pore. Furthermore, mutant 3 exhibited an improvement in at least one of parameters 1 to 5 when compared with enzyme mutant 17 which was attributed to the first at least one substitution which interacted with the sugar and/or base of one or more nucleotides in single stranded DNA (ssDNA). Clearly, making the combination of substitutions (the first at least one substitution which interacted with the sugar and/or base of one or more nucleotides in single stranded DNA (ssDNA) and the second one or more modifications in the part of the helicase which interacted with the transmembrane pore) resulted in an enzyme which exhibited improved movement control.

Enzyme ID's

Enzyme mutant 1=T4 Dda-E94C/C109A/C136A/A360C (SEQ ID NO: 8 with mutations E94C/C109A/C136A/A360C and then (ΔM1)G1))

Enzyme mutant 2=T4 Dda-E94C/F98W/C109A/C136A/K199L/A360C (SEQ ID NO: 8 with mutations E94C/F98W/C109A/C136A/K199L/A360C and then (ΔM1)G1))

Enzyme mutant 3=T4 Dda-F98W/E94C/C109A/C136A/K194L/A360C (SEQ ID NO: 8 with mutations F98W/E94C/C109A/C136A/K194L/A360C and then (ΔM1)G1))

Enzyme mutant 4=T4 Dda-S83H/E94C/F98W/C109A/ C136A/A360C (SEQ ID NO: 8 with mutations S83H/E94C/ F98W/C109A/C136A/A360C and then (ΔM1)G1))

Enzyme mutant 5=T4 Dda-E94C/F98W/C109A/C136A/ F276K/A360C (SEQ ID NO: 8 with mutations E94C/F98W/ C109A/C136A/F276K/A360C and then (ΔM1)G1))

Enzyme mutant 6=T4 Dda-E94C/F98W/C109A/C136A/ S287R/A360C (SEQ ID NO: 8 with mutations E94C/F98W/ C109A/C136A/S287R/A360C and then (ΔM1)G1))

Enzyme mutant 7=T4 Dda-E94C/F98W/C109A/C136A/ S287W/A360C (SEQ ID NO: 8 with mutations E94C/ F98W/C109A/C136A/S287W/A360C and then (ΔM1)G1))

Enzyme mutant 8=T4 Dda-E94C/F98W/C109A/C136A/ S287F/A360C (SEQ ID NO: 8 with mutations E94C/F98W/ C109A/C136A/S287F/A360C and then (ΔM1)G1))

Enzyme mutant 9=T4 Dda-E94C/F98W/C109A/C136A/ A360C (SEQ ID NO: 8 with mutations E94C/F98W/ C109A/C136A/A360C and then (ΔM1)G1))

Enzyme mutant 10=T4 Dda-P89F/E94C/C109A/C136A/ A360C (SEQ ID NO: 8 with mutations P89F/E94C/C109A/ C136A/A360C and then (ΔM1)G1))

Enzyme mutant 11=T4 Dda-E94C/C109A/C136A/V150H/ A360C (SEQ ID NO: 8 with mutations/C109A/C136A/ V150H/A360C and then (ΔM1)G1))

Enzyme mutant 12=T4 Dda-E94C/C109A/C136A/V150I/ A360C (SEQ ID NO: 8 with mutations E94C/C109A/ C136A/V150I/A360C and then (ΔM1)G1))

Enzyme mutant 13=T4 Dda-E94C/C109A/C136A/P152F/ A360C (SEQ ID NO: 8 with mutations E94C/C109A/ C136A/P152F/A360C and then (ΔM1)G1))

Enzyme mutant 14=T4 Dda-E94C/F98A/C109A/C136A/ A360C (SEQ ID NO: 8 with mutations E94C/F98A/C109A/ C136A/A360C and then (ΔM1)G1))

Enzyme mutant 15=T4 Dda-E94C/C109A/C136A/K199L/ A360C (SEQ ID NO: 8 with mutations E94C/C109A/ C136A/K199L/A360C and then (ΔM1)G1))

Enzyme mutant 16=T4 Dda-E94C/C109A/C136A/K194L/ A360C (SEQ ID NO: 8 with mutations E94C/C109A/ C136A/K194L/A360C and then (ΔM1)G1))

Enzyme mutant 17=T4 Dda-E94C/C109A/C136A/W 195A/ A360C (SEQ ID NO: 8 with mutations E94C/C109A/ C136A/W 195A/A360C and then (ΔM1)G1))

TABLE 17

| Enzyme | Number complement slips per 3.6 kb | Number complement slips per kb | % complement bases missed through slipping | Total length of complement slips | Average slip length |
|---|---|---|---|---|---|
| 1 | 16 | 4.4 | 10.5 | 377 | 23.6 |
| 2 | 6 | 1.7 | 3.6 | 129 | 21.5 |
| 3 | 3 | 0.8 | 1.9 | 70 | 23.3 |
| 4 | 6 | 1.7 | 3.4 | 121 | 24 |
| 5 | 7.7 | 2.1 | 3.9 | 140 | 22 |
| 6 | 8.1 | 2.3 | 4.4 | 158 | 27 |
| 7 | 5.8 | 1.6 | 3.1 | 112 | 27 |
| 8 | 6.7 | 1.9 | 3.7 | 134 | 28 |
| 9 | 11 | 3.1 | 6.5 | 233 | 21.2 |
| 10 | 17 | 4.7 | 10.3 | 372 | 21.9 |
| 11 | 6 | 1.7 | 3.7 | 134 | 22.3 |
| 12 | 12 | 3.3 | 8.7 | 314 | 26.2 |
| 13 | 12 | 3.3 | 9.9 | 355 | 29.6 |
| 14 | 17 | 4.7 | 11.7 | 420 | 24.7 |
| 15 | 8 | 2.2 | 5.3 | 191 | 23.9 |
| 16 | 4 | 1.1 | 2.8 | 100 | 25.0 |
| 17 | 15 | 4.2 | 10.3 | 371 | 24.7 |

Example 4

This example shows how the helicase T4 Dda-E94C/ F98W/C109A/C136A/K194L/A360C (SEQ ID NO: 8 with mutations E94C/F98W/C109A/C136A/K194L/A360C and then (ΔM1)G1)) controlled the movement of DNA construct X (see FIG. 7) through a CsgG nanopore (CsgG-Eco-(Y51T/ F56Q)-StrepII(C))9 (SEQ ID NO: 66 with mutations Y51T/ F56Q where StepII(C) is SEQ ID NO: 67 and is attached at the C-terminus).

Materials and Methods

DNA construct X helicase (T4 Dda-E94C/F98W/C109A/ C136A/K194L/A360C (SEQ ID NO: 8 with mutations E94C/F98W/C109A/C136A/K194L/A360C and then (ΔM1)G1)) pre-mix was prepared as described in the materials and methods section of Example 3.

Electrical measurements were acquired from single CsgG nanopores (CsgG-Eco-(Y51T/F56Q)-StrepII(C))9 (SEQ ID NO: 66 with mutations Y51T/F56Q where StepII(C) is SEQ ID NO: 67 and is attached at the C-terminus) inserted in block co-polymer in a similar method as described in Example 3 except the nanopore was CsgG and not MspA.

Results

Figure 8:
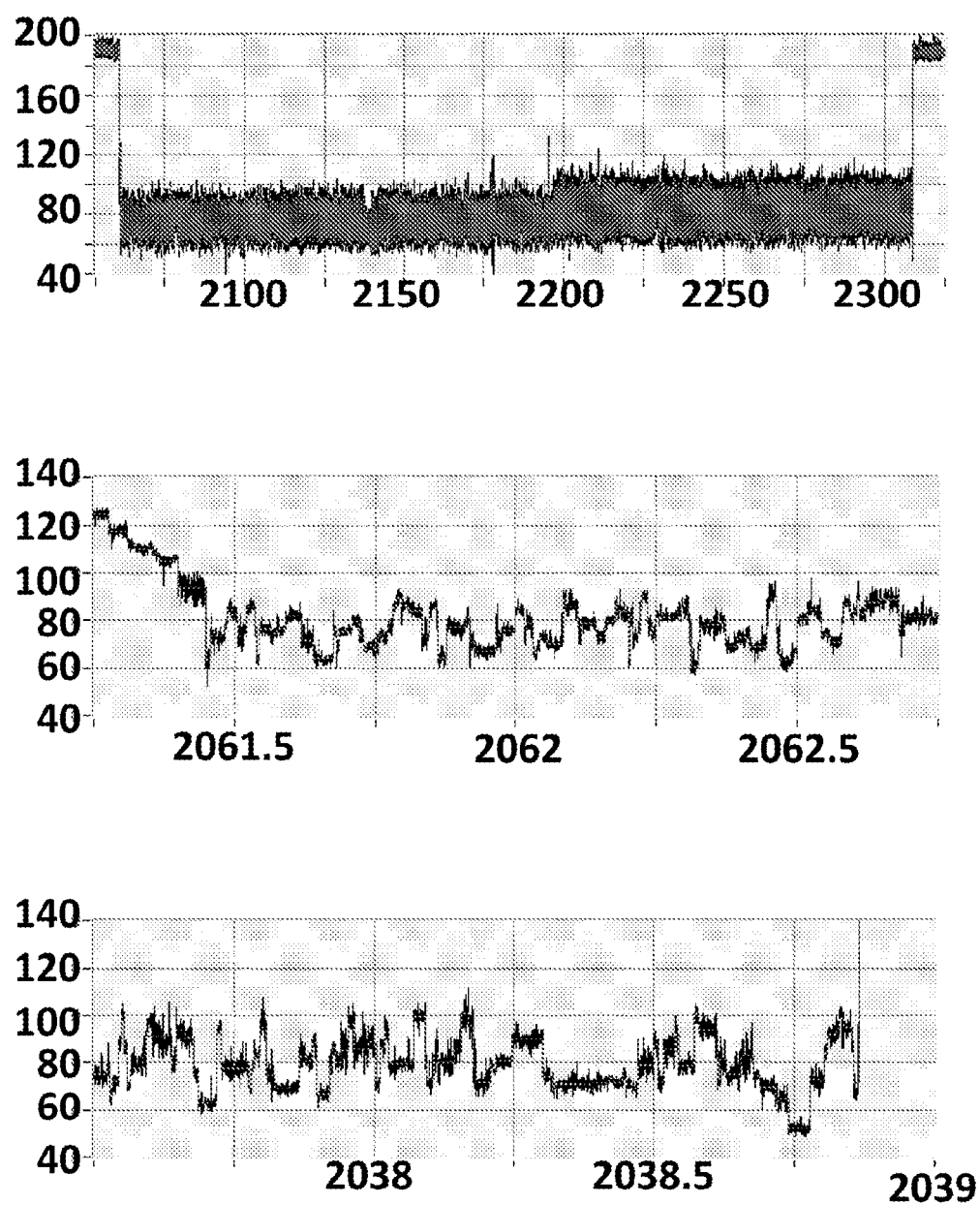
FIG. 8 shows example current traces (y-axis label=Current (pA), x-axis label=Time (s) for all three traces) of when a helicase (T4 Dda-E94C/F98W/C109A/C136A/K194L/A360C (SEQ ID NO: 8 with mutations E94C/F98W/C109A/C136A/K194L/A360C and then (ΔM1)G1)) controlled the translocation of the DNA construct X through the CsgG-Eco nanopore (CsgG-Eco-(Y51T/F56Q)-StrepII(C))9 (SEQ ID NO: 66 with mutations Y51T/F56Q where StepII(C) is SEQ ID NO: 67 and is attached at the C-terminus). Sections B and C show zoomed in regions of current trace A.

Helicase controlled DNA movement was observed as T4 Dda-E94C/F98W/C109A/C136A/K194L/A360C (SEQ ID NO: 8 with mutations E94C/F98W/C109A/C136A/K194L/ A360C and then (ΔM1)G1)) controlled the movement of DNA construct X (see FIG. 7) through a CsgG nanopore (CsgG-Eco-(Y51T/F56Q)-StrepII(C))9 (SEQ ID NO: 66 with mutations Y51T/F56Q where StepII(C) is SEQ ID NO: 67 and is attached at the C-terminus). An example of a current trace of a helicase controlled DNA movement is shown in FIG. 8A and zoomed in views of the same trace are shown in FIGS. 8B and C.

Example 5

This example shows how a hairpin was attached to the 3' end of an RNA strand and the RNA strand was reverse transcribed to create an RNA/DNA hybrid. Subsequently a non-RNA polynucleotide was attached to the 5' end of the RNA strand in the RNA/DNA hybrid to facilitate loading of a DNA helicase, T4 Dda (E94C/F98W/C109A/C136A/ K194L/A360C (SEQ ID NO: 8 with mutations E94C/F98W/ C109A/C136A/K194L/A360C and then (ΔM1)G1)). Helicase-controlled movement of the RNA/DNA construct through a nanopore was observed.

Materials and Methods

1. Hairpin Ligation

The reagents listed in Table 18 below were mixed and placed on a thermocycler set to the program in Table 19 below. The mixture was then purified using Agencourt Ampure SPRI beads at a ratio of 1.8 μL SPRI beads per μL of sample. After purification, reverse transcription was performed using Life Technologies Super Script II: reagents in Table 20 and were mixed according to the manufacturer's protocol and placed on a thermocycler set to the program in Table 21. The mixture was then purified using Agencourt Ampure SPRI beads at a ratio of 1.8 μL SPRI beads per L of sample. This sample was known as reverse transcribed sample 1.

TABLE 18

| Reagent | Volume | Stock Concentration | Final Concentration |
| --- | --- | --- | --- |
| RNA strand (3' polyadenylated with open reading frame SEQ ID NO: 68) | 0.72 ul | 556 ng/ul | 0.2 uM |
| polyT hairpin (SEQ ID NO: 72 is attached at its 5' end to a phosphate group and SEQ ID NO: 72 is attached at its 3' end to four iSpC3 spacers which are attached at the opposite end to the 5' end of SEQ ID NO: 73) | 0.4 ul | 50 uM | 1 uM |
| T4 DNA ligase buffer | 4 ul | 5x | 1x |
| T4 DNA ligase | 1 ul | 2000 U/ul | 2000 U |
| NF H₂O | 13.88 ul | | |
| Total | 20 ul | | |

TABLE 19

| Number of Cycles | Step | Temp (° C.) | Time |
| --- | --- | --- | --- |
| 1 | Ligate | 16 | 2:00:00 |

TABLE 20

| Reagent | Volume | Stock Concentration | Final Concentration |
| --- | --- | --- | --- |
| RNA after polyT hairpin ligation | 7 ul | 35.5 ng/ul | 248.5 ng/reaction |
| dNTPs | 1 ul | 10 uM each | 0.5 uM |
| NF H₂O | 5 ul | | |
| First-Strand Buffer | 4 ul | 5x | 1x |
| 0.1M DTT | 2 ul | 0.1M | 0.01M |
| Super Script II | 1 ul | 200 U | 200 U |
| Total | 20 ul | | |

TABLE 21

| Number of Cycles | Step | Temp (° C.) | Time |
| --- | --- | --- | --- |
| 1 | Reverse Transcription | 42 | 0:50:00 |
| 2 | Denaturation | 70 | 0:15:00 |

Subsequently, a "non-RNA polynucleotide" (30 SpC3 spacers attached to the 5' end of SEQ ID NO: 69 which is attached at the 3' end to the 5' end of four iSp18 spacers which were attached at the 3' end to the 5' end of SEQ ID NO: 70 which was attached at the 3' end to the 5' end of four 5-nitroindoles which were attached at the 3' end to the RNA sequence CAAGGG) was ligated to the RNA polynucleotide (which was reverse transcribed in the previous step) by mixing the reagents listed in a Table 22 and placing the mixture on a thermocycler set to the program in Table 23. The mixture was then purified using Agencourt Ampure SPRI beads at a ratio of 1.8 μL SPRI beads per μL of sample. This sample was known as ligated sample 1.

TABLE 22

| Reagent | Volume | Stock Concentration | Final Concentration |
| --- | --- | --- | --- |
| transcribed sample 1 | 1.5 ul | 166 ng/ul | 250 ng/reaction |
| T4 RNA ligase 1 reaction buffer | 2 ul | 10x | 1x |
| "non-RNA polynucleotide (see description above) | 2.4 ul | 50 uM | 8.33 uM |
| ATP | 0.4 ul | 50 mM | 1 mM |
| NF H₂O | 0.8 ul | | |
| T4 RNA ligase 1 | 2.9 ul | 10 U/ul | 29 U |
| PEG 8k | 10 ul | 50% | 25% |
| Total | 20 ul | | |

TABLE 23

| Number of Cycles | Step | Temp (° C.) | Time |
| --- | --- | --- | --- |
| 1 | Ligation | 16 | 4:00:00 |

The reagents listed in Table 24 below were mixed and incubated at 65° C. and then cooled to 4° C. at a rate of 0.1° C. per second. This sample was known as DNA/RNA construct Y.

TABLE 24

| Reagent | Volume | Concentration of Stock | Final Concentration |
| --- | --- | --- | --- |
| Ligated sample 1 | 9 μl | ~1 μM | 942 μM |
| Anchor (SEQ ID NO: 71 attached at its 3' end to the 5' end of six iSp18 spacers, two thymines and a 3' cholesterol TEG) | 0.36 μl | 100 μM | 3.77 μM |
| 10 mM TRIS pH 7.5 50 mM NaCl | 0.19 μl | 50 x | 1 x |
| Total | 9.55 μl | | |

Electrophysiology

DNA/RNA construct Y was incubated with 2 μl of 17.4 μM T4 Dda (E94C/F98W/C109A/C136A/K194L/A360C (SEQ ID NO: 8 with mutations E94C/F98W/C109A/C136A/K194L/A360C and then (ΔM1)G1)) for 20 minutes. 2.1 μl of 800 μM TMAD was then added to the incubated mixture and kept at room temperature for 10 min. This sample was then diluted into buffer (276 μL of 500 mM KCl, 25 mM potassium phosphate pH 8.0) MgCl2 (4 μL, 150 mM) and ATP (4 μL, 150 mM) giving a total volume of 300 μL.

Electrical measurements were acquired from single MspA nanopores inserted in block co-polymer in buffer (25 mM K Phosphate buffer, 150 mM Potassium Ferrocyanide, 150 mM Potassium Ferricyanide~pH 8.0). After achieving a single pore inserted in the block co-polymer, then buffer (2 mL, 25 mM K Phosphate buffer, 150 mM Potassium Ferrocyanide, 150 mM Potassium Ferricyanide, pH 8.0) was flowed through the system to remove any excess MspA nanopores.

An excess of buffer (500 mM KCl, 25 mM potassium phosphate pH 8.0) was flowed through the system prior to the addition of DNA/RNA Construct Y and helicase. Finally, (T4 Dda (E94C/F98W/C109A/C136A/K194L/A360C (SEQ ID NO: 8 with mutations E94C/F98W/C109A/C136A/K194L/A360C and then (ΔM1)G1)), bound to DNA/RNA construct Y) was then added to the nanopore system, the experiment was run at −140 mV and helicase-controlled DNA movement monitored.

Figure 9:
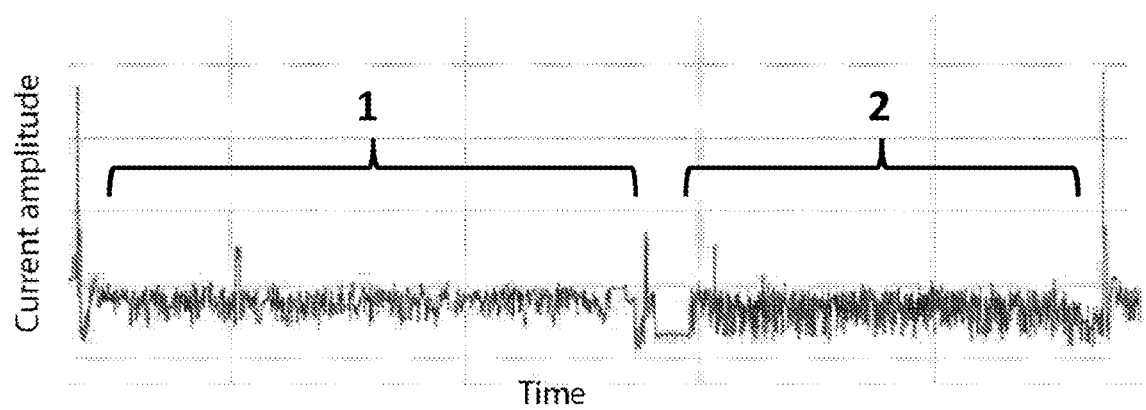
FIG. 9 show an example current trace (y-axis label=Current (pA), x-axis label=Time (s)) of when a helicase (T4 Dda-E94C/F98W/C109A/C136A/K194L/A360C (SEQ ID NO: 8 with mutations E94C/F98W/C109A/C136A/K194L/A360C and then (ΔM1)G1)) controlled the translocation of the DNA/RNA construct Y through an MspA nanopore. The region labelled 1 corresponds to an RNA region and the region labelled 2 corresponds to a DNA region.

Results:

This example shows how a non-RNA polynucleotide was attached to RNA (which had been transcribed) to facilitate loading of a DNA helicase, T4 Dda (E94C/F98W/C109A/C136A/K194L/A360C (SEQ ID NO: 8 with mutations E94C/F98W/C109A/C136A/K194L/A360C and then (ΔM1)G1)), and subsequent helicase controlled movement of the construct was observed. An example of a T4 Dda (E94C/F98W/C109A/C136A/K194L/A360C (SEQ ID NO: 8 with mutations E94C/F98W/C109A/C136A/K194L/A360C and then (ΔM1)G1)) helicase-controlled movement is shown in FIG. 9.

Figure 11:
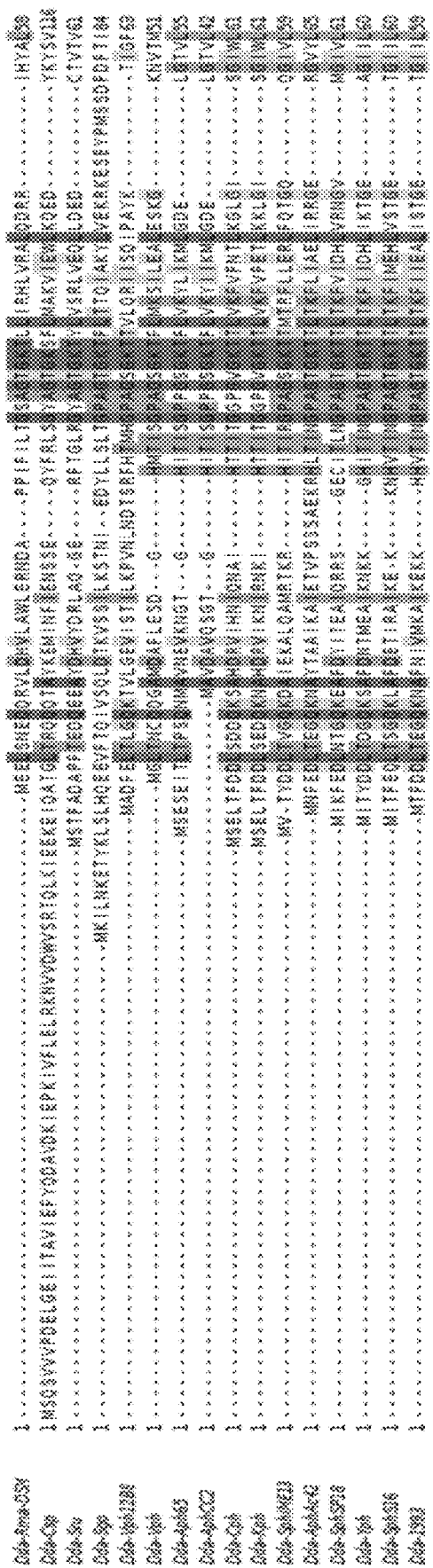
FIG. 11 shows a sequence alignment of Dda helicases, SEQ ID NOs: 8-23.

An alignment of the preferred Dda helicases of the invention (SEQ ID NOs: 8 to 23) is shown in FIG. 11.

The invention claimed is:

1. A composition for characterizing a target polynucleotide comprising a transmembrane pore and a DNA-dependent ATPase (Dda helicase in which:
   (a) the Dda helicase comprises a sequence that is at least 80% identical to the sequence set forth in SEQ ID NO: 8 and is recombinantly substituted in at least one residue corresponding to at least one of the following amino acid positions in SEQ ID NO: 8 which interacts with one or more nucleotides in single stranded DNA (ssDNA): H82, N88, P89, F98, D121, V150, P152, F240, F276, S287, H396 and/or Y415; and
   (b) the part of the Dda helicase which interacts with the transmembrane pore comprises one or more modifications at one or more residues corresponding to a position in SEQ ID NO: 8 selected from the group consisting of: 3, 4, 5, 176, 177, 179, 180, 185, 193, 194, 195, 198, 199, 200, 202, 203, 204, 207, 208, 209, 210, 211, 212, 213, 216, 221, 224, 255, 318, 347, 405, 415, 434, 437, and 438.

2. The composition according to claim 1, wherein in (a) the at least one amino acid interacts with the sugar and/or base of the one or more nucleotides in single stranded DNA (ssDNA) is substituted with an amino acid which comprises a larger side chain (R group).

3. The composition according to claim 2 wherein the at least one amino acid which interacts with the sugar and/or base of one or more nucleotides in ssDNA is at the residue corresponding to H82, N88, P89, F98, D121, V150, P152, F240, F276, S287, and H396 in SEQ ID NO: 8.

4. The composition according to claim 2, wherein the at least one amino acid which interacts with the sugar and/or base of one or more nucleotides in ssDNA is at least one amino acid which intercalates between the nucleotides in ssDNA.

5. The composition according to claim 4, wherein the at least one amino acid which intercalates between the nucleotides in ssDNA is at a residue corresponding to at least one of P89, F98, and V150 in SEQ ID NO: 8.

6. The composition according to claim 2, wherein the larger side chain (R group) contains an increased number of carbon atoms, has an increased length, has an increased molecular volume and/or has an increased van der Waals volume.

7. The composition according to claim 2, wherein the larger side chain (R group) increases the (i) electrostatic interactions, (ii) hydrogen bonding and/or (iii) cation-pi (cation-π) interactions between the at least one amino acid and the one or more nucleotides in ssDNA.

8. The composition according to claim 2, wherein the amino acid which comprises a larger side chain (R group) is not alanine (A), cysteine (C), glycine (G), selenocysteine (U), methionine (M), aspartic acid (D) or glutamic acid (E).

9. The composition according to claim 1, wherein
   histidine (H) is substituted with arginine (R), lysine (K), glutamine (Q), asparagine (N), phenylalanine (F), tyrosine (Y) or tryptophan (W);
   asparagine (N) is substituted with arginine (R), lysine (K), glutamine (Q), histidine (H), phenylalanine (F), tyrosine (Y) or tryptophan (W);
   proline (P) is substituted with arginine (R), lysine (K), glutamine (Q), asparagine (N), threonine (T), histidine (H), tyrosine (Y), phenylalanine (F), tryptophan (W), leucine (L), valine (V) or isoleucine (I);
   phenylalanine (F) is substituted with arginine (R), lysine (K), histidine (H), tyrosine (Y) or tryptophan (W);
   aspartic acid (D) is substituted with arginine (R), lysine (K), glutamine (Q), asparagine (N), histidine (H), phenylalanine (F), tyrosine (Y) or tryptophan (W);
   valine (V) is substituted with arginine (R), lysine (K), glutamine (Q), asparagine (N), histidine (H), phenylalanine (F), tyrosine (Y), tryptophan (W), isoleucine (I) or leucine (L);
   serine (S) is substituted with arginine (R), lysine (K), glutamine (Q), asparagine (N), histidine (H), phenylalanine (F), tyrosine (Y), tryptophan (W), isoleucine (I) or leucine (L); and/or
   tyrosine (Y) is substituted with arginine (R), lysine (K) or tryptophan (W).

10. The composition according to claim 1, wherein the helicase-sequence comprises a substitution corresponding to:

H82N;
H82Q;
H82W;
N88R;
N88H;
N88W;
N88Y;
P89L;
P89V;
P89I;
P89E;
P89T;
P89F;
D121H;
D121Y;
D121K;
V150I;
V150L;
V150N;
V150W;
V150H;
P152W;
P152F;
P152Y;
P152H;
P152I;
P152L;
P152V;
F240W;
F240Y;
F240H;
F276W;
F276R;
F276K;
F276H;
S287K;
S287R;
S287W;
S287F;
H396Y;
H396F;
H396Q;
H396K;
Y415W;

Y415R;
F98W/H82N;
F98W/H82Q;
F98W/H82W;
F98W/N88R;
F98W/N88H;
F98W/N88W;
F98W/N88Y;
F98W/P89L;
F98W/P89V;
F98W/P89I;
F98W/P89T;
F98W/P89F;
F98W/D121H;
F98W/D121Y;
F98W/D121K;
F98W/V150I;
F98W/V150L;
F98W/V150N;
F98W/V150W;
F98W/V150H;
F98W/P152W;
F98W/P152F;
F98W/P152Y;
F98W/P152H;
F98W/P152I;
F98W/P152L;
F98W/P152V;
F98W/F240W;
F98W/F240Y;
F98W/F240H;
F98W/F276W;
F98W/F276R;
F98W/F276K;
F98W/F276H;
F98W/S287K;
F98W/S287R;
F98W/S287W;
F98W/S287F;
F98W/H396Y;
F98W/H396F;
F98W/H396Q;
F98W/Y415W; or
F98W/Y415R in SEQ ID NO: 8.

11. The composition according to claim 2, wherein the amino acid with a larger side chain (R group) is a non-natural amino acid.

12. The composition according to claim 1, wherein the Dda helicase further comprises in (a) a substitution of at least one additional amino acid which interacts with one or more phosphate groups in one or more nucleotides in single stranded DNA (ssDNA).

13. The composition according to claim 12, wherein the substitution of at least one amino acid which interacts with one or more phosphates in one or more nucleotides in ssDNA increases the (i) electrostatic interactions, (ii) hydrogen bonding and/or (iii) cation-pi (cation-π) interactions between the at least one amino acid and the one or more phosphate groups in ssDNA.

14. The composition according to claim 13, wherein the substitution of at least one amino acid which interacts with one or more phosphates in one or more nucleotides in ssDNA increases the net positive charge of the position.

15. The composition according to claim 12, wherein the at least one amino acid which interacts with one or more phosphates in one or more nucleotides in ssDNA is at a residue corresponding to at least one of H64, T80, S83, N242, K243, N293, T394 and K397 in SEQ ID NO: 8.

16. The composition according to claim 15, wherein histidine (H) is substituted with arginine (R), lysine (K), asparagine (N), serine (S), glutamine (Q), threonine (T), phenylalanine (F), tryptophan (W) or tyrosine (Y);

threonine (T) is substituted with arginine (R), lysine (K), asparagine (N), serine (S), glutamine (Q), phenylalanine (F), tryptophan (W), tyrosine (Y) or histidine (H);

serine (S) is substituted with arginine (R), lysine (K), asparagine (N), glutamine (Q), threonine (T), phenylalanine (F), tryptophan (W), tyrosine (Y) or histidine (H);

asparagine (N) is substituted with arginine (R), lysine (K), serine (S), glutamine (Q), threonine (T), phenylalanine (F), tryptophan (W), tyrosine (Y) or histidine (H); and/or lysine (K) is substituted with arginine (R), asparagine (N), serine (S), glutamine (Q), threonine (T), phenylalanine (F), tryptophan (W), tyrosine (Y) or histidine (H).

17. The composition according to claim 12, wherein the substitution of at least one amino acid which interacts with one or more phosphates in one or more nucleotides in ssDNA, is with a non-natural amino acid.

18. The composition according to claim 12, wherein the helicase comprises one or more substitutions corresponding to one or more substitutions from the group consisting of (a) H64N, H64Q, H64K or H64F, (b) T80K, T80Q or T80N, (c) S83H, S83N, S83K, S83T, S83R, or S83Q (d) N242H or N242Q, (e) K243Q or K243H, (f) N293Q, N293K or N293H, (g) T394K, T394H or T394N and (h) K397R, K397H or K397Y in SEQ ID NO: 8.

19. The composition according to claim 1, wherein the helicase comprises substitutions at one or more residues corresponding to:

F98/H64, such as F98W/H64N, F98W/H64Q, F98W/H64K or F98W/H64F;

F98/T80, such as F98W/T80K, F98W/T80Q, F98W/T80N;

F98/H82, such as F98W/H82N, F98W/H82Q or F98W/H82W;

F98/S83, such as F98W/S83H, F98W/S83N, F98W/S83K, F98W/S83T, F98W/S83R or F98W/S83Q;

F98/N242, such as F98W/N242H, F98W/N242Q, F98W/K243Q or F98W/K243H;

F98/N293, such as F98W/N293Q, F98W/N293K, F98W/N293H, F98W/T394K, F98W/T394H, F98W/T394N, F98W/H396Y, F98W/H396F, F98W/H396Q or F98W/H396K; or F98/K397, such as F98W/K397R, F98W/K397H or F98W/K397Y in SEO ID NO: 8.

20. The composition according to claim 1, wherein the part of the helicase which interacts with a transmembrane pore comprises positions corresponding to 1, 2, 3, 4, 5, 6, 51, 176, 177, 178, 179, 180, 181, 185, 189, 191, 193, 194, 195, 197, 198, 199, 200, 201, 202, 203, 204, 207, 208, 209, 210, 211, 212, 213, 216, 219, 220, 221, 223, 224, 226, 227, 228, 229, 247, 254, 255, 256, 257, 258, 259, 260, 261, 298, 300, 304, 308, 318, 319, 321, 337, 347, 350, 351, 405, 415, 422, 434, 437, 438 in SEQ ID NO: 8;

(b) the part of the helicase which interacts with a transmembrane pore comprises positions 1, 2, 4, 51, 177, 178, 179, 180, 185, 193, 195, 197, 198, 199, 200, 202, 203, 204, 207, 208, 209, 210, 211, 212, 216, 221, 223, 224, 226, 227, 228, 229, 254, 255, 256, 257, 258, 260, 304, 318, 321, 347, 350, 351, 405, 415, 422, 434, 437 and 438 in SEQ ID NO: 8; or (c) the part of the helicase which interacts with a transmembrane pore comprises positions 1, 2, 178, 179, 180, 185, 195, 197, 198, 199, 200, 202, 203, 207, 209, 210, 212, 216, 221, 223, 226, 227, 255, 258, 260, 304, 350 and 438 in SEQ ID NO: 8.

21. The composition according to claim 20, wherein the helicase comprises a modification at one or more residues corresponding to one or more positions selected from the group consisting of (a) K194, (b) W195, (c) D198, (d) K199 and (e) E258.

22. The composition according to claim 1, wherein the helicase comprises substitutions at residues corresponding to:

F98/K194/H64, such as F98W/K194L/H64N, F98W/K194L/H64Q, F98W/K194L/H64K or F98W/K194L/H64F;

F98/K194/T80, such as F98W/K194L/T80K, F98W/K194L/T80Q or F98W/K194L/T80N;

F98/K194/H82, such as F98W/K194L/H82N, F98W/K194L/H82Q or F98W/K194L/H82W

F98/S83/K194, such as F98W/S83H/K194L, F98W/S83T/K194L, F98W/S83R/K194L, F98W/S83Q/K194L, F98W/S83N/K194L, F98W/S83K/K194L, F98W/N88R/K194L, F98W/N88H/K194L, F98W/N88K/K194L or F98W/N88Y/K194L;

F98/S83/K194/F276, such as F98W/S83H/K194L/F276K;

F98/P89/K194, such as F98W/P89L/K194L, F98W/P89V/K194L, F98W/P89I/K194L or F98W/P89T/K194L;

F98/D121/K194, such as F98W/D121H/K194L, F98W/D121Y/K194L or F98W/D121K/K194L;

F98/V150/K194, such as F98W/V150I/K194L, F98W/V150L/K194L, F98W/V150N/K194L, F98W/V150W/K194L or F98W/V150H/K194L;

F98/P152/K194, such as F98W/P152W/K194L, F98W/P152F/K194L, F98W/P152Y/K194L, F98W/P152H/K194L, F98W/P152I/K194L, F98W/P152L/K194L or F98W/P152V/K194L;

F98/F240/K194, such as F98W/F240W/K194L, F98W/F240Y/K194L or F98W/F240H/K194L;

F98/N242/K194, such as F98W/N242H/K194L or F98W/N242Q/K194L;

F98/K194/F276, such as F98W/K194L/F276K, F98W/K194L/F276H, F98W/K194L/F276W or F98W/K194L/F276R;

F98/K194/S287, such as F98W/K194L/S287K, F98W/K194L/S287R, F98W/K194L/S287W or F98W/K194L/S287F;

F98/N293/K194, such as F98W/N293Q/K194L, F98W/N293K/K194L or F98W/N293H/K194L;

F98/T394/K194, such as F98W/T394K/K194L, F98W/T394H/K194L or F98W/T394N/K194L;

F98/H396/K194, such as F98W/H396Y/K194L, F98W/H396F/K194L, F98W/H396Q/K194L or F98W/H396K/K194L;

F98/K397/K194, such as F98W/K397R/K194L, F98W/K397H/K194L or F98W/K397Y/K194L; or F98/Y415/K194, such as F98W/Y415W/K194L or F98W/Y415R/K194L in SEQ ID NO: 8.

23. The composition according to claim 1, wherein
(a) at least one cysteine residue and/or at least one non-natural amino acid have been introduced into (i) the tower domain of the Dda helicase and/or (ii) the pin domain of the Dda helicase and/or (iii) the 1A (RecA-like motor) domain of the Dda helicase;
(b) at least one cysteine residue and/or at least one non-natural amino acid have been introduced into the hook domain of the Dda helicase and/or the 2A (RecA-like motor) domain of the Dda helicase; or
(c) the Dda helicase is modified to reduce its surface negative charge.

24. The composition according to claim 1, wherein the helicase comprises substitutions corresponding to E94C, F98W, C109A, C136A, K194L and A360C in SEQ ID NO: 8.

25. The composition according to claim 1 further comprising an additional polynucleotide binding moiety, wherein the helicase is attached to the polynucleotide binding moiety.

26. The composition according to claim 25, wherein the composition comprises two or more helicases according to claim 1.

27. A kit for characterising a target polynucleotide comprising
(a) the composition according to claim 1.

28. An apparatus for characterising target polynucleotides in a sample, comprising a plurality of compositions according to claim 1.

29. The composition of claim 1, further comprising a second helicase.

30. The kit of claim 27, further comprising one or more loading moieties.

* * * * *

SEQUENCE LISTING

```
<160> NUMBER OF SEQ ID NOS: 73

<210> SEQ ID NO 1
<211> LENGTH: 552
<212> TYPE: DNA
<213> ORGANISM: Mycobacterium smegmatis

<400> SEQUENCE: 1
ggcctggata acgaacttag cctggtggac ggccaagatc gcacgctgac ggtgcaacaa      60
tgggatacct tcctgaatgg tgtgtttccg ctggatcgta accgcctgac ccgtgaatgg     120
tttcattccg gtcgcgcaaa atatatcgtc gcaggcccgg gtgctgacga attcgaaggc     180
acgctggaac tgggttatca gattggcttt ccgtggtcac tgggcgttgg tatcaacttc     240
tcgtacacca cgccgaatat tctgatcgat gacggtgata ttaccgcacc gccgtttggc     300
ctgaacagcg tgattacgcc gaacctgttt ccgggtgtta gcatctctgc cgatctgggc     360
aacggtccgg gcattcaaga agtggcaacc tttagtgtgg acgtttccgg cgctgaaggc     420
ggtgtcgcgg tgtctaatgc ccacggtacc gttacgggcg cggccggcgg tgtcctgctg     480
cgtccgttcg cgcgcctgat tgcgagcacc ggcgactctg ttacgaccta tggcgaaccg     540
tggaatatga ac                                                         552

<210> SEQ ID NO 2
<211> LENGTH: 184
<212> TYPE: PRT
<213> ORGANISM: Mycobacterium smegmatis

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
```

```
                115                 120                 125
Ala Thr Phe Ser Val Asp Val Ser Gly Ala Glu Gly Gly Val Ala Val
            130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct     300
gattactatc aagaaattc gattgataca aaaaactata tgagtacttt aacttatgga     360
ttcaacggta atgttactgg tgatgataca ggaaaaattg gcggccttat tggtgcaaat     420
gtttcgattg gtcatacact gaactatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga tgtaatatac gaacgagttc gtgatgatta ccaattgcat     780
tggacttcaa caaattggaa aggtaccaat actaaagata aatggacaga tcgttcttca     840
gaaagatata aaatcgattg ggaaaaagaa gaatgacaa attaa                      885
```

<210> SEQ ID NO 4
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80
```

```
Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
        130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
        130                 135                 140

Ser Asn Ala His Gly Thr Val Thr Gly Ala Ala Gly Gly Val Leu Leu
145                 150                 155                 160
```

```
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 6
<211> LENGTH: 184
<212> TYPE: PRT
<213> ORGANISM: Mycobacterium smegmatis

<400> SEQUENCE: 6

```
Gly Leu Asp Asn Glu Leu Ser Leu Val Asp Gly Gln Asp Arg Thr Leu
1               5                   10                  15
Thr Val Gln Gln Trp Asp Thr Phe Leu Asn Gly Val Phe Pro Leu Asp
            20                  25                  30
Arg Asn Arg Leu Thr Arg Glu Trp Phe His Ser Gly Arg Ala Lys Tyr
        35                  40                  45
Ile Val Ala Gly Pro Gly Ala Asp Glu Phe Glu Gly Thr Leu Glu Leu
    50                  55                  60
Gly Tyr Gln Ile Gly Phe Pro Trp Ser Leu Gly Val Gly Ile Asn Phe
65                  70                  75                  80
Ser Tyr Thr Thr Pro Asn Ile Leu Ile Asp Asp Gly Asp Ile Thr Gly
                85                  90                  95
Pro Pro Phe Gly Leu Glu Ser Val Ile Thr Pro Asn Leu Phe Pro Gly
            100                 105                 110
Val Ser Ile Ser Ala Asp Leu Gly Asn Gly Pro Gly Ile Gln Glu Val
        115                 120                 125
Ala Thr Phe Ser Val Asp Val Ser Gly Pro Ala Gly Gly Val Ala Val
    130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 7
<211> LENGTH: 183
<212> TYPE: PRT
<213> ORGANISM: Mycobacterium smegmatis

<400> SEQUENCE: 7

```
Val Asp Asn Gln Leu Ser Val Val Asp Gly Gln Gly Arg Thr Leu Thr
1               5                   10                  15
Val Gln Gln Ala Glu Thr Phe Leu Asn Gly Val Phe Pro Leu Asp Arg
            20                  25                  30
Asn Arg Leu Thr Arg Glu Trp Phe His Ser Gly Arg Ala Thr Tyr His
        35                  40                  45
Val Ala Gly Pro Gly Ala Asp Glu Phe Glu Gly Thr Leu Glu Leu Gly
    50                  55                  60
Tyr Gln Val Gly Phe Pro Trp Ser Leu Gly Val Gly Ile Asn Phe Ser
65                  70                  75                  80
Tyr Thr Thr Pro Asn Ile Leu Ile Asp Gly Gly Asp Ile Thr Gln Pro
                85                  90                  95
Pro Phe Gly Leu Asp Thr Ile Ile Thr Pro Asn Leu Phe Pro Gly Val
            100                 105                 110
```

Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
        130                 135                 140

Asn Ala His Gly Thr Val Thr Gly Ala Ala Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 439
<212> TYPE: PRT
<213> ORGANISM: Enterobacteria phage T4

<400> SEQUENCE: 8

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
            195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Val Met Gln
            260                 265                 270

Glu Pro Leu Phe Lys Thr Tyr Lys Ile Asp Gly Lys Pro Val Ser Glu
    275                 280                 285

Ile Ile Phe Asn Asn Gly Gln Leu Val Arg Ile Ile Glu Ala Glu Tyr

-continued

```
            290                 295                 300
Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Glu Tyr Tyr
                325                 330                 335

Arg Glu Lys Ile Lys Ile Ile Ser Ser Asp Glu Glu Leu Tyr Lys Phe
                340                 345                 350

Asn Leu Phe Leu Gly Lys Thr Ala Glu Thr Tyr Lys Asn Trp Asn Lys
                355                 360                 365

Gly Gly Lys Ala Pro Trp Ser Asp Phe Trp Asp Ala Lys Ser Gln Phe
370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
                420                 425                 430

Arg Tyr Asp Val Phe Tyr Val
                435
```

<210> SEQ ID NO 9
<211> LENGTH: 678
<212> TYPE: PRT
<213> ORGANISM: Rhodothermus marinus

<400> SEQUENCE: 9

```
Met Glu Glu Leu Ser Asn Glu Gln Gln Arg Val Leu Asp His Val Leu
1               5                   10                  15

Ala Trp Leu Glu Arg Asn Asp Ala Pro Pro Ile Phe Ile Leu Thr Gly
                20                  25                  30

Ser Ala Gly Thr Gly Lys Thr Leu Leu Ile Arg His Leu Val Arg Ala
                35                  40                  45

Leu Gln Asp Arg Arg Ile His Tyr Ala Leu Ala Ala Pro Thr Gly Arg
50                  55                  60

Ala Ala Arg Ile Leu Ser Glu Arg Thr Gly Asp His Ala Arg Thr Leu
65                  70                  75                  80

His Ser Leu Ile Tyr Ile Phe Asp Arg Tyr Gln Leu Val Glu Glu Ala
                85                  90                  95

Asp Arg Gln Thr Asp Glu Pro Leu Ser Leu Gln Leu His Phe Ala Leu
                100                 105                 110

Arg Ser Ala Glu His Asp Ala Arg Leu Ile Ile Val Asp Glu Ala Ser
                115                 120                 125

Met Val Ser Asp Thr Ala Gly Glu Glu Leu Tyr Arg Phe Gly Ser
130                 135                 140

Gly Arg Leu Leu Asn Asp Leu Leu Thr Phe Ala Arg Leu Ile Pro Lys
145                 150                 155                 160

Arg Asp Arg Pro Pro Thr Thr Arg Leu Leu Phe Val Gly Asp Pro Ala
                165                 170                 175

Gln Leu Pro Pro Val Gly Gln Ser Val Ser Pro Ala Leu Ser Ala Gln
                180                 185                 190

Tyr Leu Arg Asp Thr Phe Gly Leu Ser Ala Glu Thr Ala His Leu Arg
                195                 200                 205

Ser Val Tyr Arg Gln Arg Lys Gly His Pro Ile Leu Glu Thr Ala Thr
210                 215                 220
```

```
Ala Leu Arg Asn Ala Leu Glu Lys Gly His Tyr His Thr Phe Arg Leu
225                 230                 235                 240

Pro Glu Gln Pro Pro Asp Leu Arg Pro Val Gly Leu Glu Glu Ala Ile
            245                 250                 255

Glu Thr Thr Ala Thr Asp Phe Arg Arg Gln Asn Pro Ser Val Leu Leu
                260                 265                 270

Cys Arg Thr Asn Ala Leu Ala Arg Lys Leu Asn Ala Ala Val Arg Ala
            275                 280                 285

Arg Leu Trp Gly Arg Glu Gly Leu Pro Pro Gln Pro Gly Asp Leu Leu
        290                 295                 300

Leu Val Asn Arg Asn Ala Pro Leu His Gly Leu Phe Asn Gly Asp Leu
305                 310                 315                 320

Val Leu Val Glu Thr Val Gly Pro Leu Glu His Arg Arg Val Gly Arg
                325                 330                 335

Arg Gly Arg Pro Pro Val Asp Leu Tyr Phe Arg Asp Val Glu Leu Leu
            340                 345                 350

Tyr Pro His Glu Lys Pro Arg Asn Arg Ile Arg Cys Lys Leu Leu Glu
        355                 360                 365

Asn Leu Leu Glu Ser Pro Asp Gly Gln Leu Ser Pro Asp Ile Ile Gln
370                 375                 380

Ala Leu Leu Ile Asp Phe Tyr Arg Arg His Pro Ser Leu Lys His Gly
385                 390                 395                 400

Ser Ser Glu Phe Arg Leu Met Leu Ala Asn Asp Ala Tyr Phe Asn Ala
                405                 410                 415

Leu His Val Arg Tyr Gly Tyr Ala Met Thr Val His Lys Ala Gln Gly
            420                 425                 430

Gly Glu Trp Lys Arg Ala Thr Val Val Phe Asn Asp Trp Arg His Phe
        435                 440                 445

Arg His Ala Glu Phe Phe Arg Trp Ala Tyr Thr Ala Ile Thr Arg Ala
450                 455                 460

Arg Glu Glu Leu Leu Thr Ile Gly Ala Pro Ser Phe Glu Ala Leu Ser
465                 470                 475                 480

Asp Met Arg Trp Gln Pro Ala Pro Ser Val Pro Ala Pro Glu Gln Ala
                485                 490                 495

Ala Glu Asn Ala Thr Arg Phe Pro Leu Lys Ala Leu Glu Thr Tyr His
            500                 505                 510

Gln Arg Leu Ser Glu Ala Leu Thr Ala Ala Gly Ile Glu Thr Thr Gly
        515                 520                 525

Val Glu Leu Leu Gln Tyr Ala Val Arg Tyr His Leu Ala Arg Ala Asp
530                 535                 540

Arg Thr Thr Arg Ile Gln Tyr Tyr Arg Gly Asp Gly Gln Ile Ser
545                 550                 555                 560

Arg Ile Val Thr Leu Gly Gly Ala Asp Asp Pro Glu Leu Thr Gln Gln
            565                 570                 575

Ala Tyr Ala Leu Phe Glu Arg Ile Leu Ser Glu Pro Ala Asp Ser
        580                 585                 590

Gly Glu Leu Pro Glu Asn Pro Leu Arg Glu Phe Leu Glu Arg Ala
                595                 600                 605

His Leu Arg Leu Glu Gly Ser Gly Ile Arg Ile Val His Trp Lys Glu
            610                 615                 620

Met Pro Tyr Ala Leu Arg Leu Tyr Phe Ser Ala Asp Gly Glu Asn Val
625                 630                 635                 640

Thr Ile Asp Phe Tyr Tyr Asn Arg Arg Gly Val Trp Thr His Ala Gln
```

645                 650                 655
Glu Val Gly Arg Ser Ser Ser Gly Ala Leu Phe Ala Arg Ile Gln Ser
                    660                 665                 670

Leu Leu Gln Ala Asp Ser
            675

<210> SEQ ID NO 10
<211> LENGTH: 496
<212> TYPE: PRT
<213> ORGANISM: Cyanothece ATCC51142

<400> SEQUENCE: 10

Met Ser Gln Ser Val Val Pro Asp Glu Leu Gly Glu Ile Ile Thr
1               5                   10                  15

Ala Val Ile Glu Phe Tyr Gln Asp Ala Val Asp Lys Ile Glu Pro Lys
                20                  25                  30

Ile Val Phe Leu Glu Leu Arg Lys Asn Val Val Asp Trp Val Ser Arg
            35                  40                  45

Thr Gln Leu Lys Ile Glu Glu Lys Glu Ile Gln Ala Thr Gly Leu Thr
        50                  55                  60

Arg Gln Gln Gln Thr Ala Tyr Lys Glu Met Ile Asn Phe Ile Glu Asn
65                  70                  75                  80

Ser Ser Glu Gln Tyr Phe Arg Leu Ser Gly Tyr Ala Gly Thr Gly Lys
                85                  90                  95

Ser Phe Leu Met Ala Lys Val Ile Glu Trp Leu Lys Gln Glu Asp Tyr
                100                 105                 110

Lys Tyr Ser Val Ala Ala Pro Thr Asn Lys Ala Ala Lys Asn Leu Thr
            115                 120                 125

Gln Ile Ala Arg Ser Gln Gly Ile Lys Ile Glu Ala Thr Thr Val Ala
        130                 135                 140

Lys Leu Leu Lys Leu Gln Pro Thr Ile Asp Val Asp Thr Gly Gln Gln
145                 150                 155                 160

Ser Phe Glu Phe Asn Ser Glu Lys Glu Leu Glu Leu Lys Asp Tyr Asp
                165                 170                 175

Val Ile Ile Ile Asp Glu Tyr Ser Met Leu Asn Lys Asp Asn Phe Arg
                180                 185                 190

Asp Leu Gln Gln Ala Val Lys Gly Gly Glu Ser Lys Phe Ile Phe Val
            195                 200                 205

Gly Asp Ser Ser Gln Leu Pro Pro Val Lys Glu Lys Glu Pro Ile Val
        210                 215                 220

Ala Asn His Pro Asp Ile Arg Lys Ser Ala Asn Leu Thr Gln Ile Val
225                 230                 235                 240

Arg Tyr Asp Gly Glu Ile Val Lys Val Ala Glu Ser Ile Arg Arg Asn
                245                 250                 255

Pro Arg Trp Asn His Gln Thr Tyr Pro Phe Glu Thr Val Ala Asp Gly
            260                 265                 270

Thr Ile Ile Lys Leu Asn Thr Glu Asp Trp Leu Gln Gln Ala Leu Ser
        275                 280                 285

His Phe Glu Lys Glu Asp Trp Leu Ser Asn Pro Asp Tyr Val Arg Met
        290                 295                 300

Ile Thr Trp Arg Asn Lys Thr Ala Asp Lys Tyr Asn Gln Ala Ile Arg
305                 310                 315                 320

Glu Ala Leu Tyr Gly Glu Asn Val Glu Gln Leu Val Val Gly Asp Arg
                325                 330                 335

```
Leu Ile Ala Lys Lys Pro Val Phe Arg Ser Leu Pro Gly Gly Lys Lys
            340                 345                 350

Lys Glu Lys Ile Ile Leu Asn Asn Ser Glu Glu Cys Lys Val Ile
            355                 360                 365

Glu Thr Pro Lys Ile Asn Tyr Asn Glu Lys Tyr Lys Trp Glu Phe Tyr
            370                 375                 380

Gln Val Lys Val Arg Thr Asp Glu Gly Gly Met Ile Glu Leu Arg Ile
385                 390                 395                 400

Leu Thr Ser Glu Ser Glu Glu Lys Arg Gln Lys Lys Leu Lys Glu Leu
            405                 410                 415

Ala Lys Arg Ala Arg Glu Glu Asn Tyr Ser Glu Lys Lys Gln
            420                 425                 430

Trp Ala Ile Tyr Tyr Glu Leu Asp Glu Leu Phe Asp Asn Met Ala Tyr
            435                 440                 445

Ala Tyr Ala Leu Thr Cys His Lys Ala Gln Gly Ser Ser Ile Asp Asn
            450                 455                 460

Val Phe Leu Leu Val Ser Asp Met His Tyr Cys Arg Asp Lys Thr Lys
465                 470                 475                 480

Met Ile Tyr Thr Gly Leu Thr Arg Ala Lys Lys Cys Cys Tyr Val Gly
            485                 490                 495

<210> SEQ ID NO 11
<211> LENGTH: 421
<212> TYPE: PRT
<213> ORGANISM: Salinibacter ruber

<400> SEQUENCE: 11

Met Ser Thr Phe Ala Asp Ala Pro Phe Thr Glu Asp Gln Glu Glu Ala
1               5                   10                  15

Tyr Asp His Val Tyr Asp Arg Leu Ala Gln Gly Glu Arg Phe Thr Gly
            20                  25                  30

Leu Arg Gly Tyr Ala Gly Thr Gly Lys Thr Tyr Leu Val Ser Arg Leu
        35                  40                  45

Val Glu Gln Leu Leu Asp Glu Asp Cys Thr Val Thr Val Cys Ala Pro
    50                  55                  60

Thr His Lys Ala Val Gln Val Leu Ser Asp Glu Leu Gly Asp Ala Pro
65              70                  75                  80

Val Gln Met Gln Thr Leu His Ser Phe Leu Gly Leu Arg Leu Gln Pro
            85                  90                  95

Lys Gln Asp Gly Glu Tyr Glu Leu Val Ala Glu Glu Arg Asn Phe
        100                 105                 110

Ala Glu Gly Val Val Ile Val Asp Glu Ala Ser Met Ile Gly Arg Glu
    115                 120                 125

Glu Trp Ser His Ile Gln Asp Ala Pro Phe Trp Val Gln Trp Leu Phe
130                 135                 140

Val Gly Asp Pro Ala Gln Leu Pro Pro Val Asn Glu Asp Pro Ser Pro
145                 150                 155                 160

Ala Leu Asp Val Pro Gly Pro Thr Leu Glu Thr Ile His Arg Gln Ala
            165                 170                 175

Ala Asp Asn Pro Ile Leu Glu Leu Ala Thr Lys Ile Arg Thr Gly Ala
        180                 185                 190

Asp Gly Arg Phe Gly Ser Thr Phe Glu Asp Gly Lys Gly Val Ala Val
    195                 200                 205

Thr Arg Asn Arg Glu Glu Phe Leu Asp Ser Ile Leu Arg Ala Phe Asp
210                 215                 220
```

-continued

```
Ala Asp Ala Phe Ala Glu Asp Ala Thr His Ala Arg Val Leu Ala Tyr
225                 230                 235                 240

Arg Asn Lys Thr Val Arg Arg Tyr Asn Arg Glu Ile Arg Ala Glu Arg
                245                 250                 255

Tyr Gly Ala Asp Ala Asp Arg Phe Val Glu Gly Glu Trp Leu Val Gly
            260                 265                 270

Thr Glu Thr Trp Tyr Tyr Asp Gly Val Gln Arg Leu Thr Asn Ser Glu
        275                 280                 285

Glu Val Arg Val Lys Ala Gln Val Glu Thr Phe Glu Ala Asp Asp
    290                 295                 300

Gln Ser Glu Trp Thr Val Trp Glu Leu Lys Ile Arg Thr Pro Gly Arg
305                 310                 315                 320

Gly Leu Thr Arg Thr Ile His Val Leu His Glu Glu Arg Glu Arg
                325                 330                 335

Tyr Glu Asn Ala Leu Glu Arg Arg Gly Lys Ala Glu Asp Asp Pro
            340                 345                 350

Ser Lys Trp Asp Arg Phe Phe Glu Leu Arg Glu Arg Phe Ala Arg Val
        355                 360                 365

Asp Tyr Ala Tyr Ala Thr Thr Val His Arg Ala Gln Gly Ser Thr Tyr
370                 375                 380

Asp Thr Val Phe Val Asp His Arg Asp Leu Arg Val Cys Arg Gly Glu
385                 390                 395                 400

Glu Arg Gly Ala Leu Leu Tyr Val Ala Val Thr Arg Pro Ser Arg Arg
                405                 410                 415

Leu Ala Leu Leu Val
            420

<210> SEQ ID NO 12
<211> LENGTH: 500
<212> TYPE: PRT
<213> ORGANISM: Sullfurimonas gotlandica GD1

<400> SEQUENCE: 12

Met Lys Ile Leu Asn Lys Glu Thr Tyr Lys Leu Ser Leu His Gln Glu
1               5                   10                  15

Glu Val Phe Thr Gln Ile Val Ser Gln Leu Asp Thr Lys Val Ser Ser
            20                  25                  30

Ile Leu Lys Ser Thr Asn Ile Glu Asp Tyr Leu Leu Ser Leu Thr Gly
        35                  40                  45

Pro Ala Gly Thr Gly Lys Thr Phe Leu Thr Thr Gln Ile Ala Lys Tyr
    50                  55                  60

Leu Val Glu Lys Arg Lys Glu Ser Glu Tyr Pro Met Ser Ser Asp Phe
65                  70                  75                  80

Asp Phe Thr Ile Thr Ala Pro Thr His Lys Ala Val Gly Val Leu Ser
                85                  90                  95

Lys Leu Leu Arg Glu Asn Asn Ile Gln Ser Ser Cys Lys Thr Ile His
            100                 105                 110

Ser Phe Leu Gly Ile Lys Pro Phe Ile Asp Tyr Thr Thr Gly Glu Glu
        115                 120                 125

Lys Phe Val Val Asp Lys Thr Asn Lys Arg Lys Asp Arg Thr Ser Ile
    130                 135                 140

Leu Ile Val Asp Glu Ser Ser Met Ile Gly Asn Thr Leu Tyr Glu Tyr
145                 150                 155                 160

Ile Leu Glu Ala Ile Glu Asp Lys Arg Val Asn Val Val Leu Phe Ile
```

```
                    165                 170                 175
Gly Asp Pro Tyr Gln Leu Leu Pro Ile Glu Asn Ser Lys Asn Glu Ile
                180                 185                 190

Tyr Asp Leu Pro Asn Arg Phe Phe Leu Ser Glu Val Val Arg Gln Ala
            195                 200                 205

Glu Asn Ser Tyr Ile Ile Arg Val Ala Thr Lys Leu Arg Glu Arg Ile
        210                 215                 220

Lys Asn Gln Asp Phe Ile Ser Leu Gln Gln Phe Phe Gln Glu Asn Met
225                 230                 235                 240

Glu Asp Glu Ile Thr Phe Phe His Asn Lys Glu Ala Phe Leu Glu Asp
                245                 250                 255

Phe Tyr Lys Glu Glu Glu Trp Tyr Glu Asn Lys Ile Leu Ala Thr
            260                 265                 270

Tyr Lys Asn Lys Asp Val Asp Ala Phe Asn Lys Ile Ile Arg Asn Lys
        275                 280                 285

Phe Trp Glu Gln Lys Gly Asn Thr Thr Pro Ser Thr Leu Leu Ala Gly
        290                 295                 300

Asp Met Ile Arg Phe Lys Asp Ala Tyr Thr Val Gly Asp Ile Thr Ile
305                 310                 315                 320

Tyr His Asn Gly Gln Glu Leu Gln Leu Gly Ser Thr Glu Val Lys Tyr
                325                 330                 335

His Asp Ser Leu His Ile Glu Tyr Trp Glu Cys Lys Ser Ile Tyr Ala
            340                 345                 350

Leu Glu Gln Gln Val Phe Arg Val Val Asn Pro Asp Ser Glu Ala Val
        355                 360                 365

Phe Asn Gln Lys Leu Gln Ser Leu Ala Thr Lys Ala Lys Gln Ala Lys
    370                 375                 380

Phe Pro Asp Asn Lys Lys Leu Trp Lys Leu Tyr Tyr Glu Thr Arg Asn
385                 390                 395                 400

Met Phe Ala Asn Val Gln Tyr Ile His Ala Ser Thr Ile His Lys Leu
                405                 410                 415

Gln Gly Ser Thr Tyr Asp Val Ser Tyr Ile Asp Ile Phe Ser Leu Val
            420                 425                 430

His Asn His Tyr Met Ser Asp Glu Lys Tyr Arg Leu Leu Tyr Val
        435                 440                 445

Ala Ile Thr Arg Ala Ser Lys Asp Ile Lys Ile Phe Met Ser Ala Phe
    450                 455                 460

Asp Arg Thr Ser Asp Glu Lys Val Ile Ile Asn Asn Gln Asn Ser Glu
465                 470                 475                 480

Thr Met Asn Thr Leu Lys Gln Leu His Asp Ile Asp Ile Ile Leu Lys
                485                 490                 495

Asp Leu Asp Leu
            500

<210> SEQ ID NO 13
<211> LENGTH: 450
<212> TYPE: PRT
<213> ORGANISM: Vibrio phage henriette 12B8

<400> SEQUENCE: 13

Met Ala Asp Phe Glu Leu Thr Leu Gly Gln Lys Thr Val Leu Gly Glu
1               5                   10                  15

Val Ile Ser Thr Ile Leu Lys Pro Val Asn Leu Asn Asp Thr Ser Arg
            20                  25                  30
```

```
Phe His Thr Met His Gly Pro Ala Gly Ser Gly Lys Thr Val Leu
         35                  40                  45

Gln Arg Ile Ile Ser Gln Ile Pro Ala Tyr Lys Thr Ile Gly Phe Cys
 50                  55                  60

Ser Pro Thr His Lys Ser Val Lys Val Ile Arg Arg Met Ala Arg Glu
 65                  70                  75                  80

Ala Gly Ile Ser His Arg Val Asp Ile Arg Thr Ile His Ser Ala Leu
                 85                  90                  95

Gly Leu Val Met Lys Pro Val Arg Gly Asp Glu Val Leu Val Lys Glu
                100                 105                 110

Pro Phe Ala Glu Glu Arg Ile Tyr Asp Val Leu Ile Ile Asp Glu Ala
        115                 120                 125

Gly Met Leu Asn Asp Glu Leu Ile Met Tyr Ile Leu Glu Ser Gln Ser
130                 135                 140

Ser Lys Val Ile Phe Val Gly Asp Met Cys Gln Ile Gly Pro Ile Gln
145                 150                 155                 160

Ser Asn Leu Pro Glu Glu Asp Gly Tyr Thr Pro Thr Ser Thr Asp Asp
                165                 170                 175

Val Ser Lys Val Phe Thr Glu Val Glu Met Met Ser Ala Leu Thr Glu
                180                 185                 190

Val Val Arg Gln Ala Glu Gly Ser Pro Ile Ile Gln Leu Ala Thr Glu
        195                 200                 205

Phe Arg Leu Ala Gln Asp Asp Ile Tyr Ala Asp Leu Pro Arg Ile Val
        210                 215                 220

Thr Asn Thr Thr Pro Asp Gly Asn Gly Ile Ile Thr Met Pro Asn Gly
225                 230                 235                 240

Asn Trp Val Asp Ser Ala Val Ala Arg Phe Gln Ser Asp Gln Phe Lys
                245                 250                 255

Glu Asp Pro Asp His Cys Arg Ile Val Cys Tyr Thr Asn Ala Met Val
                260                 265                 270

Asp Leu Cys Asn Asp Leu Val Arg Lys Arg Leu Phe Gly Ala Asp Val
        275                 280                 285

Pro Glu Trp Leu Glu Asp Glu Ile Leu Val Ala Gln Glu Met Gly Ser
290                 295                 300

Thr Trp Asn Asn Ala Asp Glu Leu Arg Ile Val Ser Ile Asp Asp His
305                 310                 315                 320

Phe Asp Gln Gln Tyr Glu Val Pro Cys Trp Arg Met Gln Leu Glu Ser
                325                 330                 335

Val Glu Asp His Lys Leu His Asn Ala Leu Val Val Lys Gly Asp Tyr
                340                 345                 350

Ile Glu Asp Phe Lys Phe Arg Leu Asn Ala Ile Ala Glu Arg Ala Asn
        355                 360                 365

Thr Asp Lys Asn Met Ser Gly Met His Trp Lys Glu Phe Trp Gly Met
        370                 375                 380

Arg Lys Lys Phe Asn Thr Phe Lys Asn Val Tyr Ala Gly Thr Ala His
385                 390                 395                 400

Lys Ser Gln Gly Ser Thr Phe Asp Tyr Thr Tyr Val Phe Thr Pro Asp
                405                 410                 415

Phe Tyr Lys Phe Gly Ala Thr Met Thr Ile Lys Arg Leu Leu Tyr Thr
                420                 425                 430

Ala Ile Thr Arg Ser Arg Tyr Thr Thr Tyr Phe Ala Met Asn Thr Gly
        435                 440                 445

Ala Gln
```

<210> SEQ ID NO 14
<211> LENGTH: 421
<212> TYPE: PRT
<213> ORGANISM: Vibrio phage phi-pp2

<400> SEQUENCE: 14

```
Met Gly Leu Thr Asn Cys Gln Gln Gly Ala Met Asp Ala Phe Leu Glu
1               5                   10                  15

Ser Asp Gly His Met Thr Ile Ser Gly Pro Ala Gly Ser Gly Lys Thr
            20                  25                  30

Phe Leu Met Lys Ser Ile Leu Glu Ala Leu Glu Ser Lys Gly Lys Asn
        35                  40                  45

Val Thr Met Val Thr Pro Thr His Gln Ala Lys Asn Val Leu His Lys
    50                  55                  60

Ala Thr Gly Gln Glu Val Ser Thr Ile His Ser Leu Leu Lys Ile His
65                  70                  75                  80

Pro Asp Thr Tyr Glu Asp Gln Lys His Phe Thr Gln Ser Gly Glu Val
                85                  90                  95

Glu Gly Leu Asp Glu Ile Asp Val Leu Val Glu Glu Ala Ser Met
            100                 105                 110

Val Asp Glu Glu Leu Phe Gln Ile Thr Gly Arg Thr Met Pro Arg Lys
        115                 120                 125

Cys Arg Ile Leu Ala Val Gly Asp Lys Tyr Gln Leu Gln Pro Val Lys
    130                 135                 140

His Asp Pro Gly Val Ile Ser Pro Phe Phe Thr Lys Phe Thr Thr Phe
145                 150                 155                 160

Glu Met Asn Glu Val Val Arg Gln Ala Lys Asp Asn Pro Leu Ile Gln
                165                 170                 175

Val Ala Thr Glu Val Arg Asn Gly Gln Trp Leu Arg Thr Asn Trp Ser
            180                 185                 190

Lys Glu Arg Arg Gln Gly Val Leu His Val Pro Asn Val Asn Lys Met
        195                 200                 205

Leu Asp Thr Tyr Leu Ser Lys Val Asn Ser Pro Glu Asp Leu Leu Asp
    210                 215                 220

Tyr Arg Ile Leu Ala Tyr Thr Asn Asp Cys Val Asp Thr Phe Asn Gly
225                 230                 235                 240

Ile Ile Arg Glu His Val Tyr Asn Thr Ser Glu Pro Phe Ile Pro Gly
                245                 250                 255

Glu Tyr Leu Val Thr Gln Met Pro Val Met Val Ser Asn Gly Lys Tyr
            260                 265                 270

Pro Val Cys Val Ile Glu Asn Gly Glu Val Val Lys Ile Leu Asp Val
        275                 280                 285

Arg Gln Lys Thr Ile Asp Gly Met Leu Pro Lys Val Asp Asn Glu Ala
    290                 295                 300

Phe Asp Val Ala Val Leu Thr Val Glu Lys Glu Asp Gly Asn Val Tyr
305                 310                 315                 320

Glu Phe Thr Val Leu Trp Asp Asp Leu Gln Lys Glu Arg Phe Ala Arg
                325                 330                 335

Tyr Leu Ser Val Ala Ala Gly Thr Tyr Lys Ser Met Arg Gly Asn Thr
            340                 345                 350

Lys Arg Tyr Trp Arg Ala Phe Trp Gly Leu Lys Glu Gln Met Ile Glu
        355                 360                 365
```

-continued

```
Thr Lys Ser Leu Gly Ala Ser Thr Val His Lys Ser Gln Gly Thr Thr
    370                 375                 380

Val Lys Gly Val Cys Leu Tyr Thr Gln Asp Met Gly Tyr Ala Glu Pro
385                 390                 395                 400

Glu Ile Leu Gln Gln Leu Val Tyr Val Gly Leu Thr Arg Pro Thr Asp
                405                 410                 415

Trp Ala Leu Tyr Asn
                420

<210> SEQ ID NO 15
<211> LENGTH: 434
<212> TYPE: PRT
<213> ORGANISM: Aeromonas phage 65

<400> SEQUENCE: 15

Met Ser Glu Ser Glu Ile Thr Leu Thr Pro Ser Gln Asn Met Ala Val
1               5                   10                  15

Asn Glu Val Lys Asn Gly Thr Gly His Ile Thr Ile Ser Gly Pro Pro
            20                  25                  30

Gly Ser Gly Lys Thr Phe Leu Val Lys Tyr Leu Ile Lys Met Leu Gly
        35                  40                  45

Asp Glu Leu Gly Thr Val Leu Ala Ala Pro Thr His Gln Ala Lys Ile
    50                  55                  60

Val Leu Thr Glu Met Ser Gly Ile Glu Ala Cys Thr Ile His Ser Leu
65                  70                  75                  80

Met Lys Ile His Pro Glu Thr Leu Glu Asp Ile Gln Ile Phe Asp Gln
                85                  90                  95

Ser Lys Leu Pro Asp Leu Ser Asn Ile Arg Tyr Leu Ile Val Glu Glu
            100                 105                 110

Ala Ser Met His Ser Lys Thr Leu Phe Lys Ile Thr Met Lys Ser Ile
        115                 120                 125

Pro Pro Thr Cys Arg Ile Ile Ala Ile Gly Asp Lys Asp Gln Ile Gln
    130                 135                 140

Pro Glu Glu His Ala Gln Gly Glu Leu Ser Pro Tyr Phe Thr Asp Pro
145                 150                 155                 160

Arg Phe Ser Gln Ile Arg Leu Thr Asp Ile Met Arg Gln Ser Leu Asp
                165                 170                 175

Asn Pro Ile Ile Gln Val Ala Thr Lys Ile Arg Glu Gly Gly Trp Ile
            180                 185                 190

Glu Pro Asn Trp Asn Arg Asp Thr Lys Thr Gly Val Tyr Lys Val Ser
        195                 200                 205

Gly Ile Thr Asp Leu Val Asn Ser Tyr Leu Arg Ala Val Lys Thr Pro
    210                 215                 220

Glu Asp Leu Thr Lys Tyr Arg Phe Leu Ala Tyr Thr Asn Lys Val Val
225                 230                 235                 240

Asn Lys Val Asn Ser Ile Val Arg Glu His Val Tyr Lys Thr Lys Leu
                245                 250                 255

Pro Phe Ile Glu Gly Glu Lys Ile Val Leu Gln Glu Pro Val Met Val
            260                 265                 270

Glu His Glu Asp Thr Ile Glu Thr Ile Phe Thr Asn Gly Glu Val
        275                 280                 285

Val Thr Ile Asn Glu Ile Glu Val Phe Asp Arg Thr Ile Arg Ile Asp
    290                 295                 300

Gly Ser Pro Glu Phe Lys Val Asn Ala Ala Lys Leu Ser Val Ser Ser
305                 310                 315                 320
```

```
Asp Tyr Ser Gly Ile Glu His Asp Phe Cys Val Leu Tyr Gly Ser Glu
            325                 330                 335

Ser Arg Leu Glu Phe Glu Tyr Gln Leu Ser Glu Ser Ala Gly Asn Ile
            340                 345                 350

Lys Gln Met Gly Lys Gly Gly Asn Gln Arg Ser Ala Trp Lys Ser Phe
            355                 360                 365

Trp Ala Ala Lys Lys Met Phe Ile Glu Thr Lys Ser Leu Gly Ala Ser
            370                 375                 380

Thr Ile His Lys Ser Gln Gly Ser Thr Val Lys Gly Val Trp Leu Ala
385                 390                 395                 400

Leu His Asp Ile His Tyr Ala Asp Glu Glu Leu Lys Gln Gln Leu Val
                    405                 410                 415

Tyr Val Gly Val Thr Arg Pro Thr Asp Phe Cys Leu Tyr Phe Asp Gly
            420                 425                 430

Thr Lys

<210> SEQ ID NO 16
<211> LENGTH: 420
<212> TYPE: PRT
<213> ORGANISM: Aeromonas phage CC2

<400> SEQUENCE: 16

Met Ala Val Asp Ala Val Gln Ser Gly Thr Gly His Ile Thr Ile Ser
1               5                   10                  15

Gly Pro Pro Gly Ser Gly Lys Thr Phe Leu Val Lys Tyr Ile Ile Lys
            20                  25                  30

Met Leu Gly Asp Glu Leu Gly Thr Val Leu Ala Ala Pro Thr His Gln
            35                  40                  45

Ala Lys Ile Val Leu Thr Glu Met Ser Gly Ile Glu Ala Cys Thr Ile
        50                  55                  60

His Ser Leu Met Lys Ile His Pro Glu Thr Leu Glu Asp Ile Gln Ile
65                  70                  75                  80

Phe Asp Gln Ser Lys Met Pro Asp Leu Ser Thr Val Arg Tyr Leu Ile
                85                  90                  95

Ile Glu Glu Ala Ser Met His Ser Lys Ala Leu Phe Asn Ile Thr Met
            100                 105                 110

Lys Ser Ile Pro Pro Thr Cys Arg Ile Ala Ile Gly Asp Lys Asp
            115                 120                 125

Gln Ile Gln Pro Val Asp His Ala Pro Gly Glu Leu Ser Pro Tyr Phe
        130                 135                 140

Thr Asp Ser Arg Phe Thr Gln Ile Arg Met Thr Asp Ile Met Arg Gln
145                 150                 155                 160

Ser Leu Asp Asn Pro Ile Ile Gln Val Ala Thr Thr Ile Arg Glu Gly
                165                 170                 175

Gly Trp Ile Tyr Gln Asn Trp Asn Lys Glu Lys Lys Ser Gly Val Tyr
            180                 185                 190

Lys Val Lys Ser Ile Thr Asp Leu Ile Asn Ser Tyr Leu Arg Val Val
        195                 200                 205

Lys Thr Pro Glu Asp Leu Thr Lys Tyr Arg Phe Leu Ala Phe Thr Asn
    210                 215                 220

Lys Val Val Asp Lys Val Asn Ser Ile Val Arg Lys His Val Tyr Lys
225                 230                 235                 240

Thr Asp Leu Pro Phe Ile Glu Gly Glu Lys Leu Val Leu Gln Glu Pro
                245                 250                 255
```

```
Val Met Val Glu Tyr Asp Asp Thr Ile Glu Thr Ile Phe Thr Asn
            260             265             270

Gly Glu Val Thr Val Asp Glu Ile Glu Val Ser Asp Met Asn Ile
        275             280             285

Arg Ile Asp Gly Ser Pro Ala Phe Ser Ile Ser Val Ala Lys Leu Lys
290             295             300

Val Thr Ser Asp Phe Ser Gly Val Thr His Asp Ile Met Ser Val Tyr
305             310             315             320

Gly Glu Asp Ser Lys Ala Glu Phe Asn Tyr Gln Leu Ser Glu Ala Ala
                325             330             335

Ala Val Ile Lys Gln Met Gln Arg Gly Gln Thr Lys Ala Ala Trp Ala
            340             345             350

Ser Phe Trp Asp Ala Lys Lys Thr Phe Thr Glu Thr Lys Ser Leu Gly
        355             360             365

Ala Cys Thr Ile His Lys Ser Gln Gly Ser Val Lys Gly Val Trp
370             375             380

Leu Gly Leu His Asp Ile Ser Tyr Ala Asp Thr Asp Leu Gln Gln Gln
385             390             395             400

Leu Val Tyr Val Gly Val Thr Arg Pro Thr Asp Phe Cys Leu Tyr Phe
            405             410             415

Asp Gly Ser Lys
            420

<210> SEQ ID NO 17
<211> LENGTH: 443
<212> TYPE: PRT
<213> ORGANISM: Cronobacter phage vB CsaM GAP161

<400> SEQUENCE: 17

Met Ser Glu Leu Thr Phe Asp Asp Leu Ser Asp Asp Gln Lys Ser Ala
1               5                   10                  15

His Asp Arg Val Ile His Asn Ile Gln Asn Ala Ile His Thr Thr Ile
            20                  25                  30

Thr Gly Gly Pro Gly Val Gly Lys Thr Thr Leu Val Lys Phe Val Phe
        35                  40                  45

Asn Thr Leu Lys Gly Leu Gly Ile Ser Gly Ile Trp Leu Thr Ala Pro
50                  55                  60

Thr His Gln Ala Lys Asn Val Leu Ala Ala Thr Gly Met Asp Ala
65                  70                  75                  80

Thr Thr Ile His Ser Ala Leu Lys Ile Ser Pro Val Thr Asn Glu Glu
            85                  90                  95

Leu Arg Val Phe Glu Gln Gln Lys Gly Lys Lys Ala Pro Asp Leu Ser
        100                 105                 110

Thr Cys Arg Val Phe Val Val Glu Glu Val Ser Met Val Asp Met Asp
    115                 120                 125

Leu Phe Arg Ile Ile Arg Arg Ser Ile Pro Ser Asn Ala Val Ile Leu
130                 135                 140

Gly Leu Gly Asp Lys Asp Gln Ile Arg Pro Val Asn Ala Asp Gly Arg
145                 150                 155                 160

Val Glu Leu Ser Pro Phe Phe Asp Glu Ile Phe Asp Val Ile Arg
                165                 170                 175

Met Asp Lys Ile Met Arg Gln Ala Glu Gly Asn Pro Ile Ile Gln Val
            180                 185                 190

Ser Arg Ala Val Arg Asp Gly Lys Met Leu Lys Pro Met Ser Val Gly
```

-continued

```
                195                 200                 205
Asp Leu Gly Val Phe Gln His Ala Asn Ala Val Asp Phe Leu Arg Gln
210                 215                 220

Tyr Phe Arg Arg Val Lys Thr Pro Asp Leu Ile Glu Asn Arg Met
225                 230                 235                 240

Phe Ala Tyr Thr Asn Asp Asn Val Asp Lys Leu Asn Ala Thr Ile Arg
                245                 250                 255

Lys His Leu Tyr Lys Thr Thr Glu Pro Phe Ile Leu Asp Glu Val Ile
                260                 265                 270

Val Met Gln Glu Pro Leu Val Gln Glu Met Arg Leu Asn Gly Gln Ile
                275                 280                 285

Phe Thr Glu Ile Val Tyr Asn Asn Glu Lys Ile Arg Val Leu Glu
290                 295                 300

Ile Ile Pro Arg Arg Glu Val Ile Lys Ala Glu Lys Cys Asp Glu Lys
305                 310                 315                 320

Ile Glu Ile Glu Phe Tyr Leu Leu Lys Thr Val Ser Leu Glu Glu Glu
                325                 330                 335

Thr Glu Ala Gln Ile Gln Val Val Asp Pro Val Met Lys Asp Arg
                340                 345                 350

Leu Gly Asn Tyr Leu Ala Tyr Val Ala Ser Thr Tyr Lys Arg Ile Lys
                355                 360                 365

Gln Gln Thr Gly Tyr Lys Ala Pro Trp His Ser Phe Trp Ala Ile Lys
370                 375                 380

Asn Lys Phe Gln Asp Val Lys Pro Leu Pro Val Cys Thr Tyr His Lys
385                 390                 395                 400

Ser Gln Gly Ser Thr Tyr Asp His Ala Tyr Met Tyr Thr Arg Asp Ala
                405                 410                 415

Tyr Ala Phe Ala Asp Tyr Asp Leu Cys Lys Gln Leu Ile Tyr Val Gly
                420                 425                 430

Val Thr Arg Ala Arg Tyr Thr Val Asp Tyr Val
                435                 440
```

<210> SEQ ID NO 18
<211> LENGTH: 442
<212> TYPE: PRT
<213> ORGANISM: Klebsiella phage KP15

<400> SEQUENCE: 18

```
Met Ser Glu Leu Thr Phe Asp Asp Leu Ser Glu Asp Gln Lys Asn Ala
1               5                   10                  15

His Asp Arg Val Ile Lys Asn Ile Arg Asn Lys Ile His Thr Thr Ile
                20                  25                  30

Thr Gly Gly Pro Gly Val Gly Lys Thr Thr Leu Val Lys Phe Val Phe
                35                  40                  45

Glu Thr Leu Lys Lys Leu Gly Ile Ser Gly Ile Trp Leu Thr Ala Pro
50                  55                  60

Thr His Gln Ala Lys Asn Val Leu Ser Glu Ala Val Gly Met Asp Ala
65                  70                  75                  80

Thr Thr Ile His Ser Ala Leu Lys Ile Ser Pro Val Thr Asn Glu Glu
                85                  90                  95

Leu Arg Val Phe Glu Gln Gln Lys Gly Lys Lys Ala Ala Asp Leu Ser
                100                 105                 110

Glu Cys Arg Val Phe Val Val Glu Glu Val Ser Met Val Asp Lys Glu
                115                 120                 125
```

```
Leu Phe Arg Ile Ile Lys Arg Thr Ile Pro Ser Cys Ala Val Ile Leu
    130                 135                 140

Gly Leu Gly Asp Lys Asp Gln Ile Arg Pro Val Asn Thr Glu Gly Ile
145                 150                 155                 160

Thr Glu Leu Ser Pro Phe Phe Asp Glu Ile Phe Asp Val Ile Arg
                165                 170                 175

Met Asp Lys Ile Met Arg Gln Ala Glu Gly Asn Pro Ile Ile Gln Val
                180                 185                 190

Ser Arg Ala Ile Arg Asp Gly Lys Pro Leu Met Pro Leu Met Asn Gly
        195                 200                 205

Glu Leu Gly Val Met Lys His Glu Asn Ala Ser Asp Phe Leu Arg Arg
    210                 215                 220

Tyr Phe Ser Arg Val Lys Thr Pro Asp Asp Leu Asn Asn Arg Met
225                 230                 235                 240

Phe Ala Tyr Thr Asn Ala Asn Val Asp Lys Leu Asn Ala Val Ile Arg
                245                 250                 255

Lys His Leu Tyr Lys Thr Asp Gln Pro Phe Ile Val Gly Glu Val Val
        260                 265                 270

Val Met Gln Glu Pro Leu Val Thr Glu Gly Arg Val Asn Gly Val Ser
    275                 280                 285

Phe Val Glu Val Ile Tyr Asn Asn Asn Glu Gln Ile Lys Ile Leu Glu
290                 295                 300

Ile Ile Pro Arg Ser Asp Thr Ile Lys Ala Asp Arg Cys Asp Pro Val
305                 310                 315                 320

Gln Ile Asp Tyr Phe Leu Met Lys Thr Glu Ser Met Phe Glu Asp Thr
                325                 330                 335

Lys Ala Asp Ile Gln Val Ile Ala Asp Pro Val Met Gln Glu Arg Leu
                340                 345                 350

Gly Asp Tyr Leu Asn Tyr Val Ala Phe Gln Tyr Lys Lys Met Lys Gln
        355                 360                 365

Glu Thr Gly Tyr Lys Ala Pro Trp Tyr Ser Phe Trp Gln Ile Lys Asn
    370                 375                 380

Lys Phe Gln Thr Val Lys Ala Leu Pro Val Cys Thr Tyr His Lys Gly
385                 390                 395                 400

Gln Gly Ser Thr Tyr Asp His Ser Tyr Met Tyr Thr Arg Asp Ala Tyr
                405                 410                 415

Ala Tyr Ala Asp Tyr Glu Leu Cys Lys Gln Leu Leu Tyr Val Gly Thr
                420                 425                 430

Thr Arg Ala Arg Phe Thr Val Asp Tyr Val
            435                 440

<210> SEQ ID NO 19
<211> LENGTH: 438
<212> TYPE: PRT
<213> ORGANISM: Stenotrophomonas phage IME13

<400> SEQUENCE: 19

Met Val Thr Tyr Asp Asp Leu Thr Val Gly Gln Lys Asp Ala Ile Glu
1               5                   10                  15

Lys Ala Leu Gln Ala Met Arg Thr Lys Arg His Ile Thr Ile Arg Gly
            20                  25                  30

Pro Ala Gly Ser Gly Lys Thr Thr Met Thr Arg Phe Leu Leu Glu Arg
        35                  40                  45

Leu Phe Gln Thr Gly Gln Gln Gly Ile Val Leu Thr Ala Pro Thr His
    50                  55                  60
```

Gln Ala Lys Lys Glu Leu Ser Lys His Ala Leu Arg Lys Ser Tyr Thr
65                  70                  75                  80

Ile Gln Ser Val Leu Lys Ile Asn Pro Ser Thr Leu Glu Glu Asn Gln
                85                  90                  95

Ile Phe Glu Gln Lys Gly Thr Pro Asp Phe Ser Lys Thr Arg Val Leu
            100                 105                 110

Ile Cys Asp Glu Val Ser Phe Tyr Thr Arg Lys Leu Phe Asp Ile Leu
        115                 120                 125

Met Arg Asn Val Pro Ser His Cys Val Val Ile Gly Ile Gly Asp Lys
    130                 135                 140

Ala Gln Ile Arg Gly Val Ser Glu Asp Thr His Glu Leu Ser Pro
145                 150                 155                 160

Phe Phe Thr Asp Asn Arg Phe Glu Gln Val Glu Leu Thr Glu Val Lys
                165                 170                 175

Arg His Gln Gly Pro Ile Ile Glu Val Ala Thr Asp Ile Arg Asn Gly
            180                 185                 190

Lys Trp Ile Tyr Glu Lys Leu Asp Asp Ser Gly Asn Gly Val Lys Gln
        195                 200                 205

Phe His Thr Val Lys Asp Phe Leu Ser Lys Tyr Phe Glu Arg Thr Lys
    210                 215                 220

Thr Pro Asn Asp Leu Leu Glu Asn Arg Ile Met Ala Tyr Thr Asn Asn
225                 230                 235                 240

Ser Val Asp Lys Leu Asn Ser Val Ile Arg Lys Gln Leu Tyr Gly Ala
                245                 250                 255

Asn Ala Ala Pro Phe Leu Pro Asp Glu Ile Leu Val Met Gln Glu Pro
            260                 265                 270

Leu Met Phe Asp Ile Asp Ile Gly Gly Gln Thr Leu Lys Glu Val Ile
        275                 280                 285

Phe Asn Asn Gly Gln Asn Val Arg Val Ile Asn Val Lys Pro Ser Arg
    290                 295                 300

Lys Thr Leu Lys Ala Lys Gly Val Gly Glu Ile Glu Val Glu Cys Thr
305                 310                 315                 320

Met Leu Glu Cys Glu Ser Tyr Glu Glu Asp Gly Asp Asp Tyr Arg Arg
                325                 330                 335

Ala Trp Phe Thr Val Val His Asp Gln Asn Thr Gln Tyr Ala Ile Asn
            340                 345                 350

Glu Phe Leu Ser Ile Ile Ala Glu Lys Tyr Arg Ser Arg Glu Val Phe
        355                 360                 365

Pro Asn Trp Lys Asp Phe Trp Ala Ile Arg Asn Thr Phe Val Lys Val
    370                 375                 380

Arg Pro Leu Gly Ala Met Thr Phe His Lys Ser Gln Gly Ser Thr Phe
385                 390                 395                 400

Asp Asn Ala Tyr Leu Phe Thr Pro Cys Leu His Gln Tyr Cys Arg Asp
                405                 410                 415

Pro Asp Val Ala Gln Glu Leu Ile Tyr Val Gly Asn Thr Arg Ala Arg
            420                 425                 430

Lys Asn Val Cys Phe Val
        435

<210> SEQ ID NO 20
<211> LENGTH: 442
<212> TYPE: PRT
<213> ORGANISM: Acinetobacter phage Ac42

```
<400> SEQUENCE: 20

Met Asn Phe Glu Asp Leu Thr Glu Gly Gln Lys Asn Ala Tyr Thr Ala
1               5                   10                  15

Ala Ile Lys Ala Ile Glu Thr Val Pro Ser Ser Ala Glu Lys Arg
            20                  25                  30

His Leu Thr Ile Asn Gly Pro Ala Gly Thr Gly Lys Thr Thr Leu Thr
            35                  40                  45

Lys Phe Leu Ile Ala Glu Leu Ile Arg Arg Gly Glu Arg Gly Val Tyr
    50                  55                  60

Leu Ala Ala Pro Thr His Gln Ala Lys Lys Val Leu Ser Gln His Ala
65                  70                  75                  80

Gly Met Glu Ala Ser Thr Ile His Ser Leu Leu Lys Ile Asn Pro Thr
                85                  90                  95

Thr Tyr Glu Asp Ser Thr Thr Phe Glu Gln Lys Asp Val Pro Asp Met
            100                 105                 110

Ser Glu Cys Arg Val Leu Ile Cys Asp Glu Ala Ser Met Tyr Asp Leu
        115                 120                 125

Lys Leu Phe Gln Ile Leu Met Ser Ser Ile Pro Leu Cys Cys Thr Val
130                 135                 140

Ile Ala Leu Gly Asp Ile Ala Gln Ile Arg Pro Val Glu Pro Gly Ala
145                 150                 155                 160

Phe Glu Gly Gln Val Ser Pro Phe Phe Thr Tyr Glu Lys Phe Glu Gln
                165                 170                 175

Val Ser Leu Thr Glu Val Met Arg Ser Asn Ala Pro Ile Ile Asp Val
            180                 185                 190

Ala Thr Ser Ile Arg Thr Gly Asn Trp Ile Tyr Glu Asn Val Ile Asp
        195                 200                 205

Gly Ala Gly Val His Asn Leu Thr Ser Glu Arg Ser Val Lys Ser Phe
    210                 215                 220

Met Glu Lys Tyr Phe Ser Ile Val Lys Thr Pro Glu Asp Leu Phe Glu
225                 230                 235                 240

Asn Arg Leu Leu Ala Phe Thr Asn Lys Ser Val Asp Asp Leu Asn Lys
                245                 250                 255

Ile Val Arg Lys Lys Ile Tyr Asn Thr Leu Glu Pro Phe Ile Asp Gly
            260                 265                 270

Glu Val Leu Val Met Gln Glu Pro Leu Ile Lys Ser Tyr Thr Tyr Glu
        275                 280                 285

Gly Lys Lys Val Ser Glu Ile Val Phe Asn Asn Gly Glu Met Val Lys
    290                 295                 300

Val Leu Cys Cys Ser Gln Thr Ser Asp Glu Ile Ser Val Arg Gly Cys
305                 310                 315                 320

Ser Thr Lys Tyr Met Val Arg Tyr Trp Gln Leu Asp Leu Gln Ser Leu
                325                 330                 335

Asp Asp Pro Asp Leu Thr Gly Ser Ile Asn Val Ile Val Asp Glu Ala
            340                 345                 350

Glu Ile Asn Lys Leu Asn Leu Val Leu Gly Lys Ser Ala Glu Gln Phe
        355                 360                 365

Lys Ser Gly Ala Val Lys Ala Ala Trp Ala Asp Trp Trp Lys Leu Lys
    370                 375                 380

Arg Asn Phe His Lys Val Lys Ala Leu Pro Cys Ser Thr Ile His Lys
385                 390                 395                 400

Ser Gln Gly Thr Ser Val Asp Asn Val Phe Leu Tyr Thr Pro Cys Ile
                405                 410                 415
```

His Lys Ala Asp Ser Gln Leu Ala Gln Gln Leu Leu Tyr Val Gly Ala
            420                 425                 430

Thr Arg Ala Arg His Asn Val Tyr Tyr Ile
            435                 440

<210> SEQ ID NO 21
<211> LENGTH: 442
<212> TYPE: PRT
<213> ORGANISM: Shigella phage SP18

<400> SEQUENCE: 21

Met Ile Lys Phe Glu Asp Leu Asn Thr Gly Gln Lys Glu Ala Phe Asp
1               5                   10                  15

Tyr Ile Thr Glu Ala Ile Gln Arg Arg Ser Gly Glu Cys Ile Thr Leu
            20                  25                  30

Asn Gly Pro Ala Gly Thr Gly Lys Thr Thr Leu Thr Lys Phe Val Ile
        35                  40                  45

Asp His Leu Val Arg Asn Gly Val Met Gly Ile Val Leu Ala Ala Pro
    50                  55                  60

Thr His Gln Ala Lys Lys Val Leu Ser Lys Leu Ser Gly Gln Thr Ala
65                  70                  75                  80

Asn Thr Ile His Ser Ile Leu Lys Ile Asn Pro Thr Thr Tyr Glu Asp
                85                  90                  95

Gln Asn Ile Phe Glu Gln Arg Glu Met Pro Asp Met Ser Lys Cys Asn
            100                 105                 110

Val Leu Val Cys Asp Glu Ala Ser Met Tyr Asp Gly Ser Leu Phe Lys
        115                 120                 125

Ile Ile Cys Asn Ser Val Pro Glu Trp Cys Thr Ile Leu Gly Ile Gly
130                 135                 140

Asp Met His Gln Leu Gln Pro Val Asp Pro Gly Ser Thr Gln Gln Lys
145                 150                 155                 160

Ile Ser Pro Phe Phe Thr His Pro Lys Phe Lys Gln Ile His Leu Thr
                165                 170                 175

Glu Val Met Arg Ser Asn Ala Pro Ile Ile Glu Val Ala Thr Glu Ile
            180                 185                 190

Arg Asn Gly Gly Trp Phe Arg Asp Cys Met Tyr Asp Gly His Gly Val
        195                 200                 205

Gln Gly Phe Thr Ser Gln Thr Ala Leu Lys Asp Phe Met Val Asn Tyr
    210                 215                 220

Phe Gly Ile Val Lys Asp Ala Asp Met Leu Met Glu Asn Arg Met Tyr
225                 230                 235                 240

Ala Tyr Thr Asn Lys Ser Val Glu Lys Leu Asn Asn Ile Ile Arg Arg
                245                 250                 255

Lys Leu Tyr Glu Thr Asp Lys Ala Phe Leu Pro Tyr Glu Val Leu Val
            260                 265                 270

Met Gln Glu Pro His Met Lys Glu Leu Glu Phe Glu Gly Lys Lys Phe
        275                 280                 285

Ser Glu Thr Ile Phe Asn Asn Gly Gln Leu Val Arg Ile Lys Asp Cys
    290                 295                 300

Lys Tyr Thr Ser Thr Ile Leu Arg Cys Lys Gly Glu Ser His Gln Leu
305                 310                 315                 320

Val Ile Asn Tyr Trp Asp Leu Glu Val Glu Ser Ile Asp Glu Asp Glu
                325                 330                 335

Glu Tyr Gln Val Asp Arg Ile Lys Val Leu Pro Glu Asp Gln Gln Pro

```
            340                 345                 350
Lys Phe Gln Ala Tyr Leu Ala Lys Val Ala Asp Thr Tyr Lys Gln Met
            355                 360                 365

Lys Ala Ala Gly Lys Arg Pro Glu Trp Lys Asp Phe Trp Lys Ala Arg
        370                 375                 380

Arg Thr Phe Leu Lys Val Arg Ala Leu Pro Val Ser Thr Ile His Lys
385                 390                 395                 400

Ala Gln Gly Val Ser Val Asp Lys Ala Phe Ile Tyr Thr Pro Cys Ile
                405                 410                 415

His Met Ala Glu Ala Ser Leu Ala Ser Gln Leu Ala Tyr Val Gly Ile
            420                 425                 430

Thr Arg Ala Arg Tyr Asp Ala Tyr Tyr Val
        435                 440

<210> SEQ ID NO 22
<211> LENGTH: 439
<212> TYPE: PRT
<213> ORGANISM: Yersinia phage phiR1-RT

<400> SEQUENCE: 22

Met Ile Thr Tyr Asp Asp Leu Thr Asp Gly Gln Lys Ser Ala Phe Asp
1               5                   10                  15

Asn Thr Met Glu Ala Ile Lys Asn Lys Lys Gly His Ile Thr Ile Asn
            20                  25                  30

Gly Pro Ala Gly Thr Gly Lys Thr Thr Leu Thr Lys Phe Ile Ile Asp
        35                  40                  45

His Leu Ile Lys Thr Gly Glu Ala Gly Ile Ile Leu Cys Ala Pro Thr
    50                  55                  60

His Gln Ala Lys Lys Val Leu Ser Lys Leu Ser Gly Met Asp Ala Ser
65                  70                  75                  80

Thr Ile His Ser Val Leu Lys Ile Asn Pro Thr Thr Tyr Glu Glu Asn
                85                  90                  95

Gln Ile Phe Glu Gln Arg Glu Val Pro Asp Leu Ala Ala Cys Arg Val
            100                 105                 110

Leu Ile Cys Asp Glu Ala Ser Phe Tyr Asp Arg Lys Leu Phe Gly Ile
        115                 120                 125

Ile Leu Ala Thr Val Pro Ser Trp Cys Thr Val Ile Ala Leu Gly Asp
    130                 135                 140

Lys Asp Gln Leu Arg Pro Val Thr Pro Gly Glu Ser Glu Gln Gln Leu
145                 150                 155                 160

Ser Pro Phe Phe Ser His Ala Lys Phe Lys Gln Val His Leu Thr Glu
                165                 170                 175

Ile Lys Arg Ser Asn Gly Pro Ile Ile Gln Val Ala Thr Asp Ile Arg
            180                 185                 190

Asn Gly Gly Trp Leu Ser Glu Asn Ile Val Asp Gly Glu Gly Val His
        195                 200                 205

Ala Phe Asn Ser Asn Thr Ala Leu Lys Asp Phe Met Ile Arg Tyr Phe
    210                 215                 220

Asp Val Val Lys Thr Ala Asp Asp Leu Ile Glu Ser Arg Met Leu Ala
225                 230                 235                 240

Tyr Thr Asn Lys Ser Val Asp Lys Leu Asn Gly Ile Ile Arg Arg Lys
                245                 250                 255

Leu Tyr Glu Thr Asp Lys Pro Phe Ile Asn Gly Glu Val Leu Val Met
            260                 265                 270
```

-continued

```
Gln Glu Pro Leu Met Lys Glu Leu Glu Phe Asp Gly Lys Phe His
            275                 280                 285

Glu Ile Val Phe Asn Asn Gly Gln Leu Val Lys Ile Leu Tyr Ala Ser
290                 295                 300

Glu Thr Ser Thr Phe Ile Ser Ala Arg Asn Val Pro Gly Glu Tyr Met
305                 310                 315                 320

Ile Arg Tyr Trp Asn Leu Glu Val Glu Thr Ala Asp Ser Asp Asp Asp
                325                 330                 335

Tyr Ala Thr Ser Gln Ile Gln Val Ile Cys Asp Pro Ala Glu Met Thr
            340                 345                 350

Lys Phe Gln Met Phe Leu Ala Lys Thr Ala Asp Thr Tyr Lys Asn Ser
        355                 360                 365

Gly Val Lys Ala Tyr Trp Lys Asp Phe Trp Ser Val Lys Asn Lys Phe
370                 375                 380

Lys Lys Val Lys Ala Leu Pro Val Ser Thr Ile His Lys Ser Gln Gly
385                 390                 395                 400

Cys Thr Val Asn Asn Thr Phe Leu Tyr Thr Pro Cys Ile His Met Ala
                405                 410                 415

Asp Ala Gln Leu Ala Lys Gln Leu Leu Tyr Val Gly Ala Thr Arg Ala
            420                 425                 430

Arg Thr Asn Leu Tyr Tyr Ile
            435

<210> SEQ ID NO 23
<211> LENGTH: 441
<212> TYPE: PRT
<213> ORGANISM: Salmonella phage S16

<400> SEQUENCE: 23

Met Ile Thr Phe Glu Gln Leu Thr Ser Gly Gln Lys Leu Ala Phe Asp
1               5                   10                  15

Glu Thr Ile Arg Ala Ile Lys Glu Lys Lys Asn His Val Thr Ile Asn
                20                  25                  30

Gly Pro Ala Gly Thr Gly Lys Thr Thr Leu Thr Lys Phe Ile Met Glu
            35                  40                  45

His Leu Val Ser Thr Gly Glu Thr Gly Ile Ile Leu Thr Ala Pro Thr
50                  55                  60

His Ala Ala Lys Lys Val Leu Thr Lys Leu Ser Gly Met Glu Ala Asn
65                  70                  75                  80

Thr Ile His Lys Ile Leu Lys Ile Asn Pro Thr Thr Tyr Glu Glu Ser
                85                  90                  95

Met Leu Phe Glu Gln Lys Glu Val Pro Asp Leu Ala Ser Cys Arg Val
            100                 105                 110

Leu Ile Cys Asp Glu Ala Ser Met Trp Asp Arg Lys Leu Phe Lys Ile
        115                 120                 125

Leu Met Ala Ser Ile Pro Lys Trp Cys Thr Ile Val Ala Ile Gly Asp
130                 135                 140

Val Ala Gln Ile Arg Pro Val Asp Pro Gly Glu Thr Glu Ala His Ile
145                 150                 155                 160

Ser Pro Phe Phe Ile His Lys Asp Phe Lys Gln Leu Asn Leu Thr Glu
                165                 170                 175

Val Met Arg Ser Asn Ala Pro Ile Ile Asp Val Ala Thr Asp Ile Arg
            180                 185                 190

Asn Gly Ser Trp Ile Tyr Glu Lys Thr Val Asp Gly His Gly Val His
        195                 200                 205
```

```
Gly Phe Thr Ser Thr Thr Ala Leu Lys Asp Phe Met Met Gln Tyr Phe
    210                 215                 220
Ser Ile Val Lys Ser Pro Glu Asp Leu Phe Glu Asn Arg Met Leu Ala
225                 230                 235                 240
Phe Thr Asn Lys Ser Val Asp Lys Leu Asn Ser Ile Ile Arg Arg Arg
                245                 250                 255
Leu Tyr Gln Thr Glu Glu Ala Phe Val Val Gly Glu Val Ile Val Met
            260                 265                 270
Gln Glu Pro Leu Met Arg Glu Leu Val Phe Glu Gly Lys Lys Phe His
        275                 280                 285
Glu Thr Leu Phe Thr Asn Gly Gln Tyr Val Arg Ile Leu Ser Ala Asp
    290                 295                 300
Tyr Thr Ser Ser Phe Leu Gly Ala Lys Gly Val Ser Gly Glu His Leu
305                 310                 315                 320
Ile Arg His Trp Val Leu Asp Val Glu Thr Tyr Asp Asp Glu Glu Tyr
                325                 330                 335
Ala Arg Glu Lys Ile Asn Val Ile Ser Asp Glu Gln Glu Met Asn Lys
            340                 345                 350
Phe Gln Phe Phe Leu Ala Lys Thr Ala Asp Thr Tyr Lys Asn Trp Asn
        355                 360                 365
Lys Gly Gly Lys Ala Pro Trp Ser Glu Phe Trp Asp Ala Lys Arg Lys
370                 375                 380
Phe His Lys Val Lys Ala Leu Pro Cys Ser Thr Phe His Lys Ala Gln
385                 390                 395                 400
Gly Ile Ser Val Asp Ser Ser Phe Ile Tyr Thr Pro Cys Ile His Val
                405                 410                 415
Ser Ser Asp Asn Lys Phe Lys Leu Glu Leu Leu Tyr Val Gly Ala Thr
            420                 425                 430
Arg Gly Arg His Asp Val Phe Phe Val
        435                 440

<210> SEQ ID NO 24
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 24

Gly Thr Gly Ser Gly Ala Trp Lys Glu Trp Leu Glu Arg Lys Val Gly
1               5                   10                  15
Glu Gly Arg Ala Arg Arg Leu Ile Glu Tyr Phe Gly Ser Ala Gly Glu
            20                  25                  30
Val Gly Lys Leu Val Glu Asn Ala Glu Val Ser Lys Leu Leu Glu Val
        35                  40                  45
Pro Gly Ile Gly Asp Glu Ala Val Ala Arg Leu Val Pro Gly Gly Ser
    50                  55                  60
Ser
65

<210> SEQ ID NO 25
<211> LENGTH: 299
<212> TYPE: PRT
<213> ORGANISM: Bacteriophage RB69

<400> SEQUENCE: 25
```

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
            115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
            195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
            275                 280                 285

Asp Gly Asp Leu Asp Asp Leu Leu Ala Gly Leu
            290                 295

<210> SEQ ID NO 26
<211> LENGTH: 232
<212> TYPE: PRT
<213> ORGANISM: Bacteriophage T7

<400> SEQUENCE: 26

Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

Ala Tyr Ala Ala Ala Val Glu Glu Tyr Glu Ala Asn Pro Pro Ala Val
65                  70                  75                  80

```
Ala Arg Gly Lys Lys Pro Leu Lys Pro Tyr Glu Gly Asp Met Pro Phe
            85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
            115                 120                 125

Val Val Asp Ser Lys Gly Lys Lys Met Glu Asp Val Pro Ile Ile Gly
            130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
            180                 185                 190

Glu Val Glu Glu Asn Gly Tyr Val Ala Ser Gly Ser Ala Lys Ala Ser
            195                 200                 205

Lys Pro Arg Asp Glu Glu Ser Trp Asp Glu Asp Glu Glu Ser Glu
            210                 215                 220

Glu Ala Asp Glu Asp Gly Asp Phe
225                 230

<210> SEQ ID NO 27
<211> LENGTH: 324
<212> TYPE: PRT
<213> ORGANISM: Herpes virus 1

<400> SEQUENCE: 27

Met Asp Ser Pro Gly Gly Val Ala Pro Ala Ser Pro Val Glu Asp Ala
1               5                   10                  15

Ser Asp Ala Ser Leu Gly Gln Pro Glu Glu Gly Ala Pro Cys Gln Val
                20                  25                  30

Val Leu Gln Gly Ala Glu Leu Asn Gly Ile Leu Gln Ala Phe Ala Pro
            35                  40                  45

Leu Arg Thr Ser Leu Leu Asp Ser Leu Leu Val Met Gly Asp Arg Gly
50                  55                  60

Ile Leu Ile His Asn Thr Ile Phe Gly Glu Gln Val Phe Leu Pro Leu
65                  70                  75                  80

Glu His Ser Gln Phe Ser Arg Tyr Arg Trp Arg Gly Pro Thr Ala Ala
                85                  90                  95

Phe Leu Ser Leu Val Asp Gln Lys Arg Ser Leu Leu Ser Val Phe Arg
            100                 105                 110

Ala Asn Gln Tyr Pro Asp Leu Arg Arg Val Glu Leu Ala Ile Thr Gly
            115                 120                 125

Gln Ala Pro Phe Arg Thr Leu Val Gln Arg Ile Trp Thr Thr Thr Ser
            130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
            165                 170                 175

Leu Arg Leu Thr Arg Pro Gln Leu Thr Lys Val Leu Asn Ala Thr Gly
            180                 185                 190

Ala Asp Ser Ala Thr Pro Thr Thr Phe Glu Leu Gly Val Asn Gly Lys
            195                 200                 205

Phe Ser Val Phe Thr Thr Ser Thr Cys Val Thr Phe Ala Ala Arg Glu
```

```
                       210                 215                 220

Glu Gly Val Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
                245                 250                 255

Gly Glu Asn Thr His Arg Thr Phe Ser Val Val Asp Asp Cys Ser
                260                 265                 270

Met Arg Ala Val Leu Arg Arg Leu Gln Val Gly Gly Thr Leu Lys
                275                 280                 285

Phe Phe Leu Thr Thr Pro Val Pro Ser Leu Cys Val Thr Ala Thr Gly
                290                 295                 300

Pro Asn Ala Val Ser Ala Val Phe Leu Leu Lys Pro Gln Lys His His
305                 310                 315                 320

His His His His
```

<210> SEQ ID NO 28
<211> LENGTH: 251
<212> TYPE: PRT
<213> ORGANISM: Artificial Sequence
<220> FEATURE:
<223> OTHER INFORMATION: Synthetic polypeptide

<400> SEQUENCE: 28

```
Met Phe Lys Ile Val Tyr Pro Asn Ala Lys Asp Phe Phe Ser Phe Ile
1               5                   10                  15

Asn Ser Ile Thr Asn Val Thr Asp Ser Ile Ile Leu Asn Phe Thr Glu
                20                  25                  30

Asp Gly Ile Phe Ser Arg His Leu Thr Glu Asp Lys Val Leu Met Ala
            35                  40                  45

Ile Met Arg Ile Pro Lys Asp Val Leu Ser Glu Tyr Ser Ile Asp Ser
    50                  55                  60

Pro Thr Ser Val Lys Leu Asp Val Ser Ser Val Lys Lys Ile Leu Ser
65                  70                  75                  80

Lys Ala Ser Ser Lys Lys Ala Thr Ile Glu Leu Thr Glu Thr Asp Ser
                85                  90                  95

Gly Leu Lys Ile Ile Ile Arg Asp Glu Lys Ser Gly Ala Lys Ser Thr
            100                 105                 110

Ile Tyr Ile Lys Ala Glu Lys Gly Gln Val Glu Gln Leu Thr Glu Pro
        115                 120                 125

Lys Val Asn Leu Ala Val Asn Phe Thr Thr Asp Glu Ser Val Leu Asn
    130                 135                 140

Val Ile Ala Ala Asp Val Thr Leu Val Gly Glu Glu Met Arg Ile Ser
145                 150                 155                 160

Thr Glu Glu Asp Lys Ile Lys Ile Glu Ala Gly Glu Glu Gly Lys Arg
                165                 170                 175

Tyr Val Ala Phe Leu Met Lys Asp Lys Pro Leu Lys Glu Leu Ser Ile
            180                 185                 190

Asp Thr Ser Ala Ser Ser Ser Tyr Ser Ala Glu Met Phe Lys Asp Ala
        195                 200                 205

Val Lys Gly Leu Arg Gly Phe Ser Ala Pro Thr Met Val Ser Phe Gly
    210                 215                 220

Glu Asn Leu Pro Met Lys Ile Asp Val Glu Ala Val Ser Gly Gly His
225                 230                 235                 240

Met Ile Phe Trp Ile Ala Pro Arg Leu Leu Glu
                245                 250
```

<210> SEQ ID NO 29
<211> LENGTH: 245
<212> TYPE: PRT
<213> ORGANISM: Artificial Sequence
<220> FEATURE:
<223> OTHER INFORMATION: Synthetic polypeptide

<400> SEQUENCE: 29

```
Met Lys Ala Lys Val Ile Asp Ala Val Ser Phe Ser Tyr Ile Leu Arg
1               5                   10                  15

Thr Val Gly Asp Phe Leu Ser Glu Ala Asn Phe Ile Val Thr Lys Glu
            20                  25                  30

Gly Ile Arg Val Ser Gly Ile Asp Pro Ser Arg Val Val Phe Leu Asp
        35                  40                  45

Ile Phe Leu Pro Ser Ser Tyr Phe Glu Gly Phe Glu Val Ser Gln Glu
    50                  55                  60

Lys Glu Ile Ile Gly Phe Lys Leu Glu Asp Val Asn Asp Ile Leu Lys
65                  70                  75                  80

Arg Val Leu Lys Asp Asp Thr Leu Ile Leu Ser Ser Asn Glu Ser Lys
                85                  90                  95

Leu Thr Leu Thr Phe Asp Gly Glu Phe Thr Arg Ser Phe Glu Leu Pro
            100                 105                 110

Leu Ile Gln Val Glu Ser Thr Gln Pro Pro Ser Val Asn Leu Glu Phe
        115                 120                 125

Pro Phe Lys Ala Gln Leu Leu Thr Ile Thr Phe Ala Asp Ile Ile Asp
    130                 135                 140

Glu Leu Ser Asp Leu Gly Glu Val Leu Asn Ile His Ser Lys Glu Asn
145                 150                 155                 160

Lys Leu Tyr Phe Glu Val Ile Gly Asp Leu Ser Thr Ala Lys Val Glu
                165                 170                 175

Leu Ser Thr Asp Asn Gly Thr Leu Leu Glu Ala Ser Gly Ala Asp Val
            180                 185                 190

Ser Ser Ser Tyr Gly Met Glu Tyr Val Ala Asn Thr Thr Lys Met Arg
        195                 200                 205

Arg Ala Ser Asp Ser Met Glu Leu Tyr Phe Gly Ser Gln Ile Pro Leu
    210                 215                 220

Lys Leu Arg Phe Lys Leu Pro Gln Glu Gly Tyr Gly Asp Phe Tyr Ile
225                 230                 235                 240

Ala Pro Arg Ala Asp
                245
```

<210> SEQ ID NO 30
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 30

```
Met Lys Val Val Tyr Asp Asp Val Arg Val Leu Lys Asp Ile Ile Gln
1               5                   10                  15

Ala Leu Ala Arg Leu Val Asp Glu Ala Val Leu Lys Phe Lys Gln Asp
            20                  25                  30

Ser Val Glu Leu Val Ala Leu Asp Arg Ala His Ile Ser Leu Ile Ser
        35                  40                  45

Val Asn Leu Pro Arg Glu Met Phe Lys Glu Tyr Asp Val Asn Asp Glu
```

```
                    50                  55                  60

Phe Lys Phe Gly Phe Asn Thr Gln Tyr Leu Met Lys Ile Leu Lys Val
 65                  70                  75                  80

Ala Lys Arg Lys Glu Ala Ile Glu Ile Ala Ser Glu Ser Pro Asp Ser
                 85                  90                  95

Val Ile Ile Asn Ile Ile Gly Ser Thr Asn Arg Glu Phe Asn Val Arg
                100                 105                 110

Asn Leu Glu Val Ser Glu Gln Ile Pro Glu Ile Asn Leu Gln Phe
            115                 120                 125

Asp Ile Ser Ala Thr Ile Ser Ser Asp Gly Phe Lys Ser Ala Ile Ser
            130                 135                 140

Glu Val Ser Thr Val Thr Asp Asn Val Val Gly His Glu Asp
145                 150                 155                 160

Arg Ile Leu Ile Lys Ala Glu Gly Glu Ser Val Glu Val Glu Phe
                165                 170                 175

Ser Lys Asp Thr Gly Gly Leu Gln Asp Leu Glu Phe Ser Lys Glu Ser
            180                 185                 190

Lys Asn Ser Tyr Ser Ala Glu Tyr Leu Asp Asp Val Leu Ser Leu Thr
            195                 200                 205

Lys Leu Ser Asp Tyr Val Lys Ile Ser Phe Gly Asn Gln Lys Pro Leu
            210                 215                 220

Gln Leu Phe Phe Asn Met Glu Gly Gly Lys Val Thr Tyr Leu Leu
225                 230                 235                 240

Ala Pro Lys Val Leu Glu
                245

<210> SEQ ID NO 31
<211> LENGTH: 608
<212> TYPE: PRT
<213> ORGANISM: Bacillus subtilis phage phi29

<400> SEQUENCE: 31

Met Lys His Met Pro Arg Lys Met Tyr Ser Cys Ala Phe Glu Thr Thr
 1               5                  10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175
```

-continued

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys

-continued

```
              595                 600                 605
```

<210> SEQ ID NO 32
<211> LENGTH: 318
<212> TYPE: PRT
<213> ORGANISM: Herpes virus 1

<400> SEQUENCE: 32

```
Thr Asp Ser Pro Gly Gly Val Ala Pro Ala Ser Pro Val Glu Asp Ala
1               5                  10                  15

Ser Asp Ala Ser Leu Gly Gln Pro Glu Glu Gly Ala Pro Cys Gln Val
            20                  25                  30

Val Leu Gln Gly Ala Glu Leu Asn Gly Ile Leu Gln Ala Phe Ala Pro
        35                  40                  45

Leu Arg Thr Ser Leu Leu Asp Ser Leu Leu Val Met Gly Asp Arg Gly
    50                  55                  60

Ile Leu Ile His Asn Thr Ile Phe Gly Glu Gln Val Phe Leu Pro Leu
65                  70                  75                  80

Glu His Ser Gln Phe Ser Arg Tyr Arg Trp Arg Gly Pro Thr Ala Ala
                85                  90                  95

Phe Leu Ser Leu Val Asp Gln Lys Arg Ser Leu Leu Ser Val Phe Arg
            100                 105                 110

Ala Asn Gln Tyr Pro Asp Leu Arg Arg Val Glu Leu Ala Ile Thr Gly
        115                 120                 125

Gln Ala Pro Phe Arg Thr Leu Val Gln Arg Ile Trp Thr Thr Thr Ser
    130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
            180                 185                 190

Ala Asp Ser Ala Thr Pro Thr Thr Phe Glu Leu Gly Val Asn Gly Lys
        195                 200                 205

Phe Ser Val Phe Thr Thr Ser Thr Cys Val Thr Phe Ala Ala Arg Glu
    210                 215                 220

Glu Gly Val Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
                245                 250                 255

Gly Glu Asn Thr His Arg Thr Phe Ser Val Val Asp Asp Cys Ser
            260                 265                 270

Met Arg Ala Val Leu Arg Arg Leu Gln Val Gly Gly Thr Leu Lys
        275                 280                 285

Phe Phe Leu Thr Thr Pro Val Pro Ser Leu Cys Val Thr Ala Thr Gly
    290                 295                 300

Pro Asn Ala Val Ser Ala Val Phe Leu Leu Lys Pro Gln Lys
305                 310                 315
```

<210> SEQ ID NO 33
<211> LENGTH: 233
<212> TYPE: PRT
<213> ORGANISM: Bacteriophage RB69

<400> SEQUENCE: 33

```
Lys Gly Phe Ser Ser Glu Asp Lys Gly Glu Trp Lys Leu Lys Leu Asp
```

```
  1               5                   10                  15
Ala Ser Gly Asn Gly Gln Ala Val Ile Arg Phe Leu Pro Ala Lys Thr
                20                  25                  30
Asp Asp Ala Leu Pro Phe Ala Ile Leu Val Asn His Gly Phe Lys Lys
                35                  40                  45
Asn Gly Lys Trp Tyr Ile Glu Thr Cys Ser Ser Thr His Gly Asp Tyr
 50                  55                  60
Asp Ser Cys Pro Val Cys Gln Tyr Ile Ser Lys Asn Asp Leu Tyr Asn
 65                  70                  75                  80
Thr Asn Lys Thr Glu Tyr Ser Gln Leu Lys Arg Lys Thr Ser Tyr Trp
                85                  90                  95
Ala Asn Ile Leu Val Val Lys Asp Pro Gln Ala Pro Asp Asn Glu Gly
                100                 105                 110
Lys Val Phe Lys Tyr Arg Phe Gly Lys Lys Ile Trp Asp Lys Ile Asn
                115                 120                 125
Ala Met Ile Ala Val Asp Thr Glu Met Gly Glu Thr Pro Val Asp Val
                130                 135                 140
Thr Cys Pro Trp Glu Gly Ala Asn Phe Val Leu Lys Val Lys Gln Val
145                 150                 155                 160
Ser Gly Phe Ser Asn Tyr Asp Glu Ser Lys Phe Leu Asn Gln Ser Ala
                165                 170                 175
Ile Pro Asn Ile Asp Asp Glu Ser Phe Gln Lys Glu Leu Phe Glu Gln
                180                 185                 190
Met Val Asp Leu Ser Glu Met Thr Ser Lys Asp Lys Phe Lys Ser Phe
                195                 200                 205
Glu Glu Leu Asn Thr Lys Phe Asn Gln Val Leu Gly Thr Ala Ala Leu
                210                 215                 220
Gly Gly Ala Ala Ala Ala Ala Ser
225                 230

<210> SEQ ID NO 34
<211> LENGTH: 210
<212> TYPE: PRT
<213> ORGANISM: Bacteriophage T7

<400> SEQUENCE: 34

Ala Lys Lys Ile Phe Thr Ser Ala Leu Gly Thr Ala Glu Pro Tyr Ala
 1               5                  10                  15
Tyr Ile Ala Lys Pro Asp Tyr Gly Asn Glu Glu Arg Gly Phe Gly Asn
                20                  25                  30
Pro Arg Gly Val Tyr Lys Val Asp Leu Thr Ile Pro Asn Lys Asp Pro
                35                  40                  45
Arg Cys Gln Arg Met Val Asp Glu Ile Val Lys Cys His Glu Glu Ala
 50                  55                  60
Tyr Ala Ala Val Glu Glu Tyr Glu Ala Asn Pro Pro Ala Val Ala
 65                  70                  75                  80
Arg Gly Lys Lys Pro Leu Lys Pro Tyr Glu Gly Asp Met Pro Phe Phe
                85                  90                  95
Asp Asn Gly Asp Gly Thr Thr Thr Phe Lys Phe Lys Cys Tyr Ala Ser
                100                 105                 110
Phe Gln Asp Lys Lys Thr Lys Glu Thr Lys His Ile Asn Leu Val Val
                115                 120                 125
Val Asp Ser Lys Gly Lys Lys Met Glu Asp Val Pro Ile Ile Gly Gly
                130                 135                 140
```

```
Gly Ser Lys Leu Lys Val Lys Tyr Ser Leu Val Pro Tyr Lys Trp Asn
145                 150                 155                 160

Thr Ala Val Gly Ala Ser Val Lys Leu Gln Leu Glu Ser Val Met Leu
                165                 170                 175

Val Glu Leu Ala Thr Phe Gly Gly Glu Asp Asp Trp Ala Asp Glu
            180                 185                 190

Val Glu Glu Asn Gly Tyr Val Ala Ser Gly Ala Lys Ala Ser Lys
            195                 200                 205

Pro Arg
    210

<210> SEQ ID NO 35
<211> LENGTH: 99
<212> TYPE: PRT
<213> ORGANISM: Halorubrum lacusprofundi

<400> SEQUENCE: 35

Ser Gly Glu Glu Leu Leu Asp Leu Ala Gly Val Arg Asn Val Gly Arg
1               5                   10                  15

Lys Arg Ala Arg Arg Leu Phe Glu Ala Gly Ile Glu Thr Arg Ala Asp
                20                  25                  30

Leu Arg Glu Ala Asp Lys Ala Val Leu Gly Ala Leu Arg Gly Arg
            35                  40                  45

Glu Arg Thr Ala Glu Arg Ile Leu Glu His Ala Gly Arg Glu Asp Pro
50                  55                  60

Ser Met Asp Asp Val Arg Pro Asp Lys Ser Ala Ser Ala Ala Thr
65                  70                  75                  80

Ala Gly Ser Ala Ser Asp Glu Asp Gly Glu Gly Gln Ala Ser Leu Gly
                85                  90                  95

Asp Phe Arg

<210> SEQ ID NO 36
<211> LENGTH: 102
<212> TYPE: PRT
<213> ORGANISM: Haloferax volcanii

<400> SEQUENCE: 36

Ser Gly Glu Glu Leu Leu Asp Leu Ala Gly Val Arg Gly Val Gly Arg
1               5                   10                  15

Lys Arg Ala Arg Arg Leu Phe Glu Ala Gly Val Glu Thr Arg Ala Asp
                20                  25                  30

Leu Arg Glu Ala Asp Lys Pro Arg Val Leu Ala Ala Leu Arg Gly Arg
            35                  40                  45

Arg Lys Thr Ala Glu Asn Ile Leu Glu Ala Ala Gly Arg Lys Asp Pro
50                  55                  60

Ser Met Asp Ala Val Asp Glu Asp Ala Pro Asp Asp Ala Val Pro
65                  70                  75                  80

Asp Asp Ala Gly Phe Glu Thr Ala Lys Glu Arg Ala Asp Gln Gln Ala
                85                  90                  95

Ser Leu Gly Asp Phe Glu
            100

<210> SEQ ID NO 37
<211> LENGTH: 55
<212> TYPE: PRT
<213> ORGANISM: Artificial Sequence
<220> FEATURE:
<223> OTHER INFORMATION: Synthetic polypeptide
```

```
<400> SEQUENCE: 37

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro
    50                  55

<210> SEQ ID NO 38
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 38

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro Gly Tyr Lys Thr Leu Arg Asp Ala Gly
    50                  55                  60

Leu Thr Pro Ala Glu Ala Glu Arg Val Leu Lys Arg Tyr Gly Ser Val
65                  70                  75                  80

Ser Lys Val Gln Glu Gly Ala Thr Pro Asp Glu Leu Arg Glu Leu Gly
                85                  90                  95

Leu Gly Asp Ala Lys Ile Ala Arg Ile Leu Gly
            100                 105

<210> SEQ ID NO 39
<211> LENGTH: 132
<212> TYPE: PRT
<213> ORGANISM: Homo sapiens

<400> SEQUENCE: 39

Glu Ser Glu Thr Thr Thr Ser Leu Val Leu Glu Arg Ser Leu Asn Arg
1               5                   10                  15

Val His Leu Leu Gly Arg Val Gly Gln Asp Pro Val Leu Arg Gln Val
            20                  25                  30

Glu Gly Lys Asn Pro Val Thr Ile Phe Ser Leu Ala Thr Asn Glu Met
        35                  40                  45

Trp Arg Ser Gly Asp Ser Glu Val Tyr Gln Leu Gly Asp Val Ser Gln
    50                  55                  60

Lys Thr Thr Trp His Arg Ile Ser Val Phe Arg Pro Gly Leu Arg Asp
65                  70                  75                  80

Val Ala Tyr Gln Tyr Val Lys Lys Gly Ser Arg Ile Tyr Leu Glu Gly
                85                  90                  95

Lys Ile Asp Tyr Gly Glu Tyr Met Asp Lys Asn Asn Val Arg Arg Gln
            100                 105                 110

Ala Thr Thr Ile Ile Ala Asp Asn Ile Ile Phe Leu Ser Asp Gln Thr
        115                 120                 125

Lys Glu Lys Glu
```

130

<210> SEQ ID NO 40
<211> LENGTH: 123
<212> TYPE: PRT
<213> ORGANISM: Bacillus subtilis phage phi29

<400> SEQUENCE: 40

Glu Asn Thr Asn Ile Val Lys Ala Thr Phe Asp Thr Glu Thr Leu Glu
1               5                   10                  15

Gly Gln Ile Lys Ile Phe Asn Ala Gln Thr Gly Gly Gln Ser Phe
            20                  25                  30

Lys Asn Leu Pro Asp Gly Thr Ile Ile Glu Ala Asn Ala Ile Ala Gln
        35                  40                  45

Tyr Lys Gln Val Ser Asp Thr Tyr Gly Asp Ala Lys Glu Glu Thr Val
    50                  55                  60

Thr Thr Ile Phe Ala Ala Asp Gly Ser Leu Tyr Ser Ala Ile Ser Lys
65                  70                  75                  80

Thr Val Ala Glu Ala Ala Ser Asp Leu Ile Asp Leu Val Thr Arg His
                85                  90                  95

Lys Leu Glu Thr Phe Lys Val Lys Val Val Gln Gly Thr Ser Ser Lys
            100                 105                 110

Gly Asn Val Phe Phe Ser Leu Gln Leu Ser Leu
        115                 120

<210> SEQ ID NO 41
<211> LENGTH: 177
<212> TYPE: PRT
<213> ORGANISM: Escherichia coli

<400> SEQUENCE: 41

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asp Phe Asp Asp Ile Pro
                165                 170                 175

Phe

<210> SEQ ID NO 42

```
<211> LENGTH: 301
<212> TYPE: PRT
<213> ORGANISM: Enterobacteria phage T4

<400> SEQUENCE: 42

Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
            100                 105                 110

Thr Ser Tyr Trp Ala Asn Ile Leu Val Val Lys Asp Pro Ala Ala Pro
        115                 120                 125

Glu Asn Glu Gly Lys Val Phe Lys Tyr Arg Phe Gly Lys Lys Ile Trp
    130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Gly Gln Val Met Gly
225                 230                 235                 240

Thr Ala Val Met Gly Gly Ala Ala Thr Ala Ala Lys Lys Ala Asp
                245                 250                 255

Lys Val Ala Asp Asp Leu Asp Ala Phe Asn Val Asp Phe Asn Thr
            260                 265                 270

Lys Thr Glu Asp Asp Phe Met Ser Ser Ser Gly Ser Ser Ser
        275                 280                 285

Ala Asp Asp Thr Asp Leu Asp Leu Leu Asn Asp Leu
    290                 295                 300

<210> SEQ ID NO 43
<211> LENGTH: 177
<212> TYPE: PRT
<213> ORGANISM: Artificial Sequence
<220> FEATURE:
<223> OTHER INFORMATION: Synthetic polypeptide

<400> SEQUENCE: 43

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30
```

```
Thr Leu Ala Thr Ser Glu Ser Trp Arg Asp Lys Ala Thr Gly Glu Met
             35                  40                  45

Lys Glu Gln Thr Glu Trp His Arg Val Val Leu Phe Gly Lys Leu Ala
 50                  55                  60

Glu Val Ala Ser Glu Tyr Leu Arg Lys Gly Ser Gln Val Tyr Ile Glu
 65                  70                  75                  80

Gly Gln Leu Arg Thr Arg Lys Trp Thr Asp Gln Ser Gly Gln Asp Arg
                 85                  90                  95

Tyr Thr Thr Glu Val Val Val Asn Val Gly Gly Thr Met Gln Met Leu
                100                 105                 110

Gly Gly Arg Gln Gly Gly Gly Ala Pro Ala Gly Gly Asn Ile Gly Gly
            115                 120                 125

Gly Gln Pro Gln Gly Gly Trp Gly Gln Pro Gln Gln Pro Gln Gly Gly
            130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Ala Phe Ala Ala Ala Ile Pro
                165                 170                 175

Phe

<210> SEQ ID NO 44
<211> LENGTH: 177
<212> TYPE: PRT
<213> ORGANISM: Artificial Sequence
<220> FEATURE:
<223> OTHER INFORMATION: Synthetic polypeptide

<400> SEQUENCE: 44

Ala Ser Arg Gly Val Asn Lys Val Ile Leu Val Gly Asn Leu Gly Gln
  1               5                  10                  15

Asp Pro Glu Val Arg Tyr Met Pro Asn Gly Gly Ala Val Ala Asn Ile
                 20                  25                  30

Thr Leu Ala Thr Ser Glu Ser Trp Arg Asp Lys Ala Thr Gly Glu Met
             35                  40                  45

Lys Glu Gln Thr Glu Trp His Arg Val Val Leu Phe Gly Lys Leu Ala
 50                  55                  60

Glu Val Ala Ser Glu Tyr Leu Arg Lys Gly Ser Gln Val Tyr Ile Glu
 65                  70                  75                  80

Gly Gln Leu Arg Thr Arg Lys Trp Thr Asp Gln Ser Gly Gln Asp Arg
                 85                  90                  95

Tyr Thr Thr Glu Val Val Val Asn Val Gly Gly Thr Met Gln Met Leu
                100                 105                 110

Gly Gly Arg Gln Gly Gly Gly Ala Pro Ala Gly Gly Asn Ile Gly Gly
            115                 120                 125

Gly Gln Pro Gln Gly Gly Trp Gly Gln Pro Gln Gln Pro Gln Gly Gly
            130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asn Phe Gly Gly Asn Ile Pro
                165                 170                 175

Phe

<210> SEQ ID NO 45
<211> LENGTH: 152
<212> TYPE: PRT
<213> ORGANISM: Artificial Sequence
```

```
<220> FEATURE:
<223> OTHER INFORMATION: Synthetic polypeptide

<400> SEQUENCE: 45

Ala Ser Arg Gly Val Asn Lys Val Ile Leu Val Gly Asn Leu Gly Gln
1               5                   10                  15

Asp Pro Glu Val Arg Tyr Met Pro Asn Gly Ala Val Ala Asn Ile
            20                  25                  30

Thr Leu Ala Thr Ser Glu Ser Trp Arg Asp Lys Ala Thr Gly Glu Met
            35                  40                  45

Lys Glu Gln Thr Glu Trp His Arg Val Val Leu Phe Gly Lys Leu Ala
            50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Gln Pro Gln Gly Gly
    130                 135                 140

Asn Gln Phe Ser Gly Gly Ala Gln
145                 150

<210> SEQ ID NO 46
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 46

Ala Ser Arg Gly Val Asn Lys Val Ile Leu Val Gly Asn Leu Gly Gln
1               5                   10                  15

Asp Pro Glu Val Arg Tyr Met Pro Asn Gly Ala Val Ala Asn Ile
            20                  25                  30

Thr Leu Ala Thr Ser Glu Ser Trp Arg Asp Lys Ala Thr Gly Glu Met
            35                  40                  45

Lys Glu Gln Thr Glu Trp His Arg Val Val Leu Phe Gly Lys Leu Ala
            50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Asn Val Gly Gly Thr Met Gln Met Leu
            100                 105                 110

Gly Gly Arg Gln Gly
        115

<210> SEQ ID NO 47
<211> LENGTH: 984
<212> TYPE: PRT
<213> ORGANISM: Methanopyrus kandleri

<400> SEQUENCE: 47

Met Ala Leu Val Tyr Asp Ala Glu Phe Val Gly Ser Glu Arg Glu Phe
1               5                   10                  15
```

```
Glu Glu Glu Arg Glu Thr Phe Leu Lys Gly Val Lys Ala Tyr Asp Gly
                20                  25                  30

Val Leu Ala Thr Arg Tyr Leu Met Glu Arg Ser Ser Ser Ala Lys Asn
            35                  40                  45

Asp Glu Glu Leu Leu Glu Leu His Gln Asn Phe Ile Leu Leu Thr Gly
        50                  55                  60

Ser Tyr Ala Cys Ser Ile Asp Pro Thr Glu Asp Arg Tyr Gln Asn Val
65                  70                  75                  80

Ile Val Arg Gly Val Asn Phe Asp Glu Arg Val Gln Arg Leu Ser Thr
                85                  90                  95

Gly Gly Ser Pro Ala Arg Tyr Ala Ile Val Tyr Arg Arg Gly Trp Arg
                100                 105                 110

Ala Ile Ala Lys Ala Leu Asp Ile Asp Glu Glu Asp Val Pro Ala Ile
            115                 120                 125

Glu Val Arg Ala Val Lys Arg Asn Pro Leu Gln Pro Ala Leu Tyr Arg
        130                 135                 140

Ile Leu Val Arg Tyr Gly Arg Val Asp Leu Met Pro Val Thr Val Asp
145                 150                 155                 160

Glu Val Pro Pro Glu Met Ala Gly Glu Phe Glu Arg Leu Ile Glu Arg
                165                 170                 175

Tyr Asp Val Pro Ile Asp Glu Lys Glu Glu Arg Ile Leu Glu Ile Leu
            180                 185                 190

Arg Glu Asn Pro Trp Thr Pro His Asp Glu Ile Ala Arg Arg Leu Gly
        195                 200                 205

Leu Ser Val Ser Glu Val Glu Gly Glu Lys Asp Pro Glu Ser Ser Gly
210                 215                 220

Ile Tyr Ser Leu Trp Ser Arg Val Val Asn Ile Glu Tyr Asp Glu
225                 230                 235                 240

Arg Thr Ala Lys Arg His Val Lys Arg Asp Arg Leu Leu Glu Glu
                245                 250                 255

Leu Tyr Glu His Leu Glu Glu Leu Ser Glu Arg Tyr Leu Arg His Pro
            260                 265                 270

Leu Thr Arg Arg Trp Ile Val Glu His Lys Arg Asp Ile Met Arg Arg
        275                 280                 285

Tyr Leu Glu Gln Arg Ile Val Glu Cys Ala Leu Lys Leu Gln Asp Arg
290                 295                 300

Tyr Gly Ile Arg Glu Asp Val Ala Leu Cys Leu Ala Arg Ala Phe Asp
305                 310                 315                 320

Gly Ser Ile Ser Met Ile Ala Thr Thr Pro Tyr Arg Thr Leu Lys Asp
                325                 330                 335

Val Cys Pro Asp Leu Thr Leu Glu Ala Lys Ser Val Asn Arg Thr
            340                 345                 350

Leu Ala Thr Leu Ile Asp Glu His Gly Leu Ser Pro Asp Ala Ala Asp
        355                 360                 365

Glu Leu Ile Glu His Phe Glu Ser Ile Ala Gly Ile Leu Ala Thr Asp
370                 375                 380

Leu Glu Glu Ile Glu Arg Met Tyr Glu Glu Gly Arg Leu Ser Glu Glu
385                 390                 395                 400

Ala Tyr Arg Ala Ala Val Glu Ile Gln Leu Ala Glu Leu Thr Lys Lys
                405                 410                 415

Glu Gly Val Gly Arg Lys Thr Ala Glu Arg Leu Leu Arg Ala Phe Gly
            420                 425                 430
```

-continued

Asn Pro Glu Arg Val Lys Gln Leu Ala Arg Glu Phe Glu Ile Glu Lys
435                 440                 445

Leu Ala Ser Val Glu Gly Val Gly Glu Arg Val Leu Arg Ser Leu Val
450                 455                 460

Pro Gly Tyr Ala Ser Leu Ile Ser Ile Arg Gly Ile Asp Arg Glu Arg
465                 470                 475                 480

Ala Glu Arg Leu Leu Lys Lys Tyr Gly Gly Tyr Ser Lys Val Arg Glu
            485                 490                 495

Ala Gly Val Glu Glu Leu Arg Glu Asp Gly Leu Thr Asp Ala Gln Ile
            500                 505                 510

Arg Glu Leu Lys Gly Leu Lys Thr Leu Glu Ser Ile Val Gly Asp Leu
        515                 520                 525

Glu Lys Ala Asp Glu Leu Lys Arg Lys Tyr Gly Ser Ala Ser Ala Val
    530                 535                 540

Arg Arg Leu Pro Val Glu Glu Leu Arg Glu Leu Gly Phe Ser Asp Asp
545                 550                 555                 560

Glu Ile Ala Glu Ile Lys Gly Ile Pro Lys Lys Leu Arg Glu Ala Phe
                565                 570                 575

Asp Leu Glu Thr Ala Ala Glu Leu Tyr Glu Arg Tyr Gly Ser Leu Lys
            580                 585                 590

Glu Ile Gly Arg Arg Leu Ser Tyr Asp Asp Leu Leu Glu Leu Gly Ala
595                 600                 605

Thr Pro Lys Ala Ala Glu Ile Lys Gly Pro Glu Phe Lys Phe Leu
        610                 615                 620

Leu Asn Ile Glu Gly Val Gly Pro Lys Leu Ala Glu Arg Ile Leu Glu
625                 630                 635                 640

Ala Val Asp Tyr Asp Leu Glu Arg Leu Ala Ser Leu Asn Pro Glu Glu
                645                 650                 655

Leu Ala Glu Lys Val Glu Gly Leu Gly Glu Glu Leu Ala Glu Arg Val
            660                 665                 670

Val Tyr Ala Ala Arg Glu Arg Val Glu Ser Arg Arg Lys Ser Gly Arg
675                 680                 685

Gln Glu Arg Ser Glu Glu Glu Trp Lys Glu Trp Leu Glu Arg Lys Val
    690                 695                 700

Gly Glu Gly Arg Ala Arg Arg Leu Ile Glu Tyr Phe Gly Ser Ala Gly
705                 710                 715                 720

Glu Val Gly Lys Leu Val Glu Asn Ala Glu Val Ser Lys Leu Leu Glu
                725                 730                 735

Val Pro Gly Ile Gly Asp Glu Ala Val Ala Arg Leu Val Pro Gly Tyr
            740                 745                 750

Lys Thr Leu Arg Asp Ala Gly Leu Thr Pro Ala Glu Ala Glu Arg Val
        755                 760                 765

Leu Lys Arg Tyr Gly Ser Val Ser Lys Val Gln Glu Gly Ala Thr Pro
770                 775                 780

Asp Glu Leu Arg Glu Leu Gly Leu Gly Asp Ala Lys Ile Ala Arg Ile
785                 790                 795                 800

Leu Gly Leu Arg Ser Leu Val Asn Lys Arg Leu Asp Val Asp Thr Ala
                805                 810                 815

Tyr Glu Leu Lys Arg Arg Tyr Gly Ser Val Ser Ala Val Arg Lys Ala
            820                 825                 830

Pro Val Lys Glu Leu Arg Glu Leu Gly Leu Ser Asp Arg Lys Ile Ala
        835                 840                 845

Arg Ile Lys Gly Ile Pro Glu Thr Met Leu Gln Val Arg Gly Met Ser

```
                    850                 855                 860
Val Glu Lys Ala Glu Arg Leu Leu Glu Arg Phe Asp Thr Trp Thr Lys
865                 870                 875                 880

Val Lys Glu Ala Pro Val Ser Glu Leu Val Arg Val Pro Gly Val Gly
                885                 890                 895

Leu Ser Leu Val Lys Glu Ile Lys Ala Gln Val Asp Pro Ala Trp Lys
                900                 905                 910

Ala Leu Leu Asp Val Lys Gly Val Ser Pro Glu Leu Ala Asp Arg Leu
                915                 920                 925

Val Glu Glu Leu Gly Ser Pro Tyr Arg Val Leu Thr Ala Lys Lys Ser
                930                 935                 940

Asp Leu Met Arg Val Glu Arg Val Gly Pro Lys Leu Ala Glu Arg Ile
945                 950                 955                 960

Arg Ala Ala Gly Lys Arg Tyr Val Glu Glu Arg Ser Arg Glu
                965                 970                 975

Arg Ile Arg Arg Lys Leu Arg Gly
                980

<210> SEQ ID NO 48
<211> LENGTH: 299
<212> TYPE: PRT
<213> ORGANISM: Methanopyrus kandleri

<400> SEQUENCE: 48

Ser Gly Arg Gln Glu Arg Ser Glu Glu Glu Trp Lys Glu Trp Leu Glu
1               5                   10                  15

Arg Lys Val Gly Glu Gly Arg Ala Arg Leu Ile Glu Tyr Phe Gly
                20                  25                  30

Ser Ala Gly Glu Val Gly Lys Leu Val Glu Asn Ala Glu Val Ser Lys
                35                  40                  45

Leu Leu Glu Val Pro Gly Ile Gly Asp Glu Ala Val Ala Arg Leu Val
                50                  55                  60

Pro Gly Tyr Lys Thr Leu Arg Asp Ala Gly Leu Thr Pro Ala Glu Ala
65                  70                  75                  80

Glu Arg Val Leu Lys Arg Tyr Gly Ser Val Ser Lys Val Gln Glu Gly
                85                  90                  95

Ala Thr Pro Asp Glu Leu Arg Glu Leu Gly Leu Gly Asp Ala Lys Ile
                100                 105                 110

Ala Arg Ile Leu Gly Leu Arg Ser Leu Val Asn Lys Arg Leu Asp Val
                115                 120                 125

Asp Thr Ala Tyr Glu Leu Lys Arg Arg Tyr Gly Ser Val Ser Ala Val
130                 135                 140

Arg Lys Ala Pro Val Lys Glu Leu Arg Glu Leu Gly Leu Ser Asp Arg
145                 150                 155                 160

Lys Ile Ala Arg Ile Lys Gly Ile Pro Glu Thr Met Leu Gln Val Arg
                165                 170                 175

Gly Met Ser Val Glu Lys Ala Glu Arg Leu Leu Glu Arg Phe Asp Thr
                180                 185                 190

Trp Thr Lys Val Lys Glu Ala Pro Val Ser Glu Leu Val Arg Val Pro
                195                 200                 205

Gly Val Gly Leu Ser Leu Val Lys Glu Ile Lys Ala Gln Val Asp Pro
                210                 215                 220

Ala Trp Lys Ala Leu Leu Asp Val Lys Gly Val Ser Pro Glu Leu Ala
225                 230                 235                 240
```

```
Asp Arg Leu Val Glu Glu Leu Gly Ser Pro Tyr Arg Val Leu Thr Ala
                245                 250                 255

Lys Lys Ser Asp Leu Met Arg Val Glu Arg Val Gly Pro Lys Leu Ala
        260                 265                 270

Glu Arg Ile Arg Ala Ala Gly Lys Arg Tyr Val Glu Glu Arg Arg Ser
            275                 280                 285

Arg Arg Glu Arg Ile Arg Arg Lys Leu Arg Gly
        290                 295

<210> SEQ ID NO 49
<211> LENGTH: 853
<212> TYPE: PRT
<213> ORGANISM: Escherichia coli

<400> SEQUENCE: 49

Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
            20                  25                  30

Met Gly Asp Phe Tyr Glu Leu Phe Tyr Asp Asp Ala Lys Arg Ala Ser
        35                  40                  45

Gln Leu Leu Asp Ile Ser Leu Thr Lys Arg Gly Ala Ser Ala Gly Glu
    50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
        115                 120                 125

Gln Asp Asn Leu Leu Ala Ala Ile Trp Gln Asp Ser Lys Gly Phe Gly
    130                 135                 140

Tyr Ala Thr Leu Asp Ile Ser Ser Gly Arg Phe Arg Leu Ser Glu Pro
145                 150                 155                 160

Ala Asp Arg Glu Thr Met Ala Ala Glu Leu Gln Arg Thr Asn Pro Ala
                165                 170                 175

Glu Leu Leu Tyr Ala Glu Asp Phe Ala Glu Met Ser Leu Ile Glu Gly
            180                 185                 190

Arg Arg Gly Leu Arg Arg Arg Pro Leu Trp Glu Phe Glu Ile Asp Thr
        195                 200                 205

Ala Arg Gln Gln Leu Asn Leu Gln Phe Gly Thr Arg Asp Leu Val Gly
    210                 215                 220

Phe Gly Val Glu Asn Ala Pro Arg Gly Leu Cys Ala Ala Gly Cys Leu
225                 230                 235                 240

Leu Gln Tyr Ala Lys Asp Thr Gln Arg Thr Thr Leu Pro His Ile Arg
                245                 250                 255

Ser Ile Thr Met Glu Arg Glu Gln Asp Ser Ile Ile Met Asp Ala Ala
            260                 265                 270

Thr Arg Arg Asn Leu Glu Ile Thr Gln Asn Leu Ala Gly Gly Ala Glu
        275                 280                 285

Asn Thr Leu Ala Ser Val Leu Asp Cys Thr Val Thr Pro Met Gly Ser
    290                 295                 300

Arg Met Leu Lys Arg Trp Leu His Met Pro Val Arg Asp Thr Arg Val
305                 310                 315                 320
```

-continued

Leu Leu Glu Arg Gln Gln Thr Ile Gly Ala Leu Gln Asp Phe Thr Ala
            325                 330                 335

Gly Leu Gln Pro Val Leu Arg Gln Val Gly Asp Leu Glu Arg Ile Leu
            340                 345                 350

Ala Arg Leu Ala Leu Arg Thr Ala Arg Pro Arg Asp Leu Ala Arg Met
            355                 360                 365

Arg His Ala Phe Gln Gln Leu Pro Glu Leu Arg Ala Gln Leu Glu Thr
            370                 375                 380

Val Asp Ser Ala Pro Val Gln Ala Leu Arg Glu Lys Met Gly Glu Phe
385                 390                 395                 400

Ala Glu Leu Arg Asp Leu Leu Glu Arg Ala Ile Ile Asp Thr Pro Pro
            405                 410                 415

Val Leu Val Arg Asp Gly Gly Val Ile Ala Ser Gly Tyr Asn Glu Glu
            420                 425                 430

Leu Asp Glu Trp Arg Ala Leu Ala Asp Gly Ala Thr Asp Tyr Leu Glu
            435                 440                 445

Arg Leu Glu Val Arg Glu Arg Glu Arg Thr Gly Leu Asp Thr Leu Lys
            450                 455                 460

Val Gly Phe Asn Ala Val His Gly Tyr Tyr Ile Gln Ile Ser Arg Gly
465                 470                 475                 480

Gln Ser His Leu Ala Pro Ile Asn Tyr Met Arg Arg Gln Thr Leu Lys
            485                 490                 495

Asn Ala Glu Arg Tyr Ile Ile Pro Glu Leu Lys Glu Tyr Glu Asp Lys
            500                 505                 510

Val Leu Thr Ser Lys Gly Lys Ala Leu Ala Leu Glu Lys Gln Leu Tyr
            515                 520                 525

Glu Glu Leu Phe Asp Leu Leu Leu Pro His Leu Glu Ala Leu Gln Gln
            530                 535                 540

Ser Ala Ser Ala Leu Ala Glu Leu Asp Val Leu Val Asn Leu Ala Glu
545                 550                 555                 560

Arg Ala Tyr Thr Leu Asn Tyr Thr Cys Pro Thr Phe Ile Asp Lys Pro
            565                 570                 575

Gly Ile Arg Ile Thr Glu Gly Arg His Pro Val Val Glu Gln Val Leu
            580                 585                 590

Asn Glu Pro Phe Ile Ala Asn Pro Leu Asn Leu Ser Pro Gln Arg Arg
            595                 600                 605

Met Leu Ile Ile Thr Gly Pro Asn Met Gly Gly Lys Ser Thr Tyr Met
            610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
            645                 650                 655

Val Gly Ala Ala Asp Asp Leu Ala Ser Gly Arg Ser Thr Phe Met Val
            660                 665                 670

Glu Met Thr Glu Thr Ala Asn Ile Leu His Asn Ala Thr Glu Tyr Ser
            675                 680                 685

Leu Val Leu Met Asp Glu Ile Gly Arg Gly Thr Ser Thr Tyr Asp Gly
            690                 695                 700

Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
            725                 730                 735

```
Glu Lys Met Glu Gly Val Ala Asn Val His Leu Asp Ala Leu Glu His
                740                 745                 750
Gly Asp Thr Ile Ala Phe Met His Ser Val Gln Asp Gly Ala Ala Ser
            755                 760                 765
Lys Ser Tyr Gly Leu Ala Val Ala Ala Leu Ala Gly Val Pro Lys Glu
        770                 775                 780
Val Ile Lys Arg Ala Arg Gln Lys Leu Arg Glu Leu Glu Ser Ile Ser
785                 790                 795                 800
Pro Asn Ala Ala Ala Thr Gln Val Asp Gly Thr Gln Met Ser Leu Leu
                805                 810                 815
Ser Val Pro Glu Glu Thr Ser Pro Ala Val Glu Ala Leu Glu Asn Leu
            820                 825                 830
Asp Pro Asp Ser Leu Thr Pro Arg Gln Ala Leu Glu Trp Ile Tyr Arg
        835                 840                 845
Leu Lys Ser Leu Val
    850

<210> SEQ ID NO 50
<211> LENGTH: 64
<212> TYPE: PRT
<213> ORGANISM: Sufolobus solfataricus

<400> SEQUENCE: 50

Met Ala Thr Val Lys Phe Lys Tyr Lys Gly Glu Glu Lys Glu Val Asp
1               5                   10                  15
Ile Ser Lys Ile Lys Lys Val Trp Arg Val Gly Lys Met Ile Ser Phe
            20                  25                  30
Thr Tyr Asp Glu Gly Gly Gly Lys Thr Gly Arg Gly Ala Val Ser Glu
        35                  40                  45
Lys Asp Ala Pro Lys Glu Leu Leu Gln Met Leu Glu Lys Gln Lys Lys
    50                  55                  60

<210> SEQ ID NO 51
<211> LENGTH: 99
<212> TYPE: PRT
<213> ORGANISM: Sufolobus solfataricus P2

<400> SEQUENCE: 51

Glu Lys Met Ser Ser Gly Thr Pro Thr Pro Ser Asn Val Val Leu Ile
1               5                   10                  15
Gly Lys Lys Pro Val Met Asn Tyr Val Leu Ala Ala Leu Thr Leu Leu
            20                  25                  30
Asn Gln Gly Val Ser Glu Ile Val Ile Lys Ala Arg Gly Arg Ala Ile
        35                  40                  45
Ser Lys Ala Val Asp Thr Val Glu Ile Val Arg Asn Arg Phe Leu Pro
    50                  55                  60
Asp Lys Ile Glu Ile Lys Glu Ile Arg Val Gly Ser Gln Val Val Thr
65                  70                  75                  80
Ser Gln Asp Gly Arg Gln Ser Arg Val Ser Thr Ile Glu Ile Ala Ile
                85                  90                  95
Arg Lys Lys

<210> SEQ ID NO 52
<211> LENGTH: 88
<212> TYPE: PRT
<213> ORGANISM: Sufolobus solfataricus P2

<400> SEQUENCE: 52
```

```
Thr Glu Lys Leu Asn Glu Ile Val Val Arg Lys Thr Lys Asn Val Glu
1               5                   10                  15

Asp His Val Leu Asp Val Ile Val Leu Phe Asn Gln Gly Ile Asp Glu
                20                  25                  30

Val Ile Leu Lys Gly Thr Gly Arg Glu Ile Ser Lys Ala Val Asp Val
            35                  40                  45

Tyr Asn Ser Leu Lys Asp Arg Leu Gly Asp Gly Val Gln Leu Val Asn
        50                  55                  60

Val Gln Thr Gly Ser Glu Val Arg Asp Arg Arg Ile Ser Tyr Ile
65                  70                  75                  80

Leu Leu Arg Leu Lys Arg Val Tyr
                85

<210> SEQ ID NO 53
<211> LENGTH: 107
<212> TYPE: PRT
<213> ORGANISM: Escherichia coli

<400> SEQUENCE: 53

Ala Gln Gln Ser Pro Tyr Ser Ala Ala Met Ala Glu Gln Arg His Gln
1               5                   10                  15

Glu Trp Leu Arg Phe Val Asp Leu Leu Lys Asn Ala Tyr Gln Asn Asp
                20                  25                  30

Leu His Leu Pro Leu Leu Asn Leu Met Leu Thr Pro Asp Glu Arg Glu
            35                  40                  45

Ala Leu Gly Thr Arg Val Arg Ile Val Glu Glu Leu Leu Arg Gly Glu
        50                  55                  60

Met Ser Gln Arg Glu Leu Lys Asn Glu Leu Gly Ala Gly Ile Ala Thr
65                  70                  75                  80

Ile Thr Arg Gly Ser Asn Ser Leu Lys Ala Ala Pro Val Glu Leu Arg
                85                  90                  95

Gln Trp Leu Glu Glu Val Leu Leu Lys Ser Asp
                100                 105

<210> SEQ ID NO 54
<211> LENGTH: 237
<212> TYPE: PRT
<213> ORGANISM: Enterobacteria phage lambda

<400> SEQUENCE: 54

Met Ser Thr Lys Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
                100                 105                 110

Gly Met Phe Ser Pro Glu Leu Arg Thr Phe Thr Lys Gly Asp Ala Glu
            115                 120                 125
```

Arg Trp Val Ser Thr Lys Lys Ala Ser Asp Ser Ala Phe Trp Leu
130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Asp Glu Phe Thr Phe
            180                 185                 190

Lys Lys Leu Ile Arg Asp Ser Gly Gln Val Phe Leu Gln Pro Leu Asn
                195                 200                 205

Pro Gln Tyr Pro Met Ile Pro Cys Asn Glu Ser Cys Ser Val Val Gly
            210                 215                 220

Lys Val Ile Ala Ser Gln Trp Pro Glu Glu Thr Phe Gly
225                 230                 235

<210> SEQ ID NO 55
<211> LENGTH: 60
<212> TYPE: PRT
<213> ORGANISM: Crenarchaea

<400> SEQUENCE: 55

Met Ser Ser Gly Lys Lys Pro Val Lys Val Lys Thr Pro Ala Gly Lys
1               5                   10                  15

Glu Ala Glu Leu Val Pro Glu Lys Val Trp Ala Leu Ala Pro Lys Gly
                20                  25                  30

Arg Lys Gly Val Lys Ile Gly Leu Phe Lys Asp Pro Glu Thr Gly Lys
            35                  40                  45

Tyr Phe Arg His Lys Leu Pro Asp Asp Tyr Pro Ile
50                  55                  60

<210> SEQ ID NO 56
<211> LENGTH: 136
<212> TYPE: PRT
<213> ORGANISM: Homo sapiens

<400> SEQUENCE: 56

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
                100                 105                 110

Ile His Ala Lys Arg Val Thr Ile Met Pro Lys Asp Ile Gln Leu Ala
            115                 120                 125

Arg Arg Ile Arg Gly Glu Arg Ala
130                 135

<210> SEQ ID NO 57

```
<211> LENGTH: 89
<212> TYPE: PRT
<213> ORGANISM: Enterobacteria phage T4

<400> SEQUENCE: 57
```

| | | | | | | | | | | | | | | |
|---|---|---|---|---|---|---|---|---|---|---|---|---|---|---|
| Met | Ala | Lys | Lys | Glu | Met | Val | Glu | Phe | Asp | Glu | Ala | Ile | His | Gly | Glu |
| 1 | | | | 5 | | | | | 10 | | | | | 15 | |
| Asp | Leu | Ala | Lys | Phe | Ile | Lys | Glu | Ala | Ser | Asp | His | Lys | Leu | Lys | Ile |
| | | | 20 | | | | | 25 | | | | | 30 | | |
| Ser | Gly | Tyr | Asn | Glu | Leu | Ile | Lys | Asp | Ile | Arg | Ile | Arg | Ala | Lys | Asp |
| | | | 35 | | | | | 40 | | | | | 45 | | |
| Glu | Leu | Gly | Val | Asp | Gly | Lys | Met | Phe | Asn | Arg | Leu | Leu | Ala | Leu | Tyr |
| | 50 | | | | | 55 | | | | | 60 | | | | |
| His | Lys | Asp | Asn | Arg | Asp | Val | Phe | Glu | Ala | Glu | Thr | Glu | Glu | Val | Val |
| 65 | | | | | 70 | | | | | 75 | | | | | 80 |
| Glu | Leu | Tyr | Asp | Thr | Val | Phe | Ser | Lys | | | | | | | |
| | | | | 85 | | | | | | | | | | | |

```
<210> SEQ ID NO 58
<211> LENGTH: 339
<212> TYPE: PRT
<213> ORGANISM: Homo sapiens

<400> SEQUENCE: 58
```

| | | | | | | | | | | | | | | | |
|---|---|---|---|---|---|---|---|---|---|---|---|---|---|---|---|
| Met | Ala | Met | Gln | Met | Gln | Leu | Glu | Ala | Asn | Ala | Asp | Thr | Ser | Val | Glu |
| 1 | | | | 5 | | | | | 10 | | | | | 15 | |
| Glu | Glu | Ser | Phe | Gly | Pro | Gln | Pro | Ile | Ser | Arg | Leu | Glu | Gln | Cys | Gly |
| | | | 20 | | | | | 25 | | | | | 30 | | |
| Ile | Asn | Ala | Asn | Asp | Val | Lys | Lys | Leu | Glu | Glu | Ala | Gly | Phe | His | Thr |
| | | | 35 | | | | | 40 | | | | | 45 | | |
| Val | Glu | Ala | Val | Ala | Tyr | Ala | Pro | Lys | Lys | Glu | Leu | Ile | Asn | Ile | Lys |
| | 50 | | | | | 55 | | | | | 60 | | | | |
| Gly | Ile | Ser | Glu | Ala | Lys | Ala | Asp | Lys | Ile | Leu | Ala | Glu | Ala | Ala | Lys |
| 65 | | | | | 70 | | | | | 75 | | | | | 80 |
| Leu | Val | Pro | Met | Gly | Phe | Thr | Thr | Ala | Thr | Glu | Phe | His | Gln | Arg | Arg |
| | | | | 85 | | | | | 90 | | | | | 95 | |
| Ser | Glu | Ile | Ile | Gln | Ile | Thr | Thr | Gly | Ser | Lys | Glu | Leu | Asp | Lys | Leu |
| | | | | 100 | | | | | 105 | | | | | 110 | |
| Leu | Gln | Gly | Gly | Ile | Glu | Thr | Gly | Ser | Ile | Thr | Glu | Met | Phe | Gly | Glu |
| | | | | 115 | | | | | 120 | | | | | 125 | |
| Phe | Arg | Thr | Gly | Lys | Thr | Gln | Ile | Cys | His | Thr | Leu | Ala | Val | Thr | Cys |
| | | 130 | | | | | 135 | | | | | 140 | | | |
| Gln | Leu | Pro | Ile | Asp | Arg | Gly | Gly | Gly | Glu | Gly | Lys | Ala | Met | Tyr | Ile |
| 145 | | | | | 150 | | | | | 155 | | | | | 160 |
| Asp | Thr | Glu | Gly | Thr | Phe | Arg | Pro | Glu | Arg | Leu | Leu | Ala | Val | Ala | Glu |
| | | | | 165 | | | | | 170 | | | | | 175 | |
| Arg | Tyr | Gly | Leu | Ser | Gly | Ser | Asp | Val | Leu | Asp | Asn | Val | Ala | Tyr | Ala |
| | | | 180 | | | | | 185 | | | | | 190 | | |
| Arg | Ala | Phe | Asn | Thr | Asp | His | Gln | Thr | Gln | Leu | Leu | Tyr | Gln | Ala | Ser |
| | | | 195 | | | | | 200 | | | | | 205 | | |
| Ala | Met | Met | Val | Glu | Ser | Arg | Tyr | Ala | Leu | Leu | Ile | Val | Asp | Ser | Ala |
| | 210 | | | | | 215 | | | | | 220 | | | | |
| Thr | Ala | Leu | Tyr | Arg | Thr | Asp | Tyr | Ser | Gly | Arg | Gly | Glu | Leu | Ser | Ala |
| 225 | | | | | 230 | | | | | 235 | | | | | 240 |
| Arg | Gln | Met | His | Leu | Ala | Arg | Phe | Leu | Arg | Met | Leu | Leu | Arg | Leu | Ala |
| | | | | 245 | | | | | 250 | | | | | 255 | |

-continued

```
Asp Glu Phe Gly Val Ala Val Ile Thr Asn Gln Val Val Ala Gln
            260                 265                 270

Val Asp Gly Ala Ala Met Phe Ala Ala Asp Pro Lys Lys Pro Ile Gly
            275                 280                 285

Gly Asn Ile Ile Ala His Ala Ser Thr Thr Arg Leu Tyr Leu Arg Lys
            290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                    325                 330                 335

Ala Lys Asp

<210> SEQ ID NO 59
<211> LENGTH: 375
<212> TYPE: PRT
<213> ORGANISM: Citromicrobium bathyomarinum JL354

<400> SEQUENCE: 59

Met Lys Ala Thr Ile Glu Arg Ala Thr Leu Leu Arg Cys Leu Ser His
1               5                   10                  15

Val Gln Ser Val Val Glu Arg Arg Asn Thr Ile Pro Ile Leu Ser Asn
            20                  25                  30

Val Leu Ile Asp Ala Asp Ala Gly Gly Val Lys Val Met Ala Thr
            35                  40                  45

Asp Leu Asp Leu Gln Val Val Glu Thr Met Thr Ala Ala Ser Val Glu
    50                  55                  60

Ser Ala Gly Ala Ile Thr Val Ser Ala His Leu Leu Phe Asp Ile Ala
65                  70                  75                  80

Arg Lys Leu Pro Asp Gly Ser Gln Val Ser Leu Glu Thr Ala Asp Asn
                85                  90                  95

Arg Met Val Val Lys Ala Gly Arg Ser Arg Phe Gln Leu Pro Thr Leu
            100                 105                 110

Pro Arg Asp Asp Phe Pro Val Ile Val Glu Gly Glu Leu Pro Thr Ser
            115                 120                 125

Phe Glu Leu Pro Ala Arg Glu Leu Ala Glu Met Ile Asp Arg Thr Arg
    130                 135                 140

Phe Ala Ile Ser Thr Glu Glu Thr Arg Tyr Tyr Leu Asn Gly Ile Phe
145                 150                 155                 160

Leu His Val Ser Asp Glu Ala Arg Pro Val Leu Lys Ala Ala Ala Thr
                165                 170                 175

Asp Gly His Arg Leu Ala Arg Tyr Thr Leu Asp Arg Pro Glu Gly Ala
            180                 185                 190

Glu Gly Met Pro Asp Val Ile Val Pro Arg Lys Ala Val Gly Glu Leu
            195                 200                 205

Arg Lys Leu Leu Glu Glu Ala Leu Asp Ser Asn Val Gln Ile Asp Leu
    210                 215                 220

Ser Ala Ser Lys Ile Arg Phe Ala Leu Gly Gly Glu Gly Val Val
225                 230                 235                 240

Leu Thr Ser Lys Leu Ile Asp Gly Thr Phe Pro Asp Tyr Ser Arg Val
                245                 250                 255

Ile Pro Thr Gly Asn Asp Lys Leu Leu Arg Leu Asp Pro Lys Ala Phe
            260                 265                 270

Phe Gln Gly Val Asp Arg Val Ala Thr Ile Ala Thr Glu Lys Thr Arg
            275                 280                 285
```

| | | | | | | | | | | | |
|---|---|---|---|---|---|---|---|---|---|---|---|
| Ala | Val | Lys | Met | Gly | Leu | Asp | Glu | Asp | Lys | Val | Thr | Leu | Ser | Val | Thr |
| | 290 | | | | 295 | | | | 300 | | |

| Ser | Pro | Asp | Asn | Gly | Thr | Ala | Ala | Glu | Glu | Ile | Ala | Ala | Glu | Tyr | Lys |
|---|---|---|---|---|---|---|---|---|---|---|---|---|---|---|---|
| 305 | | | | | 310 | | | | | 315 | | | | | 320 |

| Ala | Glu | Gly | Phe | Glu | Ile | Gly | Phe | Asn | Ala | Asn | Tyr | Leu | Lys | Asp | Ile |
|---|---|---|---|---|---|---|---|---|---|---|---|---|---|---|---|
| | | | | 325 | | | | | 330 | | | | | 335 | |

| Leu | Gly | Gln | Ile | Asp | Ser | Asp | Thr | Val | Glu | Leu | His | Leu | Ala | Asp | Ala |
|---|---|---|---|---|---|---|---|---|---|---|---|---|---|---|---|
| | | | | 340 | | | | | 345 | | | | | 350 | |

| Gly | Ala | Pro | Thr | Leu | Ile | Arg | Arg | Asp | Glu | Asn | Ser | Pro | Ala | Leu | Tyr |
|---|---|---|---|---|---|---|---|---|---|---|---|---|---|---|---|
| | | | 355 | | | | | 360 | | | | | 365 | | |

| Val | Leu | Met | Pro | Met | Arg | Val |
|---|---|---|---|---|---|---|
| | 370 | | | | 375 | |

<210> SEQ ID NO 60
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 60

```
tttttttttt tt                                                         12
```

<210> SEQ ID NO 61
<211> LENGTH: 3667
<212> TYPE: DNA
<213> ORGANISM: Artificial Sequence
<220> FEATURE:
<223> OTHER INFORMATION: Synthetic polynucleotide

<400> SEQUENCE: 61

```
ggttgtttct gttggtgctg atattgcggc gtctgcttgg gtgtttaacc tgccatcaga      60
ttgtgtttgt tagtcgcttt ttttttttgg aattttttt ttggaatttt ttttttgcgc     120
taacaacctc ctgccgtttt gcccgtgcat atcggtcacg aacaaatctg attactaaac     180
acagtagcct ggatttgttc tatcagtaat cgaccttatt cctaattaaa tagagcaaat     240
ccccttattg ggggtaagac atgaagatgc cagaaaaaca tgacctgttg gccgccattc     300
tcgcggcaaa ggaacaaggc atcggggcaa tccttgcgtt tgcaatggcg taccttcgcg     360
gcagatataa tggcggtgcg tttacaaaaa cagtaatcga cgcaacgatg tgcgccatta     420
tcgcctagtt cattcgtgac cttctcgact tcgccggact aagtagcaat ctcgcttata     480
taacgagcgt gtttatcggc tacatcggta ctgactcgat tggttcgctt atcaaacgct     540
tcgctgctaa aaagccgga gtagaagatg gtagaaatca ataatcaacg taaggcgttc     600
ctcgatatgc tggcgtggtc ggagggaact gataacggac gtcagaaaac cagaaatcat     660
ggttatgacg tcattgtagg cggagagcta tttactgatt actccgatca ccctcgcaaa     720
cttgtcacgc taaacccaaa actcaaatca acaggcgccg gacgctacca gcttctttcc     780
cgttggtggg atgcctaccg caagcagctt ggcctgaaag acttctctcc gaaaagtcag     840
gacgctgtgg cattgcagca gattaaggag cgtggcgctt tacctatgat tgatcgtggt     900
gatatccgtc aggcaatcga ccgttgcagc aatatctggg cttcactgcc gggcgctggt     960
tatggtcagt tcgagcataa ggctgacagc ctgattgcaa aattcaaaga agcgggcgga    1020
acggtcagag agattgatgt atgagcagag tcaccgcgat tatctccgct ctggttatct    1080
gcatcatcgt ctgcctgtca tgggctgtta atcattaccg tgataacgcc attacctaca    1140
```

```
aagcccagcg cgacaaaaat gccagagaac tgaagctggc gaacgcggca attactgaca   1200
tgcagatgcg tcagcgtgat gttgctgcgc tcgatgcaaa atacacgaag gagttagctg   1260
atgctaaagc tgaaaatgat gctctgcgtg atgatgttgc cgctggtcgt cgtcggttgc   1320
acatcaaagc agtctgtcag tcagtgcgtg aagccaccac cgcctccggc gtggataatg   1380
cagcctcccc ccgactggca gacaccgctg aacgggatta tttcaccctc agagagaggc   1440
tgatcactat gcaaaaacaa ctggaaggaa cccagaagta tattaatgag cagtgcagat   1500
agagttgccc atatcgatgg gcaactcatg caattattgt gagcaataca cacgcgcttc   1560
cagcggagta taaatgccta aagtaataaa accgagcaat ccatttacga atgtttgctg   1620
ggtttctgtt ttaacaacat tttctgcgcc gccacaaatt ttggctgcat cgacagtttt   1680
cttctgccca attccagaaa cgaagaaatg atgggtgatg gtttcctttg gtgctactgc   1740
tgccggtttg ttttgaacag taaacgtctg ttgagcacat cctgtaataa gcagggccag   1800
cgcagtagcg agtagcattt ttttcatggt gttattcccg atgcttttg aagttcgcag   1860 aatcgtatgt gtagaaaatt aaacaaaccc taaacaatga gttgaaattt catattgtta   1920
atatttatta atgtatgtca ggtgcgatga atcgtcattg tattcccgga ttaactatgt   1980
ccacagccct gacggggaac ttctctgcgg gagtgtccgg gaataattaa aacgatgcac   2040
acagggttta gcgcgtacac gtattgcatt atgccaacgc cccggtgctg acacggaaga   2100
aaccggacgt tatgatttag cgtggaaaga tttgtgtagt gttctgaatg ctctcagtaa   2160
atagtaatga attatcaaag gtatagtaat atcttttatg ttcatggata tttgtaaccc   2220
atcggaaaac tcctgcttta gcaagatttt ccctgtattg ctgaaatgtg atttctcttg   2280
atttcaacct atcataggac gtttctataa gatgcgtgtt tcttgagaat ttaacattta   2340
caaccttttt aagtcctttt attaacacgg tgttatcgtt ttctaacacg atgtgaatat   2400
tatctgtggc tagatagtaa atataatgtg agacgttgtg acgttttagt tcagaataaa   2460
acaattcaca gtctaaatct tttcgcactt gatcgaatat ttctttaaaa atggcaacct   2520
gagccattgg taaaaccttc catgtgatac gagggcgcgt agtttgcatt atcgttttta   2580
tcgtttcaat ctggtctgac ctccttgtgt tttgttgatg atttatgtca aatattagga   2640
atgttttcac ttaatagtat tggttgcgta acaaagtgcg gtcctgctgg cattctggag   2700
ggaaatacaa ccgacagatg tatgtaaggc caacgtgctc aaatcttcat acagaaagat   2760
ttgaagtaat attttaaccg ctagatgaag agcaagcgca tggagcgaca aaatgaataa   2820
agaacaatct gctgatgatc cctccgtgga tctgattcgt gtaaaaaata tgcttaatag   2880
caccatttct atgagttacc ctgatgttgt aattgcatgt atagaacata aggtgtctct   2940
ggaagcattc agagcaattg aggcagcgtt ggtgaagcac gataataata tgaaggatta   3000
ttccctggtg gttgactgat caccataact gctaatcatt caaactattt agtctgtgac   3060
agagccaaca cgcagtctgt cactgtcagg aaagtggtaa aactgcaact caattactgc   3120
aatgccctcg taattaagtg aatttacaat atcgtcctgt tcggagggaa gaacgcggga   3180
tgttcattct tcatcacttt taattgatgt atatgctctc ttttctgacg ttagtctccg   3240
acggcaggct tcaatgaccc aggctgagaa attcccggac cctttttgct caagagcgat   3300
gttaatttgt tcaatcattt ggttaggaaa gcggatgttg cgggttgttg ttctgcgggt   3360
tctgttcttc gttgacatga ggttgccccg tattcagtgt cgctgatttg tattgtctga   3420
agttgttttt acgttaagtt gatgcagatc aattaatacg atacctgcgt cataattgat   3480
tatttgacgt ggtttgatgg cctccacgca cgttgtgata tgtagatgat aatcattatc   3540
```

```
actttacggg tcctttccgg tgaaaaaaaa ggtaccaaaa aaaacatcgt cgtgagtagt    3600
gaaccgtaag catgtaggac gtcctgtcgc tgtgtctcgg acactgattg acacggttta    3660
gtagagc                                                              3667
```

<210> SEQ ID NO 62
<211> LENGTH: 3617
<212> TYPE: DNA
<213> ORGANISM: Artificial Sequence
<220> FEATURE:
<223> OTHER INFORMATION: Synthetic polynucleotide

<400> SEQUENCE: 62

```
tttttttttt tttttttttt tttttttcg agacacagcg acaggacgtc ctacatgctt      60
acggttcact actcacgacg atgttttttt tggtaccttt tttttcaccg gaaaggaccc    120
gtaaagtgat aatgattatc atctacatat cacaacgtgc gtggaggcca tcaaaccacg    180
tcaaataatc aattatgacg caggtatcgt attaattgat ctgcatcaac ttaacgtaaa    240
aacaacttca gacaatacaa atcagcgaca ctgaatacgg gcaacctca tgtcaacgaa     300 gaacagaacc cgcagaacaa caacccgcaa catccgcttt cctaaccaaa tgattgaaca    360
aattaacatc gctcttgagc aaaaagggtc cgggaatttc tcagcctggg tcattgaagc    420
ctgccgtcgg agactaacgt cagaaaagag agcatataca tcaattaaaa gtgatgaaga    480
atgaacatcc cgcgttcttc cctccgaaca ggacgatatt gtaaattcac ttaattacga    540
gggcattgca gtaattgagt tgcagttta ccactttcct gacagtgaca gactgcgtgt     600
tggctctgtc acagactaaa tagtttgaat gattagcagt tatggtgatc agtcaaccac    660
cagggaataa tccttcatat tattatcgtg cttcaccaac gctgcctcaa ttgctctgaa    720
tgcttccaga gacaccttat gttctataca tgcaattaca acatcagggt aactcataga    780
aatggtgcta ttaagcatat tttttacacg aatcagatcc acggagggat catcagcaga    840
ttgttcttta ttcattttgt cgctccatgc gcttgctctt catctagcgg ttaaaatatt    900
acttcaaatc tttctgtatg aagatttgag cacgttggcc ttacatacat ctgtcggttg    960
tatttccctc cagaatgcca gcaggaccgc actttgttac gcaaccaata ctattaagtg   1020
aaaacattcc taatatttga cataaatcat caacaaaaca caaggaggtc agaccagatt   1080
gaaacgataa aaacgataat gcaaactacg cgccctcgta tcacatggaa ggttttacca   1140
atggctcagg ttgccatttt taagaaaata ttcgatcaag tgcgaaaaga tttagactgt   1200
gaattgtttt attctgaact aaaacgtcac aacgtctcac attatattta ctatctagcc   1260
acagataata ttcacatcgt gttagaaaac gataacaccg tgttaataaa aggacttaaa   1320
aaggttgtaa atgttaaatt ctcaagaaac acgcatctta tagaaacgtc ctatgatagg   1380
ttgaaatcaa gagaaatcac atttcagcaa tacagggaaa atcttgctaa gcaggagtt    1440 ttccgatggg ttacaaatat ccatgaacat aaaagatatt actataccctt tgataattca   1500 ttactattta ctgagagcat tcagaacact acacaaatct ttccacgcta aatcataacg   1560
tccggttcct tccgtgtcag caccggggcg ttggcataat gcaatacgtg tacgcgctaa   1620
accctgtgtg catcgtttta attattcccg gacactcccg cagagaagtt ccccgtcagg   1680
gctgtggaca tagttaatcc gggaatacaa tgacgattca tcgcacctga catacattaa   1740
taaatattaa caatatgaaa tttcaactca ttgtttaggg tttgtttaat tttctacaca   1800
tacgattctg cgaacttcaa aaagcatcgg gaataacacc atgaaaaaaa tgctactcgc   1860
```

```
tactgcgctg gccctgctta ttacaggatg tgctcaacag acgtttactg ttcaaaacaa    1920
accggcagca gtagcaccaa aggaaaccat cacccatcat ttcttcgttt ctggaattgg    1980
gcagaagaaa actgtcgatg cagccaaaat ttgtggcggc gcagaaaatg ttgttaaaac    2040
agaaacccag caaacattcg taaatggatt gctcggtttt attactttag gcatttatac    2100
tccgctggaa gcgcgtgtgt attgctcaca ataattgcat gagttgccca tcgatatggg    2160
caactctatc tgcactgctc attaatatac ttctgggttc cttccagttg tttttgcata    2220
gtgatcagcc tctctctgag ggtgaaataa tcccgttcag cggtgtctgc cagtcggggg    2280
gaggctgcat tatccacgcc ggaggcggtg gtggcttcac gcactgactg acagactgct    2340
ttgatgtgca accgacgacg accagcggca acatcatcac gcagagcatc attttcagct    2400
ttagcatcag ctaactcctt cgtgtatttt gcatcgagcg cagcaacatc acgctgacgc    2460
atctgcatgt cagtaattgc cgcgttcgcc agcttcagtt ctctggcatt tttgtcgcgc    2520
tgggctttgt aggtaatggc gttatcacgg taatgattaa cagcccatga caggcagacg    2580
atgatgcaga taaccagagc ggagataatc gcggtgactc tgctcataca tcaatctctc    2640
tgaccgttcc gcccgcttct ttgaattttg caatcaggct gtcagcctta tgctcgaact    2700
gaccataacc agcgcccggc agtgaagccc agatattgct gcaacggtcg attgcctgac    2760
ggatatcacc acgatcaatc ataggtaaag cgccacgctc cttaatctgc tgcaatgcca    2820
cagcgtcctg acttttcgga gagaagtctt tcaggccaag ctgcttgcgg taggcatccc    2880
accaacggga agaagctgg tagcgtccgg cgcctgttga tttgagtttt gggtttagcg    2940
tgacaagttt gcgagggtga tcggagtaat cagtaaatag ctctccgcct acaatgacgt    3000
cataaccatg atttctggtt ttctgacgtc cgttatcagt tccctccgac cacgccagca    3060
tatcgaggaa cgccttacgt tgattattga tttctaccat cttctactcc ggcttttta    3120 gcagcgaagc gtttgataag cgaaccaatc gagtcagtac cgatgtagcc gataaacacg    3180
ctcgttatat aagcgagatt gctacttagt ccggcgaagt cgagaaggtc acgaatgaac    3240
taggcgataa tggcgcacat cgttgcgtcg attactgttt ttgtaaacgc accgccatta    3300
tatctgccgc gaaggtacgc cattgcaaac gcaaggattg ccccgatgcc ttgttccttt    3360
gccgcgagaa tggcggccaa caggtcatgt ttttctggca tcttcatgtc ttaccccaa    3420 taagggggatt tgctctatt aattaggaat aaggtcgatt actgatagaa caaatccagg    3480
ctactgtgtt tagtaatcag atttgttcgt gaccgatatg cacgggcaaa acggcaggag    3540
gttgttagcg caaaaaaaaa attccaaaaa aaaattcca aaaaaaaaaa gcgactaaca    3600
aacacaatct gatggca                                                  3617
```

<210> SEQ ID NO 63
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 63

```
ggttaaacac ccaagcagac gccgcaatat cagcaccaac agaaacaacc tttgaggcga    60
gcggtcaa                                                            68
```

<210> SEQ ID NO 64
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 64
ttgaccgctc gcctc                                                                15

<210> SEQ ID NO 65
<211> LENGTH: 786
<212> TYPE: DNA
<213> ORGANISM: Escherichia coli

<400> SEQUENCE: 65
tgtctgaccg caccgccgaa agaagcggca cgtccgaccc tgatgccgcg tgcacagtct    60
tataaagatc tgacccatct gccggctccg acgggcaaaa ttttttgttag cgtctataac   120 atccaggacg aaaccggtca atttaaaccg taccggcga gtaatttctc cacgccgtt    180 ccgcagagtg caaccgctat gctggtcacg gcactgaaag attcccgttg gttcattccg   240
ctggaacgcc agggcctgca aaacctgctg aatgaacgta aaattatccg cgcagctcag   300
gaaaacggta ccgtggccat taacaatcgt attccgctgc aaagcctgac cgccgcaaac   360
atcatggttg aaggctctat catcggttac gaatcaaacg tcaaatcggg cggtgtgggc   420
gcacgttatt ttggcattgg tgctgatacc cagtaccaac tggaccagat cgcagttaac   480
ctgcgcgtgg ttaatgtcag caccggcgaa attctgagct ctgtgaatac cagcaaaacg   540
atcctgtctt acgaagtgca ggctggtgtt tttcgtttca ttgattatca acgcctgctg   600
gaaggcgaag tcggttacac ctcaaacgaa ccggtgatgc tgtgtctgat gtcggcgatt   660
gaaacgggtg ttatttttcct gatcaatgat ggcatcgacc gtggtctgtg ggatctgcag   720
aacaaagccg aacgtcaaaa tgacattctg gtgaaatacc gccacatgag tgttccgccg   780
gaatcc                                                              786

<210> SEQ ID NO 66
<211> LENGTH: 262
<212> TYPE: PRT
<213> ORGANISM: Escherichia coli

<400> SEQUENCE: 66

Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn

| | | 145 | | | 150 | | | | 155 | | | | 160 | |
|---|---|---|---|---|---|---|---|---|---|---|---|---|---|---|

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
            195                 200                 205

Asn Glu Pro Val Met Leu Cys Leu Met Ser Ala Ile Glu Thr Gly Val
        210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260

<210> SEQ ID NO 67
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 67

Ser Ala Trp Ser His Pro Gln Phe Glu Lys
1               5                   10

<210> SEQ ID NO 68
<211> LENGTH: 1653
<212> TYPE: RNA
<213> ORGANISM: Artificial Sequence
<220> FEATURE:
<223> OTHER INFORMATION: Synthetic polynucleotide

<400> SEQUENCE: 68

| | | |
|---|---|---|
| auggaagacg ccaaaaacau aaagaaaggc ccggcgccau ucuauccgcu ggaagaugga | | 60 |
| accgcuggag agcaacugca uaaggcuaug aagagauacg cccuguucc uggaacaauu | | 120 |
| gcuuuuacag augcacauau cgagguggac aucacuuacg cugaguacuu cgaaaugucc | | 180 |
| guucgguugg cagaagcuau gaaacgauau gggcugaaua caaaucacag aaucgucgua | | 240 |
| ugcagugaaa acucucuuca auucuuuaug ccgguguugg gcgcguuauu uaucggaguu | | 300 |
| gcaguugcgc ccgcgaacga cauuuauaau gaacgugaau ugcucaacag uaugggcauu | | 360 |
| ucgcagccua ccguggnguu cguuuccaaa aagggguugc aaaaaauuuu gaacgugcaa | | 420 |
| aaaaagcucc caaucaucca aaaaauuauu aucauggauu cuaaaacgga uuaccaggga | | 480 |
| uuucagucga uguacacguu cgucacaucu caucuaccuc ccgguuuuaa ugaauacgau | | 540 |
| uuugugccag aguccuucga uagggacaag acaauugcac ugaucaugaa cuccucugga | | 600 |
| ucuacugguc ugccuaaagg ugucgcucug ccucauagaa cugccugcgu gagauucucg | | 660 |
| caugccagag auccuauuuu uggcaaucaa aucauuccgg auacugcgau uuaagugu | | 720 |
| guuccauucc aucacgguuu uggaauguuu acuacacgg auauuugau auguggauuu | | 780 |
| cgagucgucu uaauguauag auugaagaa gagcuguuuc ugaggagccu ucaggauuac | | 840 |
| aagauucaaa gugcgcugcu ggugccaacc cuauucuccu ucuucgccaa aagcacucug | | 900 |
| auugacaaau acgauuuauc uaauuuacac gaaauugcuu cugguggcgc ucccucucu | | 960 |
| aaggaagucg gggaagcggu ugccaagagg uuccaucugc cagguaucag gcaaggauau | | 1020 |

-continued

```
gggcucacug agacuacauc agcuauucug auuacacccg aggggauga uaaaccgggc      1080 gcggucggua aaguuguucc auuuuugaa gcgaagguug uggaucugga uaccgggaaa       1140
acgcugggcg uuaaucaaag aggcgaacug ugugagag guccuaugau uauguccggu        1200
uauguaaaca auccggaagc gaccaacgcc uugauugaca aggauggaug gcuacauucu      1260
ggagacauag cuuacuggga cgaagacgaa cacuucuuca ucguugaccg ccugaagucu      1320
cugauuaagu acaaaggcua ucagguggcu cccgcugaau uggaauccau cuugcuccaa      1380
caccccaaca ucuucgacgc aggugucgca ggucuucccg acgaugacgc cggugaacuu      1440
cccgccgccg uuguuguuuu ggagcacgga aagacgauga cggaaaaaga gaucguggau      1500
uacgucgcca gucaaguaac aaccgcgaaa aaguugcgcg gaggaguugu guuuguggac      1560
gaaguaccga aaggcuuuac cggaaaacuc gacgcaagaa aaaucagaga gauccucaua      1620
aaggccaaga agggcggaaa gaucgccgug uaa                                  1653
```

<210> SEQ ID NO 69
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 69

```
ccccccccca                                                              10
```

<210> SEQ ID NO 70
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 70

```
ggttgtttct gttggtgctg atattgc                                           27
```

<210> SEQ ID NO 71
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 71

```
gcaatatcag caccaacaga aacaacct                                          28
```

<210> SEQ ID NO 72
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 72

```
cgttctgttt atgtttcttg gacactgatt gacacggttt agtagaac                    48
```

<210> SEQ ID NO 73
<211> LENGTH: 51
<212> TYPE: DNA
<213> ORGANISM: Artificial Sequence
<220> FEATURE:
<223> OTHER INFORMATION: Synthetic polynucleotide

```
<400> SEQUENCE: 73 cccccccca cccccccca cccccccca agaaacataa acagaacgtt t            51
```